(12) United States Patent
He et al.

(10) Patent No.: US 11,339,147 B2
(45) Date of Patent: May 24, 2022

(54) LACTAM COMPOUND AS FXR RECEPTOR AGONIST

(71) Applicant: CSPC ZHONGQI PHARMACEUTICAL TECHNOLOGY (SHIJIAZHUANG) CO., LTD., Shijiazhuang (CN)

(72) Inventors: Haiying He, Shanghai (CN); Jun Yu, Shanghai (CN); Shuhui Chen, Shanghai (CN)

(73) Assignee: CSPC ZHONGQI PHARMACEUTICAL TECHNOLOGY (SHIJIAZHUANG) CO., LTD., Shijiazhuang (CN)

( * ) Notice: Subject to any disclaimer, the term of this patent is extended or adjusted under 35 U.S.C. 154(b) by 0 days.

(21) Appl. No.: 16/616,632

(22) PCT Filed: May 25, 2018

(86) PCT No.: PCT/CN2018/088393
§ 371 (c)(1),
(2) Date: Nov. 25, 2019

(87) PCT Pub. No.: WO2018/214959
PCT Pub. Date: Nov. 29, 2018

(65) Prior Publication Data
US 2020/0190074 A1 Jun. 18, 2020

(30) Foreign Application Priority Data

May 26, 2017 (CN) .......................... 201710384773.8
Jun. 26, 2017 (CN) .......................... 201710523080.2
Sep. 22, 2017 (CN) .......................... 201710867863.2

(51) Int. Cl.
| | |
|---|---|
| C07D 413/14 | (2006.01) |
| C07D 413/12 | (2006.01) |
| A61P 1/16 | (2006.01) |
| C07D 417/14 | (2006.01) |
| C07D 471/04 | (2006.01) |

(52) U.S. Cl.
CPC .............. *C07D 413/12* (2013.01); *A61P 1/16* (2018.01); *C07D 413/14* (2013.01); *C07D 417/14* (2013.01); *C07D 471/04* (2013.01)

(58) Field of Classification Search
CPC ................................................... C07D 413/14
USPC ......................................................... 546/158
See application file for complete search history.

(56) References Cited

U.S. PATENT DOCUMENTS

2011/0034507 A1\* 2/2011 Akwabi-Ameyaw .........................
A61P 35/00
514/309

FOREIGN PATENT DOCUMENTS

| | | |
|---|---|---|
| CN | 101877966 | 11/2010 |
| EP | 1690538 | 8/2006 |
| JP | H05-502022 A | 4/1993 |
| JP | 2003-507327 A | 2/2003 |
| JP | 2005-330266 | 12/2005 |
| JP | 2006-514069 A | 4/2006 |
| WO | WO 9106539 A1 | 5/1991 |
| WO | WO 2001/012187 | 2/2001 |
| WO | WO 112187 A2 | 2/2001 |
| WO | WO 2004/063190 | 7/2004 |
| WO | WO 2005054213 A1 | 6/2005 |
| WO | WO 2005/082925 | 9/2005 |
| WO | WO 2009/005998 | 1/2009 |

OTHER PUBLICATIONS

Yan et al., "The pathophysiological, etc.," Pharmacology & Therapeutics 226 107867, 1-16. (Year: 2021).\*
Li et al. I, "Bile Acids, etc.," Current Protein Peptide Science, 20(10):976-983. (Year: 2019).\*
Li et al. II, "Farnesoid X, etc.," Frontiers in Pharmacology, 11, Article 12471-15. (Year: 2020).\*
Shah et al., "Emerging drugs, etc.," Expert Opinion on Emerging Drugs, 25 (3), 251-260. (Year: 2020).\*
Tanaka, "Emerging novel, etc.," Hepatology Research, 49:489-499. (Year: 2019).\*
Ning et al., "Nuclear receptors, etc.," Hindawi Mediators of Inflammation, Article ID 2624941, 1-13. (Year: 2019).\*
Stojancevic et al., "The impact, etc.," Can J Gastroenterol, 26 (9), 631-637. (Year: 2012).\*
Porez et al., "Bile acid receptors, etc.," Journal of Lipid Research, 53, 1723-1737. (Year: 2012).\*
Forman et al., "Identification of a nuclear receptor that is activated by farnesol metabolites," *Cell*, 81:687-693, 1995.
Nian et al., "Advances on Farensoid X Receptor Agonists," *Chinese Journal of Medicinal Chemistry*, 27(1):57-66, 2017. (English abstract of Chinese publication).
PCT International Search Report issued in International Application No. PCT/CN2018/088393, dated Sep. 5, 2018.
PCT International Search Report issued in International Application No. PCT/CN2018/088393, dated Sep. 5, 2018.

(Continued)

*Primary Examiner* — Patricia L Morris
(74) *Attorney, Agent, or Firm* — Parker Highlander PLLC

(57) ABSTRACT

Disclosed is a compound as shown in formula (I), an optical isomer thereof or a pharmaceutically acceptable salt thereof, and the present invention relates to the use of same in the preparation of a drug for treating FXR-related diseases.

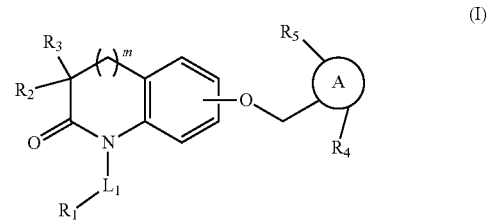

15 Claims, 3 Drawing Sheets

(56) References Cited

OTHER PUBLICATIONS

Extended European Search Report issued in European Patent Application No. 18806569.2, dated Jan. 21, 2021. Gege et al., "Knocking on FXR's Door: The "Hammerhead"-Structure Series of FXR Agonists—Amphiphilic Isoxazoles with Potent In Vitro and In Vivo Activities," *Current Topics in Medical Chemistry*, 14:2143-2158, 2014.

Office Communication issued in Japanese Application No. 2019 565423 dated Mar. 15, 2022.

English Translation of Office Communication issued in Japanese Application No. 2019 565423 dated Mar. 15, 2022.

\* cited by examiner

LACTAM COMPOUND AS FXR RECEPTOR AGONIST

CROSS REFERENCE TO RELATED APPLICATIONS

This application is a national phase application under 35 U.S.C. § 371 of International Application No. PCT/CN2018/088393, filed on May 25, 2018, which claims the priority of Chinese Patent Application No. 201710384773.8, filed on May 26, 2017 with the China National Intellectual Property Office, Chinese Patent Application No. 201710523080.2, filed on Jun. 26, 2017 with the China National Intellectual Property Office, and Chinese Patent Application No. 201710867863.2, filed on Sep. 22, 2017 with the China National Intellectual Property Office, the disclosures of which are all hereby incorporated by reference.

FIELD

The present disclosure relates to the field of medicine, and in particular to a compound of formula (I), an optical isomer thereof or a pharmaceutically acceptable salt thereof, and the use of the same in the preparation of a medicament for the treatment of FXR-related diseases.

BACKGROUND

Farnesoid X receptor (FXR), a member of the nuclear receptor superfamily, was originally cloned from rat liver cDNA libraries (B M. Forman, et al., Cell 81: 687-693 (1995)). FXR has a typical nuclear receptor structure and consists of a ligand-independent transcriptional activation domain, a DNA binding domain, a hinge region, and a ligand binding region. FXR is abundantly expressed in the liver, intestine, kidney, and adrenal glands, forms a heterodimer with retinoid X receptor (RXR), and binds to DNA to regulate gene transcription. The FXR/RXR heterodimer preferentially binds to a component composed of two nuclear receptor half sites of the consensus AG(G/T)TCA organized as an inverted repeat and separated by a single nucleotide (IR-I motif) (B M. Forman, et al., Cell 81: 687-693(1995)). FXR, as a bile acid-activated nuclear receptor, is involved in the regulation of various physiological activities, including bile acid metabolism, lipid metabolism, glucose metabolism, liver protection, and is closely related to metabolic syndrome, hepatobiliary disease, type II diabetes and other diseases. Cholic acid that serves as an endogenous ligand for FXR includes chenodeoxycholic acid (CDCA), deoxycholic acid (DCA), lithocholic acid (LCA), and the taurine and glycine conjugates of these bile acids. WO 2005082925 discloses use of the cholic acid derivative INT747 in the preparation of a medicament for the treatment of FXR-related diseases.

SUMMARY

The present disclosure provides a compound of formula (I), an optical isomer thereof or a pharmaceutically acceptable salt thereof,

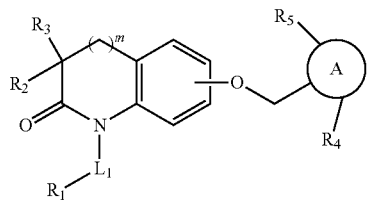

wherein,
m is selected from 0 or 1;
$L_1$ is selected from a single bond, —$CH_2$—,

$R_1$ is selected from —COOH, or selected from the following groups which are optionally substituted with 1, 2 or 3 R: phenyl, 5- to 10-membered heteroaryl, $C_{3-6}$ cycloalkyl or $C_{3-8}$ cycloalkenyl;
$R_2$ is selected from H, or selected from $C_{1-3}$ alkyl which is optionally substituted with 1, 2 or 3 R;
$R_3$ is selected from H, or selected from $C_{1-3}$ alkyl which is optionally substituted with 1, 2 or 3 R;
or, $R_2$ and $R_3$ are linked together to form a 3- to 6-membered ring;
$R_4$ is selected from H, halogen, OH, $NH_2$, or selected from the following groups which are optionally substituted with 1, 2 or 3 R: $C_{1-6}$ alkyl, phenyl or 5- to 6-membered heteroaryl;
$R_5$ is selected from H, or selected from the following groups which are optionally substituted with 1, 2 or 3 R: $C_{1-6}$ alkyl or $C_{3-6}$ cycloalkyl;
ring A is selected from 5- to 10-membered heteroaryl;
R is respectively independently selected from F, Cl, Br, I, OH, $NH_2$, CN, COOH or $CONH_2$, or selected from the following groups which are optionally substituted with 1, 2 or 3 R': $C_{1-6}$ alkyl or $C_{1-6}$ heteroalkyl;
R' is respectively independently selected from halogen, CN, OH, $NH_2$, COOH, NH(Me), $N(CH_3)_2$ or $CF_3$;
the "hetero" in the 5- to 10-membered heteroaryl, 5- to 6-membered heteroaryl, and $C_{1-6}$ heteroalkyl refers to a hetero atom or a hetero atomic group selected from —NH—, —O—, —S—, —N—, —C(=O)NH—, —C(=O)O— or —C(=O)—;
in any of the above situations, the number of the hetero atoms or hetero atomic groups is respectively independently selected from 1, 2 or 3.

In some embodiments of the present disclosure, the above compound, optical isomer thereof or pharmaceutically acceptable salt thereof is selected from

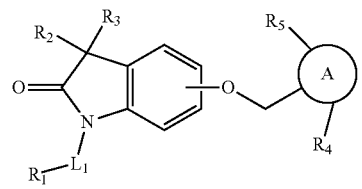

wherein, $L_1$ is selected from a single bond, —$CH_2$—,

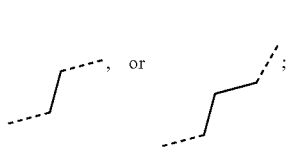

$R_1$ is selected from —COOH, or selected from the following groups which are optionally substituted with 1, 2 or 3 R: phenyl, 5- to 10-membered heteroaryl, $C_{3-6}$ cycloalkyl or $C_{3-8}$ cycloalkenyl;

$R_2$ is selected from $C_{1-3}$ alkyl which is optionally substituted with 1, 2 or 3 R;

$R_3$ is selected from $C_{1-3}$ alkyl which is optionally substituted with 1, 2 or 3 R;

or, $R_2$ and $R_3$ are linked together to form a 3- to 6-membered ring;

$R_4$ is selected from H, halogen, OH, $NH_2$, or selected from the following groups which are optionally substituted with 1, 2 or 3 R: $C_{1-6}$ alkyl, phenyl or 5- to 6-membered heteroaryl;

$R_5$ is selected from H, or selected from the following groups which are optionally substituted with 1, 2 or 3 R: $C_{1-6}$ alkyl or $C_{3-6}$ cycloalkyl;

ring A is selected from 5- to 10-membered heteroaryl;

R is respectively independently selected from F, Cl, Br, I, OH, $NH_2$, CN, COOH or $CONH_2$, or selected from the following groups which are optionally substituted with 1, 2 or 3 R': $C_{1-6}$ alkyl or $C_{1-6}$ heteroalkyl;

R' is respectively independently selected from halogen, CN, OH, $NH_2$, COOH, NH(Me), $N(CH_3)_2$ or $CF_3$;

the "hetero" in the 5- to 10-membered heteroaryl, 5- to 6-membered heteroaryl, and $C_{1-6}$ heteroalkyl refers to a hetero atom or a hetero atomic group selected from —NH—, —O—, —S—, —N—, —C(=O)NH—, —C(=O)O— or —C(=O)—;

in any of the above situations, the number of the hetero atoms or hetero atomic groups is respectively independently selected from 1, 2 or 3.

In some embodiments of the present disclosure, the above compound, optical isomer thereof or pharmaceutically acceptable salt thereof is selected from (III)

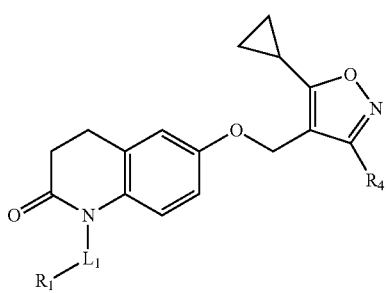

wherein, $L_1$ is selected from a single bond, —$CH_2$—,

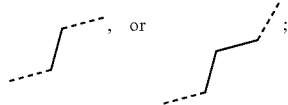

$R_1$ is selected from —COOH, or selected from the following groups which are optionally substituted with 1, 2 or 3 R: phenyl, 5- to 10-membered heteroaryl, $C_{3-6}$ cycloalkyl or $C_{3-8}$ cycloalkenyl;

$R_4$ is selected from H, halogen, OH, $NH_2$, or selected from the following groups which are optionally substituted with 1, 2 or 3 R: $C_{1-6}$ alkyl, phenyl or 5- to 6-membered heteroaryl;

R is respectively independently selected from F, Cl, Br, I, OH, $NH_2$, CN, COOH or $CONH_2$, or selected from the following groups which are optionally substituted with 1, 2 or 3 R': $C_{1-6}$ alkyl or $C_{1-6}$ heteroalkyl;

R' is selected from halogen, CN, OH, $NH_2$, COOH, NH(Me), $N(CH_3)_2$ or $CF_3$;

the "hetero" in the 5- to 10-membered heteroaryl, 5- to 6-membered heteroaryl, and $C_{1-6}$ heteroalkyl refers to a hetero atom or a hetero atomic group selected from —NH—, —O—, —S—, —N—, —C(=O)NH—, —C(=O)O— or —C(=O)—;

in any of the above situations, the number of the hetero atoms or hetero atomic groups is each independently selected from 1, 2 or 3.

In some embodiments of the present disclosure, the above R is selected from F, Cl, Br, I, OH, $NH_2$, CN, COOH, $CONH_2$, or selected from the following groups which are optionally substituted with 1, 2 or 3 R': $C_{1-3}$ alkyl, $C_{1-3}$ alkoxy or —C(=O)O—$C_{1-3}$ alkyl; and R' has a definition as defined in the present disclosure.

In some embodiments of the present disclosure, the above R is selected from F, Cl, Br, I, CN, OH, $NH_2$, COOH, $CONH_2$, Me, Et, $CF_3$,

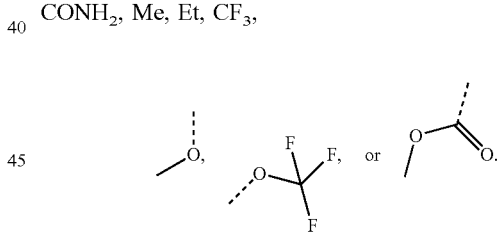

In some embodiments of the present disclosure, the above $R_1$ is selected from —COOH, or selected from the following groups which are optionally substituted with 1, 2 or 3 R: phenyl, pyridyl, pyrimidinyl, thienyl, thiazolyl, indolyl, cyclohexanyl, cyclohexenyl, bicyclo[1.1.1]pentanyl, benzopyrazolyl or benzothiazolyl; and R has a definition as defined in the present disclosure.

In some embodiments of the present disclosure, the above $R_1$ is selected from —COOH, or selected from the following groups which are optionally substituted with 1, 2 or 3 R:

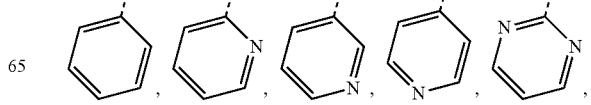

-continued

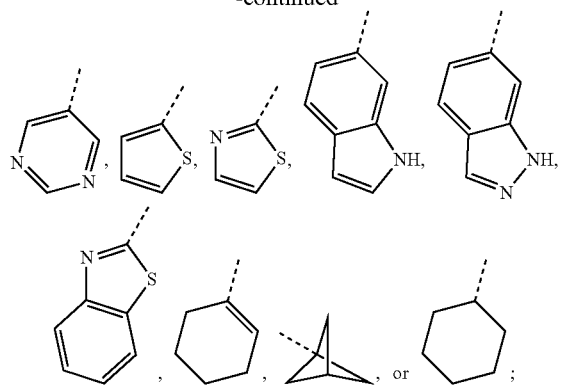

and R has a definition as defined in the present disclosure.

In some embodiments of the present disclosure, the above $R_1$ is selected from —COOH, -continued

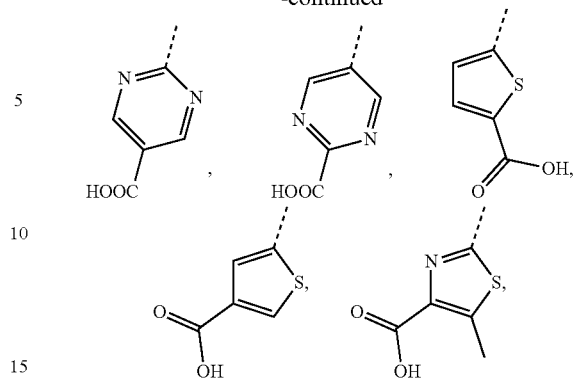

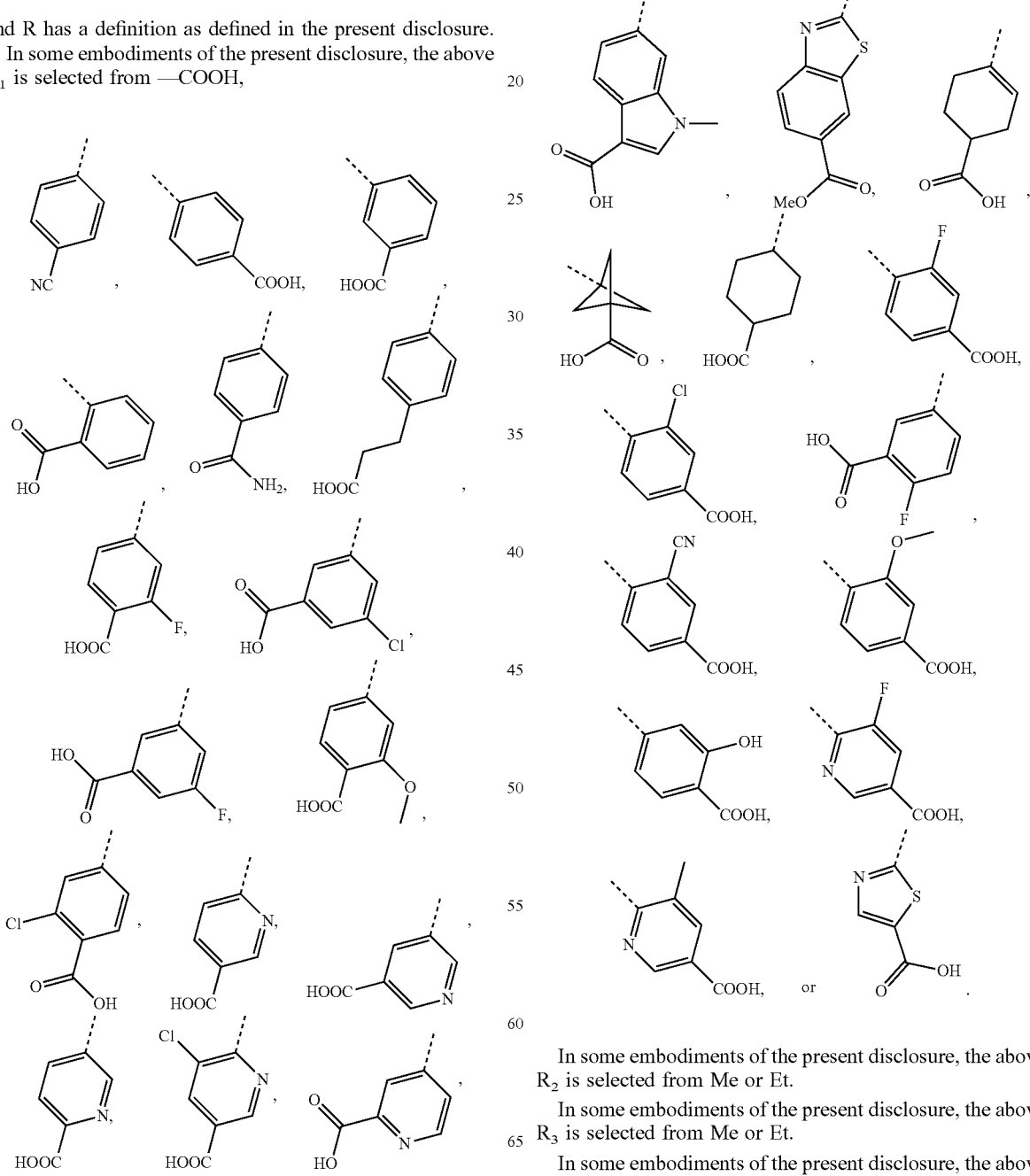

In some embodiments of the present disclosure, the above $R_2$ is selected from Me or Et.

In some embodiments of the present disclosure, the above $R_3$ is selected from Me or Et.

In some embodiments of the present disclosure, the above $R_2$ and $R_3$ are linked together to form a $C_{3-6}$ cycloalkyl.

In some embodiments of the present disclosure, the above $R_2$ and $R_3$ are linked, and the structure unit

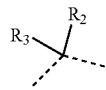

is selected from

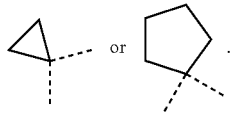

In some embodiments of the present disclosure, the above $R_4$ is selected from H, F, Cl, Br, I, OH, or $NH_2$, or selected from the following groups which are optionally substituted with 1, 2 or 3 R: $C_{1-3}$ alkyl, phenyl, or pyridyl; and R has a definition as defined in the present disclosure.

In some embodiments of the present disclosure, the above $R_4$ is selected from H, F, Cl, Br, I, OH, or $NH_2$, or selected from the following groups which are optionally substituted with 1, 2 or 3 R: Me,

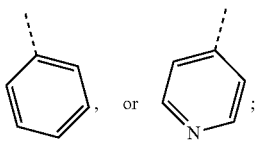

and R has a definition as defined in the present disclosure.

In some embodiments of the present disclosure, the above $R_4$ is selected from H, Cl, Me,

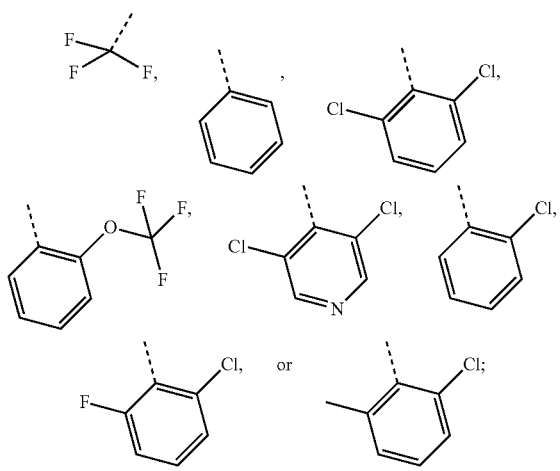

and R has a definition as defined in the present disclosure.

In some embodiments of the present disclosure, the above $R_5$ is selected from H, or selected from the following groups which are optionally substituted with 1, 2 or 3 R: Me or

and R has a definition as defined in the present disclosure.

In some embodiments of the present disclosure, the above $R_5$ is selected from H, Me or

In some embodiments of the present disclosure, the above ring A is selected from oxazolyl, isoxazolyl, pyridyl or benzothienyl.

In some embodiments of the present disclosure, the above structure unit

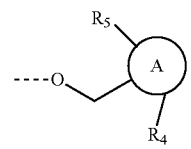

is selected from

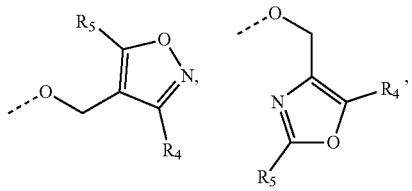

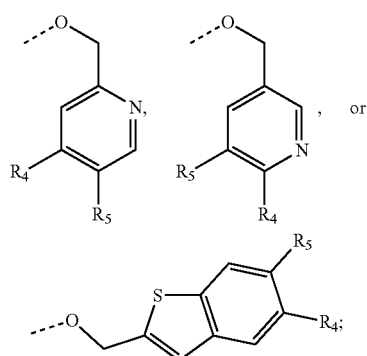

$R_4$ and $R_5$ have a definition as defined in the present disclosure.

In some embodiments of the present disclosure, the above structure unit

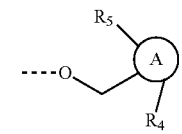

is selected from

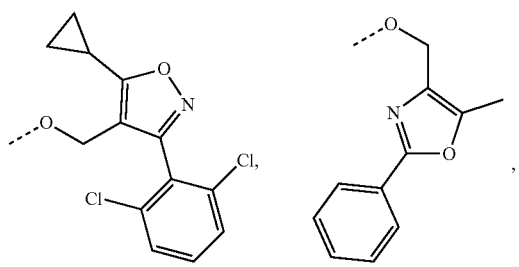 , 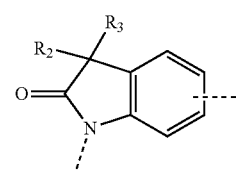 ,

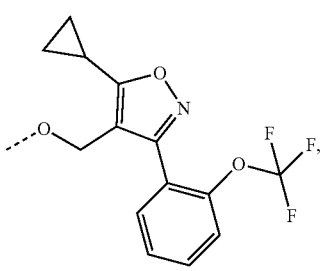 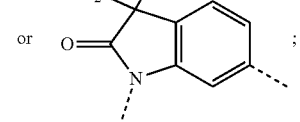

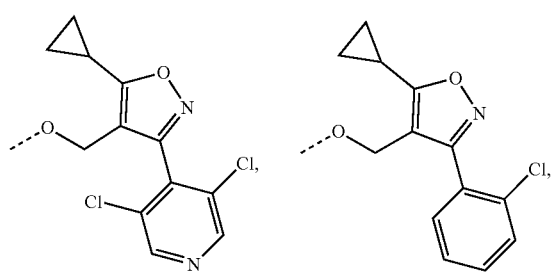

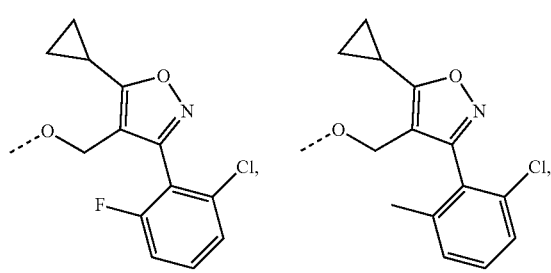 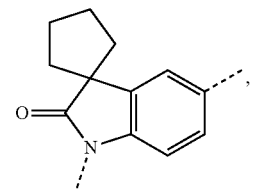

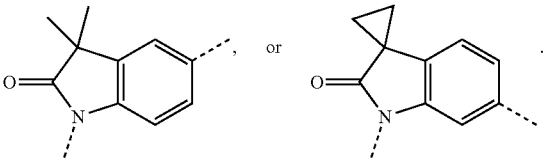

$R_4$ and $R_5$ have a definition as defined in the present disclosure.

In some embodiments of the present disclosure, the above structure unit

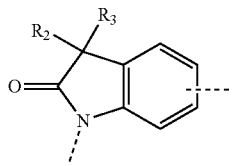

is selected from

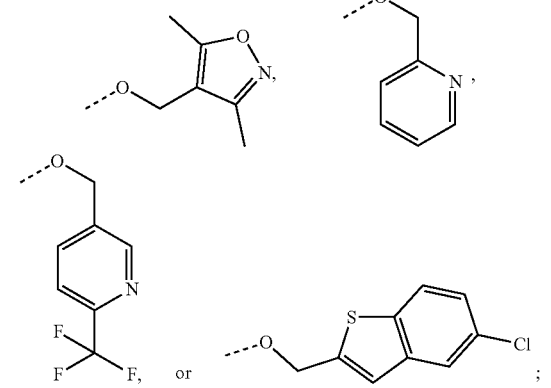

$R_2$ and $R_3$ have a definition as defined in the present disclosure.

In some embodiments of the present disclosure, the above structure unit is selected from In some embodiments of the present disclosure, the above R is selected from F, Cl, Br, I, OH, NH$_2$, CN, COOH, CONH$_2$, or selected from the following groups which are optionally substituted with 1, 2 or 3 R': C$_{1-3}$ alkyl, C$_{1-3}$ alkoxy or —C(=O)O—C$_{1-3}$ alkyl; and the other variables are as defined in the present disclosure.

In some embodiments of the present disclosure, the above R is selected from F, Cl, Br, I, CN, OH, NH$_2$, COOH, CONH$_2$, Me, Et, CF$_3$,

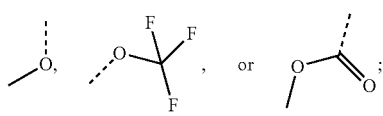

the other variables are as defined in the present disclosure.

In some embodiments of the present disclosure, the above $R_1$ is selected from —COOH, or selected from the following groups which are optionally substituted with 1, 2 or 3 R: phenyl, pyridyl, pyrimidinyl, thienyl, thiazolyl, indolyl, cyclohexanyl, cyclohexenyl, bicyclo[1.1.1]pentanyl, benzopyrazolyl or benzothiazolyl; and the other variables are as defined in the present disclosure.

In some embodiments of the present disclosure, the above $R_1$ is selected from —COOH, or selected from the following groups which are optionally substituted with 1, 2 or 3 R:

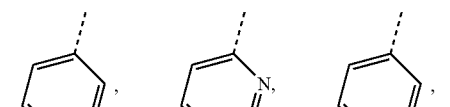

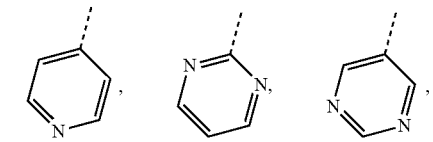

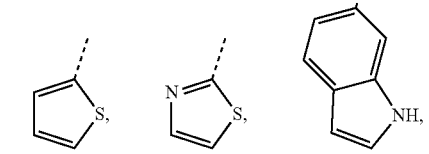

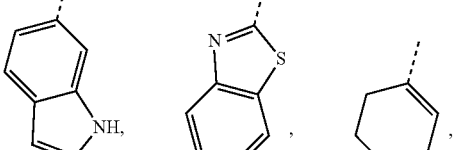

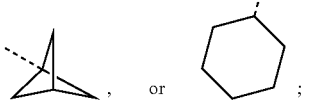

and the other variables are as defined in the present disclosure.

In some embodiments of the present disclosure, the above $R_1$ is selected from —COOH,

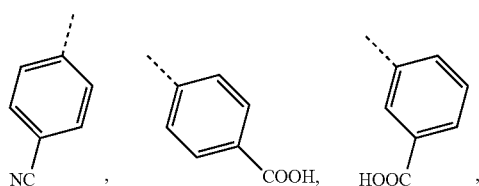

-continued

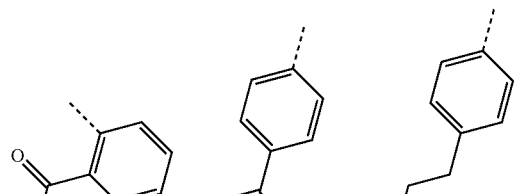

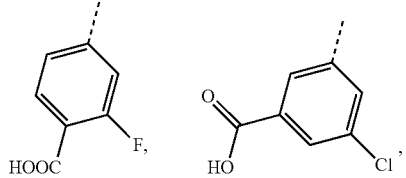

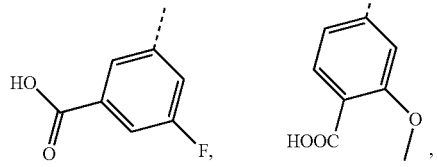

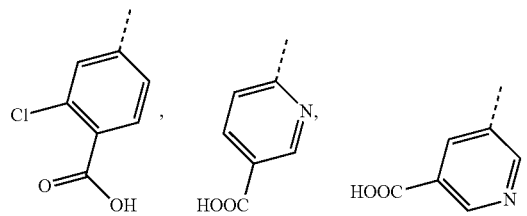

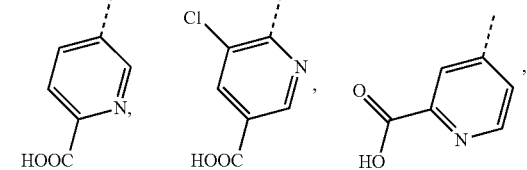

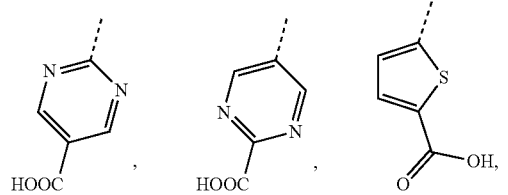

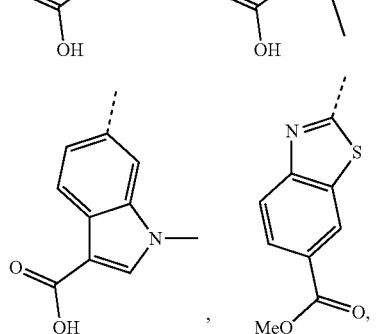

-continued

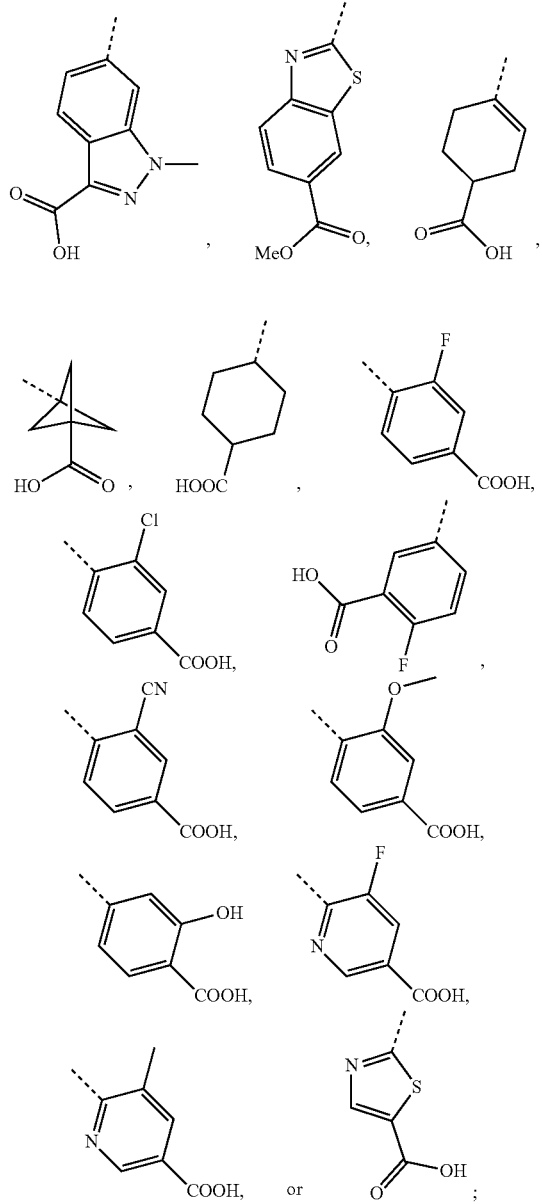

the other variables are as defined in the present disclosure.

In some embodiments of the present disclosure, the above $R_2$ is selected from Me or Et; and the other variables are as defined in the present disclosure.

In some embodiments of the present disclosure, the above $R_3$ is selected from Me or Et; and the other variables are as defined in the present disclosure.

In some embodiments of the present disclosure, the above $R_2$ and $R_3$ are linked together to form a $C_{3-6}$ cycloalkyl; and the other variables are as defined in the present disclosure.

In some embodiments of the present disclosure, the above $R_2$ and $R_3$ are linked, the structure unit

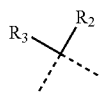

is selected from

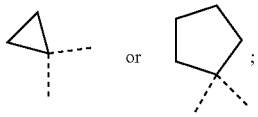

and the other variables are as defined in the present disclosure.

In some embodiments of the present disclosure, the above $R_4$ is selected from H, F, Cl, Br, I, OH, $NH_2$, or selected from the following groups which are optionally substituted with 1, 2 or 3 R: $C_{1-3}$ alkyl, phenyl or pyridyl; and the other variables are as defined in the present disclosure.

In some embodiments of the present disclosure, the above $R_4$ is selected from H, F, Cl, Br, I, OH, or $NH_2$, or selected from the following groups which are optionally substituted with 1, 2 or 3 R: Me

and the other variables are as defined in the present disclosure.

In some embodiments of the present disclosure, the above $R_4$ is selected from H, Cl, Me,

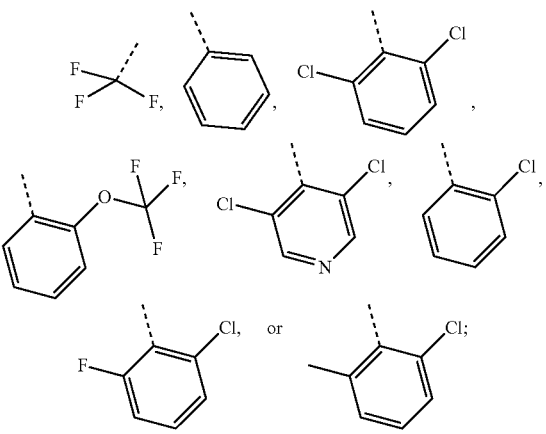

and the other variables are as defined in the present disclosure.

In some embodiments of the present disclosure, the above $R_5$ is selected from H, or selected from the following groups which are optionally substituted with 1, 2 or 3 R: Me or

and the other variables are as defined in the present disclosure.

In some embodiments of the present disclosure, the above $R_5$ is selected from H, Me or

and the other variables are as defined in the present disclosure.

In some embodiments of the present disclosure, the above ring A is selected from oxazolyl, isoxazolyl, pyridyl or benzothienyl; and the other variables are as defined in the present disclosure.

In some embodiments of the present disclosure, the above structure unit

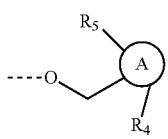

is selected from

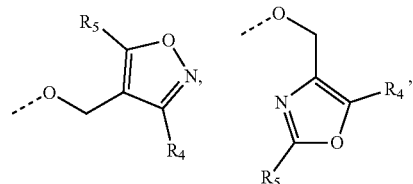

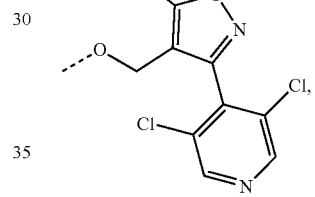

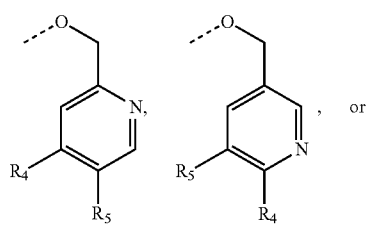

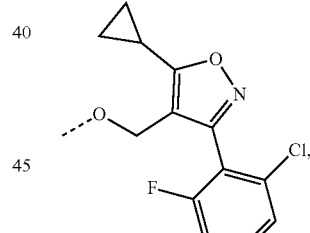

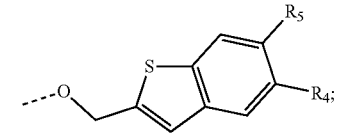

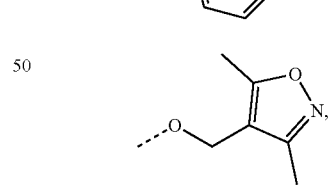

and the other variables are as defined in the present disclosure.

In some embodiments of the present disclosure, the above structure unit

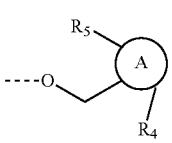

is selected from

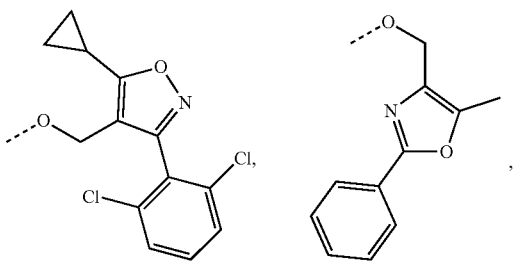

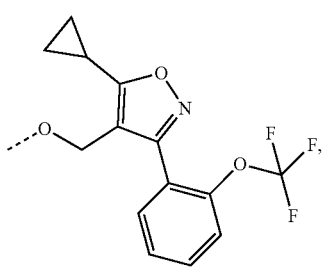

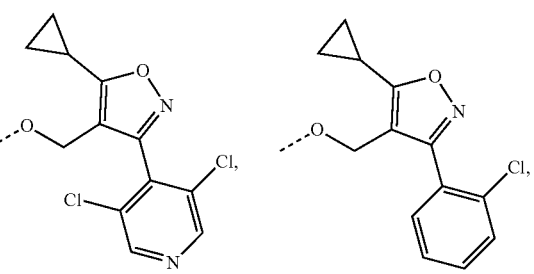

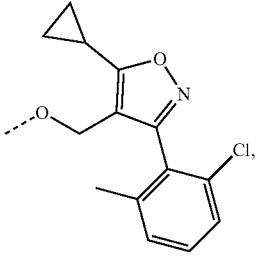

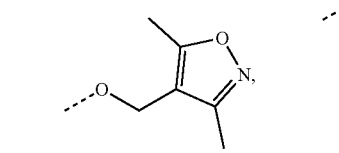

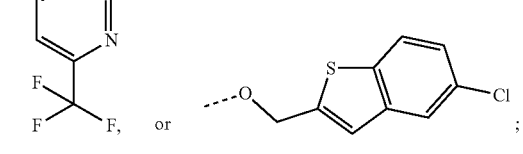

and the other variables are as defined in the present disclosure.

In some embodiments of the present disclosure, the above structure unit

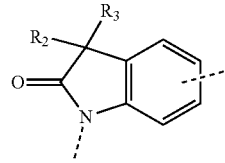

is selected from

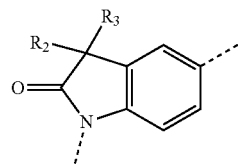 or 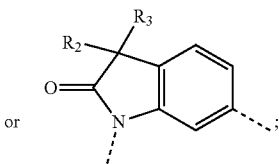

and the other variables are as defined in the present disclosure.

In some embodiments of the present disclosure, the above structure unit

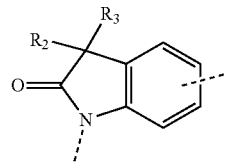

is selected from

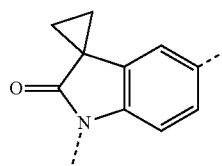, 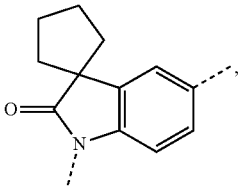

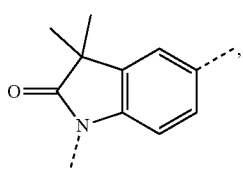, or 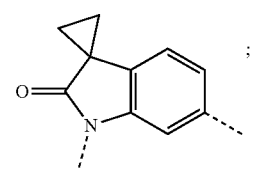;

the other variables are as defined in the present disclosure.

In some embodiments of the present disclosure, the above compound, optical isomer thereof or pharmaceutically acceptable salt thereof is selected from

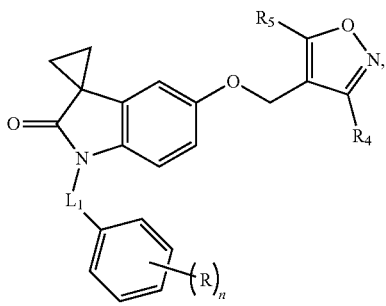

(I-1)

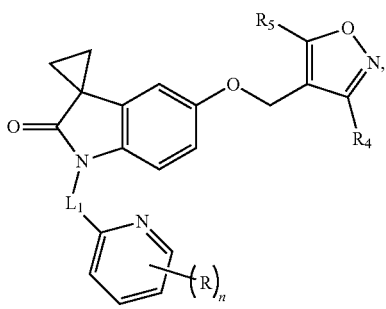

(I-2)

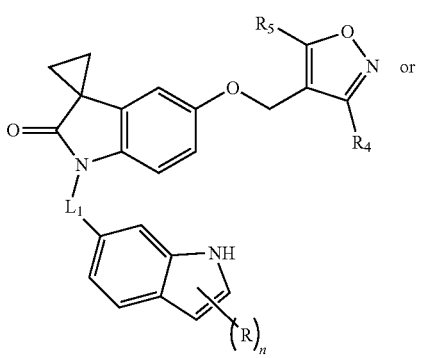

(I-3) or

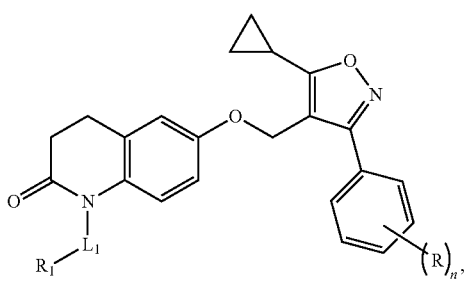

(I-4)

wherein, n is each independently selected from 0, 1 or 2;

R, $L_1$, $R_1$, $R_4$, and $R_5$ are as defined above.

The present disclosure provides a compound of formula (I), an optical isomer thereof or a pharmaceutically acceptable salt thereof,

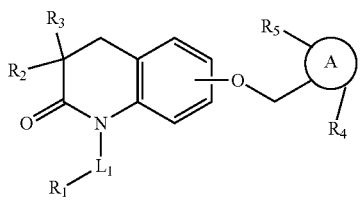

(I)

wherein,
m is selected from 0 or 1;
L₁ is selected from a single bond, —CH₂—,

R₁ is selected from —COOH, or selected from the following groups which are optionally substituted with 1, 2 or 3 R: phenyl, 5- to 10-membered heteroaryl, $C_{3-6}$ cycloalkyl or $C_{3-8}$ cycloalkenyl;

R₂ is selected from H, or selected from $C_{1-3}$ alkyl which is optionally substituted with 1, 2 or 3 R;

R₃ is selected from H, or selected from $C_{1-3}$ alkyl which is optionally substituted with 1, 2 or 3 R;

or, R₂ and R₃ are linked together to form a 3- to 6-membered ring;

R₄ is selected from H, halogen, OH, NH₂, or selected from the following groups which are optionally substituted with 1, 2 or 3 R: $C_{1-6}$ alkyl, phenyl or 5- to 6-membered heteroaryl;

R₅ is selected from H, or selected from the following groups which are optionally substituted with 1, 2 or 3 R: $C_{1-6}$ alkyl or $C_{3-6}$ cycloalkyl;

ring A is selected from 5- to 10-membered heteroaryl;

R is selected from F, Cl, Br, I, OH, NH₂, CN, COOH or CONH₂, or selected from the following groups which are optionally substituted with 1, 2 or 3 R': $C_{1-6}$ alkyl or $C_{1-6}$ heteroalkyl;

R' is selected from halogen, CN, OH, NH₂, COOH, NH(Me), N(CH₃)₂ or CF₃;

the "hetero" in the 5- to 10-membered heteroaryl, 5- to 6-membered heteroaryl, and $C_{1-6}$ heteroalkyl refers to a hetero atom or a hetero atomic group selected from —NH—, —O—, —S—, —N—, —C(=O)NH—, —C(=O)O—, —C(=O)—;

in any of the above situations, the number of the hetero atoms or hetero atomic groups is respectively independently selected from 1, 2 or 3.

In some embodiments of the present disclosure, the above compound, optical isomer thereof or pharmaceutically acceptable salt thereof is selected from

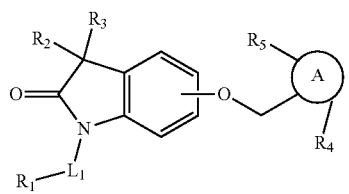

(II)

wherein,
L₁ is selected from a single bond, —CH₂—,

R₁ is selected from —COOH, or selected from the following groups which are optionally substituted with 1, 2 or 3 R: phenyl, 5- to 10-membered heteroaryl, $C_{3-6}$ cycloalkyl or $C_{3-8}$ cycloalkenyl;

R₂ is selected from $C_{1-3}$ alkyl which is optionally substituted with 1, 2 or 3 R;

R₃ is selected from $C_{1-3}$ alkyl which is optionally substituted with 1, 2 or 3 R;

or, R₂ and R₃ are linked together to form a 3- to 6-membered ring;

R₄ is selected from H, halogen, OH, NH₂, or selected from the following groups which are optionally substituted with 1, 2 or 3 R: $C_{1-6}$ alkyl, phenyl or 5- to 6-membered heteroaryl;

R₅ is selected from H, or selected from the following groups which are optionally substituted with 1, 2 or 3 R: $C_{1-6}$ alkyl or $C_{3-6}$ cycloalkyl;

ring A is selected from 5- to 10-membered heteroaryl;

R is selected from F, Cl, Br, I, OH, NH₂, CN, COOH or CONH₂, or selected from the following groups which are optionally substituted with 1, 2 or 3 R': $C_{1-6}$ alkyl or $C_{1-6}$ heteroalkyl;

R' is selected from halogen, CN, OH, NH₂, COOH, NH(Me), N(CH₃)₂ or CF₃;

the "hetero" in the 5- to 10-membered heteroaryl, 5- to 6-membered heteroaryl, and $C_{1-6}$ heteroalkyl refers to a hetero atom or a hetero atomic group selected from —NH—, —O—, —S—, —N—, —C(=O)NH—, —C(=O)O—, —C(=O)—;

in any of the above situations, the number of the hetero atoms or hetero atomic groups is respectively independently selected from 1, 2 or 3.

In some embodiments of the present disclosure, the above compound, optical isomer thereof or pharmaceutically acceptable salt thereof is selected from

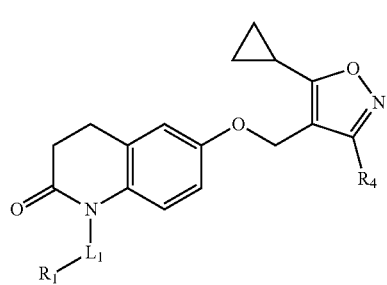

(III)

wherein,
$L_1$ is selected from a single bond, —CH$_2$—,

$R_1$ is selected from —COOH, or selected from the following groups which are optionally substituted with 1, 2 or 3 R: phenyl, 5- to 10-membered heteroaryl, $C_{3-6}$ cycloalkyl, $C_{3-8}$ cycloalkenyl;

$R_4$ is selected from H, halogen, OH, NH$_2$, or selected from the following groups which are optionally substituted with 1, 2 or 3 R: $C_{1-6}$ alkyl, phenyl, 5- to 6-membered heteroaryl;

R is selected from F, Cl, Br, I, OH, NH$_2$, CN, COOH or CONH$_2$, or selected from the following groups which are optionally substituted with 1, 2 or 3 R': $C_{1-6}$ alkyl, $C_{1-6}$ heteroalkyl;

R' is selected from halogen, CN, OH, NH$_2$, COOH, NH(Me), N(CH$_3$)$_2$, CF$_3$;

the "hetero" in the 5- to 10-membered heteroaryl, 5- to 6-membered heteroaryl, and $C_{1-6}$ heteroalkyl refers to a hetero atom or a hetero atomic group selected from —NH—, —O—, —S—, —N—, —C(=O)NH—, —C(=O)O—, —C(=O)—;

in any of the above situations, the number of the hetero atoms or hetero atomic groups is respectively independently selected from 1, 2 or 3.

In some embodiments of the present disclosure, the above R is selected from F, Cl, Br, I, OH, NH$_2$, CN, COOH, CONH$_2$, or selected from the following groups which are optionally substituted with 1, 2 or 3 R': $C_{1-3}$ alkyl, $C_{1-3}$ alkoxy, —C(=O)O—C$_{1-3}$ alkyl; and R' has a definition as described in the present disclosure.

In some embodiments of the present disclosure, the above R is selected from F, Cl, Br, I, CN, OH, NH$_2$, COOH, CONH$_2$, Me, Et, CF$_3$,

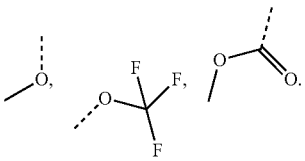

In some embodiments of the present disclosure, the above $R_1$ is selected from —COOH, or selected from the following groups which are optionally substituted with 1, 2 or 3 R: phenyl, pyridyl, pyrimidinyl, thienyl, thiazolyl, indolyl, cyclohexanyl, cyclohexenyl, bicyclo[1.1.1]pentanyl, benzopyrazolyl, benzothiazolyl; and R has a definition as described in the present disclosure.

In some embodiments of the present disclosure, the above $R_1$ is selected from —COOH, or selected from the following groups which are optionally substituted with 1, 2 or 3 R:

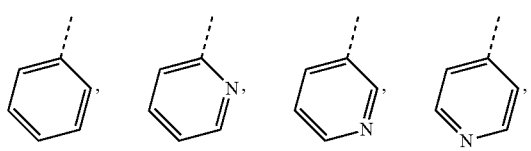

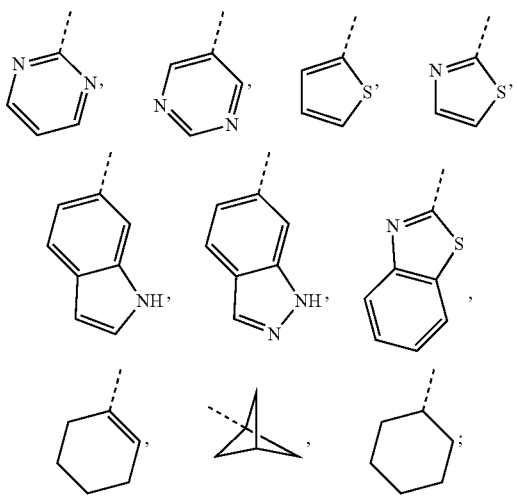

and R has a definition as described in the present disclosure.

In some embodiments of the present disclosure, the above $R_1$ is selected from —COOH,

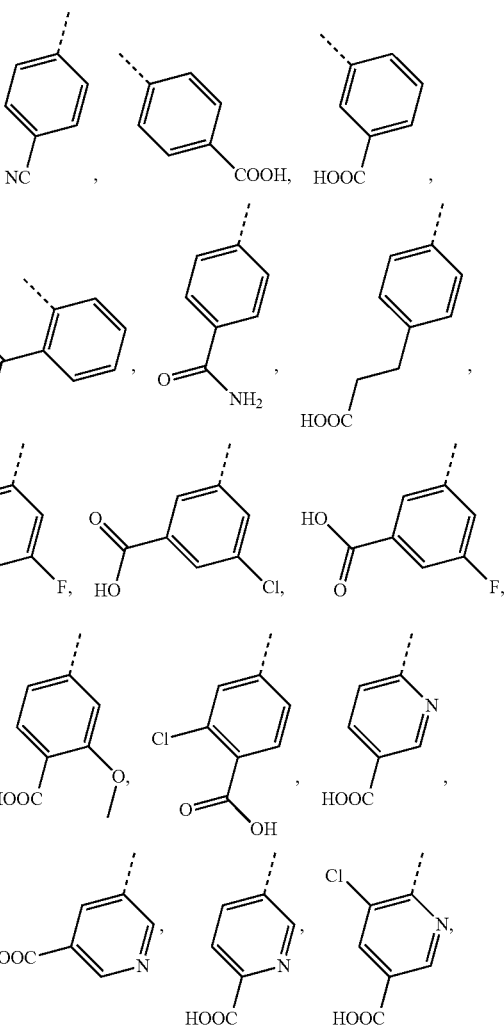

-continued

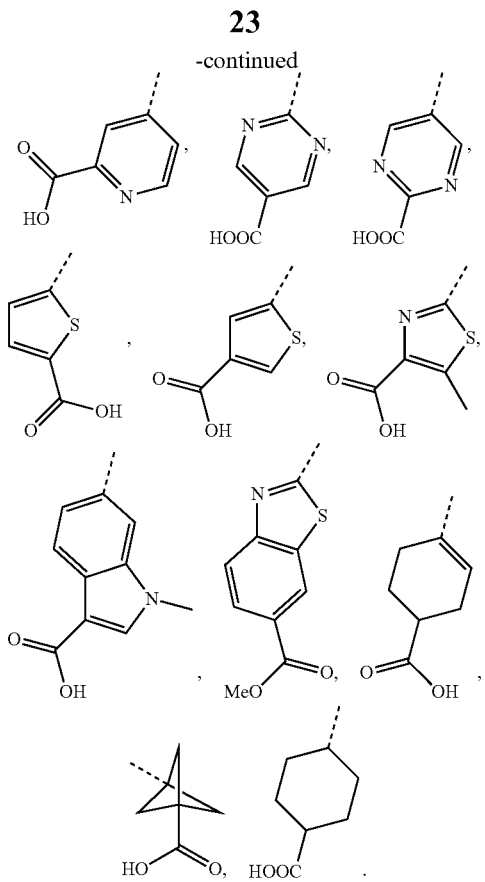

In some embodiments of the present disclosure, the above $R_2$ is selected from Me, Et.

In some embodiments of the present disclosure, the above $R_3$ is selected from Me, Et.

In some embodiments of the present disclosure, the above $R_2$ and $R_3$ are linked together to form a $C_{3-6}$ cycloalkyl.

In some embodiments of the present disclosure, the above $R_2$ and $R_3$ are linked, and the structure unit

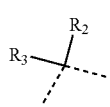

is selected from

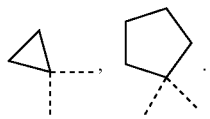

In some embodiments of the present disclosure, the above $R_4$ is selected from H, F, Cl, Br, I, OH, $NH_2$, or selected from the following groups which are optionally substituted with 1, 2 or 3 R: $C_{1-3}$ alkyl, phenyl, pyridyl; and R has a definition as described in the present disclosure.

In some embodiments of the present disclosure, the above $R_4$ is selected from H, F, Cl, Br, I, OH, $NH_2$, or selected from the following groups which are optionally substituted with 1, 2 or 3 R: Me,

and R has a definition as described in the present disclosure.

In some embodiments of the present disclosure, the above $R_4$ is selected from H, Cl, Me,

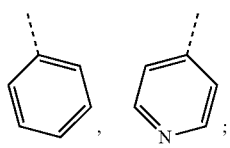

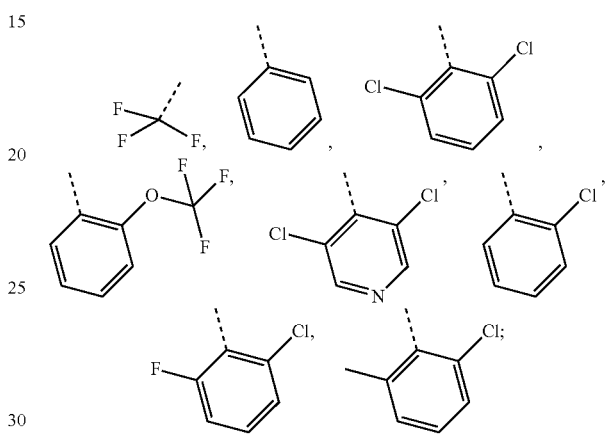

and R has a definition as described in the present disclosure.

In some embodiments of the present disclosure, the above $R_5$ is selected from H, or selected from the following groups which are optionally substituted with 1, 2 or 3 R: Me,

and R has a definition as described in the present disclosure.

In some embodiments of the present disclosure, the above $R_5$ is selected from H, Me,

In some embodiments of the present disclosure, the above ring A is selected from oxazolyl, isoxazolyl, pyridyl, benzothienyl.

In some embodiments of the present disclosure, the above structure unit

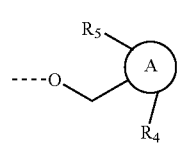

is selected from

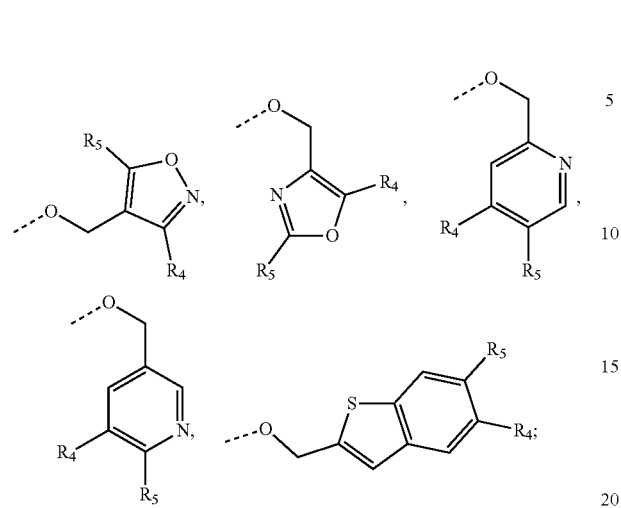

$R_4$ and $R_5$ have a definition as described in the present disclosure.

In some embodiments of the present disclosure, the above structure unit

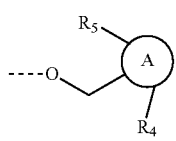

is selected from

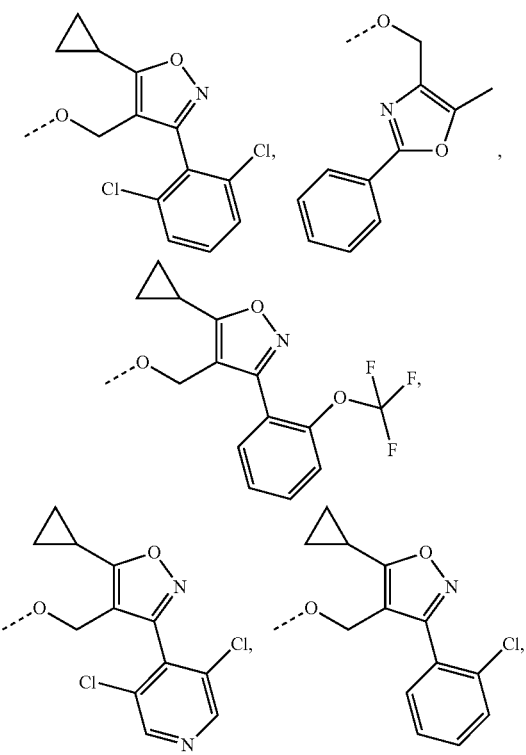

-continued

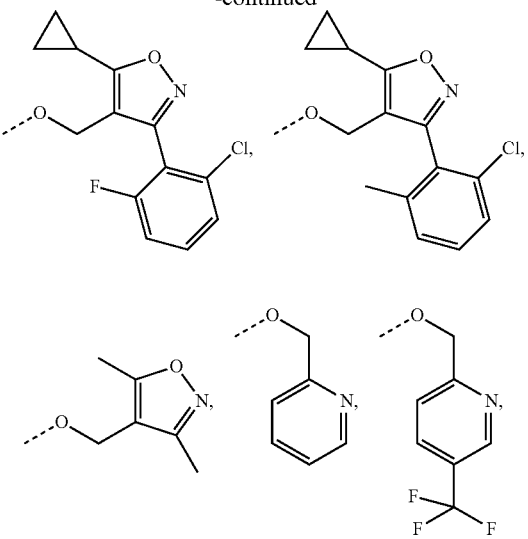

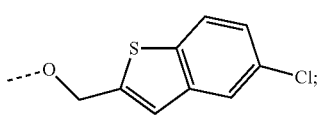

$R_4$ and $R_5$ have a definition as described in the present disclosure.

In some embodiments of the present disclosure, the above structure unit

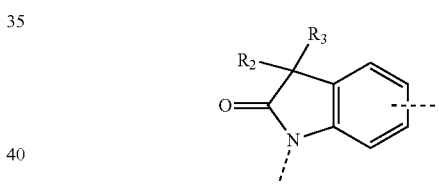

is selected from

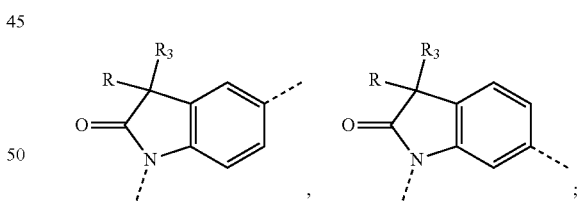

$R_2$ and $R_3$ have a definition as described in the present disclosure.

In some embodiments of the present disclosure, the above structure unit

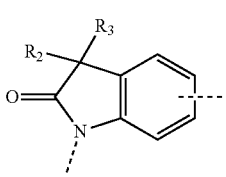

is selected from

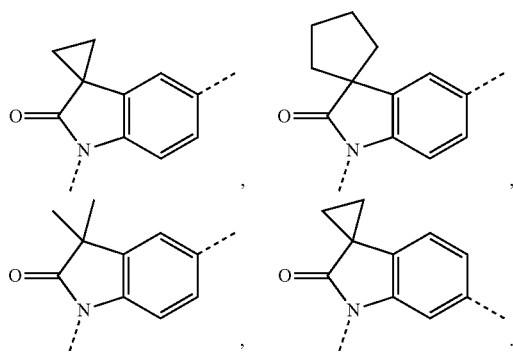

In some embodiments of the present disclosure, the above R is selected from F, Cl, Br, I, OH, NH$_2$, CN, COOH, CONH$_2$, or selected from the following groups which are optionally substituted with 1, 2 or 3 R': C$_{1-3}$ alkyl, C$_{1-3}$ alkoxy, —C(=O)O—C$_{1-3}$ alkyl; and the other variables are as defined above.

In some embodiments of the present disclosure, the above R is selected from F, Cl, Br, I, CN, OH, NH$_2$, COOH, CONH$_2$, Me, Et, CF$_3$,

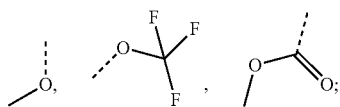

and the other variables are as defined above.

In some embodiments of the present disclosure, the above R$_1$ is selected from —COOH, or selected from the following groups which are optionally substituted with 1, 2 or 3 R: phenyl, pyridyl, pyrimidinyl, thienyl, thiazolyl, indolyl, cyclohexanyl, cyclohexenyl, bicyclo[1.1.1]pentanyl, benzopyrazolyl, benzothiazolyl; and the other variables are as defined above.

In some embodiments of the present disclosure, the above R$_1$ is selected from —COOH, or selected from the following groups which are optionally substituted with 1, 2 or 3 R:

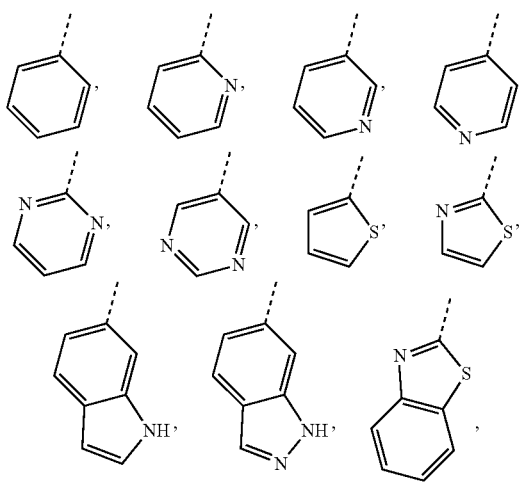

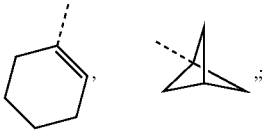

and the other variables are as defined above.

In some embodiments of the present disclosure, the above R$_1$ is selected from —COOH,

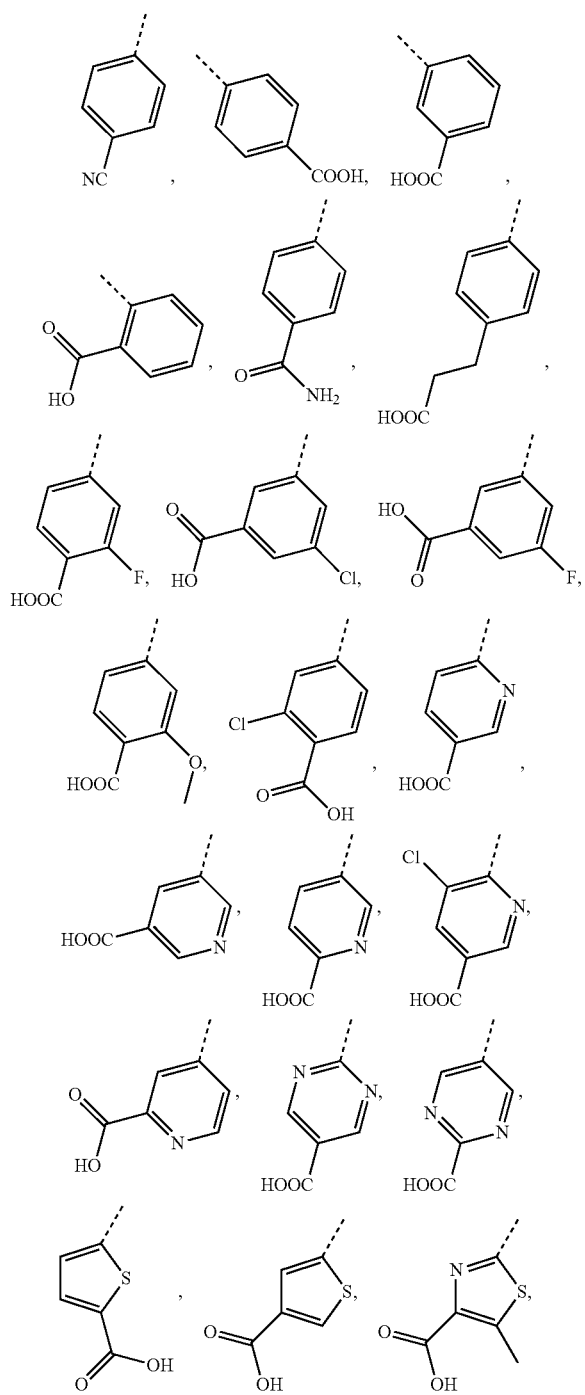

-continued

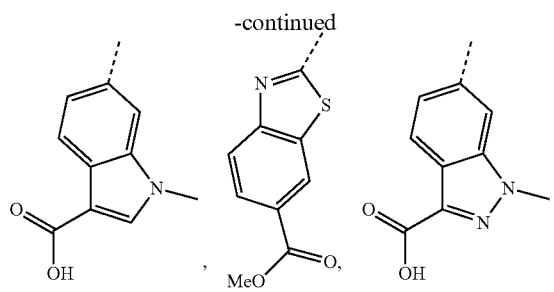

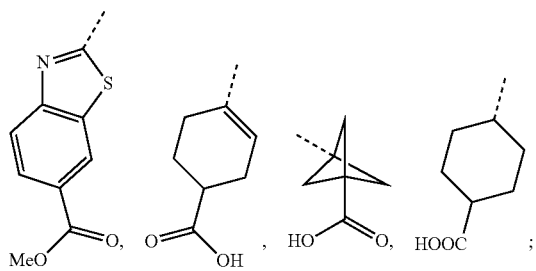

and the other variables are as defined above.

In some embodiments of the present disclosure, the above $R_2$ is selected from Me, Et; and the other variables are as defined above.

In some embodiments of the present disclosure, the above $R_3$ is selected from Me, Et; and the other variables are as defined above.

In some embodiments of the present disclosure, the above $R_2$ and $R_3$ are linked together to form a $C_{3-6}$ cycloalkyl; and the other variables are as defined above.

In some embodiments of the present disclosure, the above $R_2$ and $R_3$ are linked, the structure unit

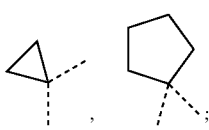

is selected from

, ;

and the other variables are as defined above.

In some embodiments of the present disclosure, the above $R_4$ is selected from H, F, Cl, Br, I, OH, $NH_2$, or selected from the following groups which are optionally substituted with 1, 2 or 3 R: $C_{1-3}$ alkyl, phenyl, pyridyl; and the other variables are as defined above.

In some embodiments of the present disclosure, the above $R_4$ is selected from H, F, Cl, Br, I, OH, or $NH_2$, or selected from the following groups which are optionally substituted with 1, 2 or 3 R: Me

, ;

and the other variables are as defined above.

In some embodiments of the present disclosure, the above $R_4$ is selected from H, Cl, Me, and the other variables are as defined above.

In some embodiments of the present disclosure, the above $R_5$ is selected from H, or selected from the following groups which are optionally substituted with 1, 2 or 3 R: Me,

;

and the other variables are as defined above.

In some embodiments of the present disclosure, the above $R_5$ is selected from H, Me

;

the other variables are as defined above.

In some embodiments of the present disclosure, the above ring A is selected from oxazolyl, isoxazolyl, pyridyl, benzothienyl; and the other variables are as defined above.

In some embodiments of the present disclosure, the above structure unit

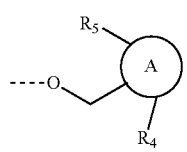

is selected from

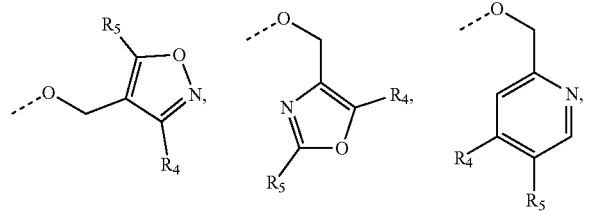

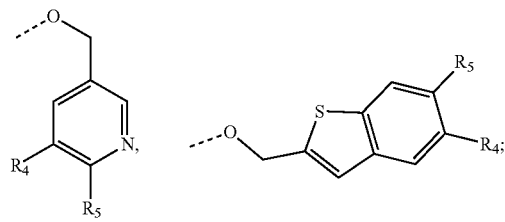

and the other variables are as defined above.

In some embodiments of the present disclosure, the above structure unit

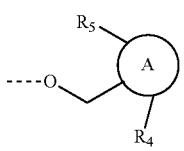

is selected from

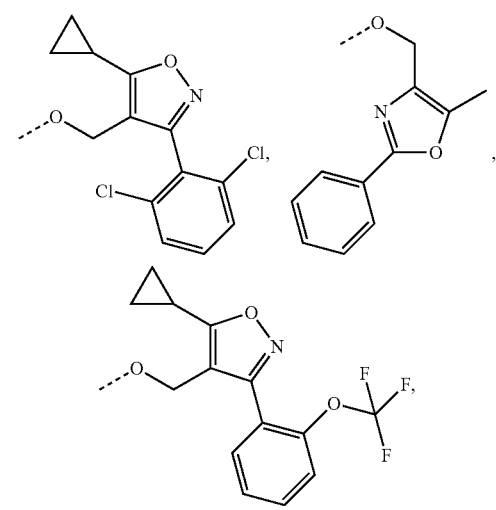

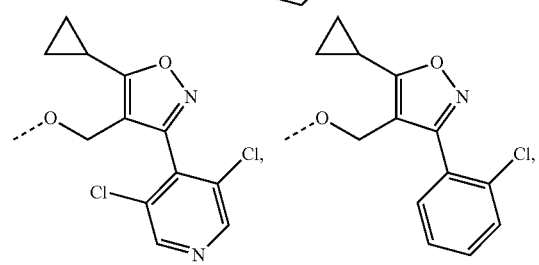

-continued

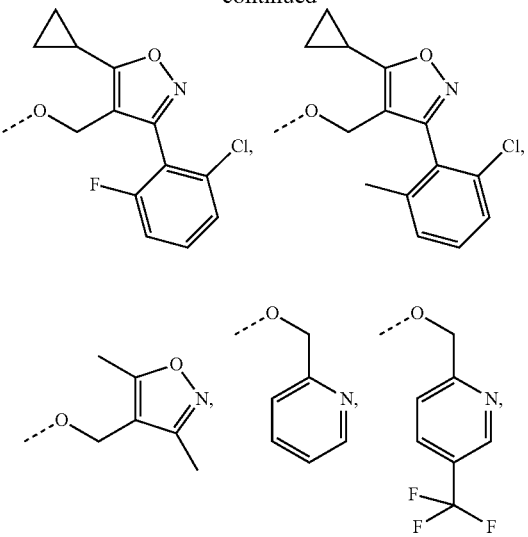

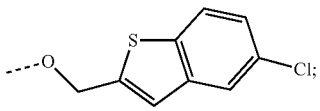

and the other variables are as defined above.

In some embodiments of the present disclosure, the above structure unit

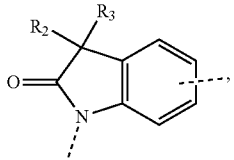

is selected from

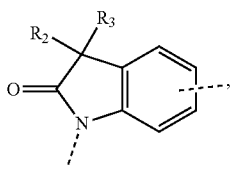

and the other variables are as defined above.

In some embodiments of the present disclosure, the above structure unit is selected from

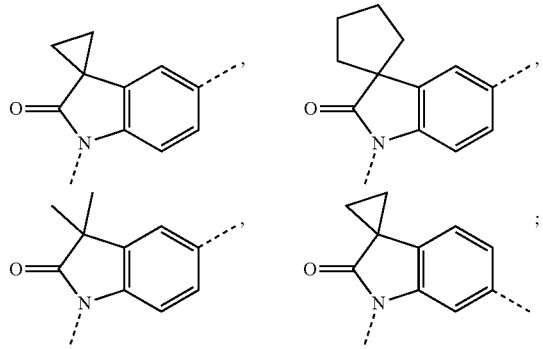

and the other variables are as defined above.

In some embodiments of the present disclosure, the above compound, optical isomer thereof or pharmaceutically acceptable salt thereof is selected from

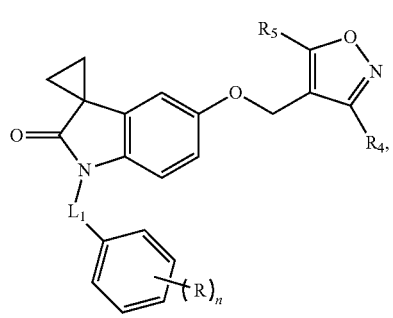
(I-1)

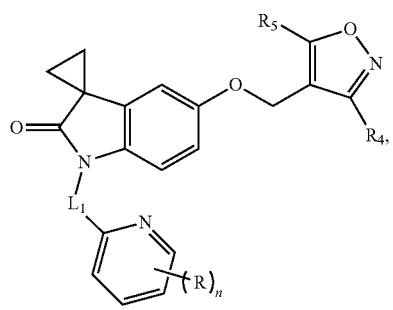
(I-2)

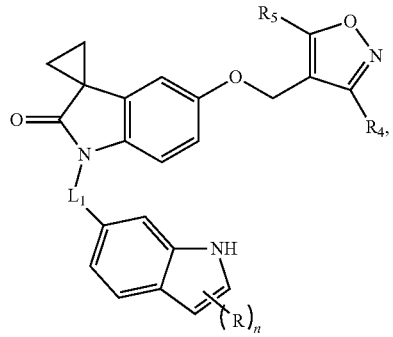
(I-3)

wherein,
n is each independently selected from 0, 1 or 2; and
R, $L_1$, $R_4$, and $R_5$ are as defined above.

The present disclosure provides a compound of formula (I) or a pharmaceutically acceptable salt thereof,

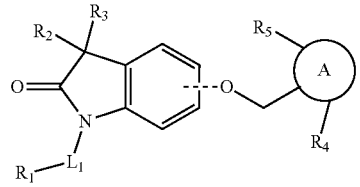
(I-A)

wherein,
$L_1$ is selected from a single bond, —$CH_2$—,

$R_1$ is selected from —COOH, or selected from the following groups which are optionally substituted with 1, 2 or 3 R: phenyl, 5- to 10-membered heteroaryl, $C_{3-6}$ cycloalkyl, $C_{3-8}$ cycloalkenyl;

$R_2$ is selected from selected from $C_{1-3}$ alkyl which is optionally substituted with 1, 2 or 3 R;

$R_3$ is selected from selected from $C_{1-3}$ alkyl which is optionally substituted with 1, 2 or 3 R;

or, $R_2$ and $R_3$ are linked together to form a 3- to 6-membered ring;

$R_4$ is selected from H, halogen, OH, $NH_2$, or selected from the following groups which are optionally substituted with 1, 2 or 3 R: $C_{1-6}$ alkyl, phenyl, 5- to 6-membered heteroaryl;

$R_5$ is selected from H, or selected from the following groups which are optionally substituted with 1, 2 or 3 R: $C_{1-6}$ alkyl, $C_{3-6}$ cycloalkyl;

ring A is selected from 5- to 10-membered heteroaryl;

R is selected from F, Cl, Br, I, OH, $NH_2$, CN, COOH, $CONH_2$, or selected from the following groups which are optionally substituted with 1, 2 or 3 R': $C_{1-6}$ alkyl, $C_{1-6}$ heteroalkyl;

R' is selected from halogen, CN, OH, $NH_2$, COOH, NH(Me), $N(CH_3)_2$, $CF_3$;

the "hetero" in the 5- to 10-membered heteroaryl, 5- to 6-membered heteroaryl, and $C_{1-6}$ heteroalkyl refers to a hetero atom or a hetero atomic group selected from —NH—, —O—, —S—, —N—, —C(=O)NH—, —C(=O)O—, —C(=O)—;

in any of the above situations, the number of the hetero atoms or hetero atomic groups is respectively independently selected from 1, 2 or 3.

In some embodiments of the present disclosure, the above R is selected from F, Cl, Br, I, OH, $NH_2$, CN, COOH, $CONH_2$, or selected from the following groups which are optionally substituted with 1, 2 or 3 R': $C_{1-3}$ alkyl, $C_{1-3}$ alkoxy, —C(=O)O—$C_{1-3}$ alkyl.

In some embodiments of the present disclosure, the above R is selected from F, Cl, Br, I, CN, OH, $NH_2$, COOH, $CONH_2$, Me, Et, $CF_3$,

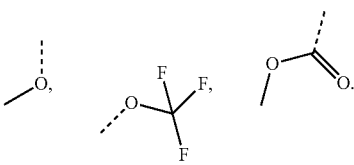

In some embodiments of the present disclosure, the above R₁ is selected from —COOH, or selected from the following groups which are optionally substituted with 1, 2 or 3 R: phenyl, pyridyl, pyrimidinyl, thienyl, thiazolyl, indolyl, cyclohexanyl, cyclohexenyl, bicyclo[1.1.1]pentanyl.

In some embodiments of the present disclosure, the above R₁ is selected from —COOH, or selected from the following groups which are optionally substituted with 1, 2 or 3 R:

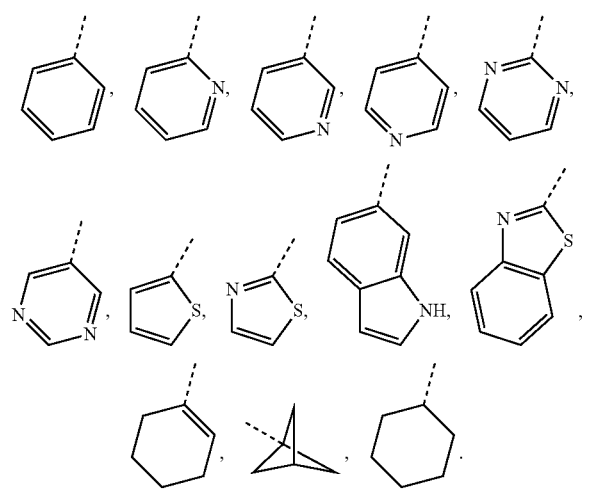

In some embodiments of the present disclosure, the above R₁ is selected from —COOH,

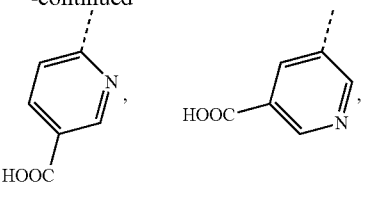

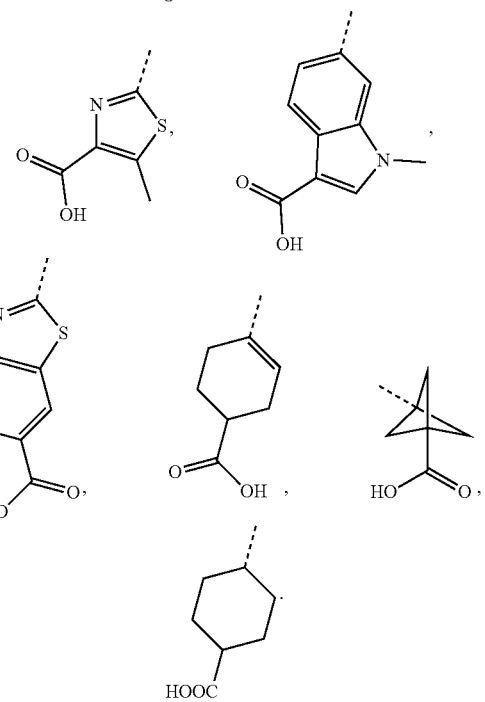

In some embodiments of the present disclosure, the above R₂ is selected from Me, Et.

In some embodiments of the present disclosure, the above R₃ is selected from Me, Et.

In some embodiments of the present disclosure, the above R₂ and R₃ are linked together to form a $C_{3-6}$ cycloalkyl.

In some embodiments of the present disclosure, the above R₂ and R₃ are linked, and the structure unit is selected from

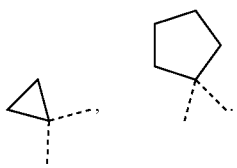

In some embodiments of the present disclosure, the above R₄ is selected from H, F, Cl, Br, I, OH, NH₂, or selected from the following groups which are optionally substituted with 1, 2 or 3 R: $C_{1-3}$ alkyl, phenyl, pyridyl.

In some embodiments of the present disclosure, the above R₄ is selected from H, F, Cl, Br, I, OH, NH₂, or selected from the following groups which are optionally substituted with 1, 2 or 3 R: Me,

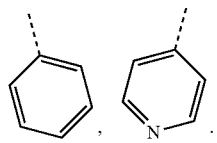

In some embodiments of the present disclosure, the above R₄ is selected from H, Cl, Me,

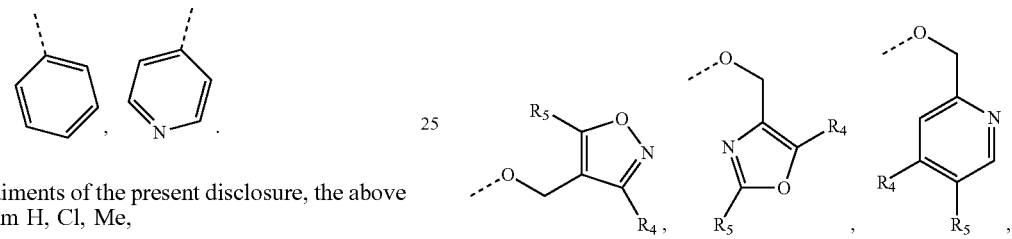

In some embodiments of the present disclosure, the above R₅ is selected from H, or selected from the following groups which are optionally substituted with 1, 2 or 3 R: Me

In some embodiments of the present disclosure, the above R₅ is selected from H, Me,

In some embodiments of the present disclosure, the above ring A is selected from oxazolyl, isoxazolyl, pyridyl, benzothienyl.

In some embodiments of the present disclosure, the above structure unit

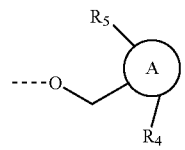

is selected from

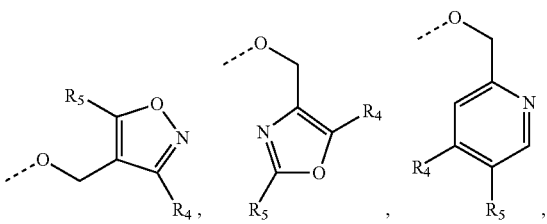

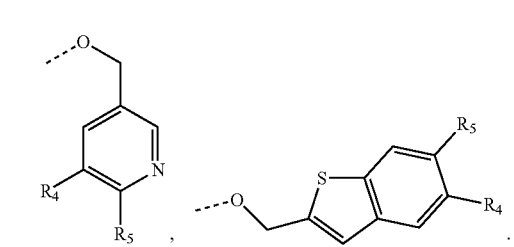

In some embodiments of the present disclosure, the above structure unit

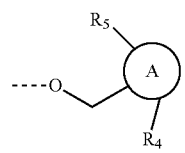

is selected from

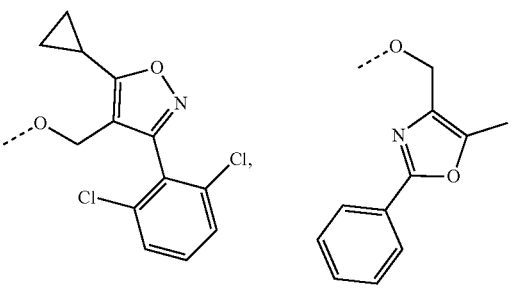

-continued

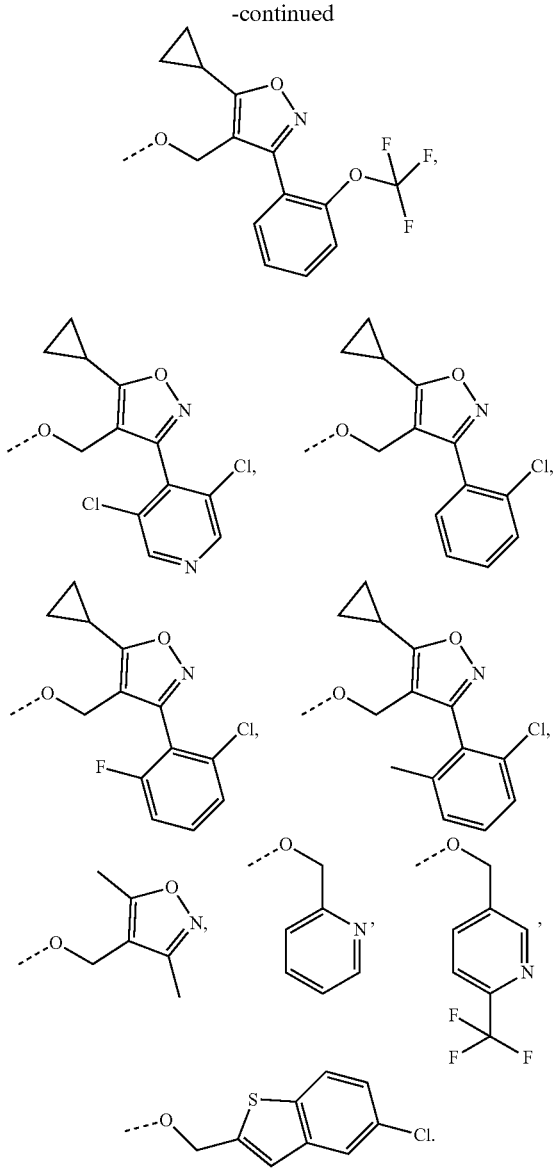

In some embodiments of the present disclosure, the above structure unit

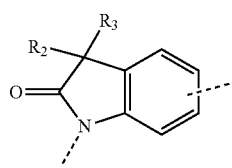

is selected from

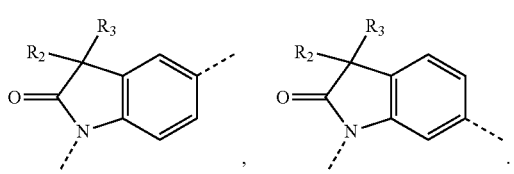

In some embodiments of the present disclosure, the above structure unit

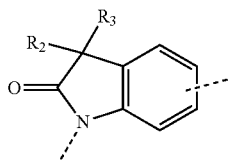

is selected from

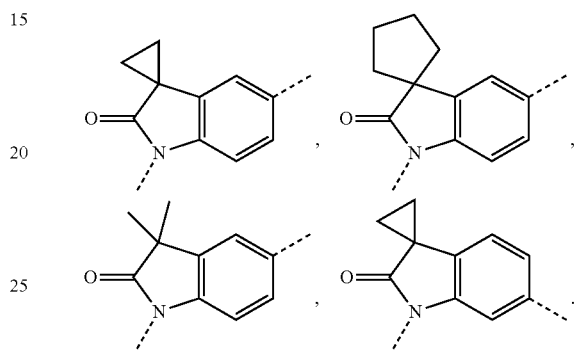

In some embodiments of the present disclosure, the above R is selected from F, Cl, Br, I, OH, $NH_2$, CN, COOH, $CONH_2$, or selected from the following groups which are optionally substituted with 1, 2 or 3 R': $C_{1-3}$ alkyl, $C_{1-3}$ alkoxy, —C(=O)O—$C_{1-3}$ alkyl; and the other variables are as defined above.

In some embodiments of the present disclosure, the above R is selected from F, Cl, Br, I, CN, OH, $NH_2$, COOH, $CONH_2$, Me, Et, $CF_3$,

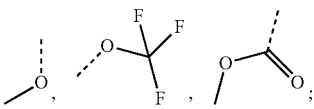

and the other variables are as defined above.

In some embodiments of the present disclosure, the above $R_1$ is selected from —COOH, or selected from the following groups which are optionally substituted with 1, 2 or 3 R: phenyl, pyridyl, pyrimidinyl, thienyl, thiazolyl, indolyl, cyclohexanyl, cyclohexenyl, bicyclo[1.1.1]pentanyl.

In some embodiments of the present disclosure, the above $R_1$ is selected from —COOH, or selected from the following groups which are optionally substituted with 1, 2 or 3 R:

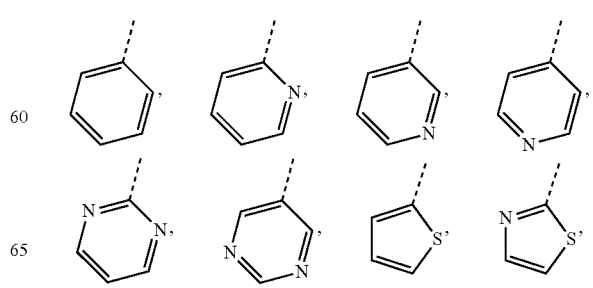

-continued

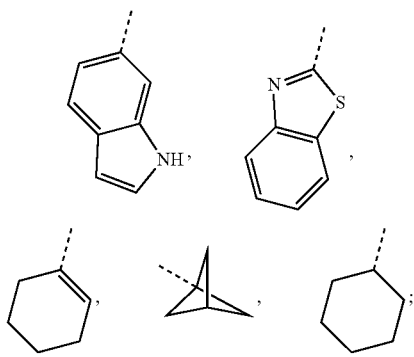

and the other variables are as defined above.

In some embodiments of the present disclosure, the above $R_1$ is selected from —COOH,

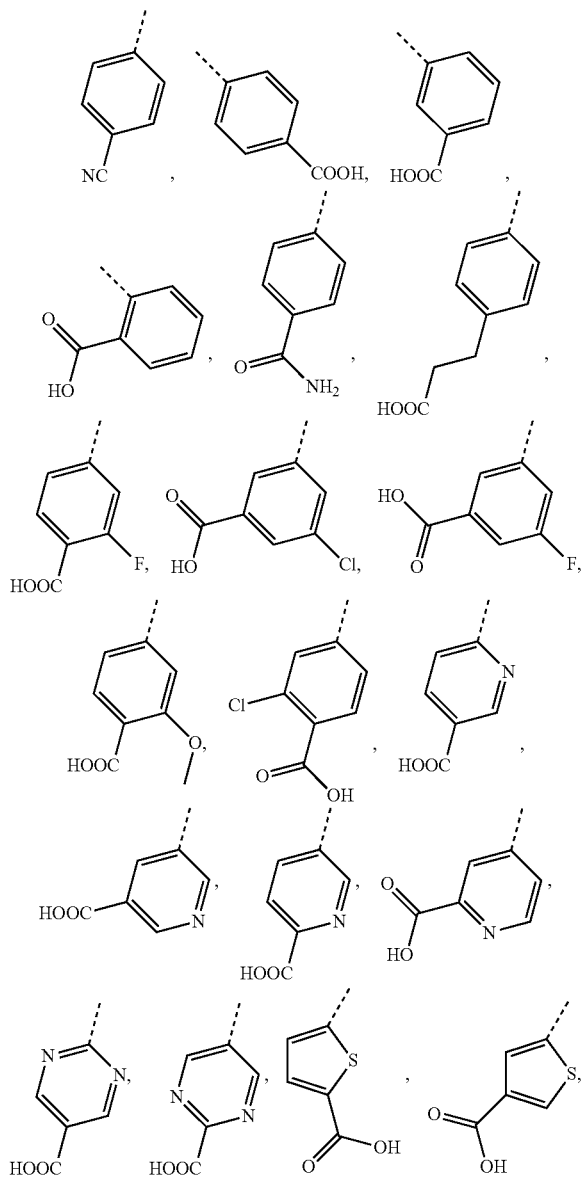

-continued

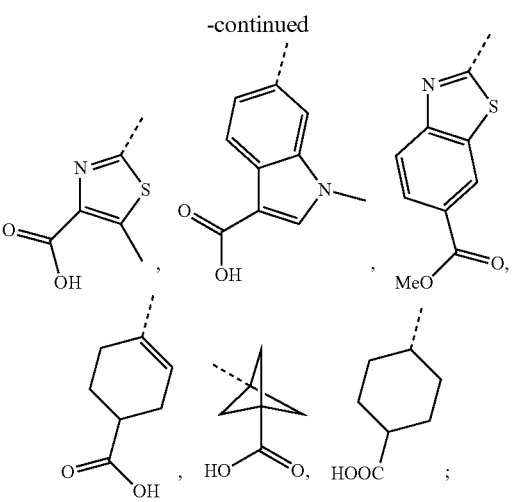

and the other variables are as defined above.

In some embodiments of the present disclosure, the above $R_2$ is selected from Me, Et; and the other variables are as defined above.

In some embodiments of the present disclosure, the above $R_3$ is selected from Me, Et; and the other variables are as defined above.

In some embodiments of the present disclosure, the above $R_2$ and $R_3$ are linked together to form a $C_{3-6}$ cycloalkyl; and the other variables are as defined above.

In some embodiments of the present disclosure, the above $R_2$ and $R_3$ are linked, the structure unit

is selected from

and the other variables are as defined above.

In some embodiments of the present disclosure, the above $R_4$ is selected from H, F, Cl, Br, I, OH, $NH_2$, or selected from the following groups which are optionally substituted with 1, 2 or 3 R: $C_{1-3}$ alkyl, phenyl, pyridyl; and the other variables are as defined above.

In some embodiments of the present disclosure, the above $R_4$ is selected from H, F, Cl, Br, I, OH, or $NH_2$, or selected from the following groups which are optionally substituted with 1, 2 or 3 R: Me,

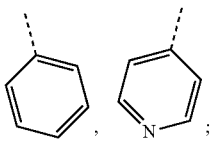

and the other variables are as defined above.

In some embodiments of the present disclosure, the above R$_4$ is selected from H, Cl, Me,

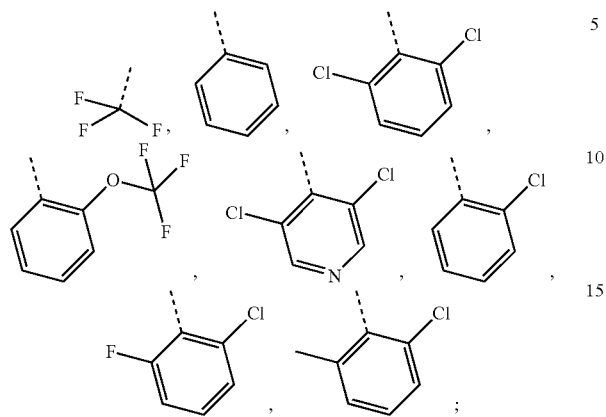

and the other variables are as defined above.

In some embodiments of the present disclosure, the above R$_5$ is selected from H, or selected from the following groups which are optionally substituted with 1, 2 or 3 R: Me,

and the other variables are as defined above.

In some embodiments of the present disclosure, the above R$_5$ is selected from H, Me,

and the other variables are as defined above.

In some embodiments of the present disclosure, the above ring A is selected from oxazolyl, isoxazolyl, pyridyl, benzothienyl; and the other variables are as defined above.

In some embodiments of the present disclosure, the above structure unit

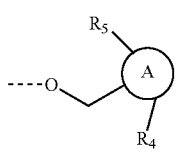

is selected from

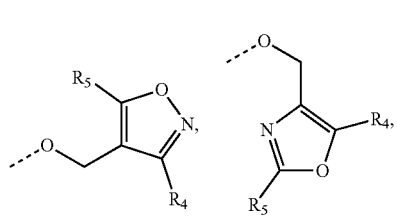

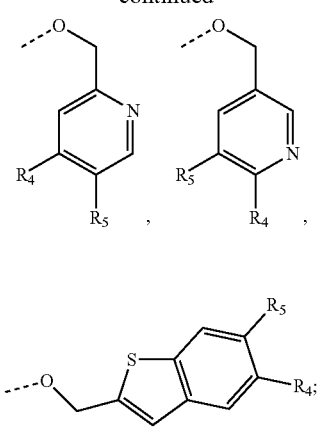

and the other variables are as defined above.

In some embodiments of the present disclosure, the above structure unit

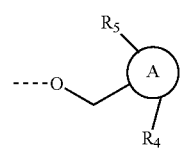

is selected from

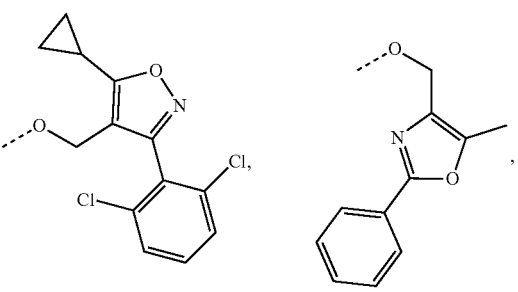

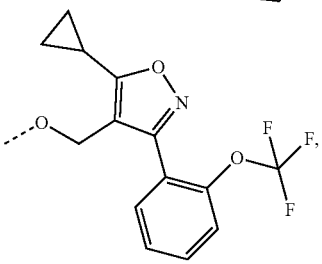

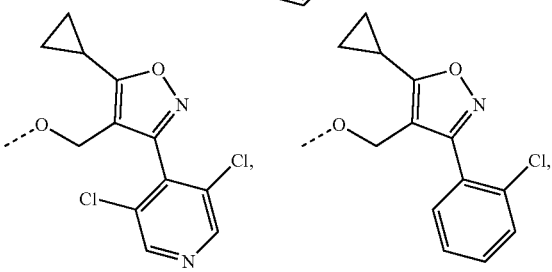

-continued

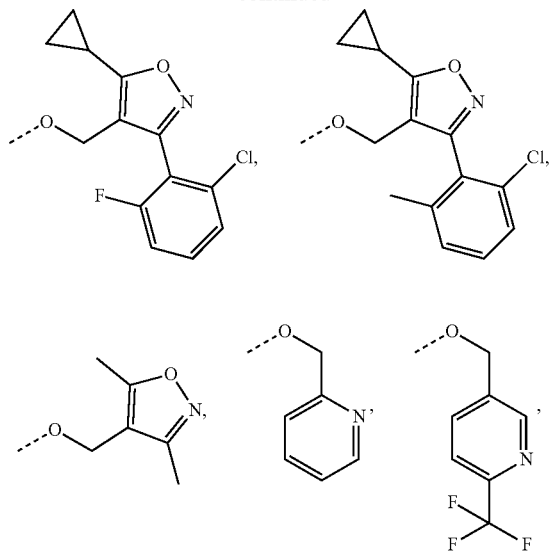

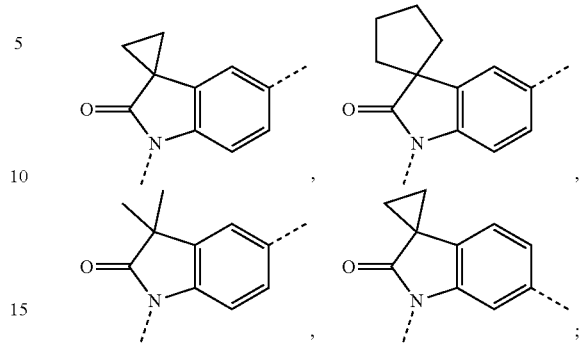

is selected from and the other variables are as defined above.

In some embodiments of the present disclosure, the above structure unit

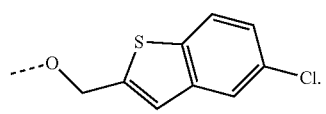

is selected from

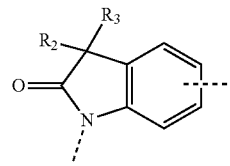

and the other variables are as defined above.

In some embodiments of the present disclosure, the above structure unit

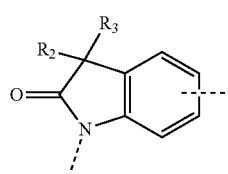

is selected from

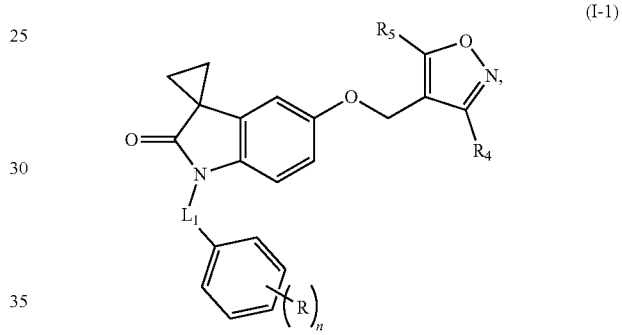

and the other variables are as defined above.

In some embodiments of the present disclosure, the above compound or a pharmaceutically acceptable salt thereof is selected from

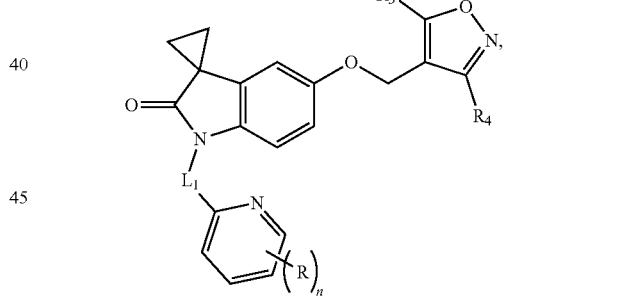
(I-1)

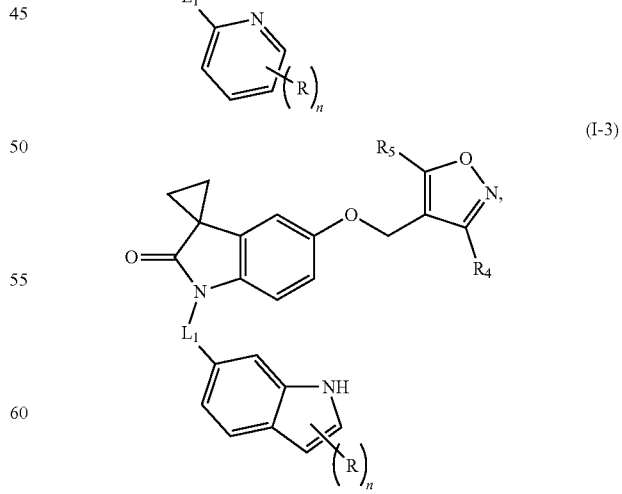
(I-2)

(I-3)

wherein,
n is each independently selected from 0, 1 or 2;
R, $L_1$, $R_4$, and $R_5$ are as defined above.

Other embodiments of the present disclosure are obtained from any combination of the above variables.
The present disclosure further provides a compound of the following formula, which is selected from
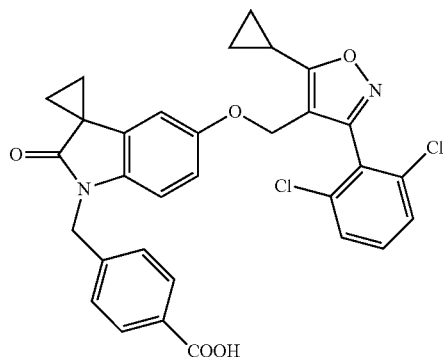
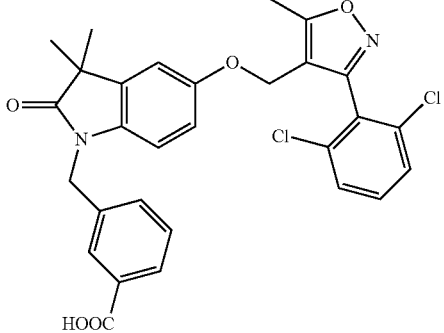
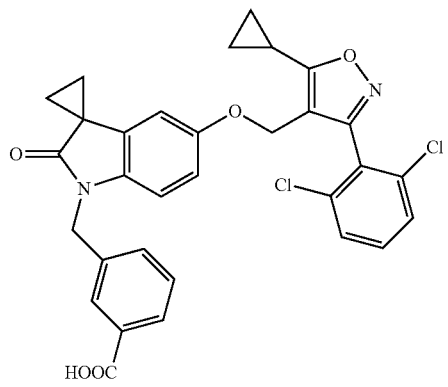
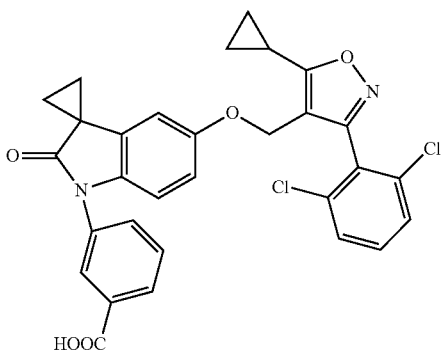
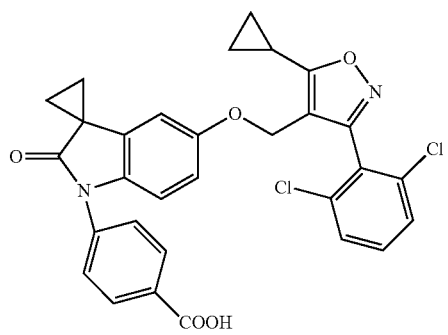
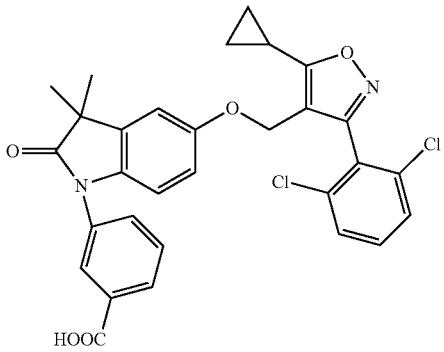
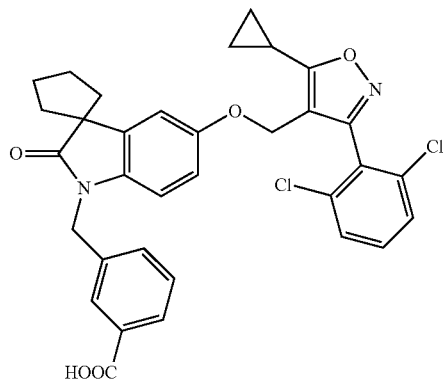
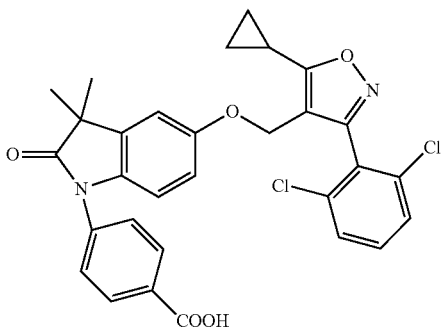

49
-continued
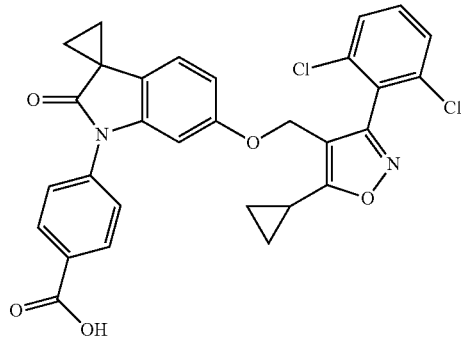
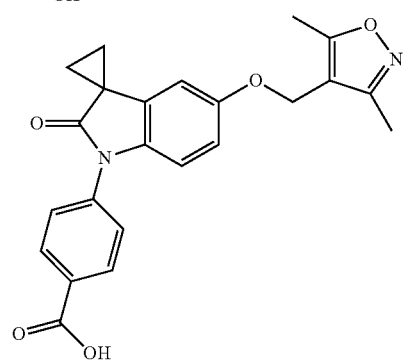
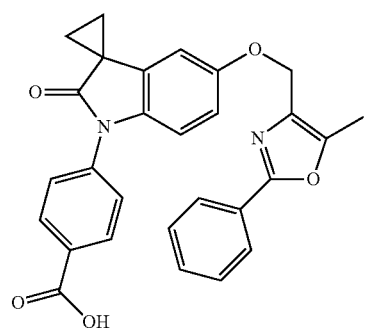
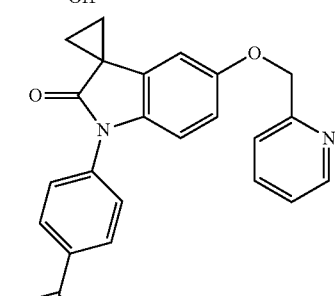
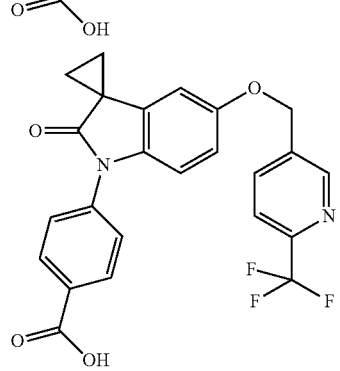
50
-continued
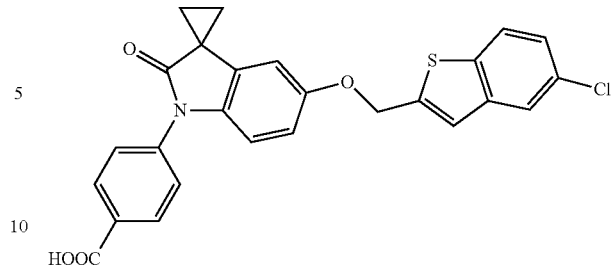
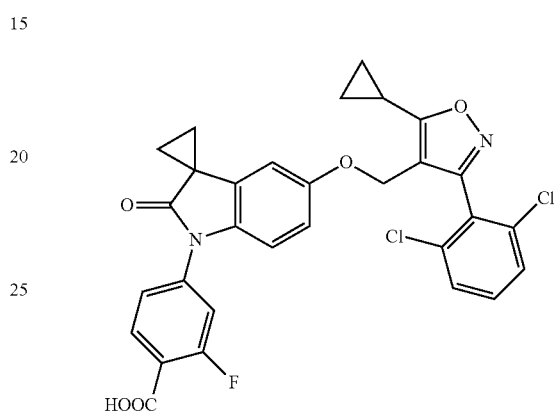
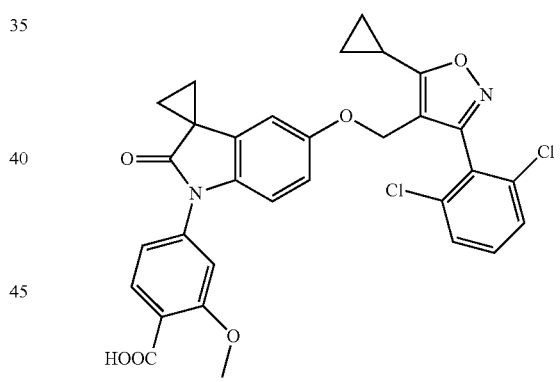
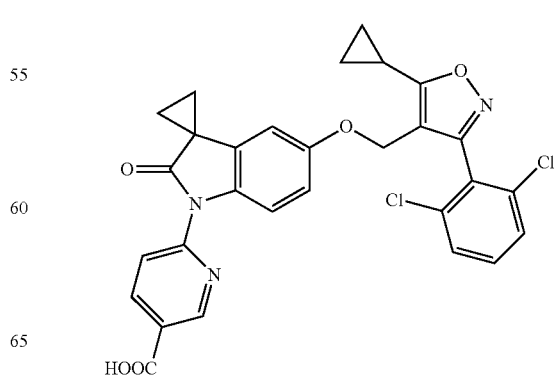

51
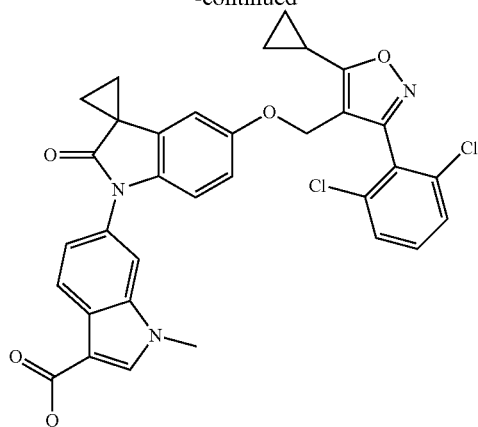
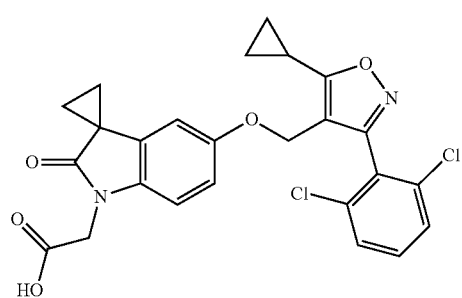
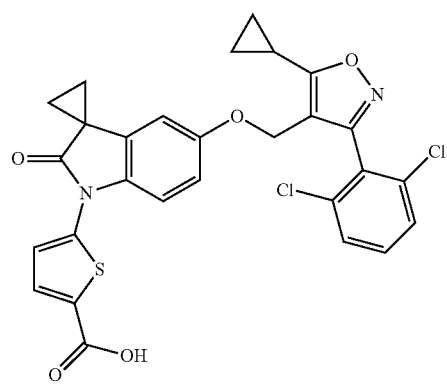
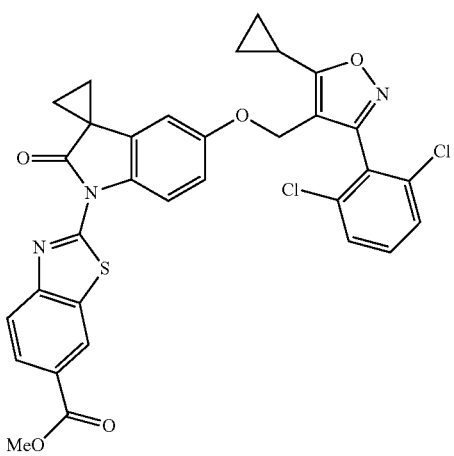
52
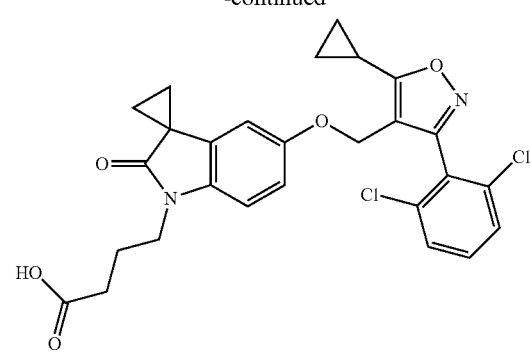
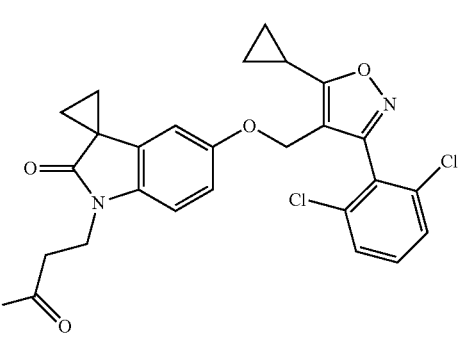
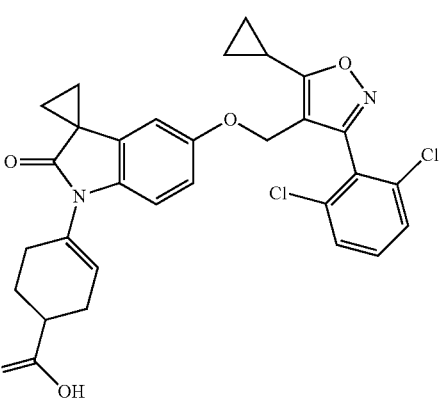
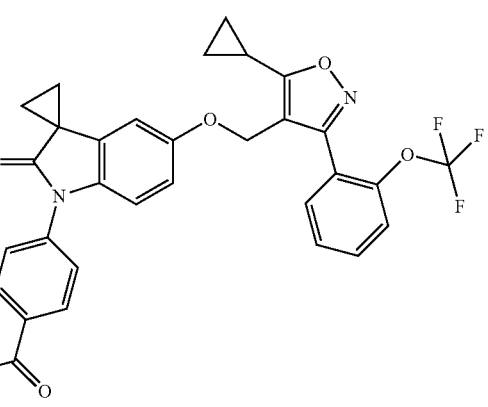

53
-continued
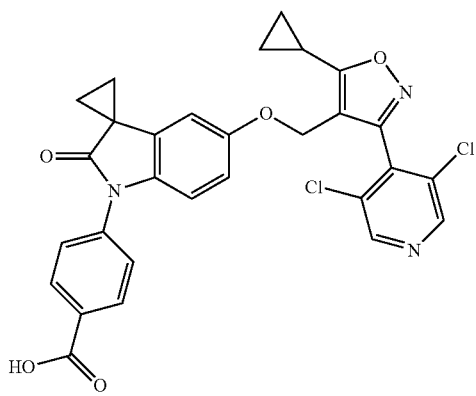
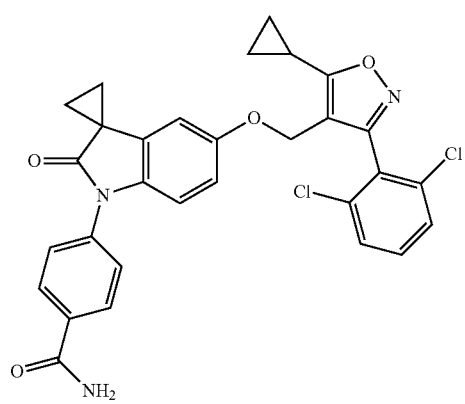
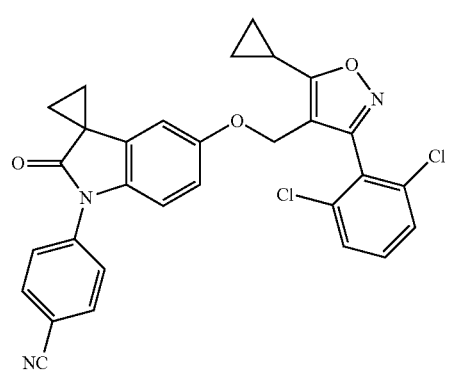
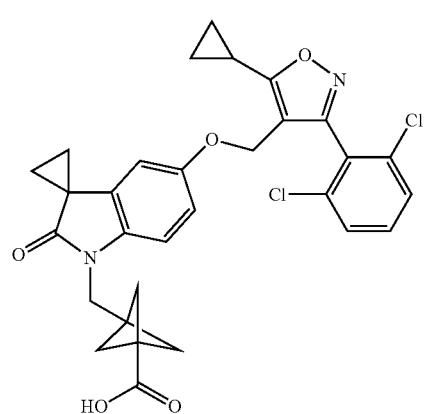
54
-continued
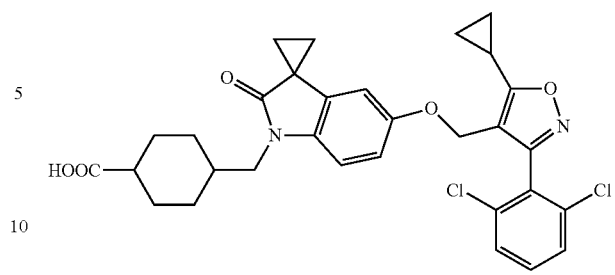
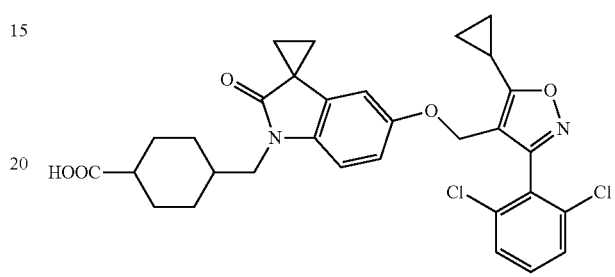
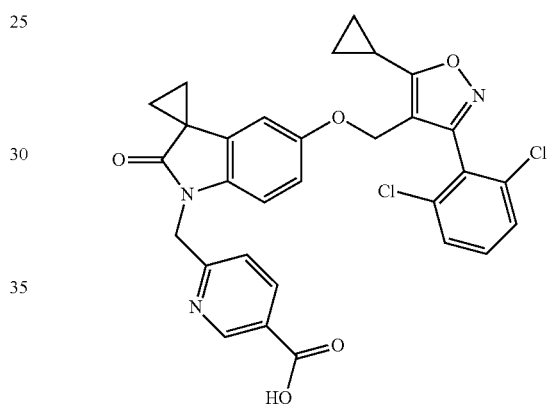
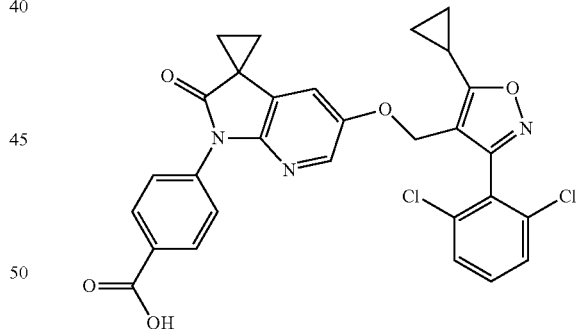
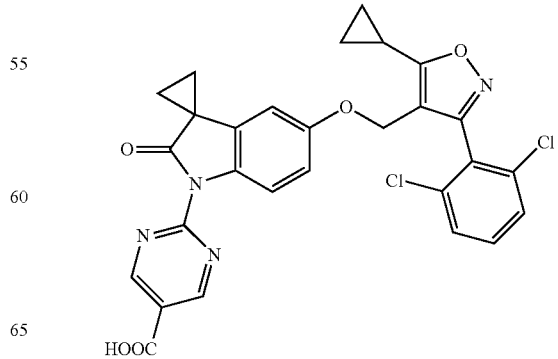

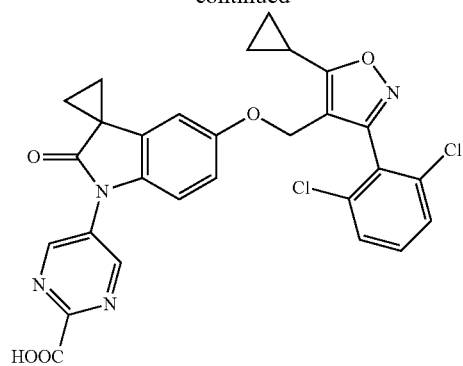
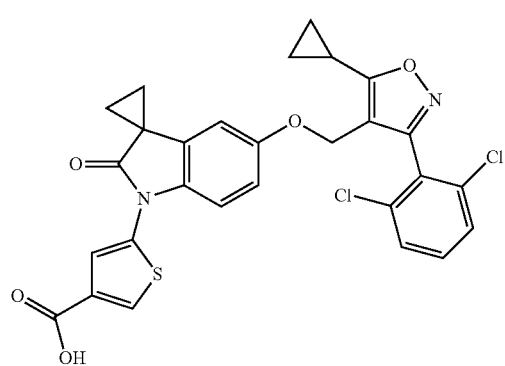
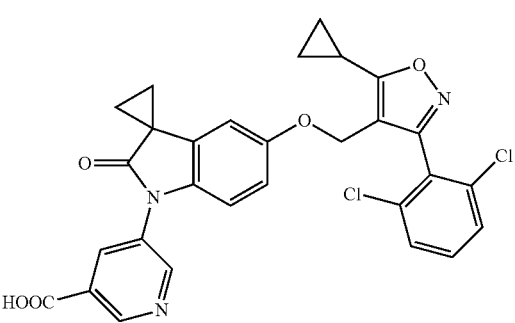
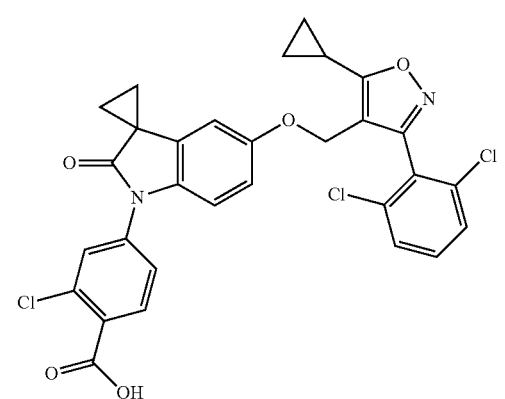
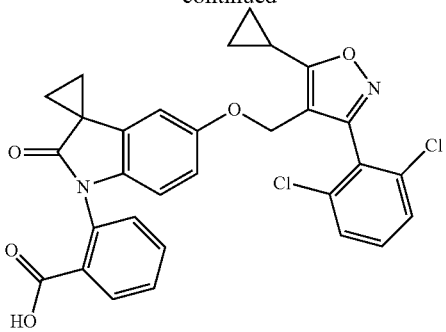
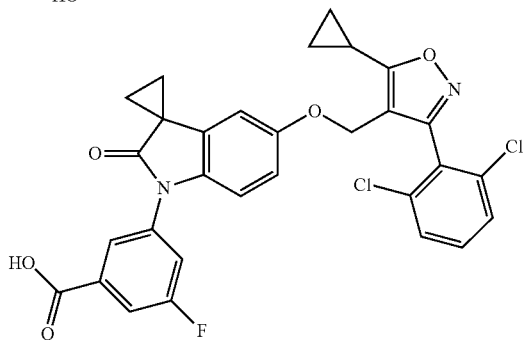
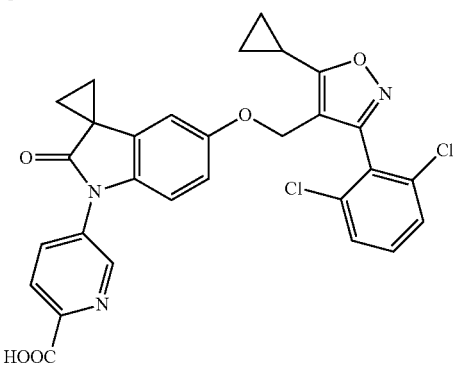
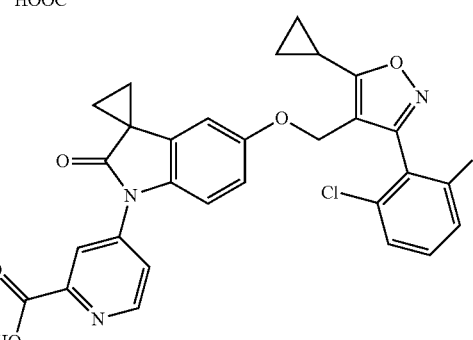
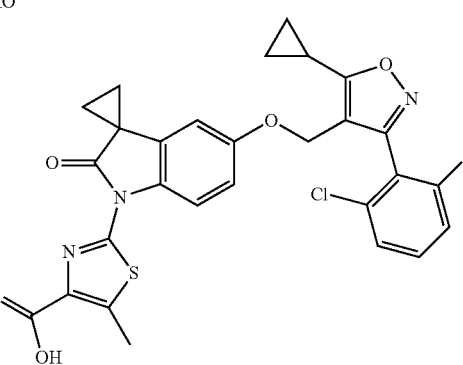

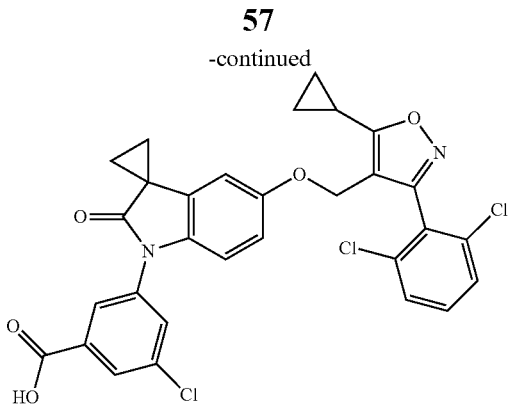

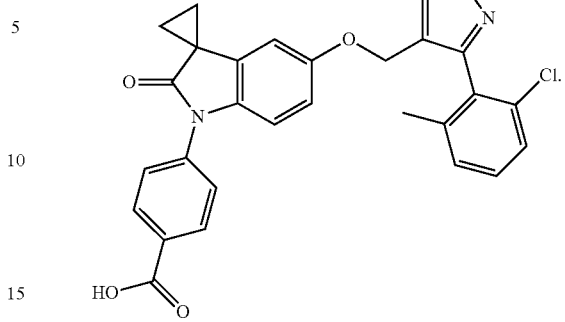

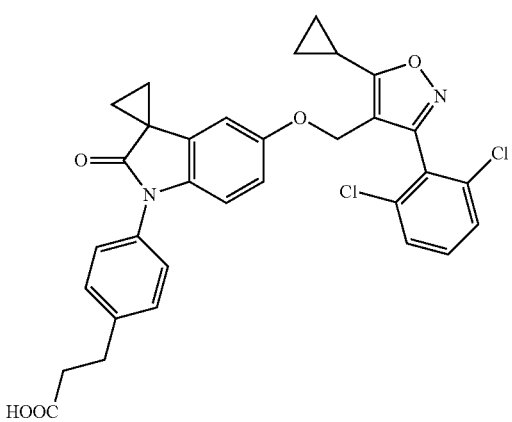

The present disclosure further provides use of the above compound, optical isomer thereof or pharmaceutically acceptable salt thereof in the preparation of a medicament for the treatment of FXR receptor-related diseases.

The present disclosure further provides use of the above compound, optical isomer thereof or pharmaceutically acceptable salt thereof in the preparation of a medicament for the treatment of RXR-related diseases.

The present disclosure further provides use of the above compound, optical isomer thereof or pharmaceutically acceptable salt thereof in the preparation of a medicament for the treatment of nonalcoholic fatty liver diseases.

Definitions and Descriptions

Unless otherwise specified, the following terms and phrases used in this text have the following meanings. A specific term or phrase should not be considered uncertain or unclear in the absence of a specific definition, and should be understood according to the common meaning. The trade name, if occurring in this text, is intended to refer to its corresponding commodity or active ingredients. The term "pharmaceutically acceptable" used herein is specific to those compounds, materials, compositions and/or dosage forms which are suitable for contacting the tissues of human and animals within the range of reliable medical judgement, but have no excessive toxicity, stimulation, allergic reactions, or create other problems or complications, matching with reasonable benefit/risk ratio.

The term "pharmaceutically acceptable salt" means a salt of a compound of this disclosure, which is prepared by a compound with specific substituent groups of the present disclosure with a relatively nontoxic acid or alkali. When the compound in this disclosure contains relatively acidic functional groups, an alkaline addition salt can be obtained by using a sufficient quantity of alkali to contact such a compound in neutral form in pure solution or suitable inert solvent. Pharmaceutically acceptable alkali addition salts include the sodium salts, potassium salts, calcium salts, ammonia salts, organic ammonia salts, magnesium salts or similar salts. When the compound in this disclosure contains relatively alkaline functional groups, an acid addition salt can be obtained by using enough quantity of acid to contact such a compound in neutral form in pure solution or suitable inert solvent. Examples of pharmaceutically acceptable acid addition salts include inorganic acid salts, wherein the inorganic acids include hydrochloric acid, hydrobromic acid, nitric acid, carbonic acid, bicarbonate radical, phosphoric acid, mono hydrogen phosphate radical, dihydrogen phosphate radical, sulfuric acid, hydrogen sulfate radical, hydroiodic acid, phosphorous acid, etc.; organic acid salts, wherein the organic acids include acetic acid, propionic acid, isobutyric acid, maleic acid, malonic acid, benzoic acid, succinic acid, octanedioic acid, fumaric acid, lactic acid, mandelic acid, phthalic acid, benzenesulfonic acid, p-toluenesulfonic acid, citric acid, tartaric acid, methanesulfonic acid, and other similar acids; salts of amino acids (such as arginine, etc.); and salts of organic acids (such as glucuronic acid). As some specific compounds in this disclosure contain alkaline and acid functional groups, they can be converted into any alkali or acid addition salts.

Preferably, the salt contacts with an alkali or acid conventionally, and then separates the parent compound to produce the neutral form of compound. The parent form of compound differs from its various salts in certain physical properties, for example, they have different solubilities in polar solvents.

The term "pharmaceutically acceptable salt" as used herein refers to a derivative of a compound of this disclosure, wherein the described parent compound can be modified in the mode of an acid or alkaline addition salt. Examples of pharmaceutically acceptable salts include but not limited to: inorganic acid salts or organic acid salts of basic groups such as amines, and alkali metal salts or organic salts of acid radicals such as carboxylic acid. The pharmaceutically acceptable salts include regular non-toxic salts of quaternary ammonium salts of parent compounds, such as a salt formed with a non-toxic inorganic acid or organic acid. Regular non-toxic salts include but not limited to the salts derived from inorganic acids and organic acids, in which the described inorganic acids or organic acids are selected from 2-acetoxybenzoic acid, 2-hydroxyethanesulfonic acid, acetic acid, ascorbic acid, benzenesulfonic acid, benzoic acid, bicarbonate radical, carbonic acid, citric acid, edetic acid, ethane disulfonic acid, ethane sulfonic acid, fumaric acid, glucoheptonic acid, gluconic acid, glutamic acid, glycolic acid, hydrobromic acid, hydrochloric acid, hydriodate, hydroxyl, hydroxyl naphthalene, isethionic acid, lactic acid, lactose, dodecyl sulfonic acid, maleic acid, malic acid, mandelic acid, methane sulfonic acid, nitric acid, oxalic acid, pamoic acid, pantothenic acid, phenylacetic acid, phosphoric acid, polygalacturonic acid, propionic acid, salicylic acid, stearic acid, folinic acid, succinic acid, sulfamic acid, sulfanilic acid, sulfuric acid, tannin, tartaric acid and p-toluenesulfonic acid.

The pharmaceutically acceptable salts in this disclosure can be prepared from parent compounds containing acid radical or basic group using conventional methods. Generally, the preparation of such salts comprises reaction of these compounds in the form of free acid or alkali with stoichiometric amounts of suitable acid or alkali in water or organic solvent or a mixture of both. Generally, ether, ethyl acetate, ethanol, isopropanol or acetonitrile and other non-aqueous media are preferred.

Certain compounds in this disclosure may have asymmetric carbon atoms (optical centers) or double bonds. Racemates, diastereomers, geometric isomers and individual isomers are included within the scope of the disclosure.

The compounds described in this disclosure can contain non-naturally proportional atomic isotopes on one or more atoms constituting such compounds. For example, radioisotopes can be used to label the compound, such as tritium ($^3$H), iodine-125 ($^{125}$I) or C-14 ($^{14}$C). All isotope-comprising forms of compounds described in this disclosure, whether radioactive or not, are included in the scope of this disclosure.

"Optional" or "optionally" means that the events or conditions described subsequently may occur but are not necessary, and this description includes the circumstances that the events or conditions described occur, as well as the circumstances that the events or conditions described do not occur.

The term "substituted" means that one or more hydrogen atoms on specific atom are substituted by a substituent group, such a hydrogen atom can include a heavy hydrogen and a variation of hydrogen, so long as the valence state of a specific atom is normal and the post-substitution compound is stable. When the substituent group is a keto group (that is, —O), it means that two hydrogen atoms are substituted. Ketone substitution never occurs on an aryl. The term "optionally substituted" means that a group can be substituted or unsubstituted. Unless otherwise specified, the type and number of said substituent groups can be arbitrarily selected on the basis of chemistry availability.

When a variable (such as R) occurs more than once in the composition or structure of compound, its definition in each case is independent from other occurrence(s). Therefore, if a group is substituted by 0-2 R groups, the groups described can be optionally substituted by two Rs at most, and the R in each case is independently chosen. A combination of substituent group(s) and/or variant(s) thereof is permitted only under the circumstances that such combination produces a stable compound.

When the number of a linking groups is 0, such as —(CRR)$_0$—, it means that this linking is a single bond.

When a variable is chosen from a single bond, it means that the two groups linked thereto are linked directly. For example, when L represents a single bond in A-L-Z, it means that this structure is actually A-Z.

When a substituent group is absent, it means that this substituent group does not exist, for example, when X is absent in A-X, it means that this structure is actually A. When a substituent group can be linked to more than one atoms on a ring, it means that this substituent group can be bonded to any atom on this ring. For example, the structural units

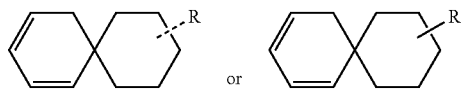

show that the substitution of substituent group R can take place in any position on cyclohexyl or cyclohexadiene. If it does not indicate that through which atom the substituent group enumerated is linked to a substituted group, this substituent group can be bonded by any atom. For example, pyridyl can be linked to the substituted group by any one carbon atom on the pyridine cycle. If the linking direction of the linking group enumerated is not indicated, its linking direction is arbitrary, for example, when the linking group L in

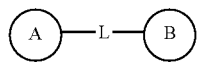

is -M-W—, the rings A and B can be linked by -M-W— to either form

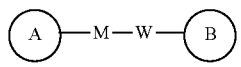

in the direction the same as reading order from left to right, or form

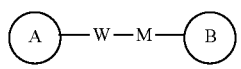

in the opposite direction to the reading order left to right. The combination of linking group(s), substituent group(s) and/or variants thereof is permitted only under the circumstances that such combination produces a stable compound.

Unless otherwise specified, a "ring" represents a substituted or unsubstituted cycloalkyl, heterocycloalkyl, cycloalkenyl, heterocycloalkenyl, aryl or heteroaryl. The term "ring" includes a monocyclic ring, a linking ring, a spiral ring, a fused ring or a bridged ring. The number of atoms on a ring is usually defined as the member number of the ring, for example, "a "5-7 membered ring" means that 5-7 atoms are arranged in an encircling way. Unless otherwise specified, the ring optionally includes 1-3 heteroatoms. Therefore, "5-7 membered ring" includes phenyl, pyridine and piperidyl. On the other hand, the term "5-7 membered heterocycloalkyl ring" includes pyridyl and piperidyl, but excludes phenyl. The term "ring" also includes a ring system containing at least one ring, wherein each "ring" is independent in accordance with the above-mentioned definition.

Unless otherwise specified, the term "heterocyclic ring" or "heterocyclic radical" means a stable monocyclic ring, dicyclic ring or tricyclic ring containing a heteroatom or a hetero-radical, which can be saturated, partly unsaturated, or unsaturated (aromatic), and contains carbon atom and one, two, three or four cyclo-heteroatoms which are independently chosen from N, O and S, wherein any above-mentioned heterocyclic ring can be fused to a benzene ring to form a dicyclic compound. Nitrogen and sulfur heteroatoms can be optionally oxidized (namely, NO and $S(O)_p$, wherein p is 1 or 2). Nitrogen atom can be substituted or unsubstituted (namely, N or NR, in which R is H or the substituent groups as defined herein). The heterocyclic ring can be attached to the side-chain group of any heteroatom or carbon atom to form a stable structure. If the compound so-produced is stable, a heterocyclic ring described herein can have substitution on carbon or on nitrogen. The nitrogen atom in the heterocyclic ring is optionally quaternized. In a preferred embodiment, the total number of S and O atoms in a heterocyclic ring is more than 1, and these atoms are not adjacent to each other. In another preferred embodiment, the total number of S and O atoms in the heterocyclic ring is not more than 1. As used herein, the term "heteroaryl" means an stable aromatic 5-, 6-, or 7-membered monocyclic ring or bicyclic ring, or stable aromatic 7-, 8-, 9- or 10 membered bicyclic heterocyclic radical which contains carbon atoms and 1, 2, 3 or 4 cyclic-heteroatoms which are independently chosen from N, O and S. Nitrogen atom can be substituted or unsubstituted (i.e., being N or NR, wherein R is H or other substituent groups as defined herein). Nitrogen and sulphur heteroatoms can optionally be oxidized (i.e., NO and $S(O)_p$, wherein p is 1 or 2). It is noteworthy that the total number of S and O atoms on aromatic heterocyclic ring is not more than 1. The bridge ring is also included in the definition of "heterocycle." The bridged ring is formed when one or more atoms (for example, C, O, N or S) link to two nonadjacent carbon atoms or nitrogen atoms. Preferred bridged rings include but not limited to one carbon atom, two carbon atoms, one nitrogen atom, two nitrogen atoms and one carbon-nitrogen radical. It is noteworthy that a bridge always converts a monocycle into a tricycle. Substitutions on the ring can also occur on the bridge in the bridged ring.

Examples of heterocyclic compounds include but not limited to acridinyl, azocinyl, benzimidazolyl, benzofuryl, benzosulfhydryl furyl, benzosulfhydryl phenyl, benzoxazolyl, benzooxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, benzodihydropyranyl, chromene, cinnolinyl-decahydroquinolinyl, 2H,6H-1,5,2-dithiazinyl, dihydrofuran-[2,3-b]tetrahydrofuranyl, furyl, furazyl, imidazolidinyl, imidazolinyl, imidazolyl, 1H-indazolyl, indolenyl, indolinyl, indolizinyl, indolyl, 3H-indolyl, isobenzofuryl, isoindolyl, isoindolinyl, isoquinolyl, isothiazolyl, isoxazolyl, methylenedioxy phenyl, morpholinyl, naphthyridinyl, octahydro-isoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidyl, phenanthridinyl, phenanthrolinyl, azophenylene, phenothiazine, benzo-xanthinyl, phenoxazinyl, phthalazinyl, piperazinyl, piperidyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridino-oxazole, pyridino-imidazole, pyridino-thiazole, pyridyl, pyrrolidyl, pyrrolinyl, 2H-pyrrolyl, pyrrolyl, quinazolinyl, quinolyl, 4H-quinolizidinyl, quinoxalinyl, quinuclidinyl, tetrahydrofuranyl, tetrahydroisoquinolinyl, tetrahydroquinolinyl, tetrazyl, 6H-1,2,5-thiadiazolyl, 1,2,3-thiadiazolyl, 1,2,4-thiadiazolyl, 1,2,5-thiadiazolyl, 1,3,4-thiadiazolyl, thianthrenyl, thiazolyl, isothiazolithiophenyl, thieno-oxazolyl, thieno-thiazolyl, thieno-imidazolyl, thienyl, triazinyl, 1,2,3-thiazolyl, 1,2,4-thiazolyl, 1,2,5-triazoly, 1,3,4-thiazolyl and xanthenyl. Fused rings and spiro rings compounds are also included.

In some embodiments, the term "heteroalkyl" whether used by itself or in combination with another term represents stable straight-chain or branched-chain hydrocarbon radicals or combinations thereof composed of a certain number of carbon atoms and at least one heteroatom. In a typical embodiment, the heteroatom is selected from B, O, N and S, wherein said nitrogen or sulphur atoms are optionally oxidized, and said nitrogen heteroatom is optionally quaternized. The heteroatom or hetero-radical can be located in any position of a hetero-hydrocarbyl, including embodiments wherein this hydrocarbyl attaches to a position of another part of a molecule, while the terms "alkoxy", "alkylamino" and "alkylsulphanyl" (or sulfo-alkoxy) are understood to be customary expressions, and respectively mean that the alkyl groups link to other parts of a molecule through a oxygen atom, amino or sulphur atom. Such examples include but not limited to —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—$S(O)_2$—$CH_3$, —$CH_2$—CH=N—$OCH_3$. At least two heteroatoms can be continuous, such as —$CH_2$—NH—$OCH_3$.

Unless otherwise specified, the term "alkyl" is used to represent a straight-chain or branched-chain saturated hydrocarbyl which can be mono-substituted (such as —$CH_2F$) or poly-substituted (such as —$CF_3$), monovalent (such as methyl), divalent (such as methylene) or multivalent (such as methenyl). Such examples of alkyl include methyl (Me), ethyl (Et), propyl (such as n-propyl and isopropyl), butyl (such as n-butyl, isobutyl, s-butyl, t-butyl), amyl (such as n-amyl, isoamyl, neo-amyl), etc.

Unless otherwise specified, "alkenyl" means an alkyl that comprises one or more carbon-carbon double bonds at any site of a chain, which can be mono-substituted or poly-substituted, and monovalent, divalent or multivalent. Such examples of alkenyl include ethenyl, propenyl, butenyl, pentenyl, hexenyl, butadienyl, pentadienyl, hexadienyl, etc.

Unless otherwise specified, cycloalkyl include any stable cyclic or polycyclic hydrocarbyl, wherein all carbon atoms are saturated which can be mono-substituted or poly-substituted, and monovalent, divalent or multivalent. Examples of these cycloalkyls include but not limited to cyclopropyl, norborneol alkyl, [2.2.2]biocyclooctane, [4.4.0]biocyclodecane, etc.

Unless otherwise specified, cycloalkenyl includes any stable cyclic or polycyclic hydrocarbyl comprising one or more unsaturated carbon-carbon double bonds at any site of a ring that can be mono-substituted or poly-substituted, and monovalent, divalent or multivalent. Examples of such a cycloalkenyl include but not limited to cyclopentenyl, cyclohexenyl, etc.

Unless otherwise specified, the term "halogenated element" or "halogen" whether used by itself or as a part of another substituent group, represents a fluorine, chlorine, bromine or iodine atom. In addition, the term "halogenated alkyl" is intended to include monohalogenated alkyl and polyhalogenated alkyl. For example, the term "halogenated ($C_1$-$C_4$) alkyl" is intended to include but not limited to trifluoromethyl, 2, 2, 2-trifluoroethyl, 4-chlorobutyl and 3-brominepropyl, etc. Unless otherwise specified, examples of such a halogenated alkyl include but not limited to trifluoromethyl, trichloromethyl, pentafluoromethyl and pentachloromethyl.

"Alkoxy" means an alkyl as defined herein comprising a specific number of carbon atoms and linked by an oxygen bridge. Unless otherwise specified, $C_{1-6}$ alkoxy includes alkoxy groups of $C_1$, $C_2$, $C_3$, $C_4$, $C_5$ and $C_6$. Examples of such an alkoxy include but not limited to methoxy, ethyoxy, n-propoxy, isopropoxy, n-butoxy, sec-butoxy, tert-butoxy, n-amoxy and S-amoxyl.

Unless otherwise specified, the term "aryl" refers to a polyunsaturated aromatic hydrocarbon group that can be mono-substituted or poly-substituted, monovalent, divalent or multivalent, and monocyclic or polycyclic (such as comprising 1-3 rings; wherein, at least one ring is aromatic) that is fused or covalently linked. The term "heteroaryl" means an aryl (or aromatic ring) containing one to four heteroatoms. In a representative example, the heteroatoms are selected from B, N, O and S, wherein, said nitrogen and sulphur atoms are optionally oxidized, and nitrogen atom is optionally quaternized. A heteroaryl can be linked to the rest of a molecule by a heteroatom. The non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furyl, thienyl, pyridyl, pyrimidyl, benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. Substituents of the above-mentioned groups on aryl or heteroaryl ring systems can be chosen from the acceptable substituent groups described hereinafter.

Unless otherwise specified, aryl, when used in conjunction with other terms (such as in aryloxy, arsulfenyl, aralkyl), includes aryl and heteroaryl as defined as above. Therefore, the term "aralkyl" is intended to include radicals in which an aryl attaches to an alkyl (such as benzyl, phenethyl, pyridylmethyl), include alkyls wherein a carbon atom (such as methylene) has been substituted by, for example, an oxygen atom, such as phenoxyl-methyl, 2-pyridine-oxymethyl, 3-(1-naphthoxy) propyl.

The compounds described in this disclosure can be prepared by many synthetic methods well known by those skilled in the art, including the embodiments described below, such embodiments used in combination with other chemical synthetic methods, or the equivalents well known by those skilled in the art, and the preferred embodiments include but are not limited to the examples in this disclosure.

The solvents used in this disclosure are available commercially. The following abbreviations are used in this disclosure: aq represents water; HATU represents O-(7-azabenzotriazole-1-yl)-N, N, N', N'-tetramethylurea-hexafluorophosphate; EDC represents N-(3-dimethylaminopropyl)-N'-ethylcarbodiimide hydrochloride; m-CPBA represents 3-chloroperoxybenzoic acid; eq represents equivalent; CDI represents carbonyldiimidazole; DCM represents dichloromethane; PE represents petroleum ether; DIAD represents diisopropyl azodicarboxylate; DMF represents N,N-dimethylformamide; DMSO represents dimethylsulfoxide; EtOAc or EA represents ethyl acetate; EtOH represents ethyl alcohol; MeOH represents methyl alcohol; CBz represents benzyloxycarbonyl which is an amino-protecting group; Boc represents t-butyloxycarboryl which is an amino-protecting group; HOAc represents acetic acid; $NaCNBH_3$ represents sodium cyanoborohydride; r.t. represents room temperature; O/N represents staying overnight; THF represents tetrahydrofuran; $Boc_2O$ represents di-tert-butyl dicarbonate; TFA represents trifluoroacetic acid; DIPEA represents N-di(isopropyl)ethylamine; $SOCl_2$ represents sulfoxide chloride; $CS_2$ represents carbon disulfide; TsOH represents p-toluenesulfonic acid; NFSI represents N-fluoro-N-(phenylsulfonyl)benzenesulfonamide; NCS represents 1-chlorine pyrrolidine-2,5-diketone; n-$Bu_4NF$ represents tetrabutylammonium fluoride; iPrOH represents 2-propanol; mp stands for melting point; LDA represents lithium diisopropylamide; EDCI represents carbodiimide; HOBt represents 1-hydroxybenzotriazole; Pd(dppf)$Cl_2$ represents [1,1'-bis(diphenylphosphine)ferrocene]palladium dichloride; $Pd_2(dba)_3$ represents tris(dibenzylideneacetone) dipalladium; PIFA represents bis(trifluoroacetyloxy)phenyliodohydrazide; X-Phos represents 2-dicyclohexylphosphine; DIBAH represents diisobutylaluminum hydride; $Pin_2B_2$ represents bis(pinacolato)diboron.

The compounds are named manually or using ChemDraw®, and commercially available compounds are referred to using the names in the catalog provided by the corresponding supplier.

Technical Effect

The compounds of the present disclosure have high in vitro FXR bioassay activity and the compounds have significant agonistic effects on the FXR receptor. The compound has high liver exposure and low plasma exposure, i.e., the liver-to-blood ratio is high, and the drug is mainly concentrated in the target organs.

DETAILED DESCRIPTION

Figure 1:
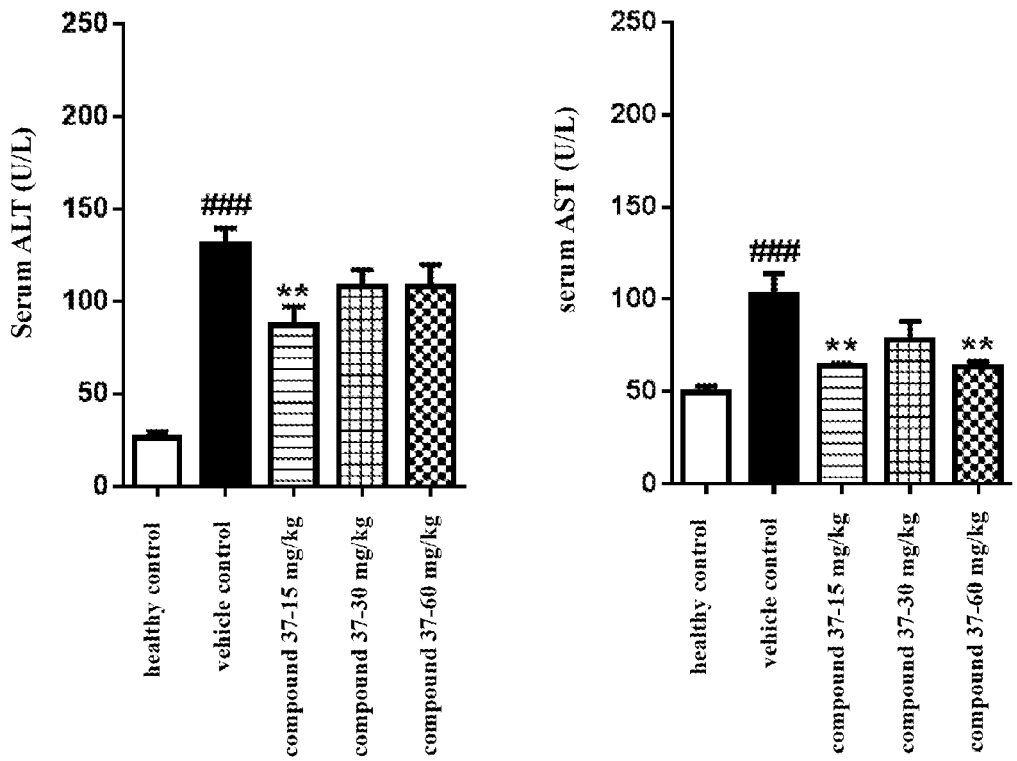
FIG. 1 shows detection of blood biochemical ALT/AST indicators. Compound 37 has a significant decrease in ALT/AST at a dose of 15 mg/kg.
Figure 2:
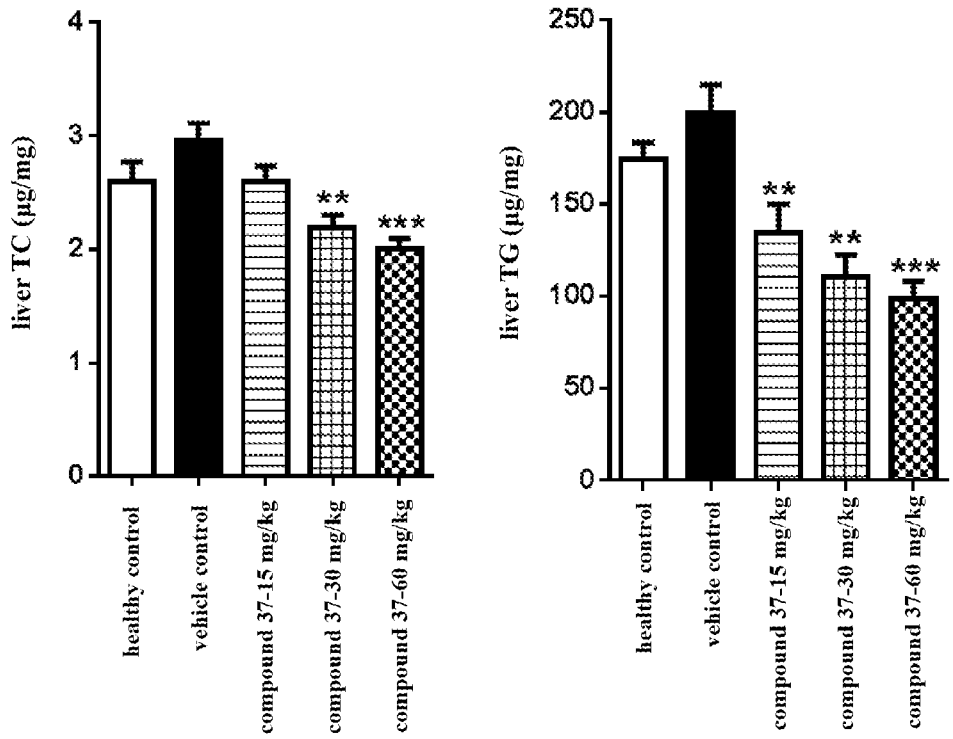
FIG. 2 is a graph of detection indicators of total cholesterol (TC) and triglyceride (TG) levels in the liver. Compound 37 has a significant decrease in TC/TG at a dose of 30 mg/kg, 60 mg/kg.
Figure 3:
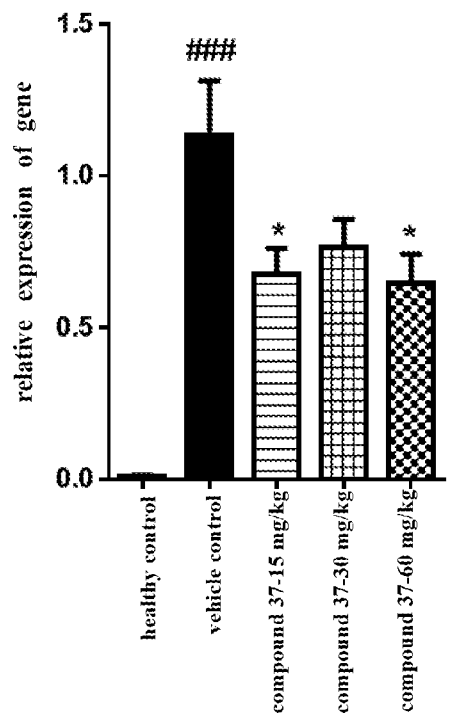
FIG. 3 shows alpha graph of gene expression of collagen in the liver. Compound 37 has a significant decrease in collagen-alpha at a dose of 15 mg/kg, 60 mg/kg.
Figure 4:
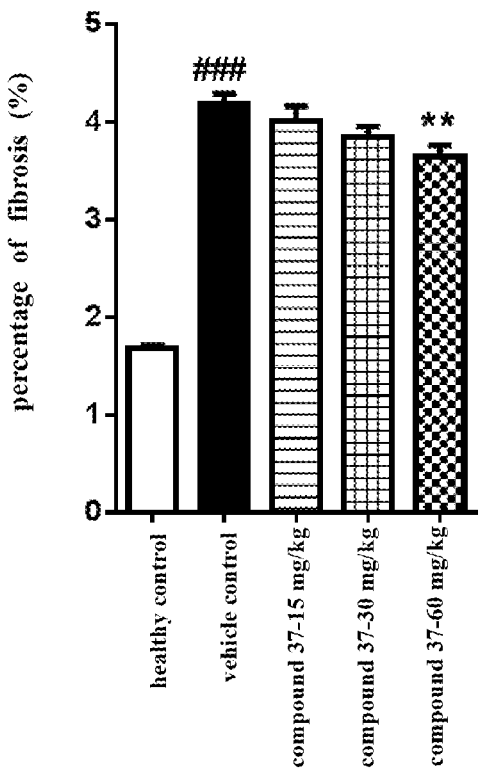
FIG. 4 is a graph of pathological tissue analysis of liver fibrosis showing that compound 37 has a significant reduction in liver fibrosis at a dose of 60 mg/kg.
Figure 5:
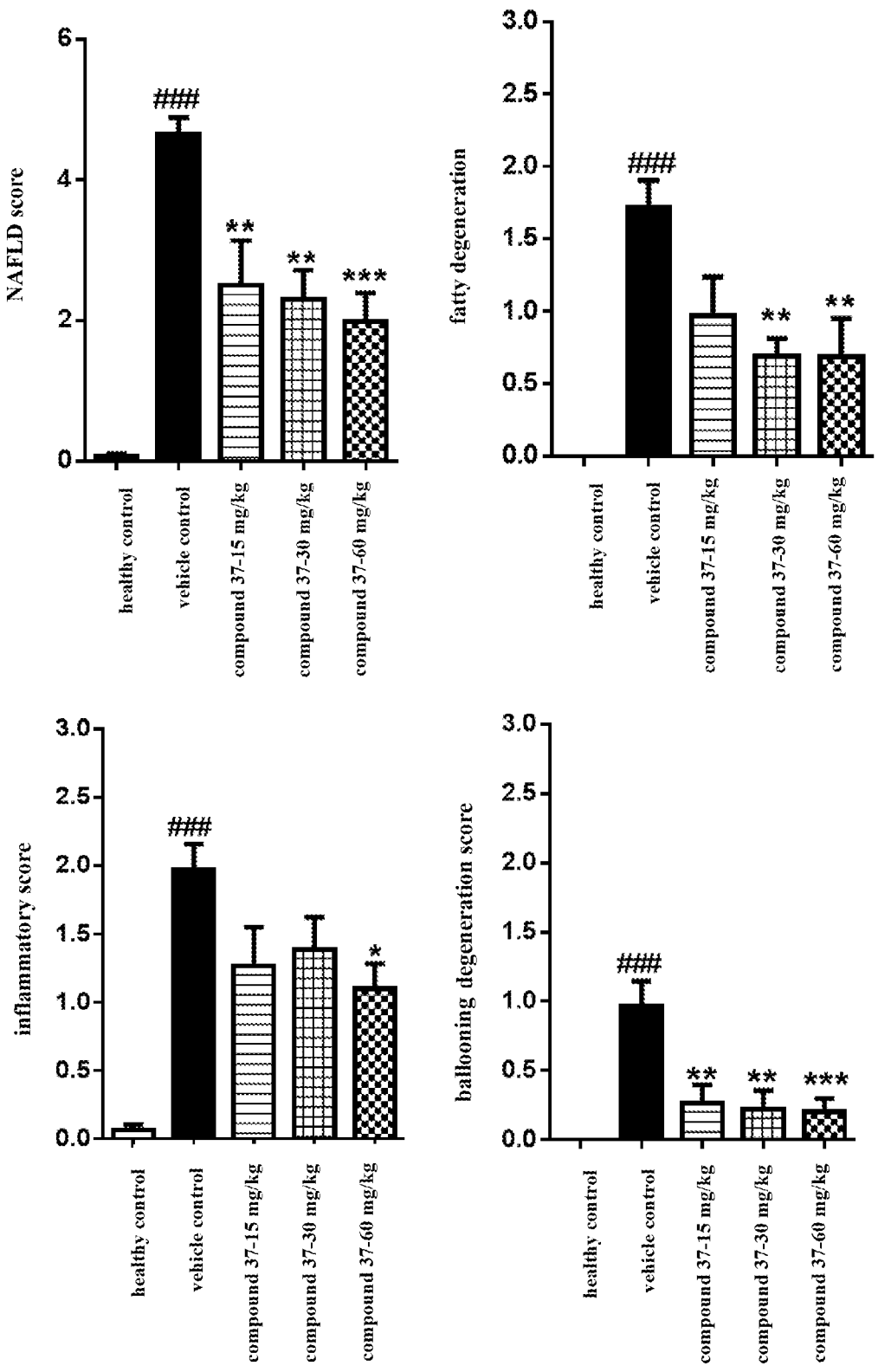
FIG. 5 is a graph of pathological tissue analysis showing that for the overall evaluation of nonalcoholic fatty liver score NAFLD, compound 37 has a significant reduction in NAFLD at a dose of 15 mg/kg, 60 mg/kg; for single steatosis, inflammatory molecules and ballooning change, compound 37 has an remarkable efficacy at 60 mg/kg.

The present invention will be described in detail by the examples below, which however do not mean any limitation to the present invention. The disclosure has described in detail the present invention, and disclosed specific embodiments thereof. It is obvious for those skilled in the art to make various modifications and improvements of the specific embodiments of the present invention without departing from the spirit and scope of this disclosure.

Reference Example 1: Fragment BB-1

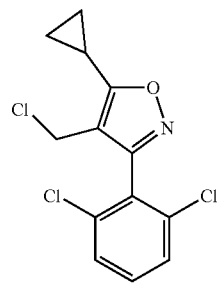 [SMILES: ClCc1c(-c2c(Cl)cccc2Cl)noc1C1CC1]

The synthesis of compound BB-1 refers to the literature (WO2011/020615).

Example 1: Compound 1

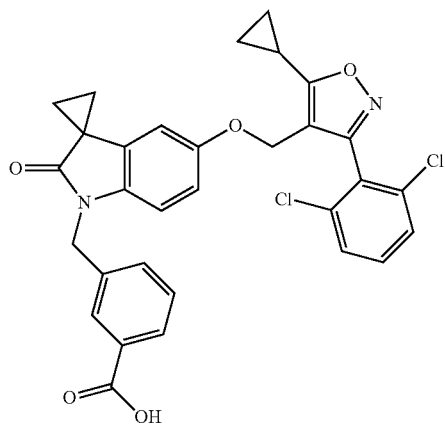 [SMILES: O=C(O)c1cccc(CN2C(=O)C3(CC3)c3cc(OCc4c(-c5c(Cl)cccc5Cl)noc4C4CC4)ccc32)c1]

Synthetic Route:

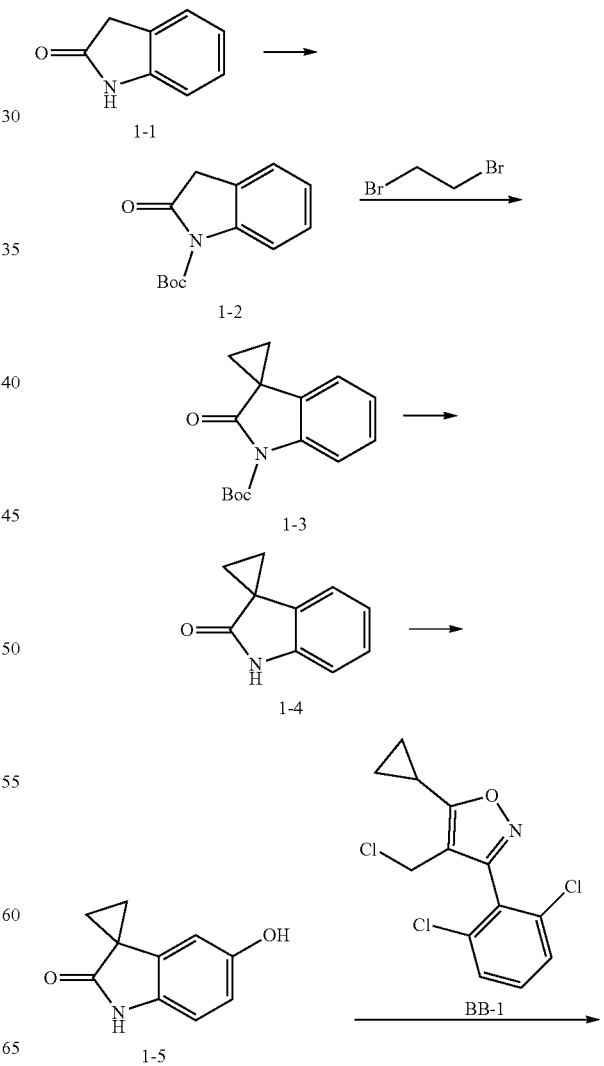

-continued

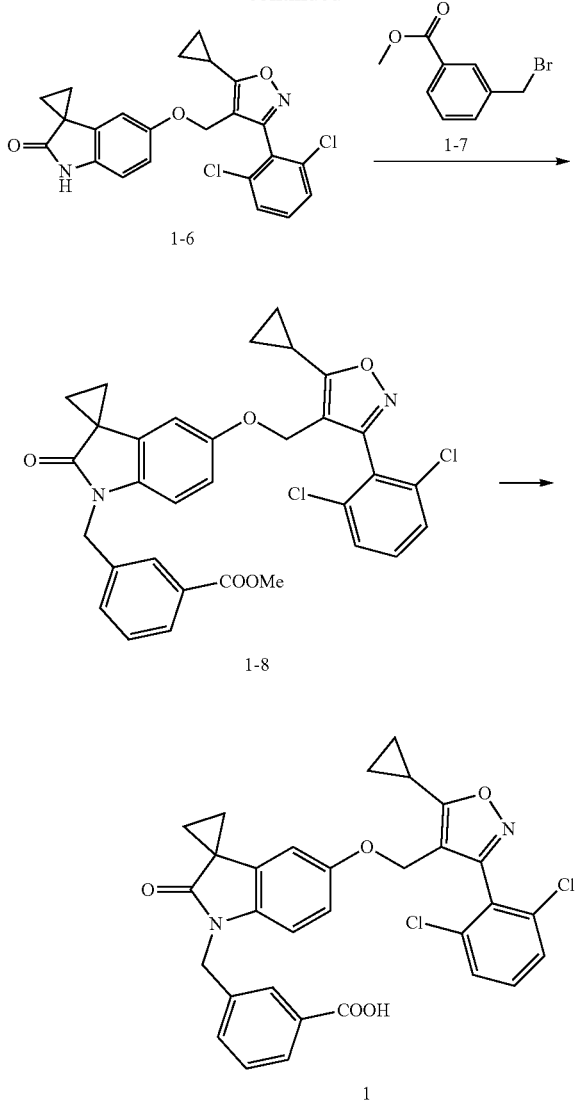

4-Dimethylaminopyridine (6.9 g, 56 mmol) and di-tert-butyl dicarbonate (90 g, 413 mmol) were added to the solution of 1-1 (50 g, 375 mmol) in acetonitrile (100 mL). The reaction liquid was stirred at 60° C. for 16 hours. TLC (petroleum ether:ethyl acetate=5:1) showed complete disappearance of the starting material and a major new point formed. The reaction liquid was concentrated under reduced pressure to remove solvent. The residue was diluted with 500 mL water and extracted with EtOAc (500 mL×3). The organic phase was combined, washed with 500 mL saturated brine once and dried over anhydrous sodium sulfate, filtered and concentrated under reduced pressure to obtain a crude product. The crude product was purified by silica gel column chromatography (petroleum ether/ethyl acetate=50/1), to give the target compound 1-2.

1-2 (60 g, 257 mmol) was dissolved in dimethyl sulfoxide (600 mL), and potassium carbonate (142 g, 1.0 mol) and 1,2-dibromoethane (70.6 g, 375.5 mmol, 28 mL, 1.46 eq.) were added. The reaction liquid was stirred at 25° C. for 12 hours. The reaction mixture was quenched with water (5000 mL), and filtered to give the target compound 1-3.

1-3 (60.0 g, 231.39 mmol) was dissolved in dichloromethane (600 mL), trifluoroacetic acid (105.5 g, 925.6 mmol, 69 mL) was added and the reaction mixture was stirred at 25° C. for 30 minutes. The reaction mixture was neutralized with a saturated sodium carbonate solution to pH=7-8, extracted with dichloromethane/methanol (10:1,500 mL×3), and the organic layer was washed with brine (100 mL×2), dried over anhydrous sodium sulfate, filtered and concentrated. The residue was washed with ethyl acetate (20 mL), and filtered to give the target compound 1-4. $^1$H NMR (400 MHz, CHLOROFORM-d) δ 8.89 (s, 1H), 7.17-7.21 (m, 1H), 6.97-6.84 (m, 2H), 6.82-6.84 (m, 1H), 1.76-1.79 (m, 2H), 1.53-1.56 (m, 2H).

1-4 (6.0 g, 37.7 mmol) was dissolved in chloroform (480 mL), and PIFA (19.5 g, 45.2 mmol) and trifluoroacetic acid (43 g, 376.9 mmol, 28 mL) were added. The reaction mixture was stirred at 25° C. for 12 hours. The reaction mixture was neutralized with a saturated sodium carbonate solution to pH=7-8, extracted with dichloromethane/methanol (100 mL×3), and the organic layer was washed with brine, dried over anhydrous sodium sulfate, filtered and concentrated. The residue was washed with petroleum ether/ethyl acetate (100 mL×2), and filtered to give the target compound 1-5. $^1$H NMR (400 MHz, CHLOROFORM-d) δ 6.68-6.70 (d, J=8.0 Hz 1H), 6.55-6.58 (m, 2H), 6.26-6.27 (d, J=2.0 Hz 1H), 1.59-1.62 (m, 2H), 1.38-1.41 (m, 2H).

1-5 (1.50 g, 8.56 mmol) was dissolved in N,N-dimethylformamide (5 mL), and potassium carbonate (2.37 g, 17.13 mmol) and BB-1 (3.11 g, 10.28 mmol) were added. The reaction mixture was stirred at 60° C. for 12 hours. The reaction was quenched with water (300 mL) at 0° C. and extracted with ethyl acetate (100 mL×3). The organic layer was washed with brine (100 mL), dried over anhydrous sodium sulfate, filtered and concentrated. The residue was separated by thin layer chromatography to give the target compound 1-6. $^1$HNMR (400 MHz, CHLOROFORM-d) δ 1.11 (m, 2H), 1.24-1.27 (m, 2H), 1.43 (d, J=4.02 Hz, 2H), 1.72 (m, 2H), 2.14 (m, 1H), 4.73 (s, 2H), 6.28 (d, J=2.51 Hz, 1H), 6.61 (dd, J=8.28, 2.26 Hz, 1H), 6.78 (d, J=8.53 Hz, 1H), 7.30-7.40 (m, 3H), 8.91 (s, 1H).

1-6 (100 mg, 226.6 μmol) and methyl 3-(bromomethyl) carboxylate (51.9 mg, 226.6 mol) were dissolved in N,N-dimethylformamide (2.0 mL), and at 0° C. sodium hydride (11 mg, 453 μmol) was added. The reaction mixture was stirred at 0° C. for one hour. At 0° C., water (20 mL) was added to quench the reaction. The reaction mixture was extracted with ethyl acetate (20 mL×3). The organic layer was washed with saturated brine (20 mL), and concentrated to obtain a crude product 1-8 which is used directly in the next step without purification.

1-8 (100 mg, 170 μmol) was dissolved in tetrahydrofuran (1 mL), methanol (1 mL) and water (1 mL), and lithium hydroxide monohydrate (41 mg, 1.7 mmol) was added. The reaction mixture was stirred at 15° C. for one hour. Water (20 mL) was added to quench the reaction. The reaction mixture was acidified with 1 M hydrochloric acid to pH=7, extracted with ethyl acetate (20 mL×3), and the organic layer was concentrated. The residue was separated by HPLC (TFA) to give the target compound 1. $^1$HNMR (400 MHz, CHLOROFORM-d) δ 1.02-1.08 (m, 2H), 1.15-1.21 (m, 2H), 1.41-1.47 (m, 2H), 1.74 (q, J=4.0 Hz, 2H), 2.01-2.10 (m, 1H), 4.66 (s, 2H), 4.92 (s, 2H), 6.26 (d, J=2.0 Hz, 1H), 6.47-6.55 (m, 2H), 7.23-7.26 (m, 1H), 7.28-7.43 (m, 4H), 7.85-7.97 (m, 2H).

Example 2: Compound 2

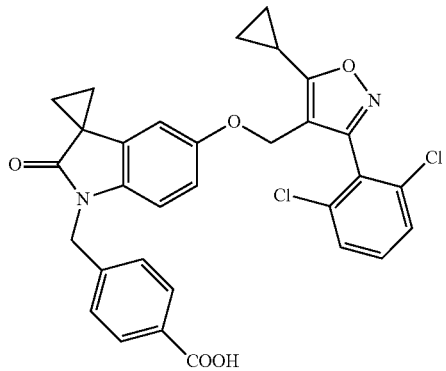 [SMILES: O=C(O)c1ccc(CN2C(=O)C3(CC3)c3cc(OCc4c(-c5c(Cl)cccc5Cl)noc4C4CC4)ccc32)cc1]

The synthesis refers to that of compound 1. ¹HNMR (400 MHz, CHLOROFORM-d) δ 1.07-1.15 (m, 2H), 1.23-1.31 (m, 2H), 1.52 (q, J=4.18 Hz, 2H), 1.84 (q, J=3.93 Hz, 2H), 2.07-2.16 (m, 1H), 4.72 (s, 2H) 5.02 (s, 2H) 7.29-7.33 (m, 1H) 7.34-7.41 (m, 4H) 8.04 (d, J=8.03 Hz, 2H).

Example 3: Compound 3

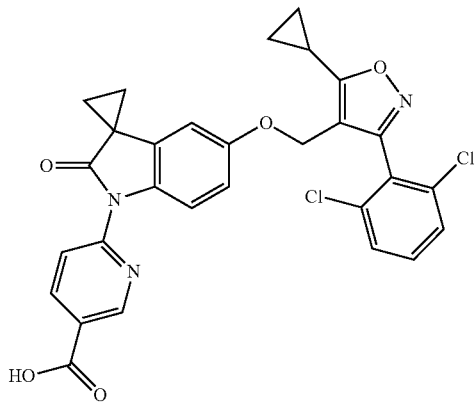 [SMILES: O=C(O)c1ccc(N2C(=O)C3(CC3)c3cc(OCc4c(-c5c(Cl)cccc5Cl)noc4C4CC4)ccc32)nc1]

Synthetic Route:

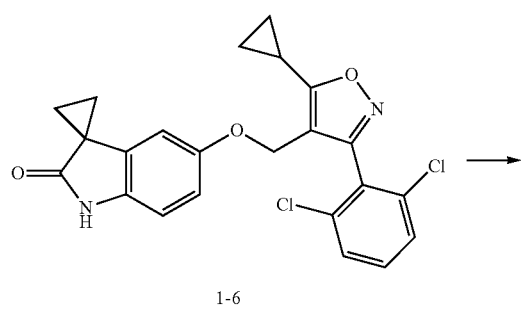

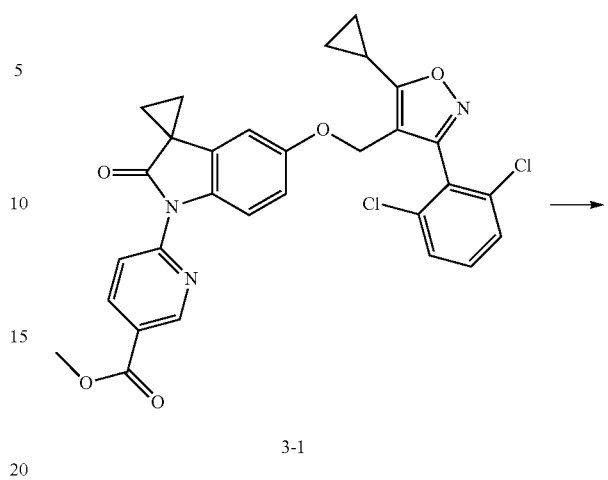

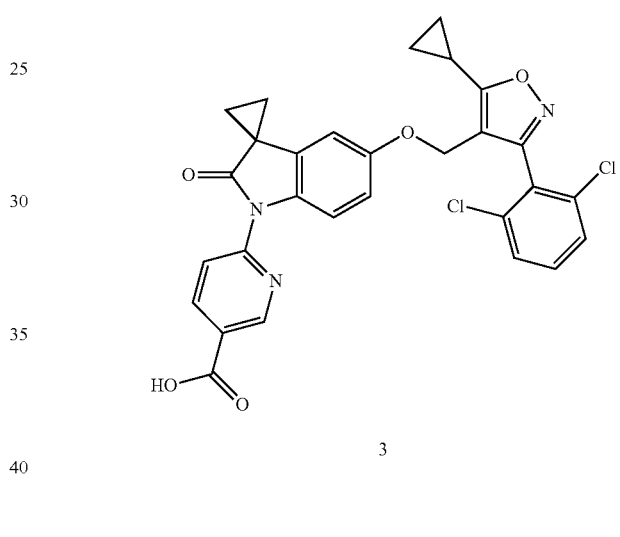

1-6 (100 mg, 227 μmol) and methyl 6-fluoronicotinate (35 mg, 227 μmol) were dissolved in N,N-dimethylformamide (2.0 mL) and cesium carbonate (148 mg, 453 mol) was added. The reaction mixture was stirred at 120° C. for 0.75 hours under microwave. Water (50 mL) was added to quench the reaction. The reaction mixture was extracted with ethyl acetate (30 mL×3). The organic layer was washed with saturated brine (50 mL×1), dried over anhydrous sodium sulfate, filtered and concentrated. The residue was separated by thin layer chromatography to give the target compound 3-1. ¹H NMR (400 MHz, CHLOROFORM-d) δ 9.15 (s, 1H), 8.39 (dd, J=2.1, 8.7 Hz, 1H), 8.12 (d, J=8.5 Hz, 1H), 7.97 (d, J=8.8 Hz, 1H), 7.43-7.29 (m, 3H), 6.72 (dd, J=2.5, 8.8 Hz, 1H), 6.33 (d, J=2.3 Hz, 1H), 4.79 (s, 2H), 3.97 (s, 3H), 2.22-2.11 (m, 1H), 1.85 (d, J=3.5 Hz, 2H), 1.32-1.24 (m, 3H), 1.14 (dd, J=2.4, 8.2 Hz, 2H).

The synthesis of compound 3 refers to that of compound 1. ¹H NMR (400 MHz, METHANOL-d₄) δ 9.14 (br. s., 1H), 8.45 (d, J=8.3 Hz, 1H), 8.04 (d, J=8.3 Hz, 1H), 7.81 (d, J=8.8 Hz, 1H), 7.53-7.38 (m, 3H), 6.71 (dd, J=2.5, 8.8 Hz, 1H), 6.45 (d, J=2.3 Hz, 1H), 4.86 (s, 2H), 2.33-2.24 (m, 1H), 1.81 (q, J=3.9 Hz, 2H), 1.64 (q, J=4.3 Hz, 2H), 1.26-1.16 (m, 4H).

Example 4: Compound 4

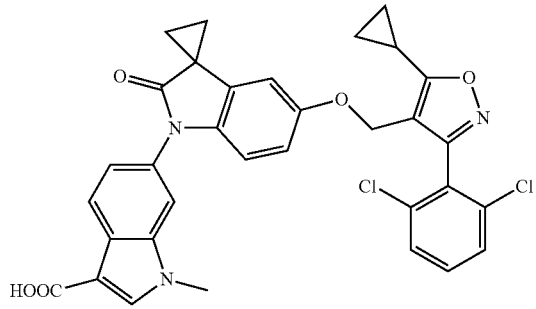 [SMILES: Cn1cc(C(=O)O)c2ccc(N3C(=O)C4(CC4)c4cc(OCc5c(-c6c(Cl)cccc6Cl)noc5C5CC5)ccc43)cc21]

Synthetic Route:

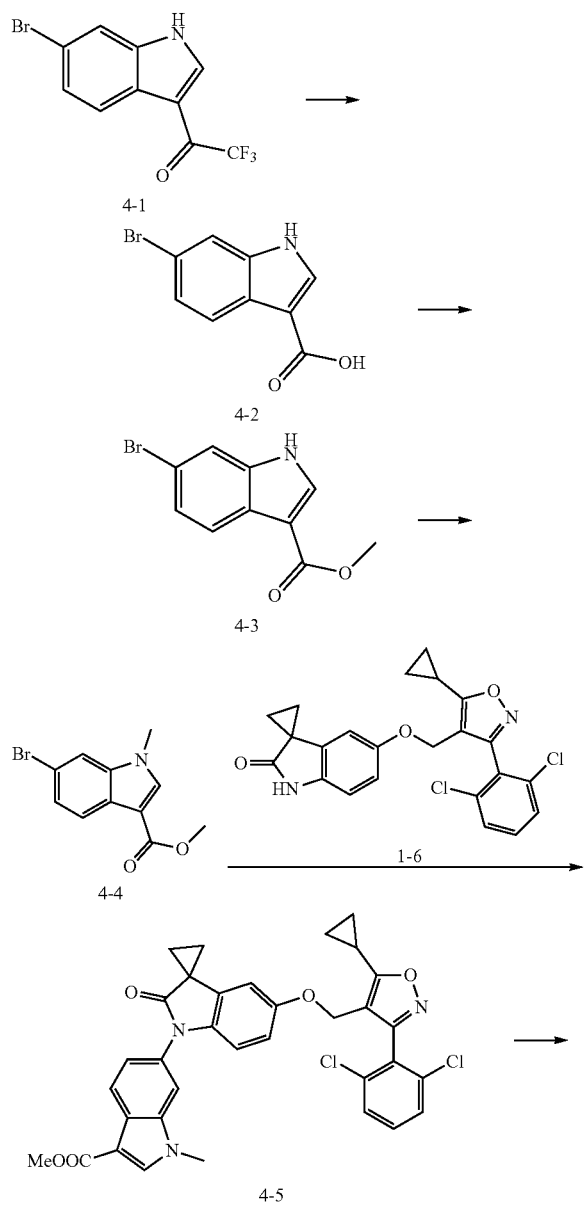

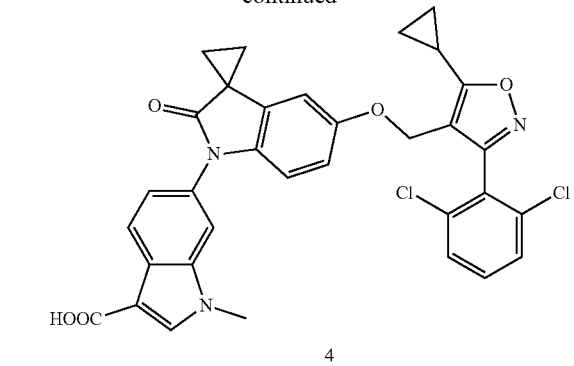

4-1 (10 g, 34.2 mmol) was placed in a flask, in which aqueous potassium hydroxide solution (19.2 g, 342.4 mmol, dissolved in water 50 ml) was added. The reaction mixture was stirred at 100° C. for 3 hours. The reaction mixture was acidified with 2 M hydrochloric acid to pH=5-6, and light yellow solid was precipitated. The reaction mixture was filtered and dried under vacuum, to give the target compound 4-2 without purification.

4-2 (8.0 g, 33.3 mmol) was dissolved in methanol (20 mL), and concentrated sulfuric acid (32.7 mg, 333.3 µmol, 18 µL, two drops) was added. The reaction mixture was stirred at 60° C. for 24 hours, concentrated to remove the solvent. The residue was purified by column chromatography to give the target compound 4-3. $^1$H NMR (400 MHz, CHLOROFORM-d) δ 8.60 (br. s., 1H), 8.05 (d, J=8.5 Hz, 1H), 7.90 (d, J=3.0 Hz, 1H), 7.63-7.56 (m, 1H), 7.43-7.35 (m, 1H), 3.98-3.85 (m, 3H).

4-3 (400 mg, 1.57 mmol) and potassium carbonate (653 mg, 4.7 mmol) were dissolved in N,N-dimethylformamide (5 mL), and iodomethane (2.9 g, 20.4 mmol, 1.27 mL) was added. The reaction mixture was stirred at 25° C. for 6 hours. Dichloromethane (20 ml) was added to the reaction mixture, and then filtered. The filtrate was concentrated to obtain a residue, to which petroleum ether/ethyl acetate (10/1, 10 mL) was added, and filtered. The obtained solid was dried under vacuum, to give the target compound 4-4 without purification. $^1$H NMR (400 MHz, CHLOROFORM-d) δ 8.02 (d, J=8.5 Hz, 1H), 7.73 (s, 1H), 7.50 (d, J=1.3 Hz, 1H), 7.37 (dd, J=1.8, 8.5 Hz, 1H), 3.93-3.87 (m, 3H), 3.84-3.75 (m, 3H).

4-4 (36.5 mg, 136 µmol) was dissolved in xylene (2 mL), and X-Phos (5.4 mg, 11 µmol), cesium carbonate (74 mg, 227 µmol) and Pd$_2$(dba)$_3$ (5.2 mg, 5.7 µmol) were added. The reaction mixture was degassed for ten minutes, and 1-6 (50 mg, 113 µmol) was added. The reaction mixture was dissolved in xylene (1 ml). The system was ventilated with nitrogen for three minutes. The reaction mixture was stirred for eleven hours and fifty minutes at 120° C. The solid was filtered off, the filtrate was concentrated, and the residue was purified by thin layer chromatography to give the target compound 4-5. $^1$H NMR (400 MHz, CHLOROFORM-d) δ 8.27 (d, J=8.5 Hz, 1H), 7.85 (s, 1H), 7.44 (d, J=1.5 Hz, 1H), 7.42-7.40 (m, 1H), 7.39 (s, 1H), 7.35-7.28 (m, 2H), 6.76-6.72 (m, 1H), 6.64-6.60 (m, 1H), 6.38 (d, J=2.5 Hz, 1H), 4.77 (s, 2H), 3.93 (s, 3H), 3.83 (s, 3H), 1.88-1.84 (m, 2H), 1.77-1.69 (m, 2H), 1.63 (br. s., 3H), 1.54 (d, J=3.5 Hz, 2H).

4-5 (58 mg, 92 µmol) was dissolved in tetrahydrofuran (1.0 mL), methanol (1.0 mL) and water (1.0 mL), and lithium hydroxide monohydrate (39 mg, 922.8 µmol) was added. The reaction mixture was stirred at 20° C. for 12 hours, warmed to 40° C. and continuously stirred for two hours. The reaction mixture was acidified with 1 M hydrochloric acid to pH=5-6, and extracted with dichloromethane/methanol (10/1, 10 mL×3). The organic layer was washed with water (10 mL), dried over anhydrous sodium sulfate, filtered and concentrated. The residue was purified by thin layer chromatography to give the target compound 4. $^1$H NMR (400 MHz, CHLOROFORM-d) δ 8.30 (d, J=8.5 Hz, 1H), 7.92 (s, 1H), 7.47 (s, 1H), 7.43-7.38 (m, 2H), 7.36-7.29 (m, 2H), 6.74 (d, J=8.5 Hz, 1H), 6.62 (dd, J=2.3, 8.5 Hz, 1H), 6.39 (d, J=2.3 Hz, 1H), 4.78 (s, 2H), 3.87 (s, 3H), 2.21-2.12 (m, 1H), 1.91-1.81 (m, 2H), 1.61-1.50 (m, 2H), 1.34-1.24 (m, 2H), 1.19-1.07 (m, 2H).

Example 5: Compound 5

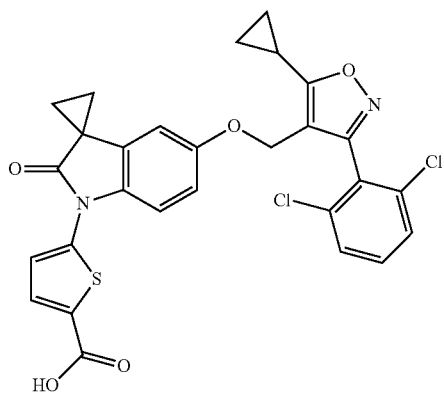 [SMILES: O=C(O)c1ccc(N2C(=O)C3(CC3)c3cc(OCc4c(-c5c(Cl)cccc5Cl)noc4C4CC4)ccc32)s1]

Synthetic Route:

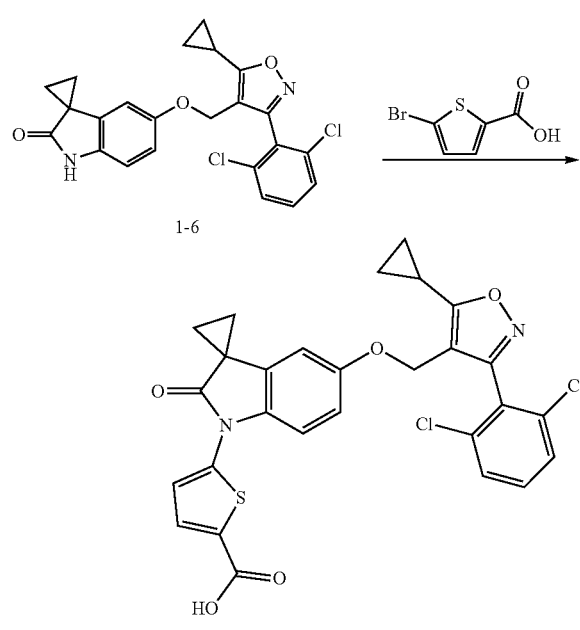

Under nitrogen protection, potassium iodide (22 mg, 113 μmol) was added to a solution of intermediate 1-6 (50 mg, 113 μmol), 5-bromo-2-carboxylic acid thiophene (35 mg, 170 μmol), potassium phosphate (72 mg, 340 μmol), (1S, 2S)-cyclohexyl-1,2-diamine (13 mg, 113 mmol) in N,N-dimethylformamide (2 mL). The reaction system was reacted at 100° C. for 12 hours. The system was adjusted to pH=2-3 with diluted hydrochloric acid. The aqueous layer was extracted with ethyl acetate (10 mL×3) and the organic layer was dried over anhydrous sodium sulfate, and concentrated. The residue was purified by preparative chromatography to give the target compound 5. $^1$H NMR (400 MHz, METHANOL-d$_4$) δ 7.79 (d, J=4.5 Hz, 1H), 7.56-7.44 (m, 2H), 7.50-7.43 (m, 1H), 7.31-7.17 (m, 2H), 6.76 (dd, J=2.3, 8.8 Hz, 1H), 6.57 (d, J=2.5 Hz, 1H), 2.34 (d, J=6.8 Hz, 1H), 1.82-1.77 (m, 2H), 1.72-1.65 (m, 2H), 1.21 (d, J=6.5 Hz, 4H).

Example 6: Compound 6

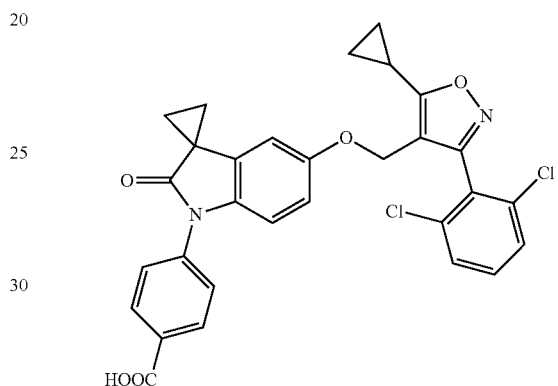

Synthetic Route:

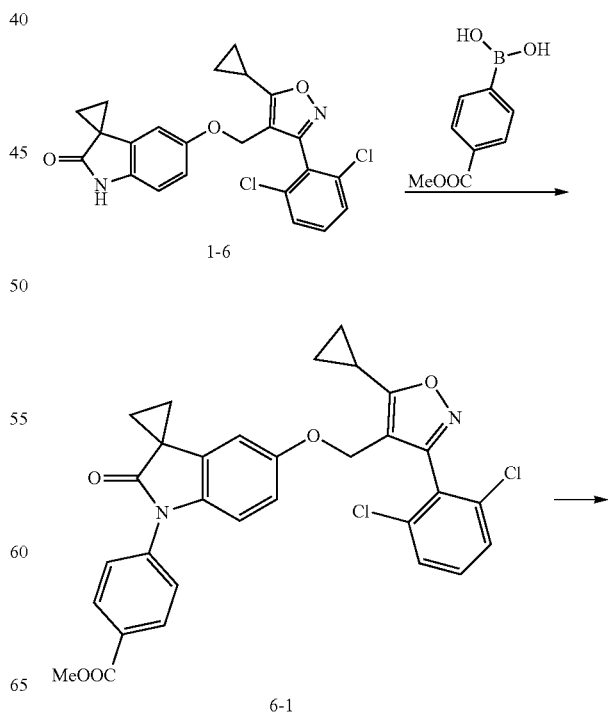

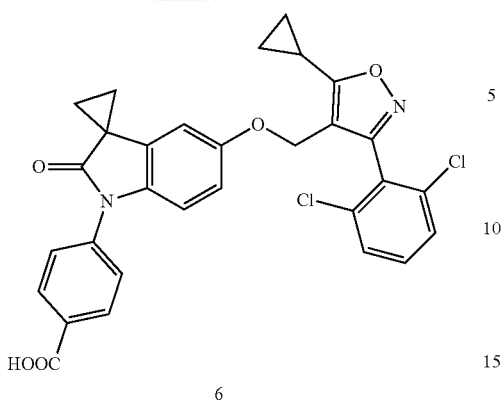

6

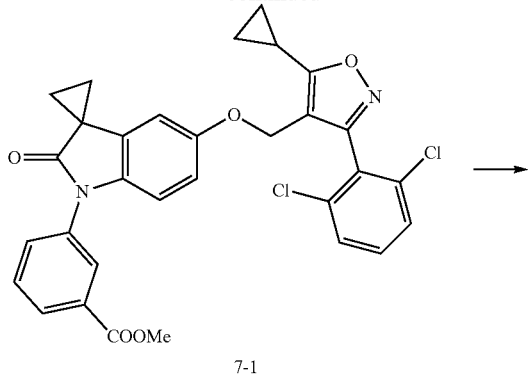

7-1

Under nitrogen protection, copper acetate (123 mg, 680 μmol) was added to a solution of 1-6 (200 mg, 453 μmol), methyl 4-carboxylate phenylboronic acid (163 mg, 906 μmol), triethylamine (92 mg, 906 μmol) in dichloromethane (2 mL). The reaction system was reacted at 15° C. for 12 hours. The solvent was evaporated to dryness. The aqueous layer was extracted with dichloromethane (20 mL×3) and the organic layer was dried over anhydrous sodium sulfate, and concentrated, to give the target compound 6-1.

The synthesis of compound 6 refers to that of compound 4. $^1$HNMR (400 MHz, CHLOROFORM-d) δ 1.10-1.19 (m, 2H), 1.25-1.34 (m, 2H), 1.51-1.61 (m, 2H), 1.84-1.90 (m, 2H), 2.11-2.22 (m, 1H), 4.79 (s, 2H), 6.38 (d, J=2.01 Hz, 1H), 6.65 (dd, J=8.53, 2.01 Hz, 1H), 6.88 (d, J=8.53 Hz, 1H), 7.29-7.37 (m, 1H), 7.38-7.45 (m, 2H), 7.60 (d, J=8.53 Hz, 2H), 8.25 (d, J=8.53 Hz, 2H).

Example 7: Compound 7

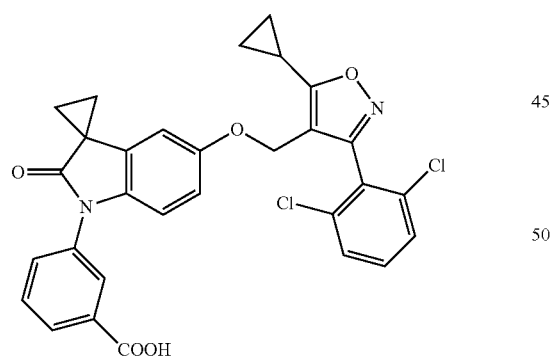

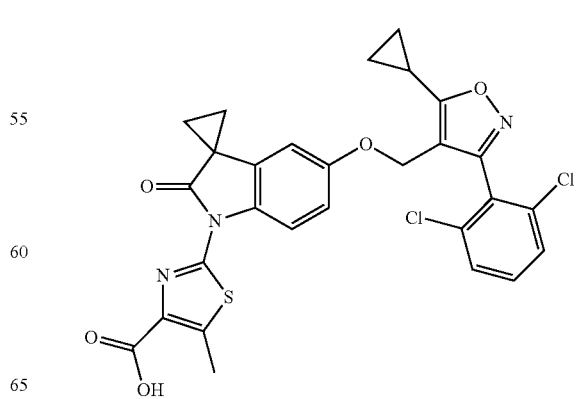

7

The synthesis of compound 7-1 refers to that of compound 4-5. $^1$H NMR (400 MHz, CHLOROFORM-d) δ 8.10-8.14 (m, 2H), 7.41-7.43 (m, 2H), 7.35-7.37 (m, 3H), 6.76-6.78 (d, J=8.8 Hz, 1H), 6.63-6.66 (d, J=4.8 Hz, 1H), 6.39 (d, J=2.0 Hz, 1H), 4.79 (s, 2H), 3.93 (s, 3H), 2.16 (m, 1H), 1.85-1.86 (m, 2H), 1.55-1.57 (m, 2H), 1.30-1.31 (m, 2H), 1.15-0.18 (m, 2H).

The synthesis of compound 7 refers to that of compound 4. $^1$H NMR (400 MHz, CHLOROFORM-d) δ 8.17 (s, 1H), 8.10-8.12 (d, J=4.0 Hz, 1H), 7.41-7.43 (m, 2H), 7.35-7.37 (m, 3H), 6.76-6.78 (d, J=8.8 Hz, 1H), 6.63-6.66 (d, J=4.8 Hz, 1H), 6.39 (s, 1H), 4.79 (s, 2H), 2.16 (m, 1H), 1.85-1.86 (m, 2H), 1.55-1.57 (m, 2H), 1.30-1.31 (m, 2H), 1.15-1.18 (m, 2H).

Example 8: Compound 8

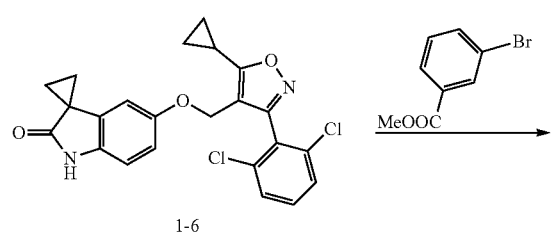

Synthetic Route:

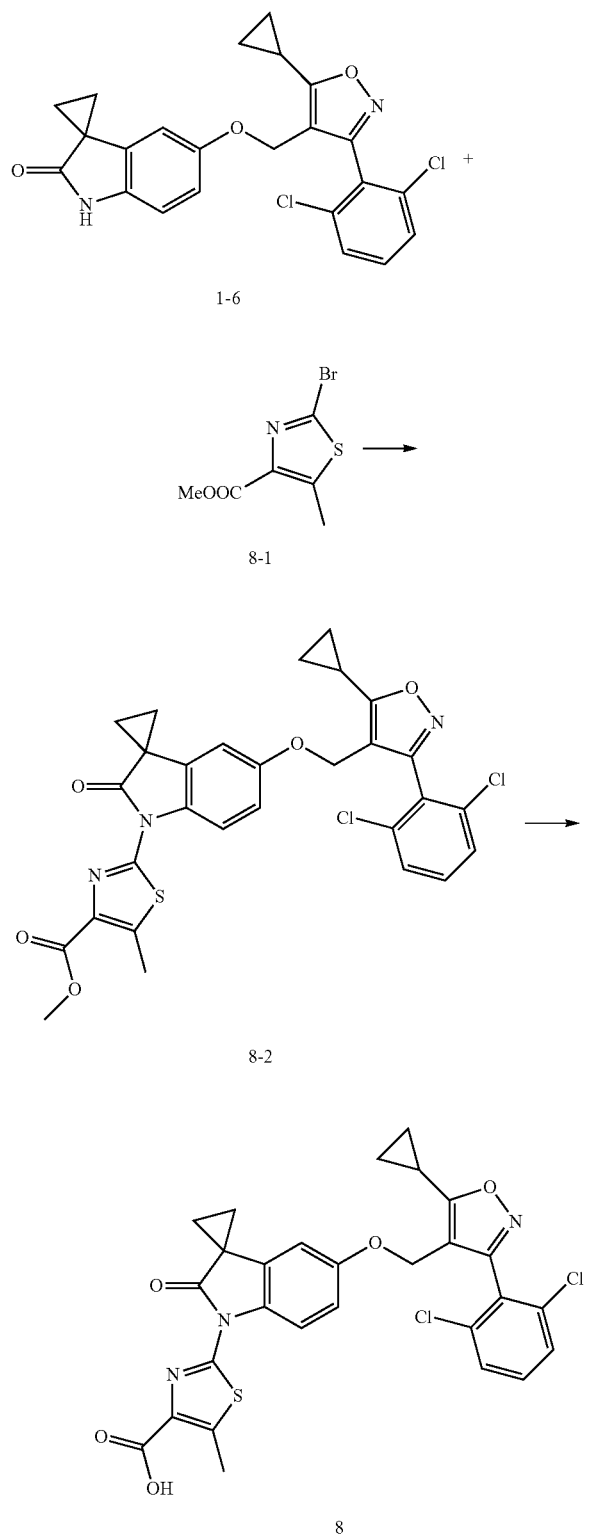

Compound 1-6 (200.00 mg, 453.20 µmol) was dissolved in dioxane (2.00 mL), and compound 8-1 (128.40 mg, 543.84 µmol), cuprous iodide (86.31 mg, 453.20 µmol), anhydrous potassium phosphate (288.60 mg, 1.36 mmol) and trans 1,2-cyclohexanediamine (51.75 mg, 453.20 µmol, 55.65 µl) were added. The reaction system was ventilated with nitrogen for 6 times, and the reaction mixture was stirred at 100° C. for 12 hours. After cooling to room temperature, the reaction system was added with ethyl acetate (20 mL), filtered and the filtrate was concentrated. The residue was separated by high performance liquid chromatography (trifluoroacetic acid) to give compound 8-2. $^1$H NMR (400 MHz, CHLOROFORM-d) δ 8.58 (d, J=8.8 Hz, 1H), 7.42-7.38 (m, 2H), 7.34-7.29 (m, 1H), 6.83 (dd, J=2.6, 8.9 Hz, 1H), 6.33 (d, J=2.5 Hz, 1H), 4.81 (s, 2H), 3.96 (s, 3H), 2.76 (s, 3H), 2.18-2.12 (m, 1H), 1.90 (q, J=3.9 Hz, 2H), 1.60 (q, J=4.4 Hz, 2H), 1.29-1.27 (m, 2H), 1.16-1.13 (m, 2H).

Compound 8-2 (15.00 mg, 25.15 µmol) was dissolved in tetrahydrofuran (1.00 ml), methanol (1.00 ml) and water (1.00 ml), and lithium hydroxide monohydrate (5.28 mg, 125.74 mol) was added. The reaction mixture was stirred at 40° C. for 12 hours. The reaction mixture was acidified with 1 M hydrochloric acid to pH=5-6, and extracted with dichloromethane/methanol (10/1, 10 mL×3). The organic layer was washed with water (10 mL), dried over anhydrous sodium sulfate, filtered and concentrated. The residue was purified by high performance liquid chromatography to give the target compound 8. $^1$H NMR (400 MHz, CHLOROFORM-d) δ 7.45-7.41 (m, 2H), 7.38-7.31 (m, 2H), 6.79 (br s, 1H), 6.74 (br d, J=8.5 Hz, 1H), 4.84 (s, 2H), 2.61 (s, 3H), 2.16 (br dd, J=3.4, 8.7 Hz, 1H), 1.67 (br s, 2H), 1.32 (br d, J=4.3 Hz, 2H), 1.18 (br d, J=5.0 Hz, 2H), 1.02 (br s, 1H).

Example 9: Compound 9

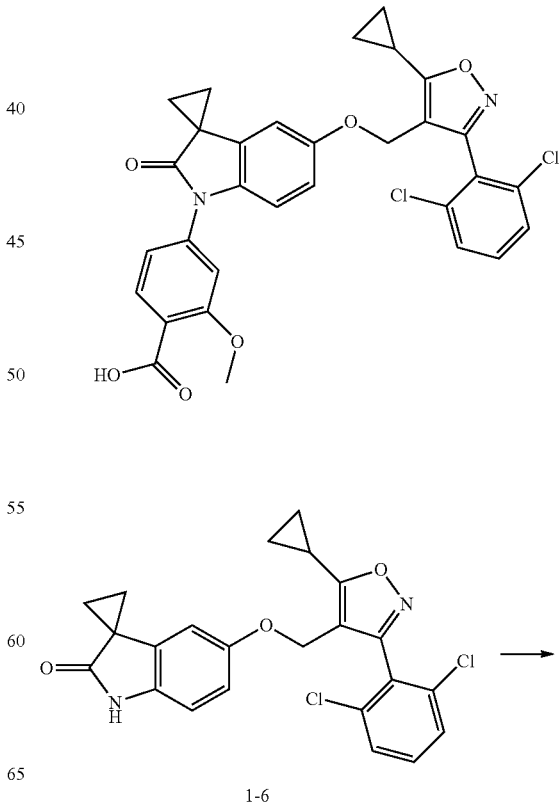

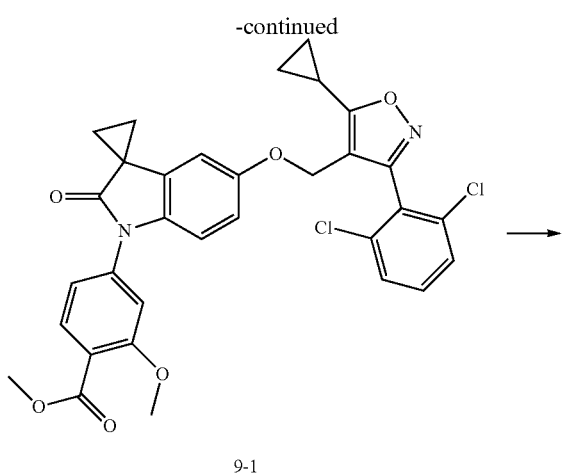
9-1
The synthesis of the target compound 9-1 refers to that of compound 4-5. ¹H NMR (400 MHz, CHLOROFORM-d) δ 7.94 (d, J=8.3 Hz, 1H), 7.43-7.30 (m, 3H), 7.12 (d, J=1.5 Hz, 1H), 7.07 (dd, J=1.8, 8.3 Hz, 1H), 6.85 (d, J=8.8 Hz, 1H), 6.64 (dd, J=2.4, 8.7 Hz, 1H), 6.37 (d, J=2.3 Hz, 1H), 4.78 (s, 2H), 3.91 (d, J=0.8 Hz, 6H), 2.22-2.11 (m, 1H), 1.84 (q, J=3.9 Hz, 2H), 1.54 (q, J=4.2 Hz, 2H), 1.32-1.24 (m, 3H), 1.18-1.10 (m, 2H).
The synthesis of the target compound 9 refers to that of compound 4. ¹H NMR (400 MHz, CHLOROFORM-d) δ 8.31 (d, J=8.5 Hz, 1H), 7.45-7.38 (m, 2H), 7.36-7.27 (m, 2H), 7.24 (d, J=8.5 Hz, 1H), 6.91 (d, J=8.5 Hz, 1H), 6.66 (dd, J=2.1, 8.7 Hz, 1H), 6.38 (d, J=2.0 Hz, 1H), 4.79 (s, 2H), 4.10 (s, 3H), 2.21-2.11 (m, 1H), 1.85 (q, J=3.8 Hz, 2H), 1.56 (q, J=3.9 Hz, 2H), 1.32-1.24 (m, 2H), 1.19-1.09 (m, 2H).
Example 10: Compound 10
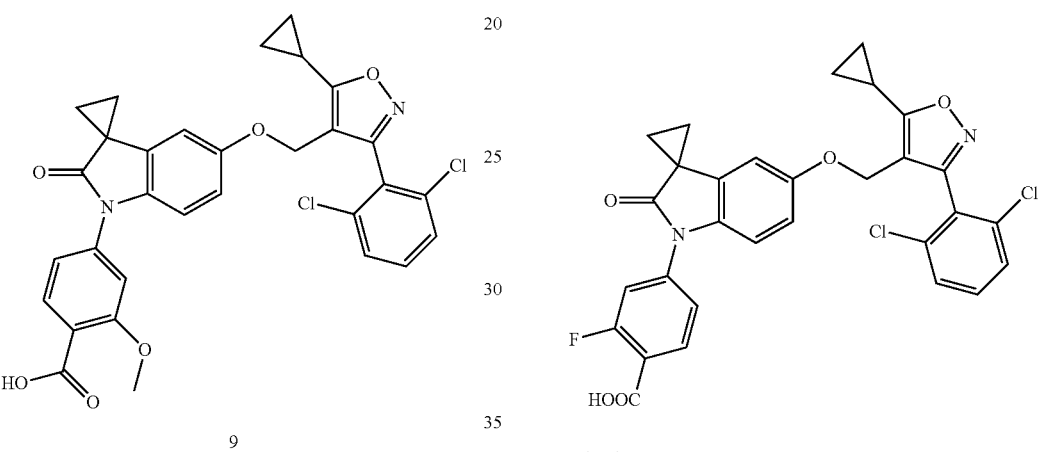
Synthetic Route:
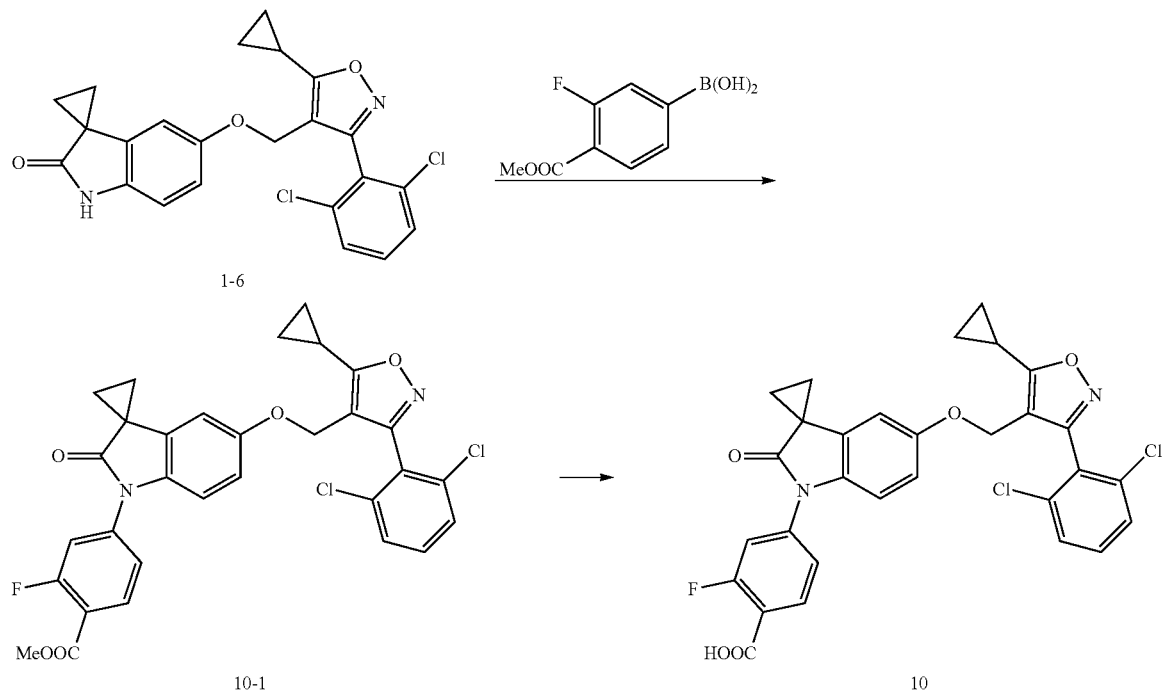

The synthesis of the target compound 10-1 refers to that of compound 6-1. LCMS (ESI): calculated value: $C_{31}H_{23}Cl_2FN_2O_5$ [M+H]$^+$: 592, measured value: 592.

The synthesis of the target compound 10 refers to that of compound 4. $^1$H NMR (400 MHz, CDCl$_3$) δ 8.18-8.14 (m, 1H), 7.42-7.33 (m, 5H), 6.95-6.93 (m, 1H), 6.68-6.67 (m, 1H), 6.37 (s, 1H), 4.79 (s, 2H), 2.16-2.05 (m, 1H), 1.87-1.86 (m, 2H), 1.57-1.56 (m, 2H), 1.30-1.28 (m, 2H), 1.16-1.14 (m, 2H).

Example 11: Compound 11

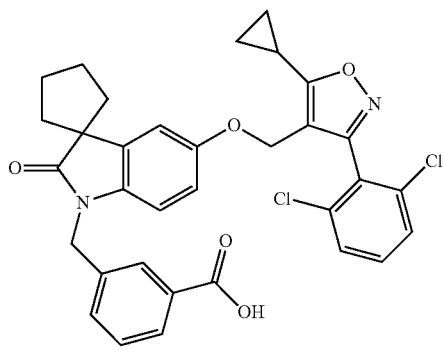 [SMILES: O=C(O)c1cccc(CN2C(=O)C3(CCCC3)c3cc(OCc4c(-c5c(Cl)cccc5Cl)noc4C4CC4)ccc32)c1]

Synthetic Route:

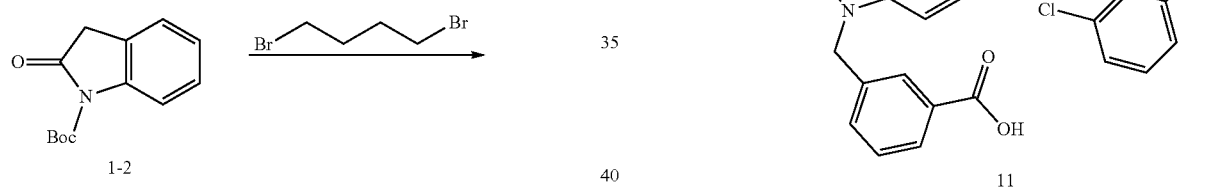

1-2

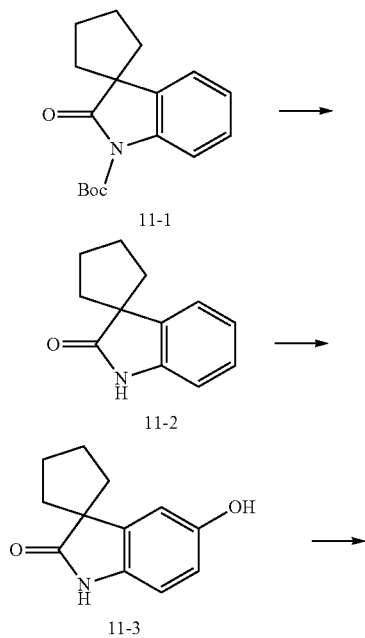

11-1

11-2

11-3

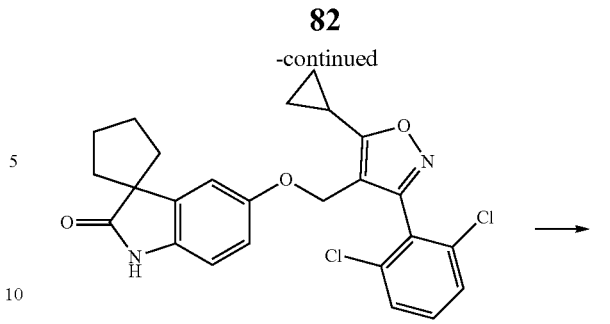

11-4

11-5

11

Cesium carbonate (11.17 g, 34.28 mmol) and 1,4-dibromobutane (2.78 g, 12.85 mmol) were added to a solution of tert-butyl 2-oxoindoline-1-carbonate (1-2) (2.00 g, 8.57 mmol) in DMSO (60.00 mL). The reaction mixture was stirred at 20° C. for 12 hours, which was then cooled to 15° C., quenched with 200 mL water, and extracted with ethyl acetate (50 mL×3). The organic phase was combined and washed with saturated saline (50 mL×2), dried over anhydrous sodium sulfate, filtered and rotary-dried to obtain a yellow oily substance. After filtration and evaporation, the residue was purified by column chromatography (petroleum ether:ethyl acetate=100:1) to give the target compound 11-1. $^1$H NMR (400 MHz, CDCl$_3$) δ 7.85 (d, J=8.0 Hz, 1H), 7.32-7.11 (m, 3H), 2.35-2.21 (m, 2H), 2.19-1.84 (m, 6H), 1.72-1.63 (m, 9H).

Trifluoroacetic acid (8 mL) was added to 11-1 (2 g, 6.96 mmol) in dichloromethane (50 mL) at 0° C. The temperature was slowly raised to 20° C. to react for 5 hours. The reaction mixture was rotary-dried, and diluted with methylene chloride (100 mL). The diluted solution was washed with 5% aqueous sodium hydrogen carbonate and dried over anhydrous sodium sulfate, filtered and evaporated to give the target compound 11-2. $^1$H NMR (400 MHz, CDCl$_3$) δ 8.14 (br. s., 1H), 7.25-7.15 (m, 2H), 7.09-7.00 (m, 1H), 6.91 (d, J=7.5 Hz, 1H), 2.28-2.16 (m, 2H), 2.15-1.84 (m, 6H).

PIFA (3.31 g, 7.69 mmol) was slowly added to a solution of 11-2 (1.20 g, 6.41 mmol) in trifluoroacetic acid (4.78 mL, 64 mmol) and chloroform (50.00 mL). The reaction was carried out at 20° C. for 12 hours. The reaction mixture was quenched with 5% sodium bicarbonate aqueous solution (200 mL), extracted with ethyl acetate (100 mL×3). The combined organic phase was washed with saturated saline (100 mL), dried over anhydrous sodium sulfate. After filtration and evaporation, the residue was purified by column chromatography (petroleum ether: ethyl acetate=2:1) to give the target compound 11-3. $^1$H NMR (400 MHz, CDCl$_3$) δ 6.79-6.55 (m, 3H), 2.24-1.72 (m, 8H).

Potassium carbonate (163.21 mg, 1.18 mmol) was added to 11-3 (80 mg, 393.6 mmol) and BB-1 (142.92 mg, 472.34 μmol) in N,N-dimethylformamide (6 ml). The reaction was carried out at 60° C. for 12 hours. The reaction mixture was cooled to 15° C., quenched with 50 ml water, extracted with ethyl acetate (30 mL×3). The organic phase was washed with saturated saline (100 mL), dried over anhydrous sodium sulfate. After filtration and evaporation, the residue was separated and purified by thin layer chromatography (petroleum ether:ethyl acetate=1:1) to give the target compound 11-4. $^1$H NMR (400 MHz, CDCl$_3$) δ 7.50-7.40 (m, 3H), 7.38-7.31 (m, 1H), 6.74-6.60 (m, 3H), 4.79 (s, 2H), 2.23-2.12 (m, 3H), 2.11-2.01 (m, 2H), 2.00-1.88 (m, 2H), 1.82 (dd, J=6.0, 12.0 Hz, 2H), 1.34-1.25 (m, 2H), 1.20-1.11 (m, 2H).

Under nitrogen protection, in an ice bath, sodium hydride (11.93 mg, 298 μmol, 60%) was added to 11-4 (70 mg, 149 μmol) in N,N-dimethylformamide (6 mL). After 0.5 hours of reaction, a solution of methyl 3-(bromomethyl)benzoate (41 mg, 179 μmol) in N,N-dimethylformamide (0.5 ml) was added dropwise to the reaction mixture. The reaction was slowly warmed to 25° C. and carried out for 2.5 hours. The reaction mixture was cooled to 0° C., quenched with water (30 ml), extracted with ethyl acetate (20 mL×3). The combined organic phase was washed with saturated saline (50 mL), dried over anhydrous sodium sulfate. After filtration and evaporation, the residue was separated and purified by thin layer chromatography (petroleum ether:ethyl acetate=2:1) to give the target compound 11-5. $^1$H NMR (400 MHz, CDCl$_3$) δ 8.02-7.91 (m, 2H), 7.46-7.35 (m, 4H), 7.34-7.26 (m, 1H), 6.71 (d, J=2.3 Hz, 1H), 6.59-6.45 (m, 2H), 4.92 (s, 2H), 4.75 (s, 2H), 3.92 (s, 3H), 2.30-2.18 (m, 3H), 2.17-2.08 (m, 2H), 2.03-1.91 (m, 2H), 1.91-1.79 (m, 2H), 1.34-1.23 (m, 2H), 1.18-1.06 (m, 2H).

Lithium hydroxide monohydrate (30.6 mg, 728 μmol) was added to a mixed liquid of 11-5 (45 mg, 73 μmol) in tetrahydrofuran (1 mL), methanol (1 mL) and water (1 mL) at 0° C. The mixture was reacted at 20° C. for 1 hour, which was then cooled to 0° C., quenched with water (20 ml). The reaction mixture was adjusted with 1 mol/l diluted hydrochloric acid to pH=3, and extracted with ethyl acetate (20 mL×3). The combined organic phase was washed with saturated saline (20 mL), dried over anhydrous sodium sulfate. After filtration and evaporation, the residue was separated and purified by preparative high performance liquid chromatography (trifluoroacetic acid system) to give the target compound 11. $^1$H NMR (400 MHz, CDCl$_3$) δ 8.02-8.04 (m, 2H), 7.56-7.30 (m, 5H), 6.72 (d, J=2.0 Hz, 1H), 6.62-6.44 (m, 2H), 4.94 (s, 2H), 4.76 (s, 2H), 2.33-2.07 (m, 5H), 2.02-1.77 (m, 4H), 1.34-1.23 (m, 2H), 1.18-1.06 (m, 2H)

Example 12: Compound 12

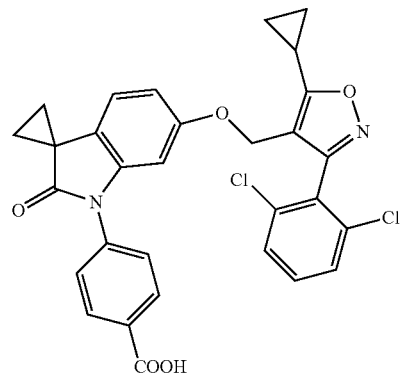 [SMILES: O=C(O)c1ccc(N2C(=O)C3(CC3)c3ccc(OCc4c(-c5c(Cl)cccc5Cl)noc4C4CC4)cc32)cc1]

Synthetic Route:

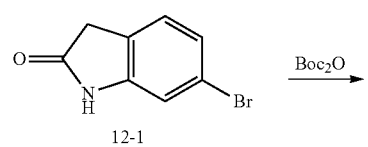

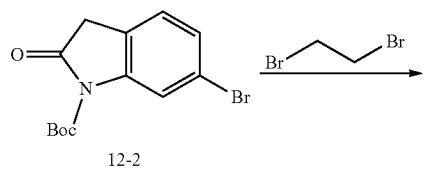

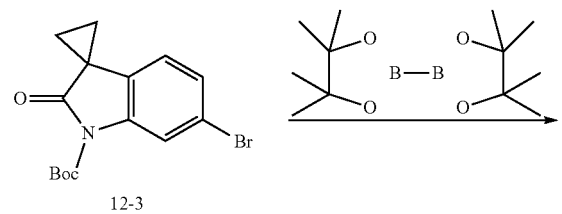

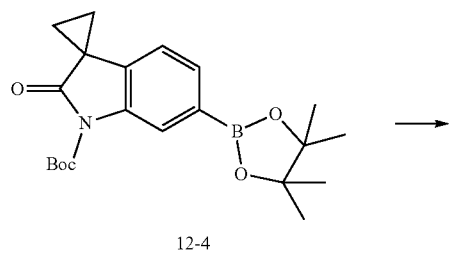

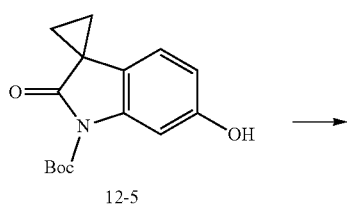

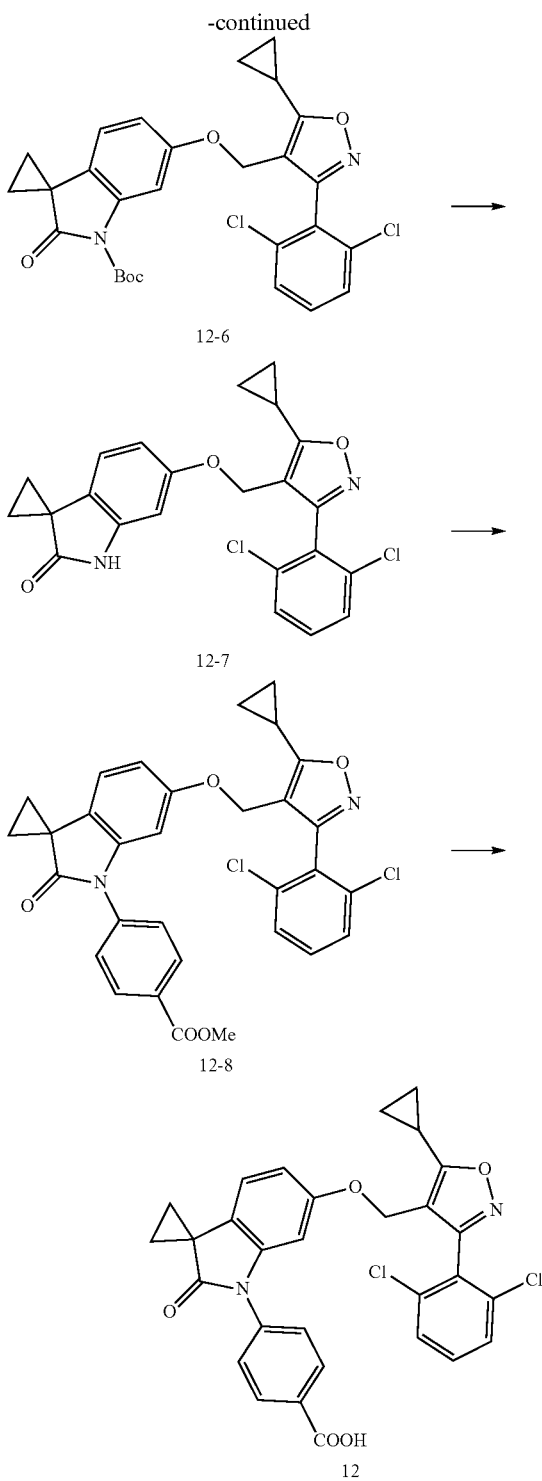

DMAP (576 mg, 4.7 mmol) and di-tert-butyl dicarbonate (10.29 g, 47.16 mmol) were added to a solution of 12-1 (5 g, 23.58 mmol) in acetonitrile, and the reaction mixuture was reacted at 20° C. for 15 hours. After the reaction mixuture was evaporated, the residue was purified by column chromatography (petroleum ether:ethyl acetate=10:1) to give the target compound 12-2. $^1$H NMR (400 MHz, CDCl$_3$) δ 8.03 (d, J=0.8 Hz, 1H), 7.27-7.30 (m, 1H), 7.10 (d, J=8.0 Hz, 1H), 3.59 (s, 2H), 1.65 (s, 9H).

Potassium carbonate (1.77 g, 12.8 mmol) and 1,2-dibromoethane (901.7 mg, 4.8 mmol) were added to a solution of 12-2 (1.00 g, 3.20 mmol) in DMSO (30.00 mL). The reaction mixture was reacted at 20° C. for 12 hours, cooled to 15° C., quenched with 200 ml water, extracted with ethyl acetate (50 mL×3). The organic phase was combined and washed with saturated saline (50 mL×2), dried over anhydrous sodium sulfate, filtered and rotary-dried to obtian a yellow oily substance. After filtration and evaporation, the residue was purified by column chromatography (petroleum ether:ethyl acetate=20:1) to give the target compound 12-3. LCMS (ESI): calculated value C$_{15}$H$_{16}$BrNO$_3$ [M+H]$^+$: 338, 340, measured value: 338, 340. $^1$H NMR (400 MHz, CDCl$_3$) δ 8.16 (d, J=1.5 Hz, 1H), 7.30 (d, J=1.8 Hz, 1H), 6.70 (d, J=8.0 Hz, 1H), 1.86 (q, J=3.9 Hz, 2H), 1.70-1.61 (m, 9H), 1.53 (q, J=3.9 Hz, 2H).

12-3 (300 mg, 887 μmol), pinacol borate (338 mg, 1.3 mmol), Pd(dppf)Cl$_2$ (130 mg, 177 μmol), potassium acetate (261 mg, 2.7 m) Mole) were dissolved in dioxane (10 ml), replaced with nitrogen for three times, and then reacted under nitrogen at 80° C. for 20 hours. The reaction mixture was filtered, and the filtrate was concentrated to give a crude title compound 12-4. LCMS (ESI): calculated value C$_{21}$H$_{28}$BNO$_5$ [M+H]$^+$: 386, measured value: 386.

12-4 (500 mg, 1.3 mmol) was dissolved in tetrahydrofuran (6.0 ml), and sodium hydroxide aqueous solution (1 M, 4.0 mL) and hydrogen peroxide (883 mg, 7.8 mmol, 30%) was added to the reaction mixture. The reaction was carried out at 20° C. for 2 hours, which was then cooled to 0° C., and quenched with water (50 mL). The reaction mixture was adjusted with 1N hydrochloric acid aqueous solution to pH=7, and extracted with ethyl acetate (5 mL×3). The organic phase was washed with saturated saline (50 mL), dried over anhydrous sodium sulfate. After filtration and evaporation, the residue was separated and purified by column chromatography (petroleum ether:ethyl acetate=20:1) to give the target compound 12-5. LCMS (ESI): calculated value C$_{15}$H$_{17}$NO$_4$ [M+H]$^+$: 276, measured value: 276; $^1$H NMR (400 MHz, CDCl$_3$) δ 7.54 (d, J=2.3 Hz, 1H), 6.73-6.59 (m, 2H), 4.95 (s, 1H), 1.78 (q, J=4.1 Hz, 2H), 1.67 (s, 9H), 1.49 (q, J=4.2 Hz, 2H).

Potassium carbonate (271 mg, 2.0 mmol) was added to 12-5 (180 mg, 654 mmol) and BB-1 (237 mg, 784.6 μmol) in N,N-dimethylformamide (10 ml). The reaction was carried out at 60° C. for 12 hours, cooled to 15° C., quenched with 50 ml water, extracted with ethyl acetate (40 mL×3). The organic phase was washed with saturated saline (30 mL), dried over anhydrous sodium sulfate. After filtration and evaporation, the residue was separated and purified by thin layer chromatography (petroleum ether:ethyl acetate=3:1) to give the target compound 12-6. LCMS (ESI): calculated value C$_{28}$H$_{26}$Cl$_2$N$_2$O$_5$ [M+H]$^+$: 541, measured value: 541; $^1$H NMR (400 MHz, CDCl$_3$) δ 7.51 (d, J=2.0 Hz, 1H), 7.42-7.36 (m, 2H), 7.34-7.28 (m, 1H), 6.66-6.59 (m, 1H), 6.58-6.52 (m, 1H), 4.82 (s, 2H), 2.15-2.22 (m, 1H), 1.75 (q, J=3.7 Hz, 2H), 1.64 (s, 9H), 1.48-1.40 (m, 2H), 1.32-1.22 (m, 2H), 1.18-1.10 (m, 2H).

12-6 (230 mg, 425 μmol) was dissolved in dichloromethane (15 ml), and the reaction mixture was cooled to 0° C., and trifluoroacetic acid (4.6 g, 40.5 mmol, 3.0 ml) was added dropwise to the reaction mixture, which was then slowly warmed to 25° C. and reacted for 2 hours. The reaction mixture was concentrated. The residue was diluted with dichloromethane (20 mL), washed with 5% sodium bicarbonate aqueous solution (10 mL). The organic phase was dried over anhydrous sodium sulfate, filtered and evaporated to give the target compound 12-7. $^1$H NMR (400 MHz, CDCl$_3$) δ 7.67 (br. s., 1H), 7.45-7.38 (m, 2H), 7.36-7.29 (m, 1H), 6.65 (d, J=8.0 Hz, 1H), 6.50-6.38 (m, 2H), 4.78 (s, 2H), 2.25-2.09 (m, 1H), 1.68 (q, J=4.0 Hz, 2H), 1.44 (q, J=3.8 Hz, 2H), 1.34-1.22 (m, 2H), 1.19-1.07 (m, 2H).

12-7 (50 mg, 113 μmol), methyl 4-carboxylate phenylboronic acid (41 mg, 226.6 μmol), triethylamine (22.9 mg, 226.6 μmol), copper acetate (31 mg, 1705 μmol) and 4 Å molecular sieve (200 mg) was suspended in dichloromethane (4 ml), and the mixture was stirred at 25° C. for 12 hours under nitrogen atmosphere. The reaction mixture was filtered. After filtration and evaporation, the residue was seperated and purified by thin layer chromatography (petroleum ether:ethyl acetate=2:1) to give the target compound 12-8. LCMS (ESI): calculated value C$_{31}$H$_{24}$Cl$_2$N$_2$O$_5$ [M+H]$^+$: 575, measured value: 575. $^1$H NMR (400 MHz, CDCl$_3$) δ 8.22 (d, J=8.5 Hz, 2H), 7.55 (d, J=8.5 Hz, 2H), 7.41-7.33 (m, 2H), 7.30 (br. s., 1H), 6.76 (d, J=8.0 Hz, 1H), 6.57-6.43 (m, 2H), 4.78 (s, 2H), 3.99 (s, 3H), 2.12 (s, 1H), 1.81 (q, J=3.8 Hz, 2H), 1.55 (q, J=4.4 Hz, 2H), 1.34-1.23 (m, 2H), 1.18-1.06 (m, 2H).

Lithium hydroxide monohydrate (7.29 mg, 173.8 μmol) was added to a mixed liquid of 12-8 (20 mg, 325 μmol) in tetrahydrofuran (1 mL), methanol (1 mL) and water (1 mL) at 0° C. The mixture was reacted at 20° C. for 2 hour. The reaction mixture was cooled to 0° C., quenched with water (20 ml). The reaction mixture was adjusted with 1 mol/l diluted hydrochloric acid to pH=3, and extracted with ethyl acetate (10 mL×3). After the organic phase was evaporated, the residue was separated and purified by preparative high performance liquid chromatography (trifluoroacetic acid system) to give the target compound 12. LCMS (ESI): calculated value C$_{30}$H$_{22}$Cl$_2$N$_2$O$_5$ [M+H]$^+$: 561, measured value: 561. $^1$H NMR (400 MHz, CDCl$_3$) δ 8.27 (d, J=8.5 Hz, 2H), 7.57 (d, J=8.5 Hz, 2H), 7.41-7.33 (m, 2H), 7.28 (d, J=7.5 Hz, 1H), 6.75 (d, J=8.5 Hz, 1H), 6.59-6.42 (m, 2H), 4.77 (s, 2H), 2.19-2.06 (m, 1H), 1.81 (q, J=3.7 Hz, 2H), 1.59-1.48 (m, 2H), 1.32-1.21 (m, 2H), 1.15-1.04 (m, 2H).

Example 13: Compound 13

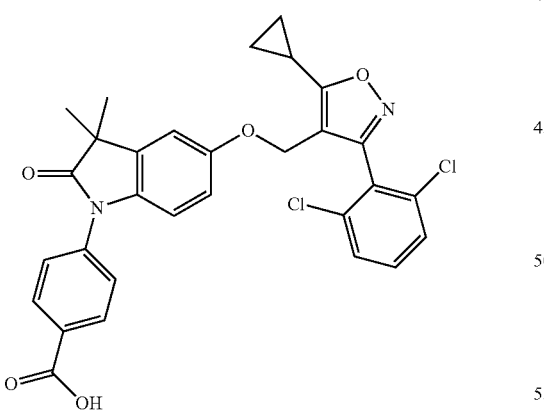

Synthetic Route:

1-2

-continued

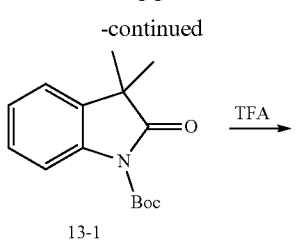

13-1

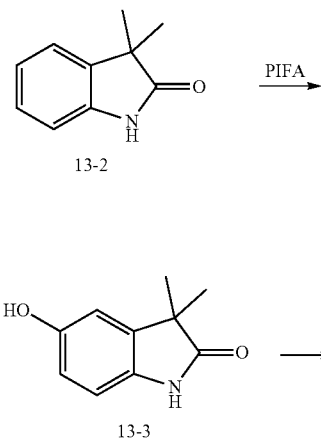

13-2

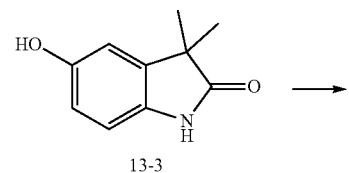

13-3

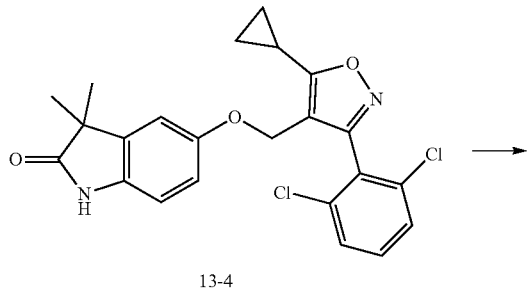

13-4

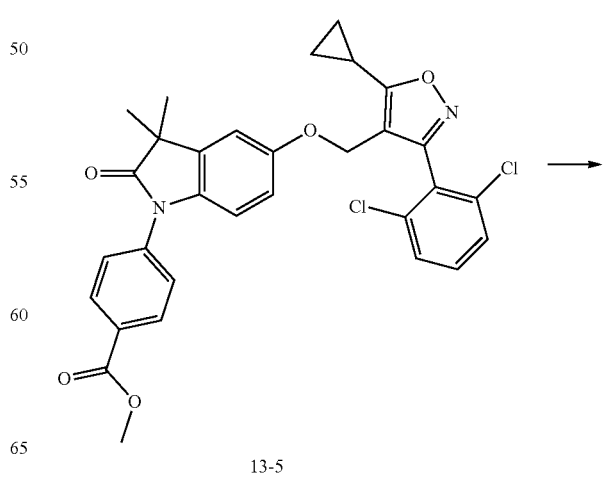

13-5

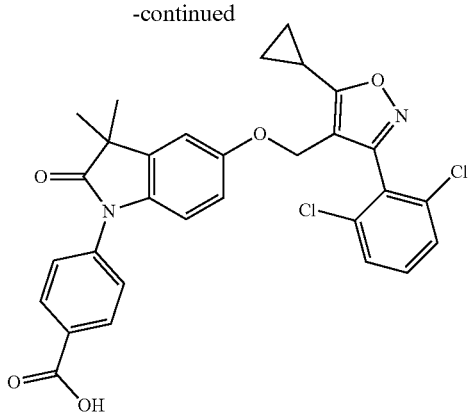

13

Potassium carbonate (4.74 g, 34.28 mmol) and methyl iodide (3.04 g, 21.43 mmol, 1.33 mL) were added to a solution of 1-2 (2.00 g, 8.57 mmol) in DMSO (20.00 mL). The reaction mixture was stirred at 25° C. for one hour. The reaction mixture was quenched with 100 ml water, extracted with ethyl acetate (100 mL×3). The organic phase was combined and washed with saturated saline (50 mL×2), dried over anhydrous sodium sulfate, filtered, and concentrated under reduced pressure to give a crude product. The crude product was purified by silica gel column chromatography (petroleum ether:ethyl acetate=10:1) to give the target compound 13-1.

Trifluoroacetic acid (3.14 g, 27.56 mmol) was added to a solution of 13-1 (1.8 g, 6.89 mmol) in dichloromethane (20 mL). The reaction mixture was stirred at 25° C. for 0.5 h. The reaction mixture was adjusted with a saturated sodium carbonate solution to pH=7-8, extracted with dichloromethane/methanol (10:1, 100 mL×3), and the combined organic layer was washed with saturated brine (100 mL×2), dried over anhydrous sodium sulfate, filtered and concentrated under reduced pressure to give the target compound 13-2. $^1$H NMR (400 MHz, CHLOROFORM-d) δ 7.18-7.21 (m, 2H), 7.02-7.06 (m, 1H), 6.91-6.93 (m, 1H), 1.40 (s, 6H).

PIFA (2.72 g, 6.32 mmol) and trifluoroacetic acid (6.01 g, 52.7 mmol, 3.90 mL) were added to a solution of 13-2 (850.00 mg, 5.27 mmol) in chloroform (80.00 mL). The reaction mixture was stirred at 25° C. for 12 hours. The reaction mixture was adjusted with a saturated sodium carbonate solution to pH=7-8, extracted with dichloromethane/methanol (10:1, 100 mL×3), and the combined organic layer was washed with saturated brine (50 mL×2), dried over anhydrous sodium sulfate, filtered and concentrated under reduced pressure to give a crude product. The crude product was purified by silica gel column chromatography (petroleum ether: ethyl acetate=1:1) to give the target compound 13-3. $^1$H NMR (400 MHz, CHLOROFORM-d) δ 6.73-6.78 (m, 2H), 6.63-6.65 (m, 1H), 1.27 (s, 6H).

Potassium carbonate (78.00 mg, 564.33 μmol) and BB-1 (102.45 mg, 338.60 μmol) were added to a solution of 13-3 (50.00 mg, 282.17 μmol) in N,N-dimethylformamide (5.00 mL). The reaction mixture was stirred at 60° C. for 12 hours. The reaction was quenched with water (50 mL) and extracted with ethyl acetate (50 mL×3). The organic layer was combined, washed with saturated brine (50 mL×1), dried over anhydrous sodium sulfate, filtered and concentrated under reduced pressure to give a crude product. The crude product was purified by thin layer chromatography (petroleum ether:ethyl acetate=1:1) to give the target compound 13-4. $^1$H NMR (400 MHz, CHLOROFORM-d) δ 8.15 (s, 1H), 7.30-7.41 (m, 3H), 6.73-6.75 (m, 1H), 6.61-6.66 (m, 1H), 4.77 (s, 2H), 2.15 (m, 1H), 1.68 (m, 2H), 1.34 (s, 6H), 1.12-1.13 (m, 2H).

The synthesis of subject compound 13-5 refers to that of compound 6-1. $^1$H NMR (400 MHz, CHLOROFORM-d) δ 8.18-8.20 (m, 2H), 7.53-7.55 (s, 2H), 7.34-7.44 (m, 3H), 6.78-6.81 (m, 2H), 6.67-6.77 (m, 1H), 4.82 (s, 2H), 3.97 (s, 3H), 2.17 (m, 1H), 1.46 (s, 6H), 1.30-1.32 (m, 2H), 1.15-1.18 (m, 2H).

The synthesis of subject compound 13 refers to that of compound 4. $^1$H NMR (400 MHz, CHLOROFORM-d) δ 8.22-8.24 (d, J=8.0 Hz, 2H), 7.55-7.57 (d, J=8.0 Hz, 2H), 7.33-7.42 (m, 3H), 6.80-6.82 (d, J=8.0 Hz, 2H), 6.76-6.77 (d, J=2.0 Hz, 1H), 6.65 (d, J=2.4 Hz, 1H), 4.81 (s, 2H), 2.16 (m, 1H), 1.45 (s, 6H), 1.28-1.31 (m, 2H), 1.13-1.16 (m, 2H).

Example 14: Compound 14

Synthetic Route:

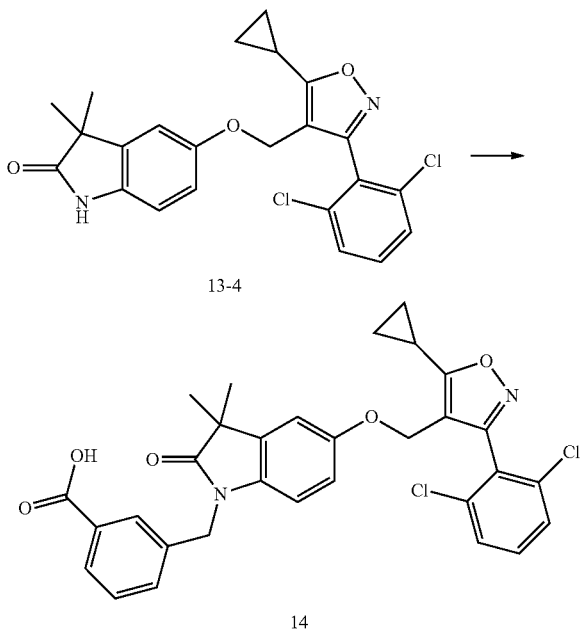

Sodium hydride (3.28 mg, 81.88 mol, 60% purity) was added to a solution of 13-4 (33 mg, 74.44 mol) in N,N-dimethylformamide (2.00 ml). The reaction mixture was stirred at 0-25° C. for 30 minutes. Methyl-3(bromomethyl) benzoate (17.05 mg, 74.44 μmol) was added to the reaction mixture. The reaction mixture was stirred for 1 h. At 0° C., 20 ml of water was added to the reaction mixture, and the pH was adjusted to 5 with 1 N hydrochloric acid. The mixture was extracted with dichloromethane/methanol (10:1, 20 ml×3), and the combined organic phase was washed with saturated brine (30 ml×1), dried over anhydrous sodium sulfate, filtered, and concentrated under reduced pressssure to obtain a crude product. The crude product was purified by preparative high-performance liquid chromatography (trifluoroacetic acid) to give the target compound 14. 1H NMR (400 MHz, CHLOROFORM-d) δ 7.98 (s, 2H), 7.28-7.46 (m, 5H), 6.71 (s, 1H), 6.48-6.54 (m, 2H), 4.92 (s, 2H), 4.74 (s, 2H), 2.12 (m, 1H), 1.40 (s, 6H), 1.25 (m, 2H), 1.09-1.11 (m, 2H).

Example 15: Compound 15

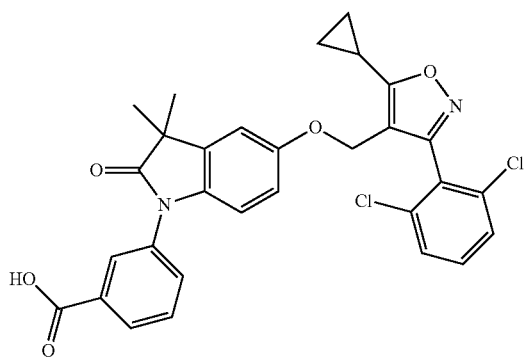 [SMILES: CC1(C)C(=O)N(c2cccc(C(=O)O)c2)c2ccc(OCc3c(-c4c(Cl)cccc4Cl)noc3C3CC3)cc21]

Synthetic Route:

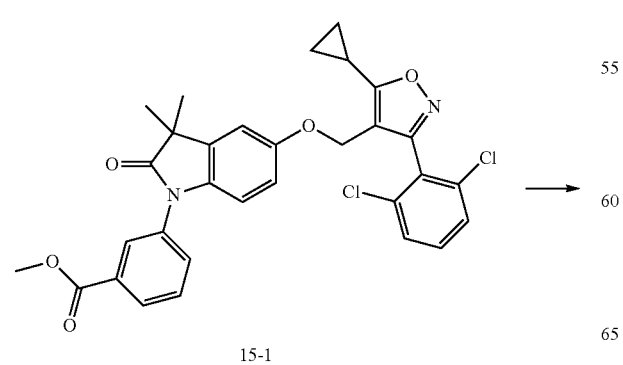

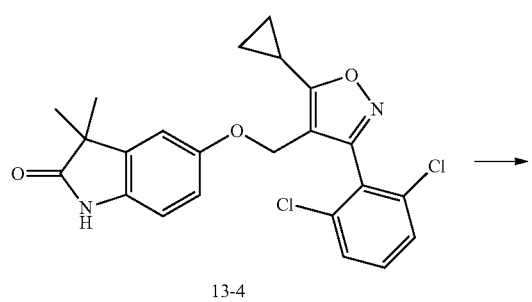

15

A solution of 13-4 (50 mg, 112.79 μmol), (3-methoxycarbonylphenyl)-boric acid (20.30 mg, 112.79 μmol), copper acetate (30.73 mg, 169.19 μmol), 3 A molecular sieve (112.79 μmol) and triethylamine (22.83 mg, 225.58 μmol, 31.27 microliters) in dichloromethane (30 ml) was degassed and charged with nitrogen gas for three times. The reaction mixture was stirred at 25° C. for 12 hours under a nitrogen atmosphere. The reaction mixture was diluted with 10 mL dichloromethane, filtered, and concentrated under reduced pressure to give a crude product. The crude product was purified by preparative silica gel thin layer chromatography (petroleum ether: ethyl acetate=3:1) to give the target compound 15-1. $^1$H NMR (400 MHz, CHLOROFORM-d) δ 8.04-8.08 (m, 1H), 7.58-7.61 (m, 2H), 7.30-7.41 (m, 3H), 6.73-6.75 (m, 1H), 6.68-6.70 (m, 1H), 6.62-6.63 (d, 1H), 4.80 (s, 2H), 3.93 (s, 3H), 2.15 (m, 1H), 1.44 (s, 6H), 1.26-1.23 (m, 4H), 1.12-1.13 (m, 2H).

The synthesis of subject compound 15 refers to that of compound 4. $^1$H NMR (400 MHz, CHLOROFORM-d) δ 8.13 (m, 2H), 7.62-7.69 (m, 2H), 7.32-7.41 (m, 3H), 6.75-6.76 (s, 1H), 6.70 (d, 1H), 6.63 (d, 2H), 4.80 (s, 2H), 2.10 (m, 1H), 1.45 (s, 6H), 1.26-1.23 (m, 4H), 1.13-1.16 (m, 2H).

Example 16: Compound 16

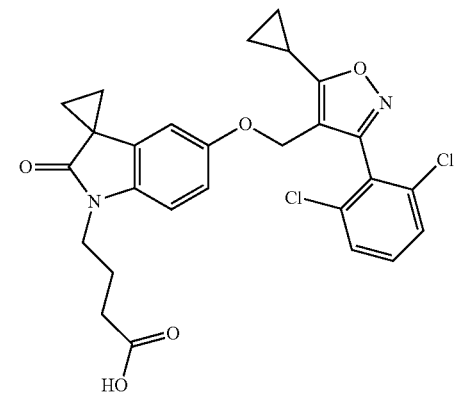 [SMILES: O=C(O)CCCN1C(=O)C2(CC2)c2cc(OCc3c(-c4c(Cl)cccc4Cl)noc3C3CC3)ccc21]

Synthetic Route:

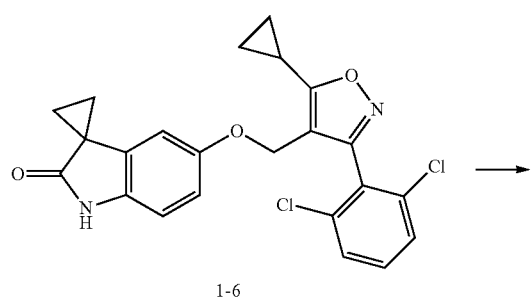

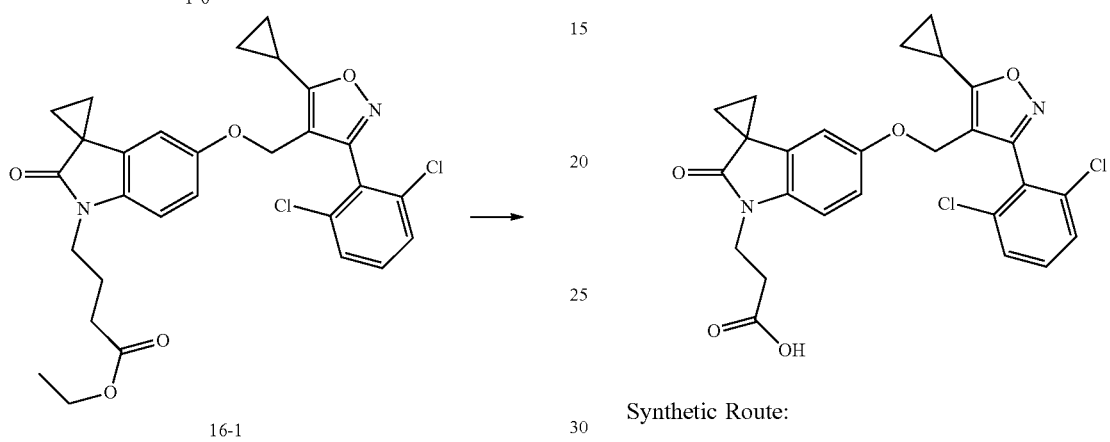

1-6 (100.00 mg, 226.60 μmol) was dissolved in N,N-dimethylformamide (6.00 mL), and sodium hydride (27.19 mg, 679.80 μmol, 60% purity) was added at 0° C. The mixture is stirred for half an hour at 0° C. Ethyl 4-bromobutyrate (66.30 mg, 339.90 μmol, 48.75 μL) in N,N-dimethylformamide (0.5 mL) was added dropwise. The reaction mixture was stirred at 25° C. for 4.5 hours. The reaction mixture was added dropwise with water (50 ml) at 0° C., acidified to pH=3 with 1 mol hydrochloric acid, and extracted with ethyl acetate (30 ml×3). The organic layer was washed with saturated brine (50 ml) and concentrated. The crude product was used directly in the next reaction without purification to give the target compound 16-1.

16-1 (120.00 mg, 216.04 μmol) was dissolved in tetrahydrofuran (4.00 ml) and water (4.00 ml). Lithium hydroxide monohydrate (90.65 mg, 2.16 mmol) was added and the reaction mixture was stirred at 20° C. for 1 hour. Water (40 ml) was added dropwise at 0° C., the mixture was acidified to pH=3 with 1 mol hydrochloric acid, and extracted with ethyl acetate (30 ml×3). The organic layer was concentrated. The residue was separated by preparative high performance liquid chromatography (trifluoroacetic acid) to give the target compound 16. $^{1}$H NMR: (400 MHz, CDCl$_3$) δ 7.44-7.37 (m, 2H), 7.36-7.29 (m, 1H), 6.82 (d, J=8.5 Hz, 1H), 6.69 (dd, J=2.0, 8.5 Hz, 1H), 6.33 (d, J=2.0 Hz, 1H), 4.76 (s, 2H), 3.84 (t, J=7.0 Hz, 2H), 2.44 (t, J=7.0 Hz, 2H), 2.22-2.10 (m, 1H), 2.02 (quin, J=6.9 Hz, 2H), 1.77 (q, J=3.7 Hz, 2H), 1.47 (q, J=3.8 Hz, 2H), 1.33-1.24 (m, 2H), 1.18-1.08 (m, 2H).

Example 17: Compound 17

Synthetic Route:

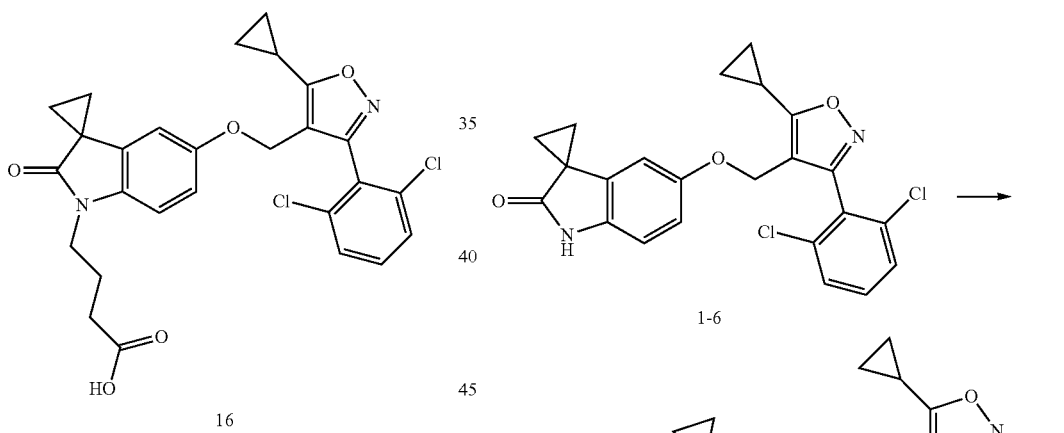

1-6 (100.00 mg, 226.60 μmol) was dissolved in N,N-dimethylformamide (6.00 mL), and sodium hydride (27.19 mg, 679.80 μmol, 60% purity) was added at 0° C. After stirring for half an hour at 0° C., ethyl 3-bromobutyrate (61.53 mg, 339.90 μL) in N,N-dimethylformamide (0.5 mL) was added dropwise. The reaction mixture was stirred at 15° C. for 12 hours. Water (40 ml) was added dropwise at 0° C., the mixture was acidified to pH=3 with 1 mol hydrochloric acid, and extracted with ethyl acetate (30 ml×3). The organic layer was concentrated. The residue was separated by preparative high performance liquid chromatography (trifluoroacetic acid) to give the target compound 17. ¹H NMR: (400 MHz, CDCl₃) δ 7.44-7.37 (m, 2H), 7.35-7.29 (m, 1H), 6.82 (d, J=8.5 Hz, 1H), 6.68 (dd, J=2.0, 8.5 Hz, 1H), 6.31 (d, J=2.5 Hz, 1H), 4.75 (s, 2H), 4.05 (t, J=7.3 Hz, 2H), 2.76 (t, J=7.3 Hz, 2H), 2.10-2.18 (s, 1H), 1.74 (q, J=3.7 Hz, 2H), 1.44 (q, J=4.0 Hz, 2H), 1.31-1.24 (m, 2H), 1.17-1.08 (m, 2H).

Example 18: Compound 18

Synthetic Route:

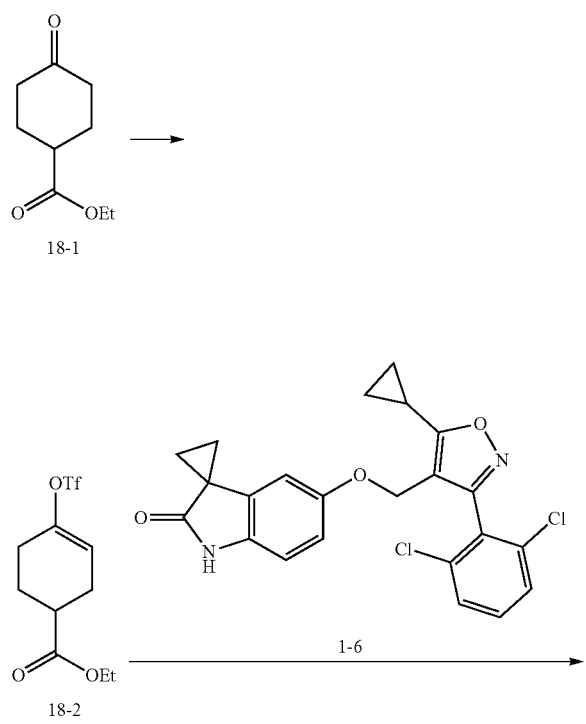

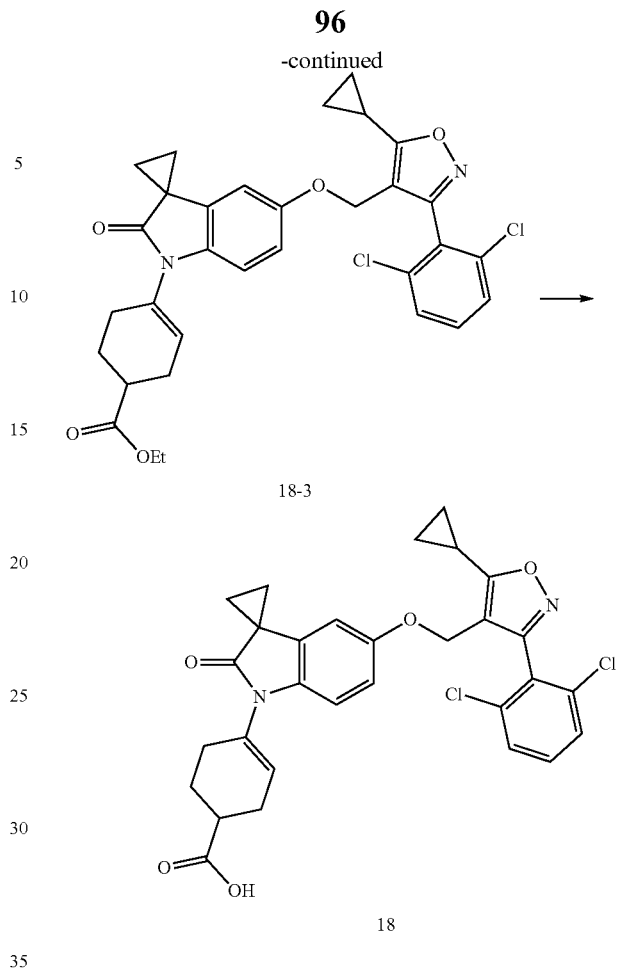

18-1 (5.00 g, 29.38 mmol, 4.67 ml) was dissolved in tetrahydrofuran (60.00 mL). Under nitrogen protection, LiHMDS (1 mol/L, 44.07 mL) was added dropwise at −78° C. After the addition, the reaction mixture was stirred at this temperature for half an hour, and 1,1,1-trifluoro-N-phenyl-N-[(trifluoromethyl)sulfonyl]methanesulfonamide (11.55 g, 32.32 mmol) in tetrahydrofuran (20.00 ml) was added dropwise. The reaction mixture was stirred at −78° C. for 1.5 hours, and then warmed to 10° C. and stirred for 10 hours. The reaction mixture was added with water (200 ml) at 0° C., and extracted with ethyl acetate (100 ml×3). The organic layer was washed with saturated saline (100 mL) and concentrated. The residue was subjected to column chromatography (silica gel) to give the target compound 18-2. ¹H NMR: (400 MHz, CDCl₃) δ 5.78 (br. s., 1H), 4.17 (q, J=7.0 Hz, 2H), 2.65-2.55 (m, 1H), 2.50-2.35 (m, 4H), 2.22-2.07 (m, 1H), 1.99-1.83 (m, 1H), 1.33-1.13 (m, 3H).

1-6 (100.00 mg, 226.60 μmol), 18-2 (136.99 mg, 453.20 μmol), Pd(dba)₂ (13.03 mg, 22.66 μmol), potassium carbonate (93.95 mg, 679.80 μmol) and 2-di-tert-butylphosphino-2',4',6'-triisopropylbiphenyl (19.24 mg, 45.32 μmol) was dissolved in tert-butanol (6.00 mL), and the reaction system was ventilated with nitrogen for three times, and stirred for 12 hours at 80° C. The reaction mixture was quenched with water (40 ml) at 15° C., and extracted with ethyl acetate (30 ml×3). The organic layer was washed with saturated brine (20 mL), dried dried over anhydrous sodium sulfate, filtered, and concentrated. The residue was seperated by thin layer chromatography to give the target compound 18-3. ¹H NMR: (400 MHz, CDCl₃) 7.46-7.23 (m, 3H), 6.76-6.68 (m, 1H), 6.66-6.57 (m, 1H), 6.30 (d, J=2.5 Hz, 1H), 5.85 (br. s., 1H), 4.74 (s, 2H), 4.25-4.13 (m, 2H), 2.80-2.65 (m, 1H), 2.61-2.26 (m, 3H), 2.24-2.08 (m, 2H), 2.01-1.88 (m, 1H), 1.72 (q, J=3.7 Hz, 2H), 1.43 (q, J=3.8 Hz, 2H), 1.34-1.22 (m, 6H), 1.18-1.06 (m, 2H).

Example 18-3 (40.00 mg, 67.40 μmol) was dissolved in tetrahydrofuran (3.00 ml) and water (3.00 ml), and then, at 0° C. lithium hydroxide monohydrate (14.14 mg, 337.00 μmol) was added. The reaction solution was stirred at 15° C. for 12 hours. The reaction was quenched with water (40 mL), acidified to pH=3 with 1 mol hydrochloric acid, and extracted with ethyl acetate (30 ml×3). The organic layer was concentrated. The crude product was separated by preparative high performance liquid chromatography (trifluoroacetic acid) to give the target compound 18. ¹H NMR: (400 MHz, CDCl₃) δ 7.44-7.30 (m, 3H), 6.79-6.70 (m, 1H), 6.68-6.60 (m, 1H), 6.31 (d, J=2.0 Hz, 1H), 5.88 (br. s., 1H), 4.75 (s, 2H), 2.82 (d, J=7.0 Hz, 3H), 2.39 (br. s., 2H), 2.28-1.95 (m, 3H), 1.75 (q, J=3.7 Hz, 2H), 1.45 (q, J=4.0 Hz, 2H), 1.33-1.23 (m, 2H), 1.18-1.07 (m, 2H).

Example 19: Compound 19

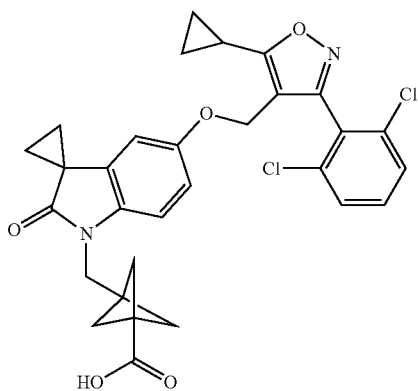 [SMILES: O=C(O)C12CC(CN3C(=O)C4(CC4)c4cc(OCc5c(-c6c(Cl)cccc6Cl)noc5C5CC5)ccc43)(C1)C2]

Synthetic Route:

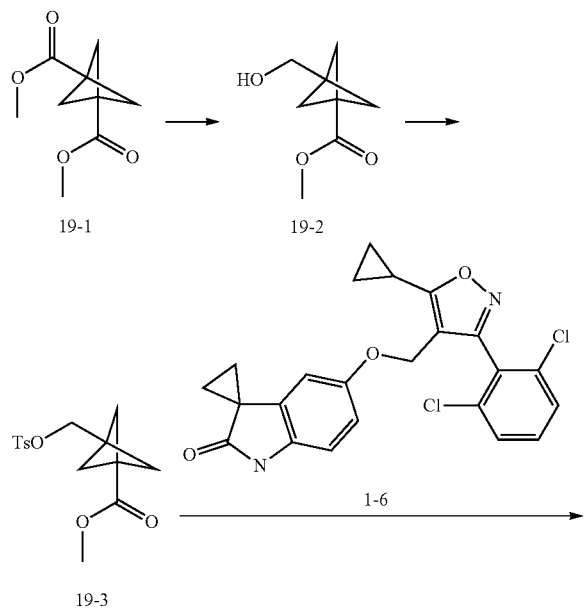

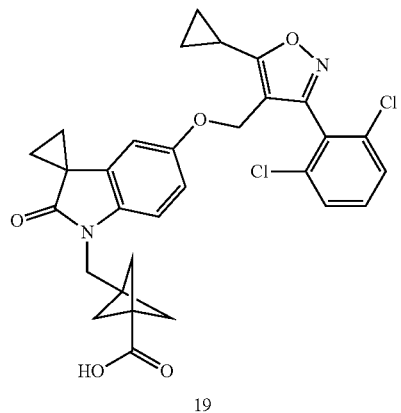

19-1 (500.0 mg, 2.71 mmol) was dissolved in tetrahydrofuran (10.00 mL), and lithium borohydride (60 mg, 2.71 mmol) was added at 0° C. The reaction mixture was stirred at 15° C. for 15 hours. The reaction mixture was quenched with water (30 mL) at 0° C., extracted with ethyl acetate (30 ml×3). The organic layer was dried over anhydrous sodium sulfate, filtered and concentrated. The residue was seperated by column chromatography to give the target compound 19-2. ¹H NMR: (400 MHz, CDCl₃) δ 3.70 (s, 3H), 3.66 (s, 2H), 2.02 (s, 6H).

19-2 (290.00 mg, 1.86 mmol) was dissolved in dichloromethane (10.00 mL), and at 25° C., TosCl (531.91 mg, 2.79 mmol), DMAP (227.24 mg, 1.86 mmol) and triethyl amine (188.21 mg, 1.86 mmol, 257.82 μL) were added. The reaction mixture was stirred at 25° C. for 12 hours, and concentrated to remove the solvent. The residue was seperated by column chromatography to give the target compound 19-3. ¹H NMR: (400 MHz, CDCl₃) δ 7.80 (d, J=8.3 Hz, 2H), 7.37 (d, J=8.3 Hz, 2H), 4.06 (s, 2H), 3.69 (s, 3H), 2.48 (s, 3H), 2.06-1.92 (m, 6H).

19-3 (100.00 mg, 226.60 μmol) was dissolved in N,N-dimethylformamide (5 mL), and at 0° C., sodium hydride (18.13 mg, 453.20 μmol, 60% purity) was added. The mixture was stirred for half an hour and then 1-6 (84.39 mg, 271.92 μmol) in N,N-dimethylformamide (1 ml) was added dropwise. The reaction mixture was stirred at 15° C. for 23.5 hours. The reaction mixture was quenched with water (20 mL) at 0° C., acidified to pH=3 with 1 mol hydrochloric acid, and extracted with ethyl acetate (30 ml×3). The organic layer was concentrated. The residue was separated by preparative high performance liquid chromatography (trifluoroacetic acid) to give the target compound 19. ¹H NMR: (400 MHz, CDCl₃) δ 7.48-7.30 (m, 3H), 6.74-6.62 (m, 2H), 6.33 (s, 1H), 4.77 (s, 2H), 3.87 (s, 2H), 2.24-2.11 (m, 1H), 2.02 (s, 6H), 1.82-1.68 (m, 2H), 1.46 (d, J=3.0 Hz, 2H), 1.29 (d, J=2.5 Hz, 2H), 1.15 (d, J=5.8 Hz, 2H).

Example 20, Example 21: Compound 20 and Compound 21

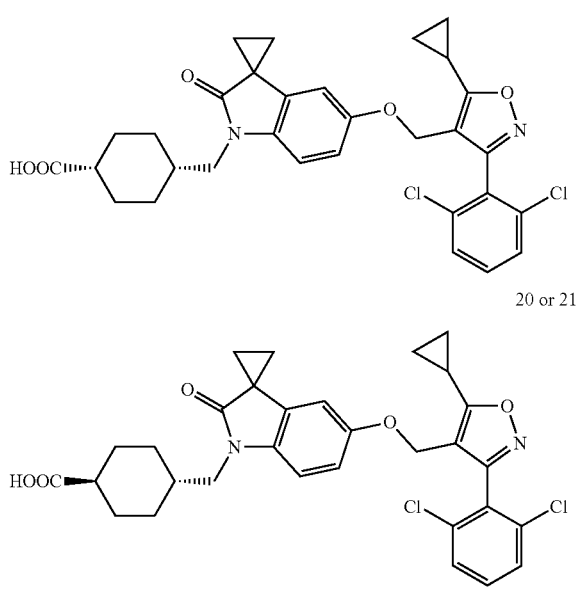

Synthetic Route:

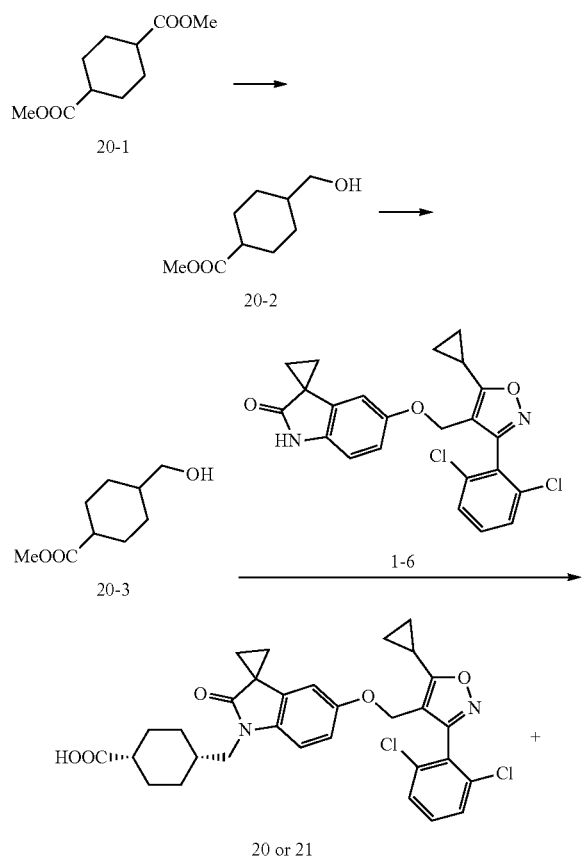

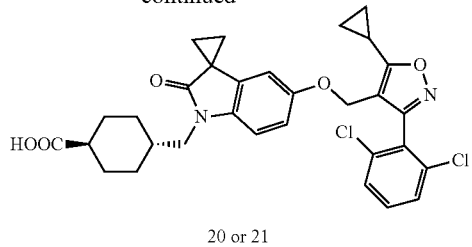

20-1 (5.00 g, 24.97 mmol) was dissolved in tetrahydrofuran (30.00 ml), and lithium borohydride (543.87 mg, 24.97 mmol) was added at 0° C. in batches. The reaction mixture was stirred at 15° C. for 12 hours. Water (35 ml) was added to the reaction system, which was then extracted with ethyl acetate (40 ml×3). The organic layer was washed with water (10 ml), dried over anhydrous sodium sulfate, filtered and concentrated to give the target compound 20-2 without purifying the residue. $^1$H NMR (400 MHz, CHLOROFORM-d) δ 3.70 (s, 3H), 3.54-3.45 (m, 2H), 2.50 (br. s., 1H), 2.07-2.01 (m, 2H), 1.94-1.89 (m, 2H), 1.72-1.66 (m, 3H), 1.34-1.28 (m, 2H).

20-2 (500.00 mg, 2.90 mmol) and carbon tetrabromide (1.20 g, 3.62 mmol) were dissolved in dichloromethane (5.00 mL), and triphenylphosphine (950.80 mg, 3.62 mmol) was added at 0° C. in three batches. The reaction mixture was stirred at 15° C. for three hours, concentrated and the solvent was removed. Ethyl acetate/petroleum ether (1:1, 20 mL) was added to the residue. White solid was precipitated, and then filtered. The filtrate was washed with water (10 mL), dried over anhydrous sodium sulfate, filtered and concentrated. The residue was seperated by column chromatography (silica gel) to give the target compound 20-3. $^1$H NMR (400 MHz, CHLOROFORM-d) δ 3.61 (s, 3H), 3.28-3.18 (m, 2H), 2.41 (br. s., 1H), 1.99-1.92 (m, 2H), 1.86-1.81 (m, 2H), 1.70-1.60 (m, 4H), 1.27 (d, J=10.5 Hz, 1H).

Sodium hydride (18.13 mg, 453.20 μmol, 60% purity) was suspended in N,N-dimethylformamide (1 mL), and examples 1-6 (100.00 mg, 226.60 μmol) were added at 0° C. After ten minutes, example 20-3 (79.92 mg, 339.90 μmol, dissolved in N,N-dimethylformamide (1 ml)) was added, and the reaction mixture was stirred at 50° C. for 12 hours. The reaction mixture was acidified with one mole of hydrochloric acid to pH=5-6, and extracted with dichloromethane/methanol (10/1, 20 mL×3). The organic layer was washed with water (10 ml), dried over anhydrous sodium sulfate, filtered and concentrated. The crude product was separated by thin layer chromatography and then by high performance liquid chromatography (trifluoroacetic acid) to give the target compound 20 (retention time: 3.772 min), $^1$H NMR (400 MHz, CHLOROFORM-d) δ 7.44-7.39 (m, 2H), 7.37-7.32 (m, 1H), 6.77-6.66 (m, 2H), 6.34 (d, J=2.0 Hz, 1H), 4.77 (s, 2H), 3.61 (d, J=6.8 Hz, 2H), 2.31 (t, J=12.3 Hz, 1H), 2.23-2.13 (m, 1H), 2.06 (d, J=14.6 Hz, 2H), 1.83 (d, J=11.0 Hz, 3H), 1.75 (q, J=3.8 Hz, 2H), 1.50-1.34 (m, 4H), 1.34-1.26 (m, 2H), 1.21-1.04 (m, 4H). and the target compound 21 (retention time: 3.870 min). $^1$H NMR (400 MHz, CHLOROFORM-d) δ 7.44-7.39 (m, 2H), 7.37-7.32 (m, 1H), 6.77-6.66 (m, 2H), 6.34 (d, J=2.0 Hz, 1H), 4.77 (s, 2H), 3.61 (d, J=6.8 Hz, 2H), 2.31 (t, J=12.3 Hz, 1H), 2.23-2.13 (m, 1H), 2.06 (d, J=14.6 Hz, 2H), 1.83 (d, J=11.0 Hz, 3H), 1.75 (q, J=3.8 Hz, 2H), 1.50-1.34 (m, 4H), 1.34-1.26 (m, 2H), 1.21-1.04 (m, 4H).

Example 22: Compound 22

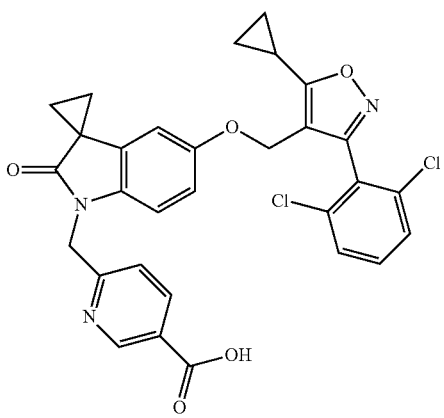 [SMILES: O=C(O)c1ccc(CN2C(=O)C3(CC3)c3cc(OCc4c(-c5c(Cl)cccc5Cl)noc4C4CC4)ccc32)nc1]

Synthetic Route:

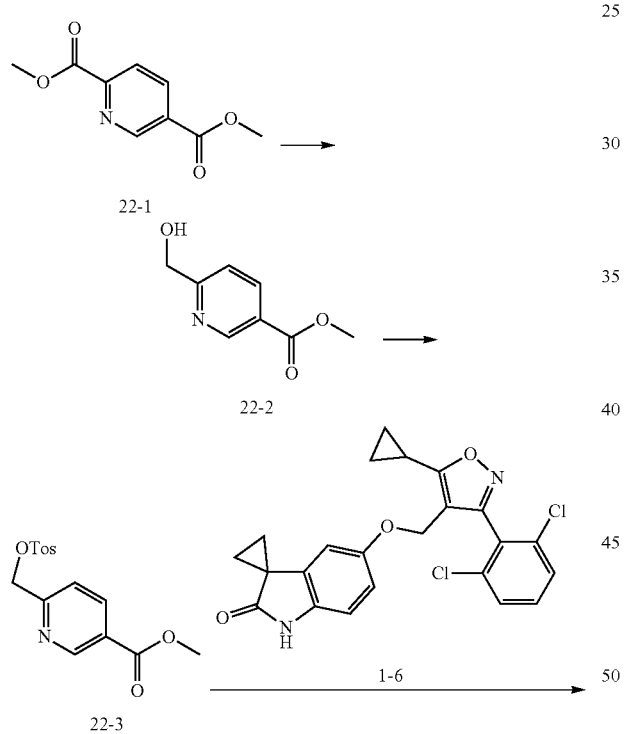

22-1 (1.00 g, 5.12 mmol) and calcium chloride (2.27 g, 20.48 mmol) were dissolved in tetrahydrofuran (15.00 ml) and methanol (15.00 ml), and stirred at 0° C. for half an hour. At this temperature, sodium borohydride (484.22 mg, 12.80 mmol) was added in batches and the reaction mixture was continously stirred at 0° C. for five hours. The reaction mixture was quenched with a saturated aqueous solution of ammonium chloride (50 ml), and extracted with ethyl acetate (50 mL×3). The organic layer was washed with saturated brine, dried over anhydrous sodium sulfate, filtered and concentrated, to give a cude product of the target compound 22-2 which was used directly in the next step. $^1$H NMR: (400 MHz, CDCl$_3$) δ 9.19 (s, 1H), 8.32 (d, J=7.8 Hz, 1H), 7.38 (d, J=8.0 Hz, 1H), 4.86 (s, 2H), 4.05-3.92 (m, 3H).

22-2 (200.00 mg, 1.20 mmol) and triethylamine (364.28 mg, 3.60 mmol, 499.02 μL) were dissolved in dichloromethane (10.00 mL), and TosCl (343.17 mg, 1.80 mmol) was added at 0° C.). The reaction mixture was stirred at 15° C. for four hours. At 0° C., the reaction mixture was quenched with water (50 ml) and extrated with ethyl acetate (40 ml×3). The organic layer was washed with saturated brine, dried over anhydrous sodium sulfate, filtered and concentrated. The residue was separated by column chromatography to give the target compound 22-3. $^1$H NMR: (400 MHz, CDCl$_3$) δ 9.12 (d, J=1.3 Hz, 1H), 8.33 (dd, J=2.0, 8.3 Hz, 1H), 7.87 (d, J=8.3 Hz, 2H), 7.55 (d, J=8.3 Hz, 1H), 7.38 (d, J=8.0 Hz, 2H), 5.21 (s, 2H), 4.04-3.89 (m, 3H), 2.47 (s, 3H).

1-6 (100.00 mg, 226.60 μmol) was dissolve in N,N-dimethylformamide (9.00 ml), and sodium hydride (18.13 mg, 453.20 μmol, 60% purity) was added at 0° C. under nitrogen protection. The reaction mixture was stirred at 0° C. for half an hour. 22-3 (80.10 mg, 249.26 μmol, dissolved in N,N-dimethylformamide (1 ml)) was added dropwise, and the reaction mixture was stirred at 15° C. for 12 hours. The reaction mixture was acidified to (pH=7) with 1 mol hydrochloric acid and then concentrated. The residue was seperated by high performance liquid chromatography to give the target compound 22. $^1$H NMR: (400 MHz, CDCl$_3$) δ 9.13 (br. s., 1H), 8.15 (d, J=6.5 Hz, 1H), 7.40-7.33 (m, 2H), 7.30 (br. s., 1H), 7.18 (d, J=7.0 Hz, 1H), 6.72-6.52 (m, 2H), 6.33 (s, 1H), 5.08 (br. s., 2H), 4.73 (s, 2H), 2.29-2.06 (m, 1H), 1.80 (br. s., 2H), 1.49 (br. s., 2H), 1.26 (br. s., 2H), 1.11 (d, J=6.3 Hz, 2H).

Example 23: Compound 23

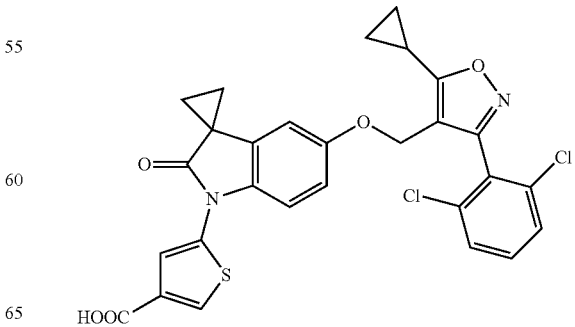

Synthetic Route:

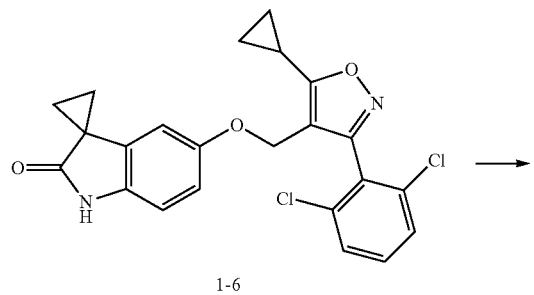

1-6

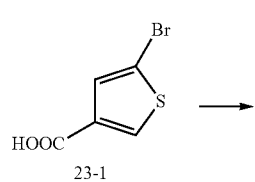

23-1

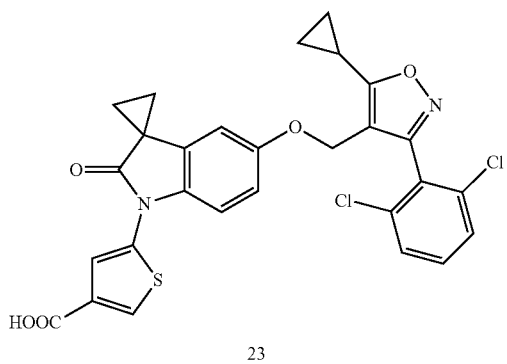

23

Compound 1-6 (50.00 mg, 113.30 μmol) was dissolved in N,N-dimethylformamide (2.00 mL), and 23-1 (28.15 mg, 135.96 μmol), anhydrous potassium phosphate (72.15 mg, 339.90 μmol), cuprous iodide (21.58 mg, 113.30 μmol) and trans 1,2-cyclohexanediamine (12.94 mg, 113.30 μmol, 13.91 μL) were added. The reaction system was ventilated with nitrogen gas for 6 times, and the reaction mixture was stirred at 100° C. for 12 hours. After cooling to room temperature, ethyl acetate (20 mL) was added to the reaction system, which was then filtered and the filtrate was concentrated. The residue was separated by high performance liquid chromatography (trifluoroacetic acid) to give the target compound 23. $^1$H NMR (400 MHz, CHLOROFORM-d) δ 8.14 (d, J=1.3 Hz, 1H), 7.55 (d, J=1.5 Hz, 1H), 7.43-7.38 (m, 2H), 7.36-7.29 (m, 1H), 7.05 (d, J=8.8 Hz, 1H), 6.69 (dd, J=2.4, 8.7 Hz, 1H), 6.36 (d, J=2.5 Hz, 1H), 4.79 (s, 2H), 2.18-2.14 (m, 1H), 1.87 (q, J=4.1 Hz, 2H), 1.59-1.55 (m, 2H), 1.31-1.27 (m, 2H), 1.18-1.13 (m, 2H).

Example 24: Compound 24

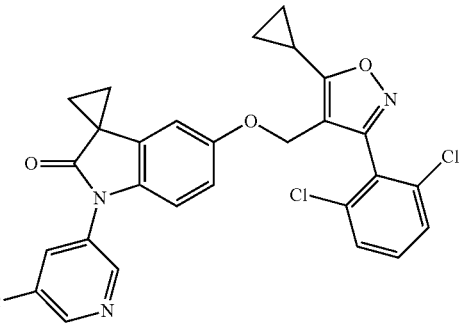

Synthetic Route:

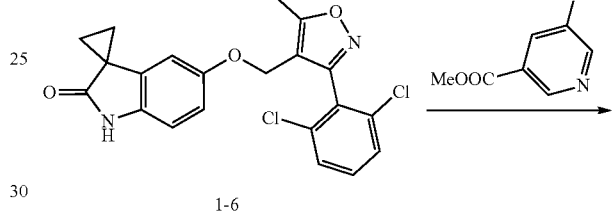

1-6

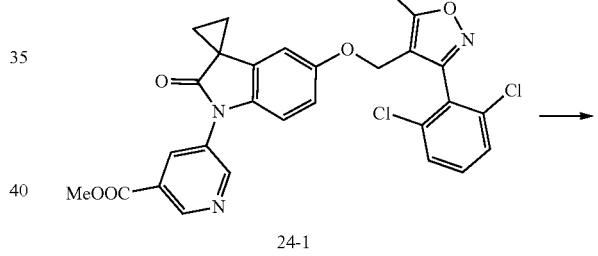

24-1

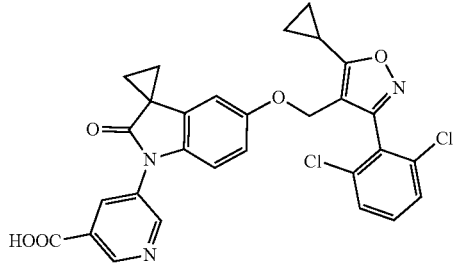

24

Compound 1-6 (100.00 mg, 226.60 μmol) was dissolved in 1,4-dioxane (2.00 mL), and methyl 5-bromopyridine-3-carboxylate (58.74 mg, 271.92 μmol), cuprous iodide (43.16 mg, 226.60 μmol), anhydrous potassium phosphate (144.30 mg, 679.80 μmol) and trans 1,2-cyclohexanediamine (25.88 mg, 226.60 μmol, 27.83 μL) were added. The reaction system was ventilated with nitrogen for 6 times, and the reaction mixture was stirred at 100° C. for 12 hours. After cooling to room temperature, ethyl acetate (20 mL) was added to the reaction system, which was then filtered and the filtrate was concentrated. The residue was separated by thin layer chromatography to give the target compound 24-1. $^1$H NMR (400 MHz, CHLOROFORM-d) δ 9.21 (d, J=1.8 Hz, 1H), 8.93 (d, J=2.3 Hz, 1H), 8.42 (t, J=2.3 Hz, 1H), 7.43-7.38 (m, 2H), 7.35-7.30 (m, 1H), 6.78 (d, J=8.5 Hz, 1H), 6.64 (dd, J=2.5, 8.5 Hz, 1H), 6.38 (d, J=2.3 Hz, 1H), 4.83-4.73 (m, 2H), 3.98 (s, 3H), 3.83-3.83 (m, 1H), 3.63-3.57 (m, 1H), 2.21-2.10 (m, 1H), 1.87 (q, J=3.9 Hz, 2H), 1.57 (q, J=4.4 Hz, 2H), 1.33-1.27 (m, 3H), 1.18-1.10 (m, 3H), 1.07-0.75 (m, 2H).

24-1 (90.00 mg, 156.13 μmol) was dissolved in tetrahydrofuran (1.00 ml), water (1.00 ml) and methanol (1.00 ml), and lithium hydroxide monohydrate (65.51 mg, 1.56 mmol) was added. The reaction mixture was stirred at 15° C. for 12 hours. The reaction mixture was acidified with one mole of hydrochloric acid to pH=5-6, and extracted with dichloromethane/methanol (10/1, 10 mL×3). The organic layer was washed with water (10 ml), dried over anhydrous sodium sulfate, filtered and concentrated. The residue was separated by high performance liquid chromatography (trifluoroacetic acid) to give the target compound 24. $^1$H NMR (400 MHz, CHLOROFORM-d) δ 9.27 (d, J=1.8 Hz, 1H), 9.05 (d, J=2.5 Hz, 1H), 8.61 (t, J=2.1 Hz, 1H), 7.43-7.39 (m, 2H), 7.36-7.31 (m, 1H), 6.84 (d, J=8.5 Hz, 1H), 6.67 (dd, J=2.5, 8.5 Hz, 1H), 6.40 (d, J=2.5 Hz, 1H), 4.80 (s, 2H), 2.16 (br t, J=5.0 Hz, 1H), 1.92-1.89 (m, 2H), 1.61 (d, J=4.0 Hz, 2H), 1.29 (dd, J=2.4, 4.9 Hz, 2H), 1.18-1.15 (m, 2H).

Example 25: Compound 25

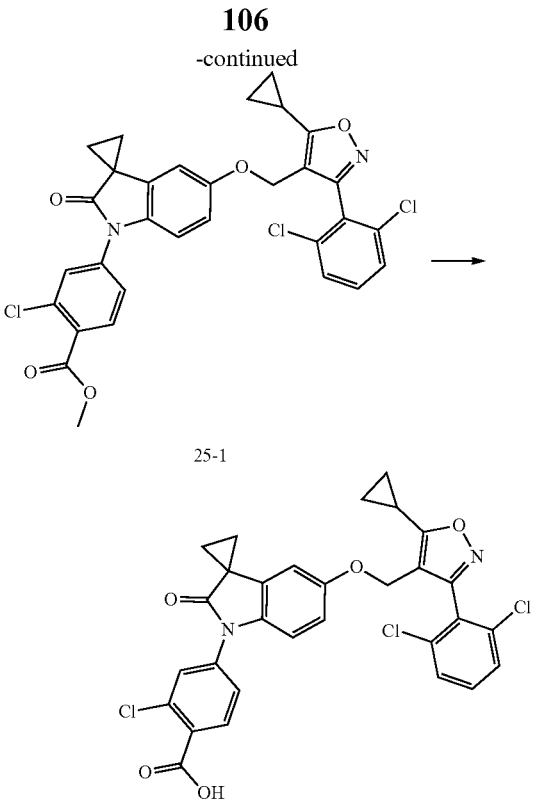

25-1

25

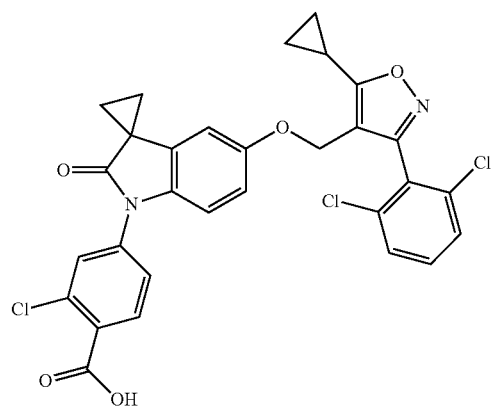 [SMILES: O=C(O)c1ccc(N2C(=O)C3(CC3)c3cc(OCc4c(-c5c(Cl)cccc5Cl)noc4C4CC4)ccc32)cc1Cl]

Synthetic Route:

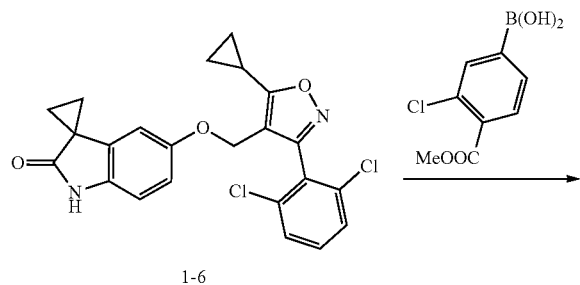

1-6 (50.00 mM, 113.30 μmol), 3-chloro-4-methoxycarbonylbenzeneboronic acid (36.44 mg, 169.95 μmol), anhydrous copper acetate (41.16 mg, 226.60 μmol), triethylamine (17.20 mg, 169.95 μmol, 23.56 μL), pyridine (13.44 mg, 169.95 μmol, 13.71 μL) and 4 A molecular sieve (100.00 mg) were dissolved in dichloromethane (2.00 mL), and the reaction mixture was stirred at 15° C. for 12 hours. Ethyl acetate (20 mL) was added to the reaction mixture, which was then filtered and the filtrate was concentrated. The residue was separated by thin layer chromatography to give the target compound 25-1. $^1$H NMR (400 MHz, CHLOROFORM-d) δ 7.92 (d, J=8.5 Hz, 1H), 7.54 (d, J=2.0 Hz, 1H), 7.39 (dd, J=2.0, 8.5 Hz, 1H), 7.35-7.30 (m, 2H), 7.28-7.22 (m, 1H), 6.78 (d, J=8.5 Hz, 1H), 6.57 (dd, J=2.5, 8.5 Hz, 1H), 6.29 (d, J=2.3 Hz, 1H), 4.71 (s, 2H), 3.95-3.83 (m, 3H), 3.41 (s, 8H), 2.08 (tt, J=5.0, 8.4 Hz, 1H), 1.77 (q, J=4.0 Hz, 2H), 1.47 (q, J=4.2 Hz, 2H), 1.21 (dd, J=2.4, 4.9 Hz, 2H), 1.10-1.05 (m, 2H).

25-1 (45.00 mg, 73.79 μmol) was dissolved in tetrahydrofuran (1.00 ml), water (1.00 ml) and methanol (1.00 ml), and lithium hydroxide monohydrate (30.96 mg, 737.90 μmol) was added. The reaction mixture was stirred at 18° C. for 12 hours. The reaction mixture was acidified with one mole of hydrochloric acid to pH=5-6, and extracted with dichloromethane/methanol (10 mL×3). The organic layer was washed with water (10 ml), dried over anhydrous sodium sulfate, filtered and concentrated. The residue was separated by high performance liquid chromatography to give the target compound 25. $^1$H NMR (400 MHz, CHLOROFORM-d) δ 8.18 (d, J=8.5 Hz, 1H), 7.68 (d, J=1.8 Hz, 1H), 7.53 (dd, J=1.8, 8.5 Hz, 1H), 7.46-7.40 (m, 2H), 7.38-7.32 (m, 1H), 6.91 (d, J=8.5 Hz, 1H), 6.68 (dd, J=2.3, 8.5 Hz, 1H), 6.39 (d, J=2.3 Hz, 1H), 4.81 (s, 2H), 2.20-2.16 (m, 1H), 1.88 (q, J=3.9 Hz, 2H), 1.58 (q, J=4.3 Hz, 2H), 1.34-1.27 (m, 2H), 1.20-1.11 (m, 2H).

Example 26: Compound 26

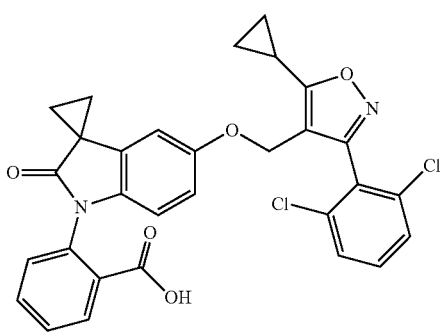 [SMILES: O=C(O)c1ccccc1N1C(=O)C2(CC2)c2cc(OCc3c(-c4c(Cl)cccc4Cl)noc3C3CC3)ccc21]

Synthetic Route:

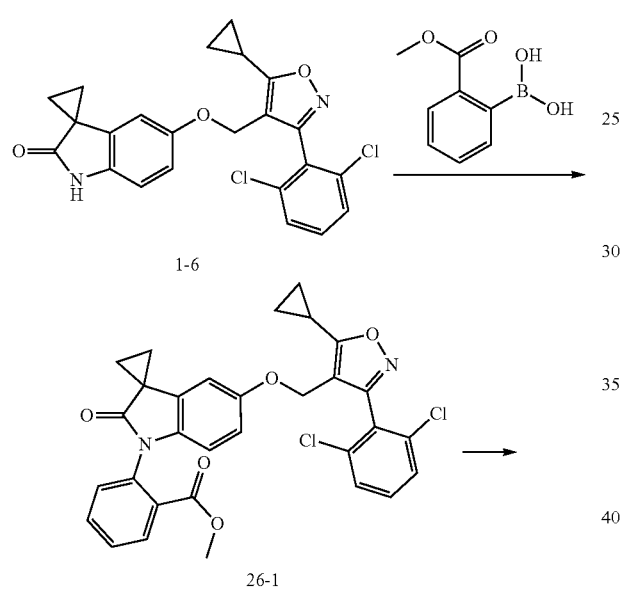

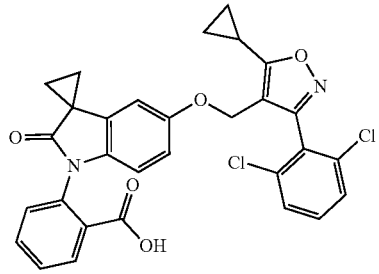

1-6 (100.00 mg, 226.60 μmol), 2-methoxycarbonylbenzeneboronic acid (81.56 mg, 453.20 μmol) and copper acetate (61.74 mg, 339.90 μmol) were dissolved in dichloromethane (5.00 mL). The reaction system was ventilated with nitrogen gas for 3 times, and the reaction mixture was stirred at 20° C. for 1 hour. Triethylamine (68.79 mg, 679.80 μmol, 94.23 μl) was added, and the reaction mixture was stirred at 20° C. for 24 hours. Dichloromethane (30 ml) was added to the reaction mixture, which was then washed with water (20 mL×2) and saturated saline (20 mL), and concentrated to obtain the crude product, which was separated by thin layer chromatography to give the target compound 26-1. $^1$H NMR (400 MHz, CHLOROFORM-d) δ 8.01 (dd, J=1.3, 7.8 Hz, 1H), 7.67-7.56 (m, 1H), 7.46-7.40 (m, 1H), 7.37-7.30 (m, 4H), 6.51 (dd, J=2.5, 8.5 Hz, 1H), 6.45-6.39 (m, 1H), 6.30 (d, J=2.3 Hz, 1H), 4.68 (s, 2H), 3.60 (s, 3H), 2.12-2.03 (m, 1H), 1.73 (d, J=4.3 Hz, 2H), 1.48-1.43 (m, 2H), 1.23-1.20 (m, 2H), 1.09-1.04 (m, 2H).

26-1 (55.00 mg, 95.58 μmol) was dissolved in tetrahydrofuran (1.00 ml), methanol (1.00 ml) and water (1.00 ml), and lithium hydroxide monohydrate (40.11 mg, 955.80 μmol) was added. The reaction mixture was stirred at 20° C. for 17 hours. Water (20 mL) was added to the reaction mixture, which was then acidified with one mole of hydrochloric acid to pH=4-5, and extracted with dichloromethane (2×20 mL). The organic layer was washed with saturated saline (20 ml), dried over anhydrous sodium sulfate, filtered and concentrated. The residue was separated by high performance liquid chromatography to give the target compound 26. $^1$H NMR (400 MHz, CHLOROFORM-d) δ 8.11 (br s, 1H), 7.76-7.64 (m, 1H), 7.51 (br s, 1H), 7.45-7.33 (m, 3H), 7.33-7.24 (m, 1H), 6.63-6.48 (m, 2H), 6.35 (br s, 1H), 4.76 (s, 2H), 2.14 (br s, 1H), 1.78 (br s, 2H), 1.47 (br d, J=15.3 Hz, 2H), 1.26 (br s, 2H), 1.12 (br d, J=6.3 Hz, 2H).

Example 27: Compound 27

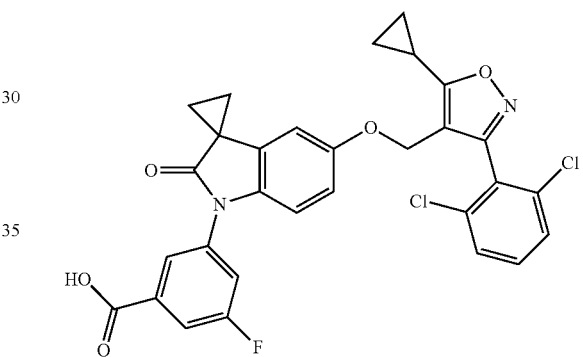

Synthetic Route:

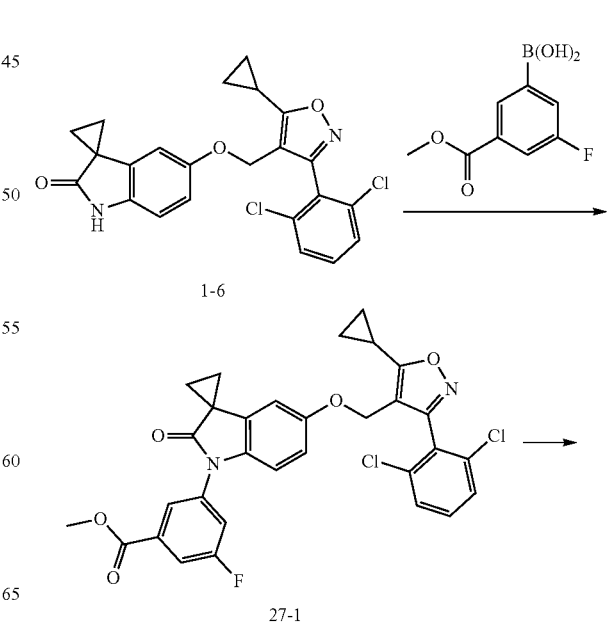

-continued

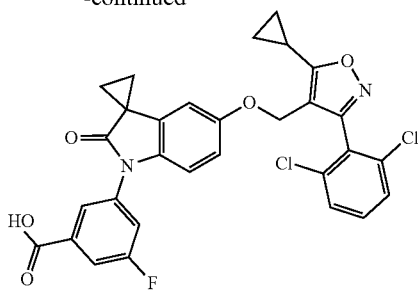

27-1

1-6 (100.00 mg, 226.60 μmol), 3-fluoro-5-methoxycarbonylphenylboronic acid (89.72 mg, 453.20 μmol), triethylamine (68.79 mg, 679.80 μmol, 94.23 μL), 4 A molecular sieve (200.00 mg) and copper acetate (61.74 mg, 339.90 μmol) were dissolved in dichloromethane (10.00 mL). The reaction system was ventilated with nitrogen gas for 3 times, and the reaction mixture was stirred at 15° C. for 12 hours. The reaction mixture was concentrated. The residue was separated by thin layer chromatography to give the target compound 27-1. $^1$H NMR (400 MHz, CDCl$_3$) δ 7.91-7.85 (m, 1H), 7.71-7.63 (m, 1H), 7.41-7.22 (m, 4H), 6.75 (d, J=8.5 Hz, 1H), 6.57 (dd, J=2.5, 8.5 Hz, 1H), 6.30 (d, J=2.5 Hz, 1H), 4.71 (s, 2H), 3.87 (s, 3H), 2.09 (tt, J=5.1, 8.4 Hz, 1H), 1.77 (q, J=4.1 Hz, 2H), 1.55-1.41 (m, 2H), 1.30-1.15 (m, 2H), 1.15-0.99 (m, 2H).

27-1 (120.00 mg, 202.21 μmol) was dissolved in tetrahydrofuran (5.00 ml) and water (2.00 ml), and lithium hydroxide monohydrate (169.69 mg, 4.04 mmol) was added, and the reaction mixture was stirred at 40° C. for 12 hours. Water (30 ml) was added to the reaction mixture at 0° C., which was then acidified with one mole of hydrochloric acid to pH=3, and extracted with ethyl acetate (30 mL×3). The organic layer was concentrated to give a crude product, which was separated by high performance liquid chromatography to give the target compound 27. $^1$H NMR (400 MHz, CDCl$_3$) δ 8.02 (s, 1H), 7.81 (dd, J=2.0, 8.0 Hz, 1H), 7.55-7.48 (m, 1H), 7.46-7.40 (m, 2H), 7.39-7.32 (m, 1H), 6.85 (d, J=8.5 Hz, 1H), 6.67 (dd, J=2.5, 8.8 Hz, 1H), 6.40 (d, J=2.5 Hz, 1H), 4.81 (s, 2H), 2.24-2.13 (m, 1H), 1.89 (q, J=4.1 Hz, 2H), 1.59 (q, J=4.4 Hz, 2H), 1.35-1.27 (m, 2H), 1.20-1.09 (m, 2H).

Example 28: Compound 28

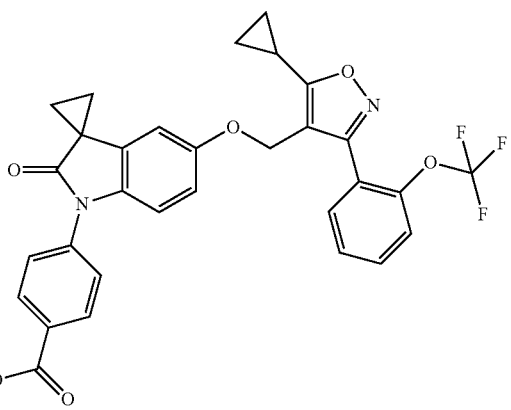

Synthetic Route:

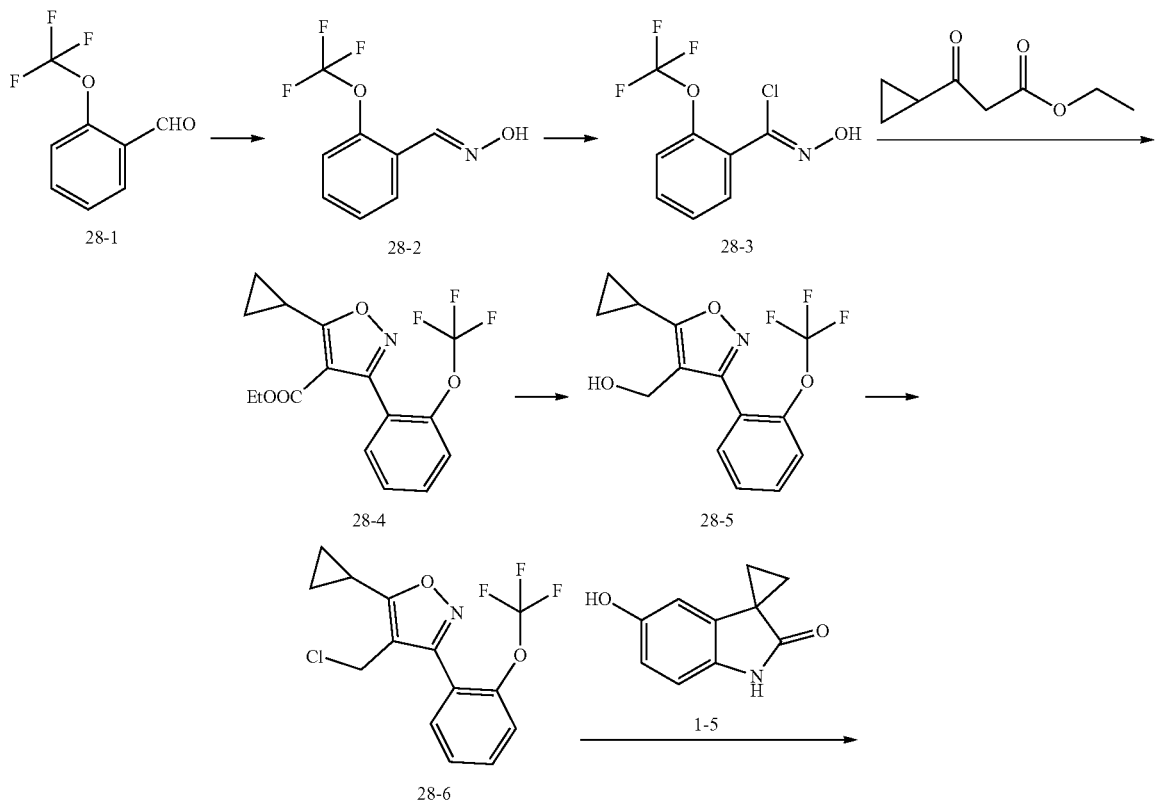

-continued

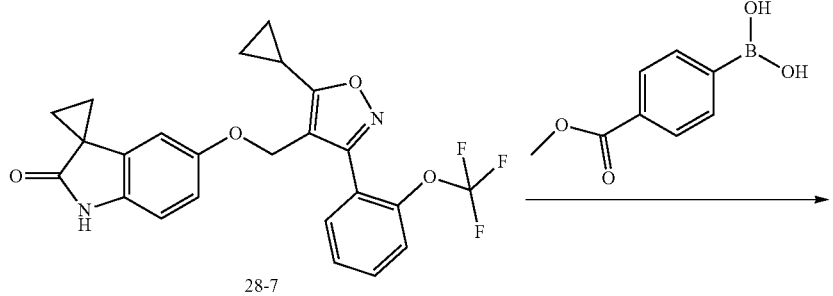

28-7

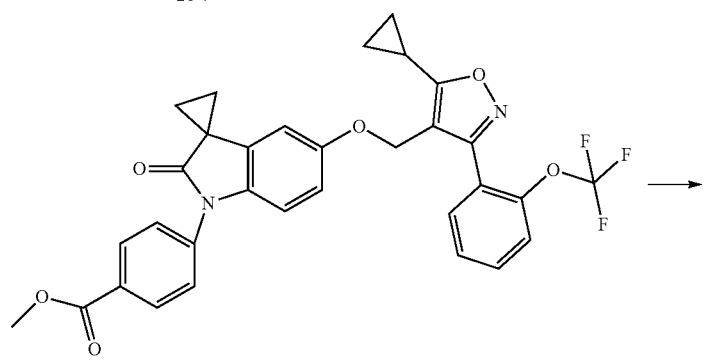

28-8

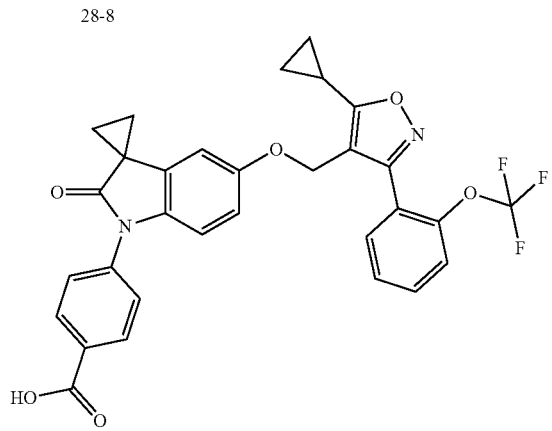

28

Hydroxylamine hydrochloride (8.11 g, 116.71 mmol) and sodium hydroxide (4.63 g, 115.72 mmol) were dissolved in water (80.00 mL) and 2-trifluoromethoxybenzaldehyde (28-1) (20.00 g, 105.20 mmol, dissolved in ethanol (240.00 ml)) was added. The reaction mixture was stirred at 90° C. for one hour. The reaction mixture was concentrated to remove the solvent, and water (10 mL) was added. The solid was filtered to give the target compound 28-2. $^1$H NMR (400 MHz, CHLOROFORM-d) δ 8.47-8.39 (m, 1H), 8.25-8.09 (m, 1H), 7.89 (dd, J=1.3, 7.8 Hz, 1H), 7.49-7.40 (m, 1H), 7.35-7.27 (m, 2H).

N-chlorosuccinimide (13.02 g, 97.50 mmol) was added to a solution of 28-2 (20.00 g, 97.50 mmol) in N,N-dimethylformamide (25.00 mL), and the reaction mixture was stirred at 20° C. for three hours. The reaction mixture was poured into ice water (25 mL), extracted with ethyl acetate (30 mL×3). The organic layer was dried over anhydrous sodium sulfate, filtered and concentrated to give the target compound 28-3. $^1$H NMR (400 MHz, CHLOROFORM-d) δ 7.60 (dd, J=1.4, 7.7 Hz, 1H), 7.50-7.44 (m, 1H), 7.38-7.30 (m, 2H).

28-3 (6.80 g, 28.38 mmol) was dissolved in triethylamine (14.36 g, 141.90 mmol, 19.67 ml), and ethyl 3-cyclopropyl-3-carbonyl-propanoate (4.43 g, 28.38 mmol) were added. The reaction mixture was stirred at 20° C. for 16 hours. The reaction mixture was concentrated to remove the solvent, water (200 mL) was added, and the mixture was filtered. The residue was separated by column chromatography to give the target compound 28-4. $^1$H NMR (400 MHz, CHLOROFORM-d) δ 7.54-7.46 (m, 2H), 7.39-7.32 (m, 2H), 4.18-4.13 (m, 2H), 2.92-2.83 (m, 1H), 1.38-1.33 (m, 2H), 1.25-1.21 (m, 2H), 1.07 (t, J=7.0 Hz, 3H).

28-4 (2.90 g, 8.50 mmol) was dissolved in tetrahydrofuran (20.00 mL), and DIBAH (1 M, 17.00 mL) was added. At 0° C., the reaction mixture was stirred at 20° C. under nitrogen atmosphere for 4 hours. Water (15 ml) and diluted hydrochloric acid (1M, 30 mL) were added to the reaction mixture, which was then extracted with ethyl acetate (30 mL×3). The organic layer was dried over anhydrous sodium sulfate, filtered and concentrated. The residue was separated by column chromatography to give the target compound 28-5. $^1$H NMR (400 MHz, CHLOROFORM-d) δ 7.60-7.50

(m, 2H), 7.44-7.37 (m, 2H), 4.50 (s, 2H), 2.24-2.15 (m, 1H), 1.28-1.22 (m, 2H), 1.16-1.10 (m, 2H).

At 0° C., thionyl chloride (596.04 mg, 5.01 mmol, 363.44 μl) was added to 1H-benzo[D][1,2,3]triazole (597.09 mg, 5.01 mmol) in dichloromethane (15 ml). After stirring at 20° C. for one hour, the mixture was added to a solution of 28-5 (1.50 g, 5.01 mmol) in dichloromethane (5 mL), and the reaction mixture was stirred at 20° C. for 1.5 hours. Water (10 ml) was added to the reaction mixture, which was then extracted with dichloromethane (25 ml×3). The organic layer was dried over anhydrous sodium sulfate, filtered and concentrated. The residue was separated by column chromatography to give the target compound 28-6. $^1$H NMR (400 MHz, CHLOROFORM-d) δ 7.61-7.52 (m, 2H), 7.43 (t, J=7.5 Hz, 2H), 4.46 (s, 2H), 2.18-2.10 (m, 1H), 1.30-1.24 (m, 2H), 1.21-1.15 (m, 2H)

1-5 (275.03 mg, 1.57 mmol) was dissolved in acetone (10.00 mL), and potassium carbonate (433.98 mg, 3.14 mmol), sodium iodide (47.07 mg, 314.00 μmol) and 28-6 (500.00 mg, 1.57 mmol) were added. The reaction mixture was stirred at 60° C. for 12 hours. Water (20 ml) was added to the reaction mixture, which was then extracted with ethyl acetate (20 mL×3). The organic layer was dried over anhydrous sodium sulfate, filtered and concentrated. The residue was separated by column chromatography to give the target compound 28-7. $^1$H NMR (400 MHz, CHLOROFORM-d) δ 7.63 (br. s., 1H), 7.56-7.48 (m, 2H), 7.37 (t, J=6.9 Hz, 2H), 6.78 (d, J=8.3 Hz, 1H), 6.63 (dd, J=2.3, 8.3 Hz, 1H), 6.27 (d, J=2.3 Hz, 1H), 4.82 (s, 2H), 2.16-2.09 (m, 1H), 1.73 (q, J=3.8 Hz, 2H), 1.43 (q, J=4.2 Hz, 2H), 1.26-1.22 (m, 2H), 1.15-1.08 (m, 2H).

The synthesis of target compound 28-8 refers to that of compound 27-1. $^1$H NMR (400 MHz, CHLOROFORM-d) δ 8.18 (d, J=8.5 Hz, 2H), 7.59-7.49 (m, 4H), 7.38 (t, J=7.0 Hz, 2H), 6.86 (d, J=8.5 Hz, 1H), 6.64 (dd, J=2.5, 8.5 Hz, 1H), 6.35 (d, J=2.5 Hz, 1H), 4.85 (s, 2H), 3.95 (s, 3H), 2.19-2.11 (m, 1H), 1.85 (q, J=4.0 Hz, 2H), 1.53 (q, J=4.0 Hz, 2H), 1.29-1.22 (m, 2H), 1.16-1.09 (m, 2H).

The synthesis of target compound 28 refers to that of compound 27. $^1$H NMR (400 MHz, CHLOROFORM-d) δ 8.25 (d, J=8.0 Hz, 2H), 7.61 (d, J=8.5 Hz, 2H), 7.57-7.50 (m, 2H), 7.41-7.36 (m, 2H), 6.89 (d, J=8.5 Hz, 1H), 6.65 (dd, J=2.3, 8.8 Hz, 1H), 6.36 (d, J=2.0 Hz, 1H), 4.86 (s, 2H), 2.20-2.11 (m, 1H), 1.88 (d, J=3.0 Hz, 2H), 1.56 (d, J=3.5 Hz, 2H), 1.27-1.24 (m, 2H), 1.17-1.11 (m, 2H).

Example 29: Compound 29

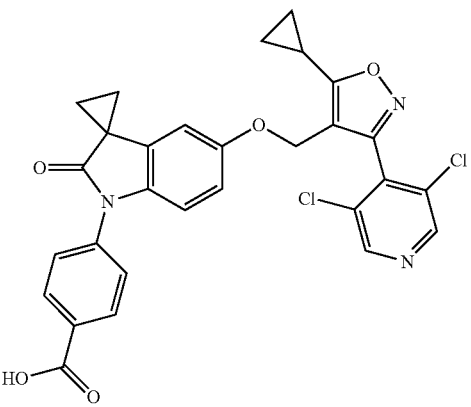 [SMILES: O=C(O)c1ccc(N2C(=O)C3(CC3)c3cc(OCc4c(-c5c(Cl)cncc5Cl)noc4C4CC4)ccc32)cc1]

Synthetic Route:

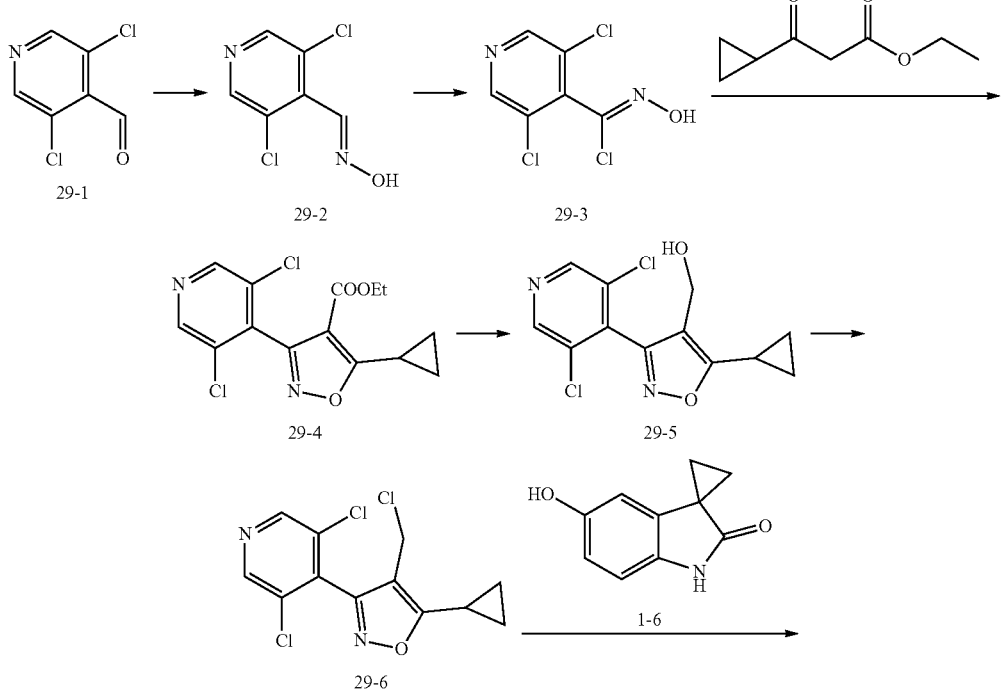

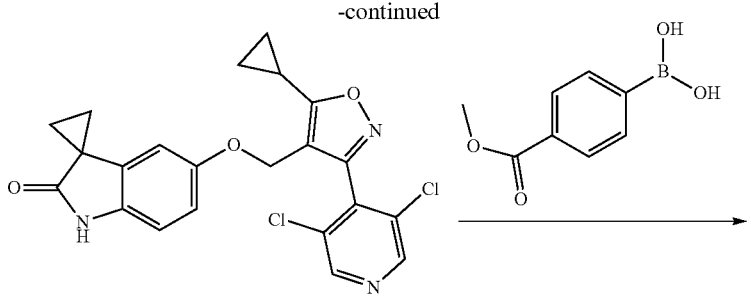

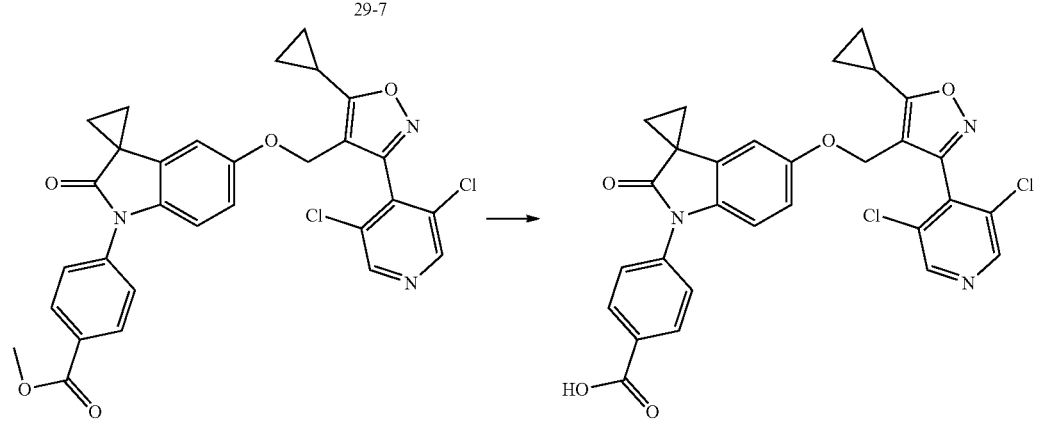

Hydroxylamine hydrochloride (789.41 mg, 11.36 mmol) and sodium hydroxide (454.55 mg, 11.36 mmol) were dissolved in water (8.00 mL) and 3,5-dichloropyridine-4-carbaldehyde (29-1) (2.00 g, 11.36 mmol, dissolved in ethanol (24.00 ml)) was added. The reaction mixture was stirred at 90° C. for one hour. The reaction mixture was concentrated to remove the solvent, and water (10 mL) was added. The solid was filtered to give the target compound 29-2. $^1$H NMR (400 MHz, CHLOROFORM-d) δ 8.56 (s, 2H), 8.38 (s, 1H), 8.05 (s, 1H).

N-chlorosuccinimide (7.38 g, 55.23 mmol) was added to a solution of 29-2 (10.55 g, 55.23 mmol) in N,N-dimethyl-formamide (25.00 mL), and the reaction mixture was stirred at 20° C. for three hours. The reaction mixture was poured into ice water (50 mL), extracted with ethyl acetate (100 mL×3). The organic layer was dried over anhydrous sodium sulfate, filtered and concentrated to give the target compound 29-3. $^1$H NMR (400 MHz, CHLOROFORM-d) δ 8.55 (s, 2H).

29-3 (3.30 g, 14.64 mmol) was dissolved in triethylamine (10.20 g, 100.85 mmol, 13.98 ml), and ethyl 3-cyclopropyl-3-carbonyl-propanoate (3.43 g, 21.96 mmol) was added dropwise. The reaction mixture was stirred at 20° C. for 16 hours. The reaction mixture was concentrated to remove the solvent. Water (10 mL) was added to the residue, the solid was precipitated and filtered. The solid was washed with petroleum ether (10 mL). The obtained solid was separated by column chromatography to give the target compound 29-4. $^1$H NMR (400 MHz, CHLOROFORM-d) δ 8.57 (s, 2H), 4.11 (q, J=7.3 Hz, 2H), 1.41-1.29 (m, 2H), 1.31-1.26 (m, 3H), 1.02 (t, J=7.2 Hz, 3H).

29-4 (2.00 g, 6.11 mmol) was dissolved in tetrahydrofuran (15.00 mL), and DIBAH (1 M, 12.22 mL) was added at 0° C. under nitrogen atmosphere. The reaction mixture was stirred 30° C. for 4 hours. Water (10 ml) and diluted hydrochloric acid (1M, 25 mL) were added to the reaction mixture, which was then extracted with ethyl acetate (25 mL×3). The organic layer was dried over anhydrous sodium sulfate, filtered and concentrated. The residue was separated by column chromatography to give the target compound 29-5. $^1$H NMR (400 MHz, CHLOROFORM-d) δ 8.62 (s, 2H), 4.45 (s, 2H), 2.22-2.14 (m, 1H), 1.31-1.28 (m, 2H), 1.21-1.15 (m, 2H).

At 0° C., thionyl chloride (500.70 mg, 4.21 mmol, 305.30 μl) was added to 1H-benzo[D][1,2,3]triazole (501.33 mg, 4.21 mmol) in dichloromethane (15 ml). After stirring at 20° C. for one hour, the mixture was added to a solution of 29-5 (1.20 g, 4.21 mmol) in dichloromethane (5 mL), and the reaction mixture was stirred at 20° C. for 1.5 hours. Water (10 ml) was added to the reaction mixture, which was then extracted with dichloromethane (25 ml×3). The organic layer was dried over anhydrous sodium sulfate, filtered and concentrated. The residue was separated by column chromatography to give the target compound 29-6. $^1$H NMR (400 MHz, CHLOROFORM-d) δ 8.65 (s, 2H), 4.36 (s, 2H), 2.20-2.09 (m, 1H), 1.33-1.28 (m, 2H), 1.24-1.19 (m, 2H)

29-6 (500.00 mg, 1.65 mmol) was dissolved in acetone (10.00 mL), and potassium carbonate (456.09 mg, 3.30 mmol), sodium iodide (49.46 mg, 330.00 μmol) and 1-5 (289.05 mg, 1.65 mmol) were added. The reaction mixture was stirred at 60° C. for 12 hours. Water (20 ml) was added to the reaction mixture, which was then extracted with ethyl acetate (20 mL×3). The organic layer was dried over anhydrous sodium sulfate, filtered and concentrated. The residue was separated by column chromatography to give the target compound 29-7. 1H NMR (400 MHz, CHLOROFORM-d) δ 8.59 (s, 2H), 7.59 (br. s., 1H), 6.76 (d, J=8.0 Hz, 1H), 6.58 (dd, J=2.5, 8.5 Hz, 1H), 6.23 (d, J=2.0 Hz, 1H), 4.78 (s, 2H), 2.19-2.10 (m, 1H), 1.75 (q, J=3.7 Hz, 2H), 1.45 (q, J=3.8 Hz, 2H), 1.30 (d, J=2.5 Hz, 2H), 1.20-1.15 (m, 2H).

The synthesis of compound 29-8 refers to that of compound 27-1. ¹H NMR (400 MHz, CHLOROFORM-d) δ 8.59 (s, 2H), 8.18 (d, J=8.5 Hz, 2H), 7.55 (d, J 8.0 Hz, 2H), 6.84 (d, J=8.5 Hz, 1H), 6.59 (dd, J=2.5, 8.5 Hz, 1H), 6.31 (d, J=2.5 Hz, 1H), 4.81 (s, 2H), 3.95 (s, 3H), 2.19-2.11 (m, 1H), 1.85 (q, J=3.7 Hz, 2H), 1.55-1.53 (m, 2H), 1.33-1.28 (m, 2H), 1.21-1.15 (m, 2H).
The synthesis of target compound 29 refers to that of compound 27. ¹H NMR (400 MHz, CHLOROFORM-d) δ 8.60 (s, 2H), 8.24 (d, J=8.3 Hz, 2H), 7.60 (d, J=8.5 Hz, 2H), 6.87 (d, J=8.5 Hz, 1H), 6.59 (dd, J=2.4, 8.7 Hz, 1H), 6.32 (d, J=2.3 Hz, 1H), 4.82 (s, 2H), 2.20-2.11 (m, 1H), 1.87 (q, J=3.8 Hz, 2H), 1.56 (q, J=4.1 Hz, 2H), 1.34-1.27 (m, 2H), 1.22-1.15 (m, 2H).
Example 30: Compound 30
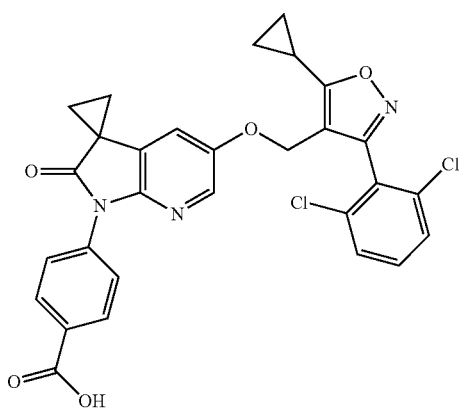 [SMILES: O=C(O)c1ccc(N2C(=O)C3(CC3)c3cc(OCc4c(-c5c(Cl)cccc5Cl)noc4C4CC4)cnc32)cc1]
Synthetic Route:
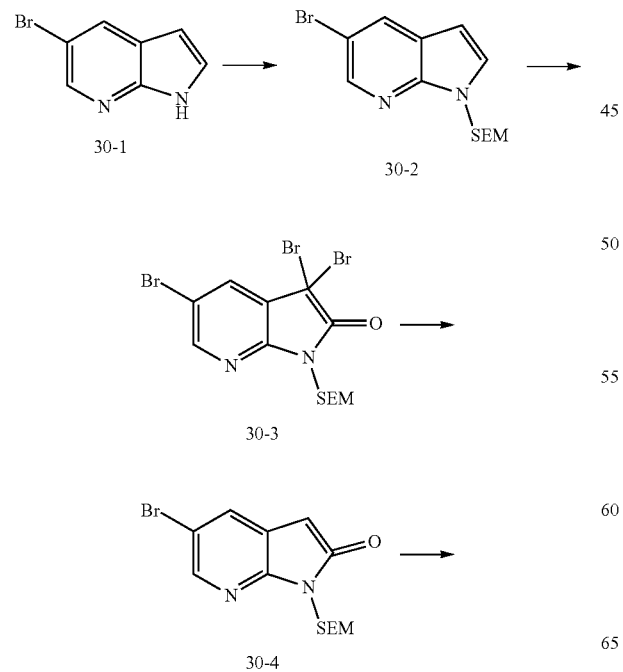
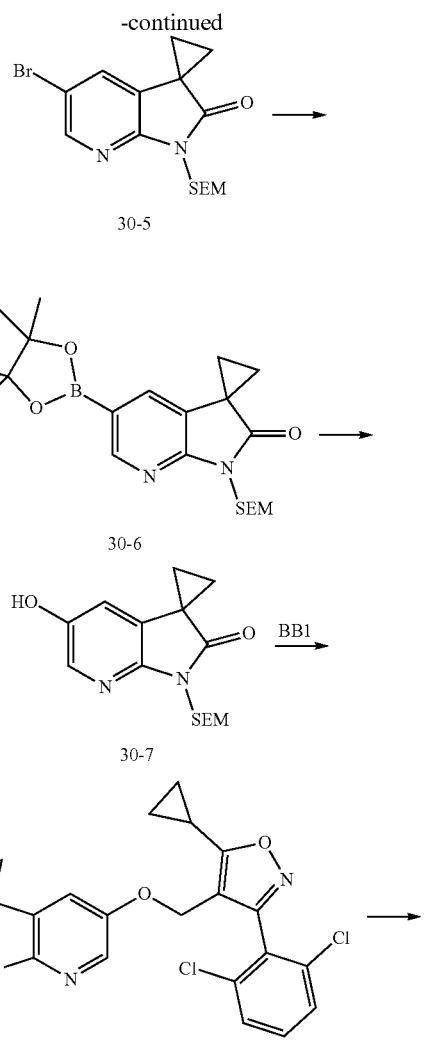

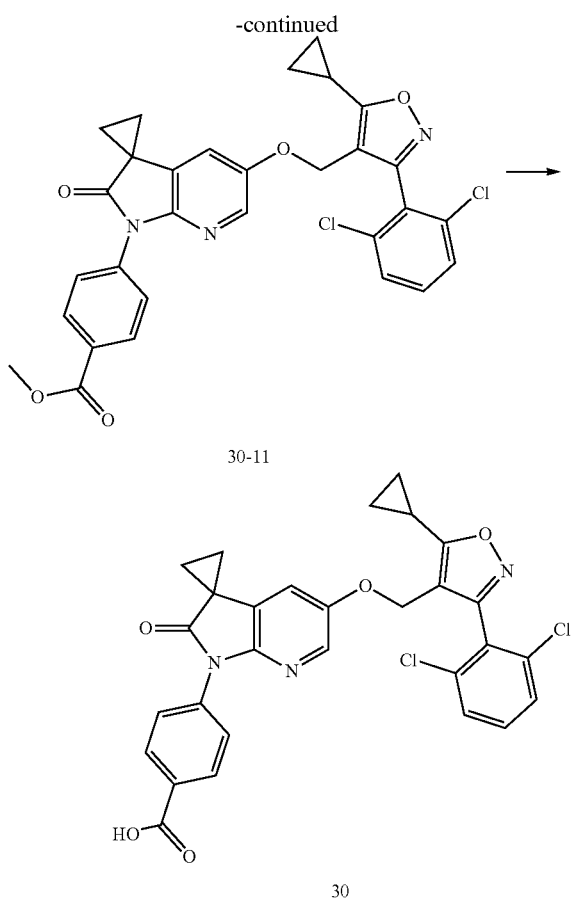

5-Bromo-7-azaindole (5.00 g, 25.38 mmol) was dissolved in N,N-dimethylformamide (60.00 mL), and at 0° C. under nitrogen protection, sodium hydride (1.22 g, 30.46 mmol, 60% purity) was added. After stirring for one hour, 2-(trimethylsilyl)ethoxymethyl chloride (5.08 g, 30.46 mmol, 5.40 mL) was added dropwise. The mixture was continuously stirred at 0° C. for 2 hours. The reaction mixture was quenched with water (300 mL) at 0° C., and extracted with ethyl acetate (100 mlx3). The organic layer was washed with saturated saline (100 mlx2), dried over anhydrous sodium sulfate, filtered and concentrated to obtain a crude product of the target compound 30-2, which was used directly for the next step. $^1$H NMR (400 MHz, CDCl$_3$) δ 8.42 (d, J=2.0 Hz, 1H), 8.10 (d, J=2.0 Hz, 1H), 7.42 (d, J=3.5 Hz, 1H), 6.53 (d, J=3.5 Hz, 1H), 5.71 (s, 2H), 3.65-3.51 (m, 2H), 0.03-0.90 (m, 2H), 0.01 (s, 9H).

30-2 (7.00 g, 21.39 mmol) was dissolved in 1,4-dioxane (80 ml) and the mixture was added dropwise to a solution of tribromopyridine (34.20 g, 106.95 mmol) in 1,4-dioxane (80 ml) at 15° C. The reaction solution was stirred at 15° C. for one hour. The reaction mixture was quenched with water (100 mL), and extracted with ethyl acetate (100 mlx3). The organic layer was washed with water (100 mL) and saturated saline (100 mL), dried over anhydrous sodium sulfate, filtered and concentrated. Dichloromethane (50 mL) was added to the residue, which was then filtered. The solid was washed with dichloromethane (600 mL). The filtrate was washed with saturated aqueous solution of sodium carbonate (100 mL) and saturated saline (100 mL), dried over anhydrous sodium sulfate, filtered and concentrated to obtain a crude product of the target compound 30-3, which was used directly for the next step. $^1$H NMR (400 MHz, CDCl$_3$) δ 8.43-8.31 (m, 1H), 8.00 (d, J=2.0 Hz, 1H), 5.31 (s, 2H), 3.75-3.66 (m, 2H), 1.03-0.92 (m, 2H), 0.01 (s, 9H).

30-3 (11.50 g, 22.95 mmol) was dissolved in tetrahydrofuran (120.00 ml) and a saturated aqueous solution of ammonium chloride (30.00 ml). At 15° C., zinc powder (15.01 g, 229.50 mmol) was added. The reaction mixture was stirred at 15° C. for three hours. The reaction mixture was filtered. Ethyl acetate (200 ml) and water (100 ml) were added to the filtrate, which was then extracted with ethyl acetate (200 mlx2). The organic layer was washed with saturated brine (100 mL), dried over anhydrous sodium sulfate, filtered and concentrated to obatin the crude product of the title compound 30-4, which was used directly for the next step. $^1$H NMR (400 MHz, CDCl$_3$) δ 8.31 (s, 1H), 7.67 (s, 1H), 5.27 (s, 2H), 3.76-3.67 (m, 2H), 3.64 (s, 2H), 1.08-0.94 (m, 2H), 0.03 (s, 9H)

30-4 (500.00 mg, 1.46 mmol) was dissolved in dimethyl sulfoxide (12.00 mL), and potassium carbonate (403.57 mg, 2.92 mmol) and 1,2-dibromoethane (411.41 mg, 2.19 mmol, 165.23 µL) were added. The reaction liquid was stirred at 25° C. for twelve hours. The reaction was quenched with water (50 mL), and extratcted with ethyl acetate (50 mlx3). The organic layer was washed with saturated brine (50 mL), dried over anhydrous sodium sulfate, filtered and concentrated. The residue was separated by thin layer chromatography to give the target compound 30-5. $^1$H NMR (400 MHz, CDCl$_3$) δ 8.27 (d, J=2.0 Hz, 1H), 7.23 (d, J=2.0 Hz, 1H), 5.31 (s, 2H), 3.79-3.62 (m, 2H), 1.89 (q, J=4.2 Hz, 2H), 1.62 (q, J=4.4 Hz, 2H), 1.09-0.91 (m, 2H), 0.00 (s, 9H)

36-5 (70.00 mg, 189.53 µmol), Pin$_2$B$_2$ (96.26 mg, 379.06 µmol), Pd(dppf)Cl$_2$ (13.87 mg, 18.95 µmol), potassium acetate (55.80 mg, 568.60 µmol) were dissolved in 1,4-dioxane (10.00 mL). The reaction system was ventilated with nitrogen gasvfor three times and stirred at 80° C. for 12 hours. The solid was filtered off, the filtrate was concentrated to give the target compound 30-6, which was used directly for the next step.

30-6 (300.00 mg, 720.48 µmol) was dissolved in tetrahydrofuran (6.00 mL), and aqueous solution of sodium hydroxide (1 M, 2.16 mL) and water (490.07 mg, 4.32 mmol, 415.31 µL, 30% purity) were added. The reaction mixture was stirred at 20° C. for two hours. At 0° C., water (50 ml) was added, The reaction mixture was acidified with one mole of hydrochloric acid to pH=7, and extracted with ethyl acetate (50 mlx3). The organic layer was washed with saturated brine (50 mL), dried over anhydrous sodium sulfate, filtered and concentrated. The residue was separated by thin layer chromatography to give the target compound 30-7. $^1$H NMR (400 MHz, CDCl$_3$) δ 7.84 (d, J=2.5 Hz, 1H), 6.76 (d, J=2.5 Hz, 1H), 5.34 (s, 2H), 3.76-3.65 (m, 2H), 1.86 (q, J=4.1 Hz, 2H), 1.56 (q, J=4.4 Hz, 2H), 1.04-0.96 (m, 2H), 0.01 (s, 9H).

30-7 (50.00 mg, 163.17 µmol) was dissolved in acetone (10.00 mL), and potassium iodide (5.42 mg, 32.63 µmol), 4-(chloromethyl)-5-cyclopropyl-3-(2, 6-dichlorophenyl) isoxazole (59.25 mg, 195.80 µmol) and potassium carbonate (45.10 mg, 326.34 µmol) were added. The reaction mixture was stirred at 60° C. for 12 hours. The reaction mixture was filtered and the filtrate was concentrated. The residue was separated by thin layer chromatography to give the target compound 30-8. $^1$H NMR (400 MHz, CDCl$_3$) δ 7.78 (d, J=2.5 Hz, 1H), 7.46-7.32 (m, 3H), 6.60 (d, J=2.5 Hz, 1H), 5.28 (s, 2H), 4.83 (s, 2H), 3.77-3.62 (m, 2H), 2.21-2.09 (m, 1H), 1.83 (q, J=4.1 Hz, 2H), 1.50 (q, J=4.2 Hz, 2H), 1.36-1.24 (m, 2H), 1.21-1.12 (m, 2H), 1.05-0.92 (m, 2H), 0.01 (s, 9H).

30-8 (100.00 mg, 174.66 μmol) was dissolved in four moles of hydrochloric acid/methanol (10.00 mL), and the reaction mixture was stirred at 40° C. for 6 hours. The reaction mixture was concentrated to give a crude product of the target compound 30-9, which was used directly for the next step.

30-9 (100.00 mg, 196.55 μmol, hydrochloride salt) was dissolved in methanol (8.00 mL), and ethylenediamine (141.75 mg, 2.36 mmol, 157.50 μL) was added. The reaction mixture was stirred at 25° C. for 9 hours, and concentrated. The residue was separated by thin layer chromatography to give the target compound 30-10. $^1$H NMR ES2816-194-p1A: (400 MHz, CDCl$_3$) δ 8.66 (br. s., 1H), 7.47-7.39 (m, 2H), 7.38-7.32 (m, 1H), 6.61 (s, 1H), 4.83 (s, 2H), 2.21-2.10 (m, 1H), 1.82 (q, J=4.1 Hz, 2H), 1.54-1.45 (m, 2H), 1.37-1.24 (m, 2H), 1.22-1.13 (m, 2H).

30-10 (30.00 mg, 67.83 μmol), 4-methyl formate phenylboronic acid (24.41 mg, 135.65 μmol), triethylamine (20.59 mg, 203.48 μmol, 28.21 μL), 4 A molecular sieve (200.00 mg) and anhydrous copper acetate (18.48 mg, 101.74 micromoles) were dissolved in dichloromethane (8.00 ml), ventilated with nitrogen gas for three times, and stirred at 20° C. for twelve hours. The mixture was filtered and the filtrate was concentrated. The residue was separated by thin layer chromatography to give the target compound 30-11. $^1$H NMR (400 MHz, CDCl$_3$) δ 8.17 (d, J=8.5 Hz, 2H), 7.74 (d, J=8.5 Hz, 3H), 7.47-7.37 (m, 2H), 7.35-7.29 (m, 1H), 6.66 (d, J=2.5 Hz, 1H), 4.83 (s, 2H), 3.94 (s, 3H), 2.22-2.09 (m, 1H), 1.91 (q, J=4.1 Hz, 2H), 1.64-1.53 (m, 2H), 1.37-1.24 (m, 2H), 1.21-1.10 (m, 2H).

30-11 (40.00 mg, 69.39 μmol) was dissolved in tetrahydrofuran (5.00 mL) and water (1.00 mL). At 0° C., lithium hydroxide monohydrate (29.12 mg, 693.90 μmol) was added. The reaction mixture was stirred at 20° C. for 12 hours. The reaction mixture was acidified with 1 mol of hydrochloric acid to pH=7, and concentrated. The residue was separated by high performance liquid chromatography (trifluoroacetic acid) to give the target compound 30. $^1$H NMR (400 MHz, CDCl$_3$) δ 8.22 (d, J=8.5 Hz, 2H), 7.76 (d, J=8.3 Hz, 3H), 7.47-7.32 (m, 3H), 6.71 (d, J=2.0 Hz, 1H), 4.86 (s, 2H), 2.16 (t, J=5.0 Hz, 1H), 1.97 (q, J=4.1 Hz, 2H), 1.63 (q, J=4.3 Hz, 2H), 1.38-1.26 (m, 2H), 1.24-1.12 (m, 2H).

Example 31: Compound 31

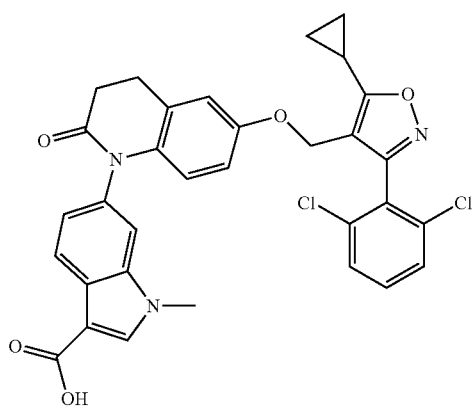 [SMILES: Cn1cc(C(=O)O)c2ccc(N3C(=O)CCc4cc(OCc5c(-c6c(Cl)cccc6Cl)noc5C5CC5)ccc43)cc21]

Synthetic Route:

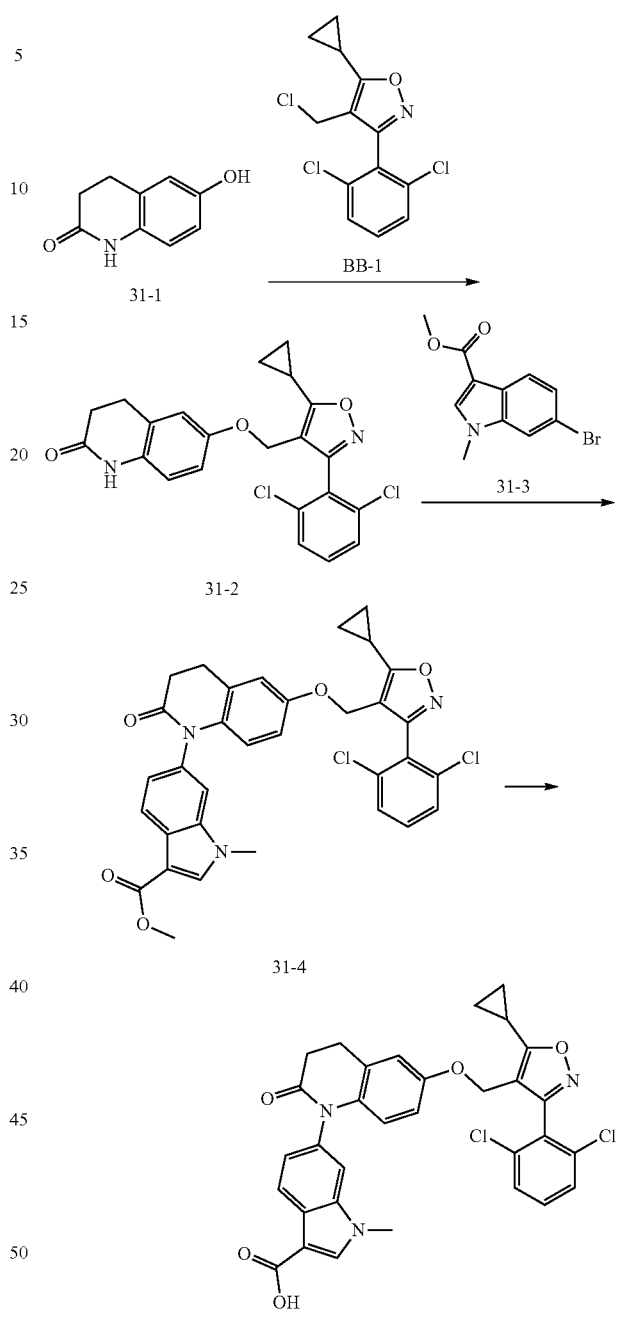

31-1 (1 g, 6.13 mmol) and BB-1 (2.23 g, 7.35 mmol) were dissolved in acetone (20 mL), and potassium carbonate (1.69 g, 12.26 mmol) and potassium iodide (200 mg, 1.20 mmol) were added. The reaction mixture was stirred at 60° C. for 12 hours and then stirred at 80° C. for 4 hours. The reaction mixture was directly filtrated and concentrated, and the crude product was separated by thin layer chromatography to give the target compound 31-2. $^1$H NMR (400 MHz, CHLOROFORM-d) δ=7.75 (br s, 1H), 7.45-7.38 (m, 2H), 7.37-7.30 (m, 1H), 6.61 (s, 3H), 4.77 (s, 2H), 2.93-2.85 (m, 2H), 2.59 (br t, J=7.5 Hz, 2H), 2.21-2.12 (m, 1H), 1.28 (br d, J=4.0 Hz, 2H), 1.14 (br d, J=6.0 Hz, 2H).

31-2 (200 mg, 465.88 μmol) and 31-3 (190 mg, 708.67 μmol) were dissolved in toluene (10 mL), and cuprous iodide (90 mg, 472.56 μmol), cesium carbonate (300 mg, 920.76 μmol) and N1,N2-dimethyl-1,2-cyclohexanediamine (70 mg, 492.13 μmol) were added. The reaction mixture was stirred at 110° C. for 12 hours, and water (20 ml) and aqueous ammonia (5 ml) were added. The mixture was extracted with ethyl acetate (30 mL×3). The combined organic layer was washed with saturated brine (30 mL), dried over anhydrous sodium sulfate, filtered and concentrated. The crude product was separated by thin layer chromatography to give the target compound 31-4.

31-4 (50 mg, 81.10 μmol) was dissolved in tetrahydrofuran (2 ml), methanol (2 ml) and water (2 ml), and lithium hydroxide monohydrate (70 mg, 1.67 mmol) was added. The reaction mixture was stirred at 20° C. for 12 hours. Water (10 ml) was added to the reaction mixture, which was then adjusted with 1 mol/L of diluted hydrochloric acid to pH=6, and then extracted with ethyl acetate (20 ml×3). The combined organic phase was washed with saturated brine (20 mL), dried over anhydrous sodium sulfate, filtered and concentrated. The crude product was separated by high performance liquid chromatography (formic acid) to give the target compound 31.

$^1$H NMR (400 MHz, METHANOL-d4) δ=8.20 (br d, J=8.5 Hz, 1H), 8.00 (s, 1H), 7.52-7.34 (m, 4H), 7.01 (br d, J=8.0 Hz, 1H), 6.69 (br s, 1H), 6.44 (br d, J=7.0 Hz, 1H), 6.16 (br d, J=8.5 Hz, 1H), 4.82-4.79 (m, 2H), 3.85 (s, 3H), 3.00 (br d, J=6.5 Hz, 2H), 2.78 (br d, J=7.0 Hz, 2H), 2.35-2.23 (m, 1H), 1.17 (br d, J=6.5 Hz, 4H).

Example 32: Compound 32

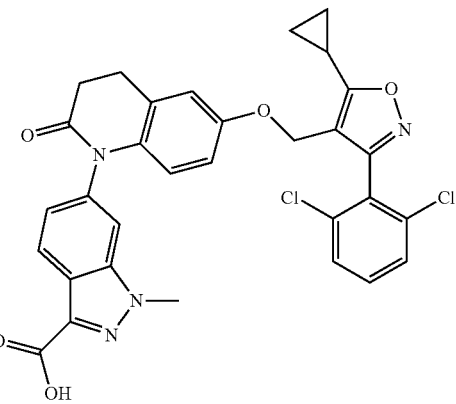

Synthetic Route:

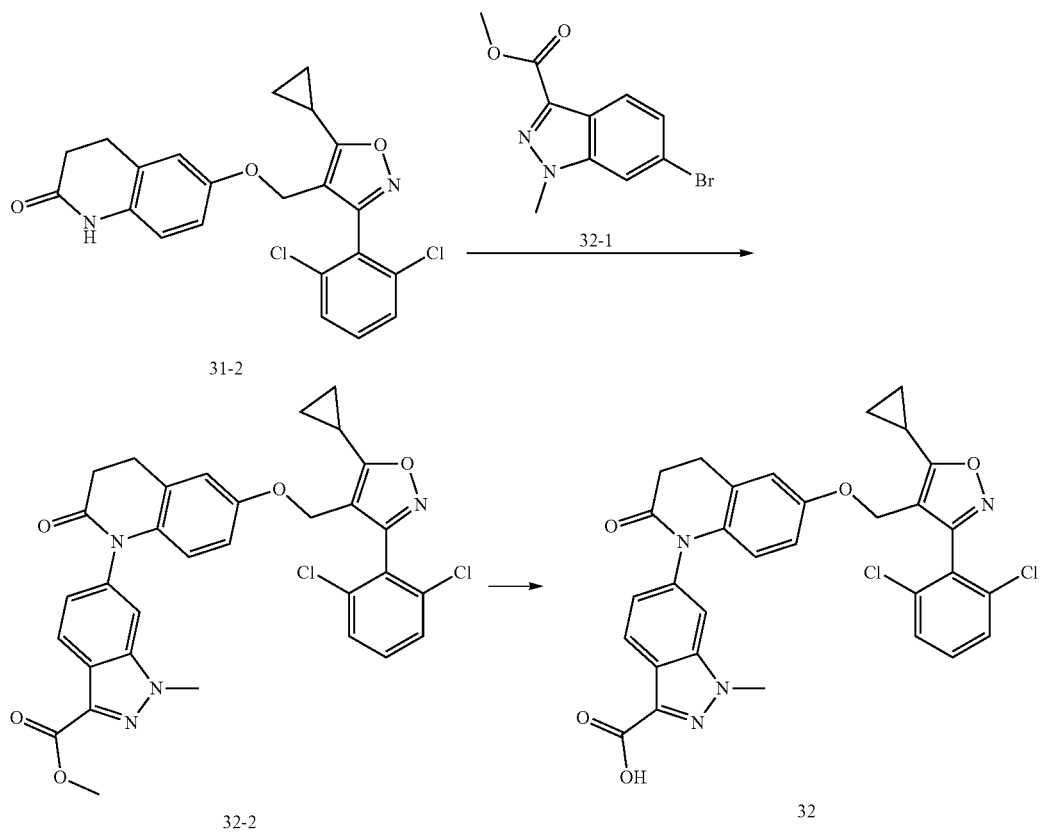

31-2 (500 mg, 1.16 mmol) and 32-1 (470 mg, 1.75 mmol) were dissolved in toluene (20 mL), and cuprous iodide (220 mg, 1.16 mmol), cesium carbonate (760 mg, 2.33 mmol) and N,N-dimethyl-1,2-cyclohexanediamine (165 mg, 1.16 mmol) were added. The reaction mixture was stirred at 110° C. for 12 hours, and water (10 ml) and aqueous ammonia (5 ml) were added. The mixture was extracted with ethyl acetate (20 mL×3). The combined organic layer was washed with saturated brine (20 mL), dried over anhydrous sodium sulfate, filtered and concentrated. The crude product was separated by thin layer chromatography to give the target compound 32-2.

32-2 (210 mg, 340.09 μmol) was dissolved in tetrahydrofuran (5 ml), methanol (5 ml) and water (5 ml), and lithium hydroxide monohydrate (150 mg, 3.57 mmol) was added. The reaction mixture was stirred at 20° C. for 12 hours. Water (10 ml) was added to the reaction mixture, which was then adjusted with 1 mol/L of diluted hydrochloric acid to pH=6, and then extracted with ethyl acetate (20 ml×3). The combined organic phase was washed with saturated brine (20 mL), dried over anhydrous sodium sulfate, filtered and concentrated. The crude product was separated by high performance liquid chromatography (formic acid) to give the target compound 32. $^1$H NMR (400 MHz, METHANOL-d4) δ=8.26 (d, J=9.0 Hz, 1H), 7.63 (s, 1H), 7.52-7.38 (m, 3H), 7.14-7.06 (m, 1H), 6.71 (d, J=2.5 Hz, 1H), 6.47 (dd, J=2.8, 8.8 Hz, 1H), 6.17 (d, J=9.0 Hz, 1H), 4.83-4.79 (m, 2H), 4.14 (s, 3H), 3.06-2.98 (m, 2H), 2.82-2.73 (m, 2H), 2.29 (quin, J=6.7 Hz, 1H), 1.21-1.13 (m, 4H).

Example 33: Compound 33

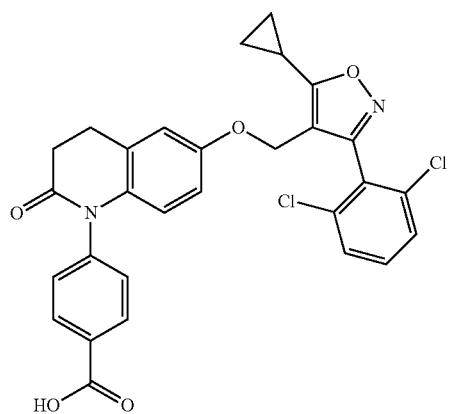 [SMILES: O=C(O)c1ccc(N2C(=O)CCc3cc(OCc4c(-c5c(Cl)cccc5Cl)noc4C4CC4)ccc32)cc1]

Synthetic Route:

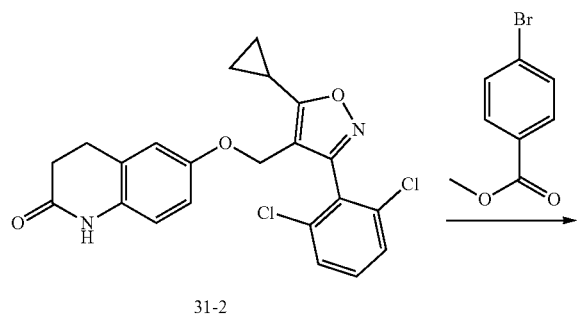

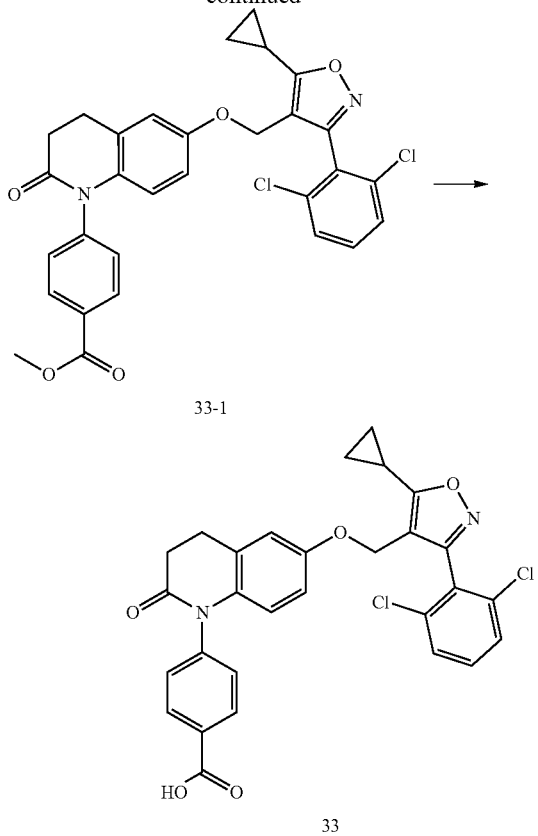

To a solution of 31-2 (300 mg, 698.82 μmol) and methyl p-bromobenzoate (301 mg, 1.40 mmol) in toluene (5 mL), cuprous iodide (133 mg, 698.82 μmol), potassium phosphate (445 mg, 2.10 mmol) and trans-N,N-dimethylcyclohexyl-1,2-diamine (274 mg, 698.82 μmol) were added. The reaction mixture was stirred at 100° C. for 14 hours. After the reaction was completed, the mixture was filtered and concentrated, and water (30 ml) was added to the concentrated solution. The mixture was extracted with ethyl acetate (30 mL) for 3 times. The combined organic layer was washed with saturated brine (30 mL) and water (30 mL) in order, and then dried over anhydrous sodium sulfate, filtered and concentrated to give a crude product 33-1.

To a solution of 33-1 (400 mg, 709.94 μmol) in tetrahydrofuran (2 ml), methanol (2 ml) and water (2 ml), lithium hydroxide monohydrate (149 mg, 3.55 mmol) was added. The reaction mixture was stirred at 25° C. for 0.5 hours. After the reaction was completed, water (45 ml) was added to the mixture, which was then adjusted with 1 M of hydrochloric acid to pH=5, and extracted with ethyl acetate (50 ml) for 3 times. The combined organic phase was washed with saturated brine (50 mL) and water (50 mL) respectively, dried over anhydrous sodium sulfate, filtered and concentrated to obtain a crude product. The crude product was separated by preparative high performance liquid chromatography to give the target compound 33. $^1$H NMR (400 MHz, CHLOROFORM-d) δ=8.22 (d, J=8.5 Hz, 2H), 7.47-7.39 (m, 2H), 7.38-7.32 (m, 3H), 6.68 (d, J=2.3 Hz, 1H), 6.51 (dd, J=2.9, 8.9 Hz, 1H), 6.24 (d, J=9.0 Hz, 1H), 4.78 (s, 2H), 3.01 (br t, J=6.9 Hz, 2H), 2.85-2.79 (m, 2H), 2.19-2.15 (m, 1H), 1.34-1.28 (m, 2H), 1.19-1.12 (m, 2H). MS m/z: 548.9 [M+H]$^+$.

Example 34: Compound 34

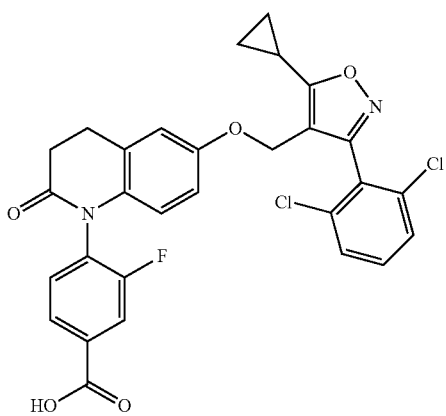 [SMILES: O=C(O)c1ccc(N2C(=O)CCc3cc(OCc4c(-c5c(Cl)cccc5Cl)noc4C4CC4)ccc32)c(F)c1]

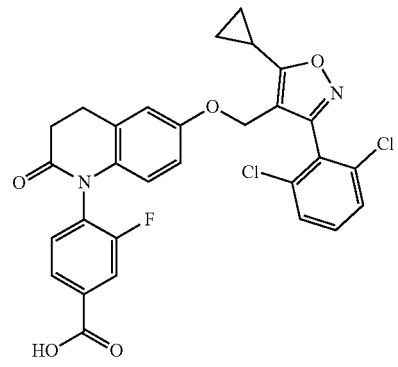
34

Synthetic Route:

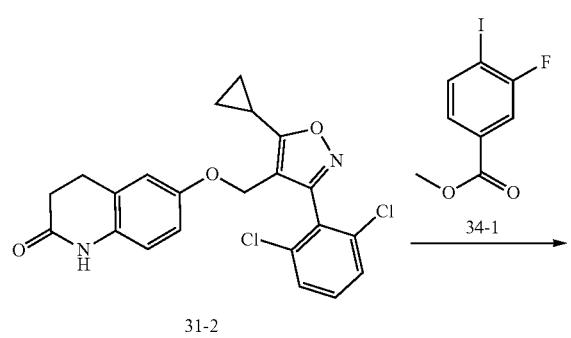

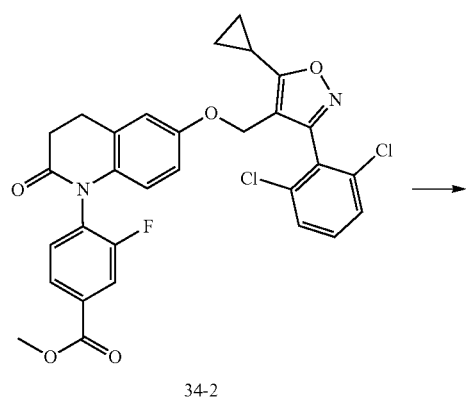
34-2

To a solution of 31-2 (200 mg, 465.88 μmol) and 34-1 (260 mg, 931.76 μmol) in toluene (5 mL), cuprous iodide (89 mg, 465.88 μmol), cesium carbonate (304 mg, 931.76 μmol) and trans-N,N-dimethylcyclohexyl-1,2-diamine (183 mg, 465.88 μmol) were added. The reaction mixture was stirred at 100° C. for 14 hours. After the reaction was completed, the mixture was filtered and concentrated, and water (30 ml) was added to the concentrated solution. The mixture was extracted with ethyl acetate (30 mL) for 3 times. The combined organic layer was washed with saturated brine (30 mL) and water (30 mL) in order, and then dried over anhydrous sodium sulfate, filtered and concentrated to give a crude product. The crude product was separated by preparative thin layer chromatography (petroleum ether:ethyl acetate=2:1) to give the target compound 34-2. MS m/z: 581.1 [M+H]$^+$.

To a solution of 34-2 (45 mg, 77.40 μmol) in tetrahydrofuran (2 ml), methanol (2 ml) and water (2 ml), lithium hydroxide monohydrate (16 mg, 386.98 μmol) was added. The reaction mixture was stirred at 25° C. for 0.5 hours. After the reaction was completed, water (45 ml) was added to the mixture, which was then adjusted with 1 M of hydrochloric acid to pH=5, and extracted with ethyl acetate (50 ml) for 3 times. The combined organic phase was washed with saturated brine (50 mL) and water (50 mL) respectively, dried over anhydrous sodium sulfate, filtered and concentrated to obtain a crude product. The crude product was separated by preparative high performance liquid chromatography to give the target compound 34. $^1$H NMR (400 MHz, CHLOROFORM-d) δ=7.98 (br s, 2H), 7.40 (br s, 4H), 6.84-6.40 (m, 2H), 6.24 (br s, 1H), 4.79 (br s, 2H), 3.24-2.65 (m, 4H), 2.19-2.01 (m, 1H), 1.44-1.02 (m, 4H)

Example 35: Compound 35

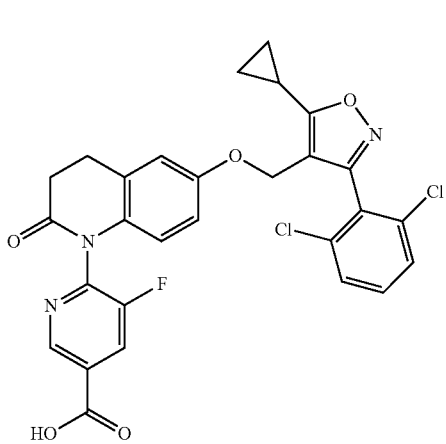 [SMILES: O=C(O)c1cnc(N2C(=O)CCc3cc(OCc4c(-c5c(Cl)cccc5Cl)noc4C4CC4)ccc32)c(F)c1]

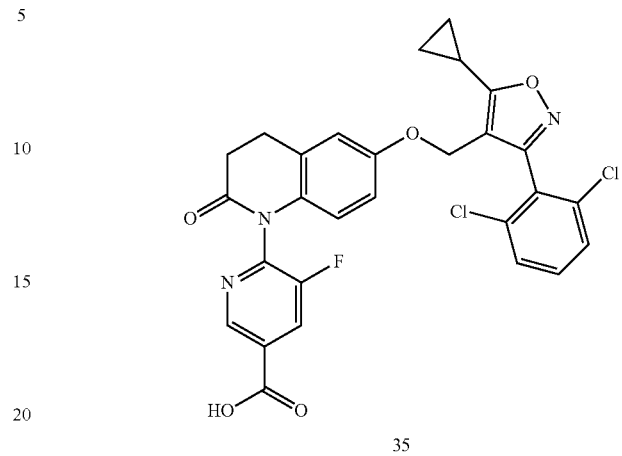

35

Synthetic Route:

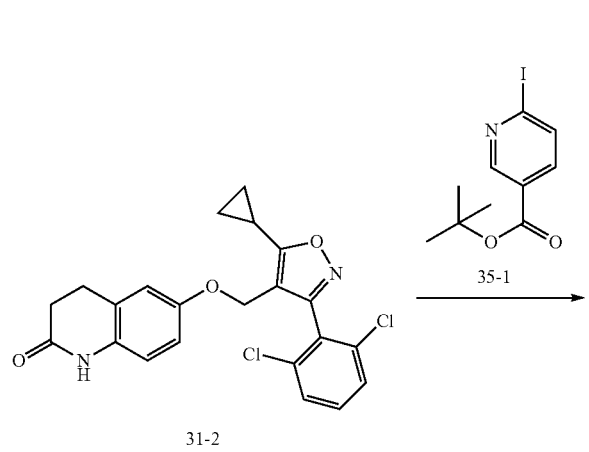

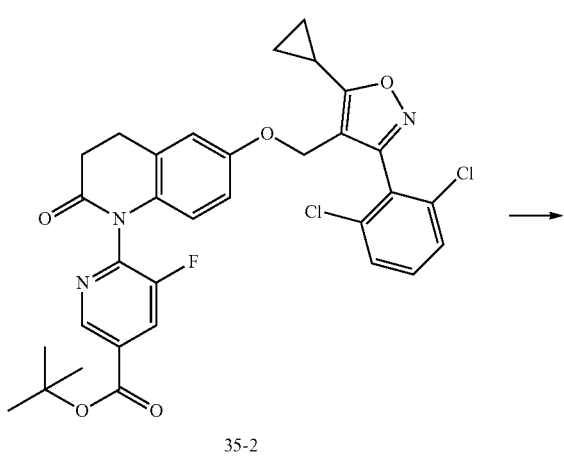

To a solution of 31-2 (200 mg, 465.88 μmol) and 35-1 (162 mg, 698.82 μmol) in toluene (5 mL), cuprous iodide (89 mg, 465.88 μmol), cesium carbonate (304 mg, 931.76 μmol) and trans-N,N-dimethylcyclohexyl-1,2-diamine (183 mg, 465.88 μmol) were added. The reaction mixture was stirred at 100° C. for 14 hours. After the reaction was completed, the mixture was filtered and concentrated, and water (30 ml) was added to the concentrated solution. The mixture was extracted with ethyl acetate (30 mL) for 3 times. The combined organic layer was washed with saturated brine (30 mL) and water (30 mL) in order, and then dried over anhydrous sodium sulfate, filtered and concentrated to give a crude product. The crude product was separated by thin layer chromatography (petroleum ether: ethyl acetate=1:1) to give the target compound 35-2. To a solution of 35-2 (50 mg, 80.07 μmol) in dichloromethane (6 ml), trifluoroacetic acid (2 ml, 27.01 mmol) was added. The reaction mixture was stirred at 25° C. for 0.5 hours. The reaction mixture was concentrated, and water (20 ml) was added to the concentrated solution. The mixture was extracted with ethyl acetate (30 mL) for 3 times. The combined organic layer was washed with saturated brine (30 mL) and water (30 mL) respectively, and then dried over anhydrous sodium sulfate, filtered and concentrated to give a crude product. The crude product was separated by preparative high performance liquid chromatography to give the target compound 35. $^1$H NMR (400 MHz, METHANOL-d4) δ=9.00 (br s, 1H), 8.34 (br d, J=8.0 Hz, 1H), 7.63-7.33 (m, 3H), 6.77 (br s, 1H), 6.56 (br d, J=8.0 Hz, 1H), 6.20 (br d, J=8.3 Hz, 1H), 4.83-4.64 (m, 2H), 3.04 (br s, 2H), 2.80 (br s, 2H), 2.32 (br s, 1H), 1.20 (br d, J=5.3 Hz, 4H) MS m/z: 568.0 [M+H]$^+$

Example 36: Compound 36

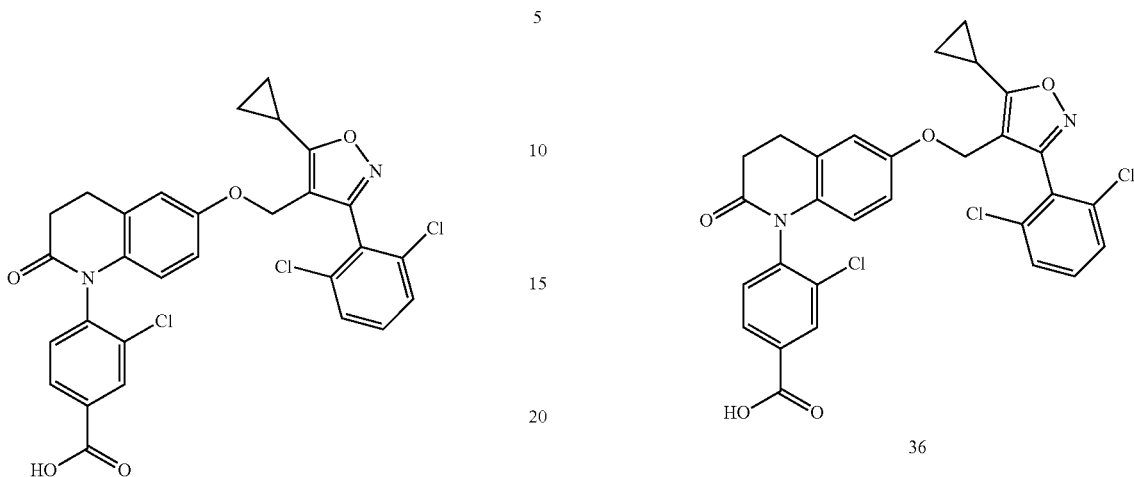

Synthetic Route:

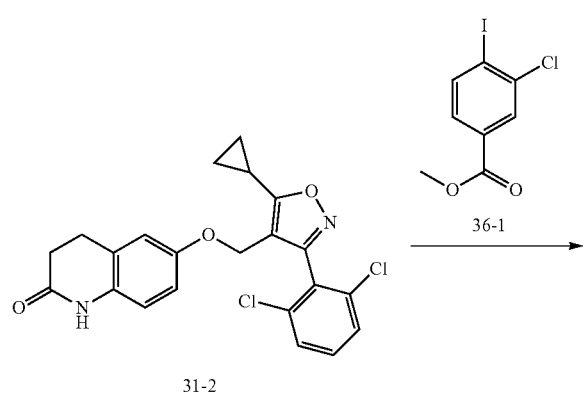

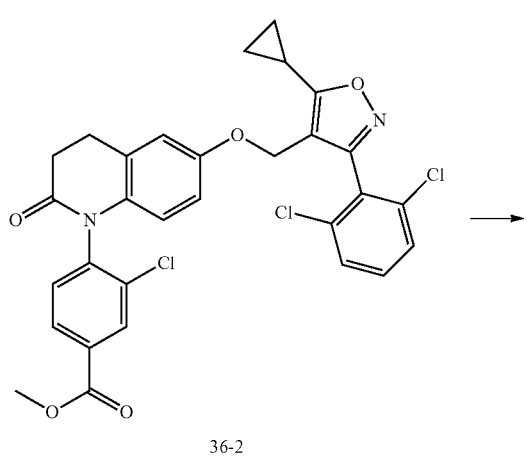

To a solution of 31-2 (200 mg, 465.88 μmol) and 36-1 (180 mg, 605.64 μmol) in toluene (5 mL), cuprous iodide (89 mg, 465.88 μmol), cesium carbonate (304 mg, 931.76 μmol) and trans-N,N-dimethylcyclohexyl-1,2-diamine (183 mg, 465.88 μmol) were added. The reaction mixture was stirred at 100° C. for 14 hours. After the reaction was completed, the mixture was filtered and concentrated, and water (30 ml) was added to the concentrated solution. The mixture was extracted with ethyl acetate (30 mL) for 3 times. The combined organic layer was washed with saturated brine (30 mL) and water (30 mL) in order, and then dried over anhydrous sodium sulfate, filtered and concentrated to give a crude product. The crude product was separated by preparative thin layer chromatography (petroleum ether:ethyl acetate=1:1) to give the target compound 36-2. MS m/z: 597.0 [M+H]$^+$.

To a solution of 36-2 (40 mg, 67.13 μmol) in tetrahydrofuran (2 ml), methanol (2 ml) and water (2 ml), lithium hydroxide monohydrate (3 mg, 67.13 μmol) was added. The reaction mixture was stirred at 25° C. for 14 hours. After the reaction was completed, water (30 ml) was added to the mixture, which was then adjusted with 1 M of hydrochloric acid to pH=5, and extracted with ethyl acetate (30 ml) for 3 times. The combined organic phase was washed with saturated brine (30 mL) and water (30 mL) respectively, dried over anhydrous sodium sulfate, filtered and concentrated to obtain a crude product. The crude product was separated by preparative chromatography to give the target compound 36. $^1$H NMR (400 MHz, METHANOL-d$_4$) δ=8.10 (br s, 2H), 7.59-7.40 (m, 4H), 6.74 (s, 1H), 6.53 (br d, J=7.5 Hz, 1H), 6.08 (br d, J=9.0 Hz, 1H), 4.77-4.50 (m, 1H), 3.12-2.94 (m, 2H), 2.84-2.72 (m, 2H), 2.40-2.27 (m, 1H), 1.20 (d, J=6.8 Hz, 4H)

Example 37: Compound 37

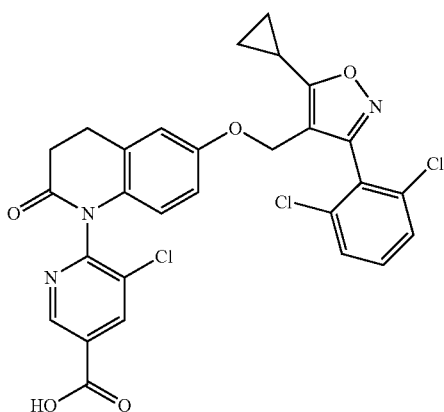 [SMILES: O=C(O)c1cnc(N2C(=O)CCc3cc(OCc4c(-c5c(Cl)cccc5Cl)noc4C4CC4)ccc32)c(Cl)c1]

Synthetic Route:

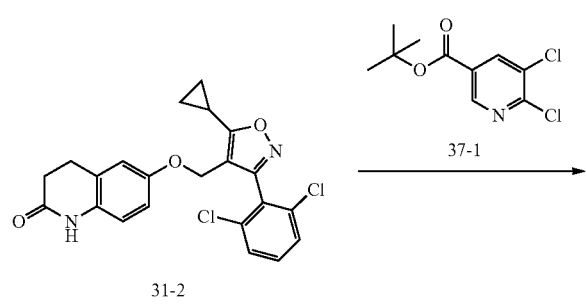

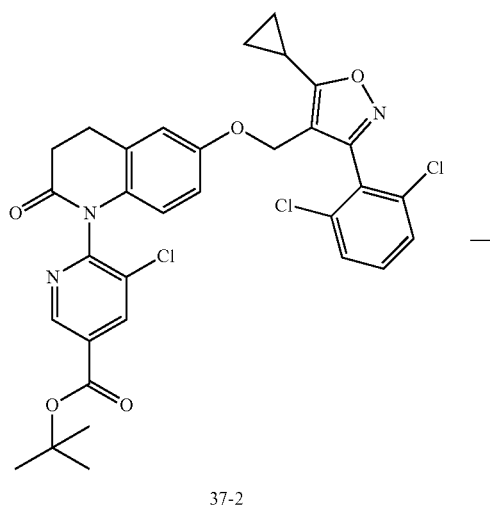

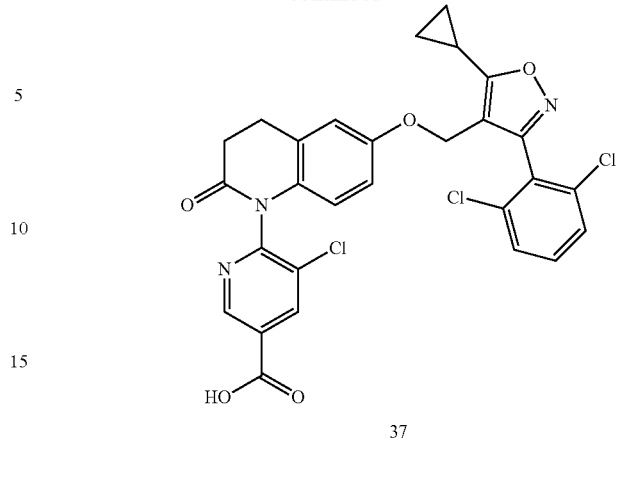

37-1 (289 mg, 1.16 mmol), Pd$_2$(dba)$_3$ (85 mg, 93 μmol), cesium carbonate (455 mg, 1.40 mmol) and BINAP (58 mg, 93 μmol) were added to a solution of 31-2 (200 mg, 0.47 mmol) in toluene (10 ml). Under nitrogen proteciton, the mixture was heated to 120° C. and stirred for 12 hours. After the reaction was completed, the reaction mixture was concentrated. The residue was purified by column chromatography (petroleum ether:ethyl acetate=30:1-3:1) to give the target compound 37-2.

At 25° C., trifluoroacetic acid (2 ml, 27.01 mmol) was added dropwise to a solution of 37-2 (138 mg, 0.22 mmol) in dichloromethane (10 ml), and the reaction mixture was stirred at 25° C. for 2 hours. After the reaction was completed, the reaction mixture was concentrated under reduced pressure. The residue was separated by high performance liquid chromatography (formic acid) to give the target compound 37. $^1$H NMR (400 MHz, CHLOROFORM-d) δ=9.00 (br s, 1H), 8.37 (br s, 1H), 7.28 (br s, 1H), 7.23-7.11 (m, 2H), 6.58 (br s, 1H), 6.39 (br d, J=7.3 Hz, 1H), 5.94 (br d, J=8.5 Hz, 1H), 4.63 (s, 2H), 2.93 (br d, J=6.3 Hz, 2H), 2.72 (br d, J=6.8 Hz, 2H), 2.02 (br s, 1H), 1.15 (br s, 2H), 1.01 (br d, J=6.3 Hz, 2H).

Example 38: Compound 38

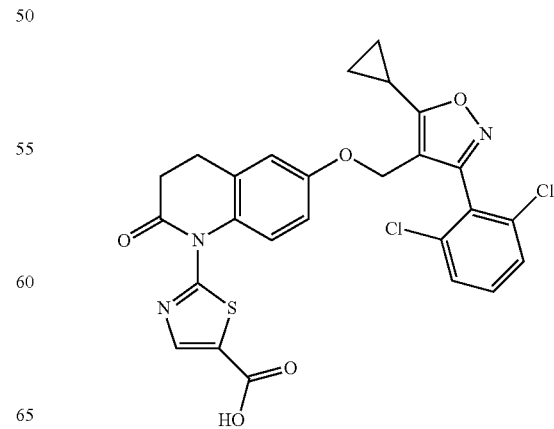

Synthetic Route:

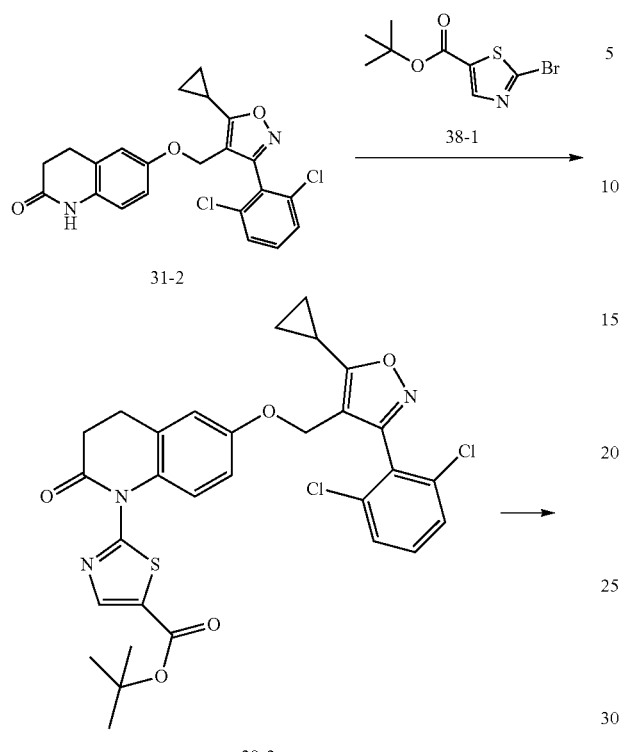
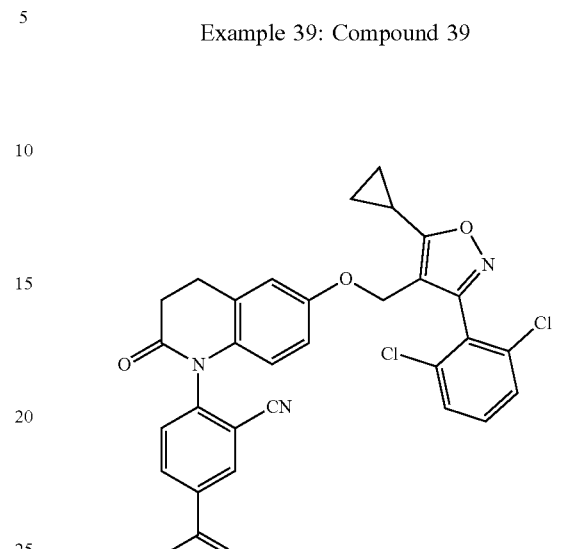

38-1 (123 mg, 0.47 mmol), Pd$_2$(dba)$_3$ (85 mg, 93 μmol), cesium carbonate (455 mg, 1.40 mmol) and BINAP (58 mg, 93 μmol) were added to a solution of 31-2 (200 mg, 0.47 mmol) in toluene (10 ml). Under nitrogen proteciton, the mixture was heated to 120° C. and stirred for 12 hours. After the reaction was completed, the reaction mixture was concentrated. The residue was purified by thin layer chromatography (petroleum ether:ethyl acetate=30:1-3:1) to give the target compound 38-.3.

At 25° C., trifluoroacetic acid (1.5 ml, 20.26 mmol) was added dropwise to a solution of 38-2 (100 mg, 0.16 mmol) in dichloromethane (10 ml), and the reaction mixture was stirred at 25° C. for 2 hours. After the reaction was completed, the reaction mixture was concentrated under reduced pressure. The residue was separated by high performance liquid chromatography (formic acid) to give the target compound 38. $^1$H NMR (400 MHz, CHLOROFORM-d) δ=8.22 (br s, 1H), 7.63 (br d, J=8.3 Hz, 1H), 7.45-7.29 (m, 3H), 6.83-6.62 (m, 2H), 4.80 (br s, 2H), 2.96-2.76 (m, 3H), 2.54 (br s, 1H), 2.16 (br s, 1H), 1.37-1.12 (m, 4H).

Example 39: Compound 39

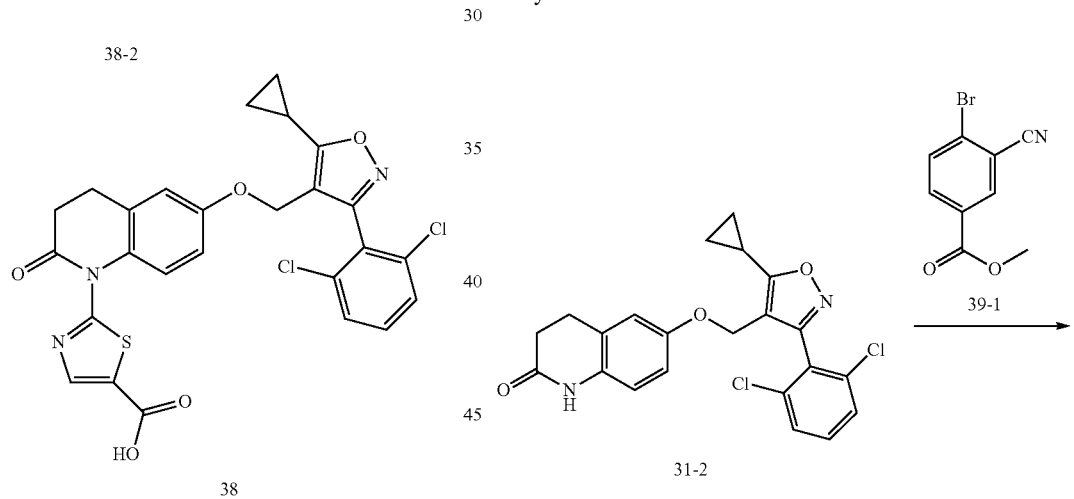

Synthetic Route:

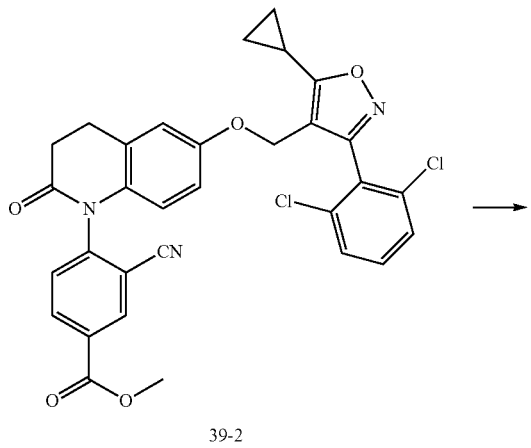

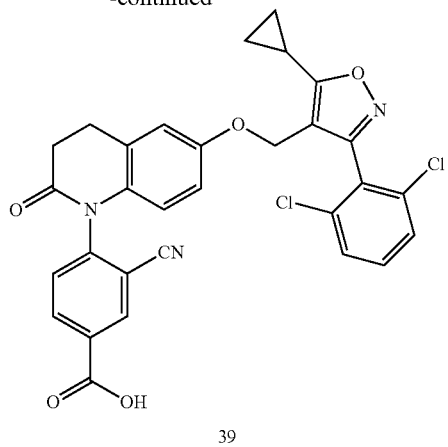

39

31-2 (100 mg, 0.23 mmol), Pd$_2$(dba)$_3$ (25 mg, 27 μmol), cesium carbonate (230 mg, 0.71 mmol) and BINAP (29 mg, 47 μmol) were added to a solution of 39-1 (116 mg, 0.48 mmol) in toluene (8 ml). Under nitrogen proteciton, the mixture was heated to 100° C. and stirred for 16 hours. After the reaction was completed, 20 ml water was added to the reaction mixture at 25° C., which was then extracted with ethyl acetate (20 mL×3). The organic phase was combined, washed with saturated brine (20 mL), dried over anhydrous sodium sulfate, filtered and concentrated under reduced pressure. The residue was purified by thin layer chromatography (petroleum ether:ethyl acetate=1:1) to give the target compound 39-2.

At 25° C., lithium hydroxide monohydrate (50 mg, 1.19 mmol) was added in batches to a solution of 39-2 (70 mg, 1.19 mmol) in tetrahydrofuran (5 mL), methanol (2 mL) and water (2). The mixture was stirred at 25° C. for 2 hours. After the reaction was completed, the reaction mixture was diluted with 30 mL water, adjusted with 1 N of hydrochloric acid to pH=3, and extracted with ethyl acetate (30 mL×3). The organic phase was combined, dried over anhydrous sodium sulfate, filtered and concentrated under reduced pressure. The residue was separated by high performance liquid chromatography (formic acid) to give the target compound 39. $^1$H NMR (400 MHz, CHLOROFORM-d) δ=8.50 (s, 1H), 8.41 (d, J=7.8 Hz, 1H), 7.63-7.31 (m, 4H), 6.73 (s, 1H), 6.54 (d, J=7.0 Hz, 1H), 6.11 (d, J=8.8 Hz, 1H), 4.79 (s, 2H), 3.17-2.79 (m, 4H), 2.22-2.11 (m, 1H), 1.35-1.26 (m, 2H), 1.21-1.09 (m, 2H)

Example 40: Compound 40

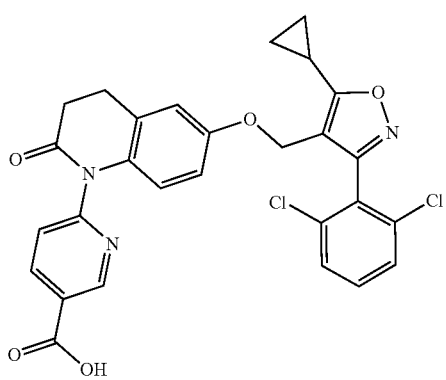 [SMILES: O=C(O)c1ccc(N2C(=O)CCc3cc(OCc4c(-c5c(Cl)cccc5Cl)noc4C4CC4)ccc32)nc1]

Synthetic Route:

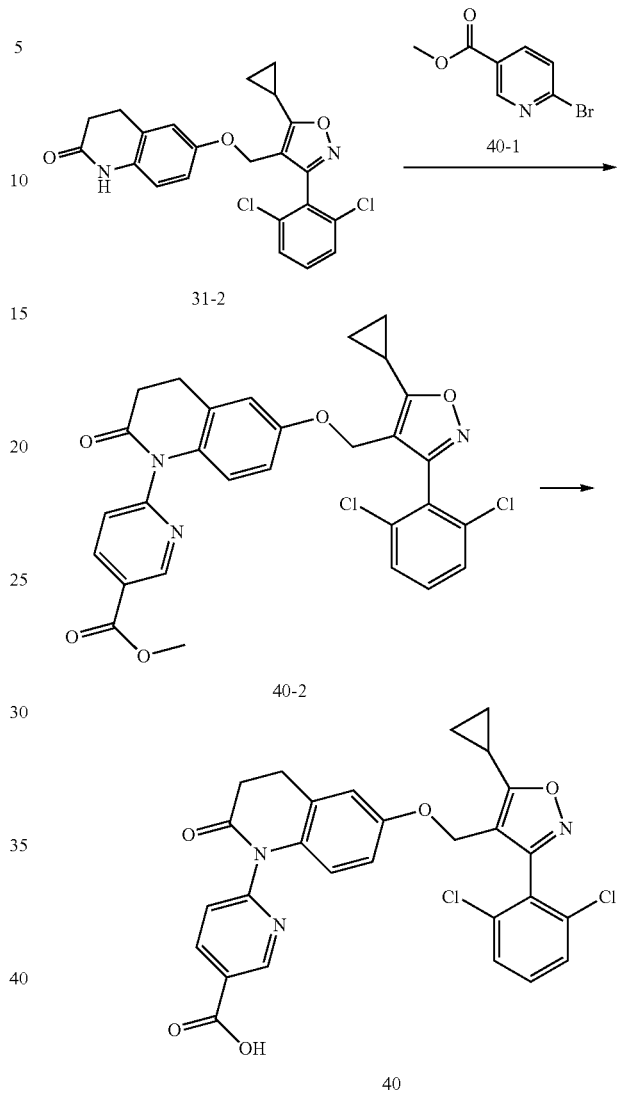

To a solution of 31-2 (200 mg, 465.88 μmol) and 40-1 (150 mg, 694.34 μmol) in toluene (10 mL), cuprous iodide (90 mg, 472.56 μmol), cesium carbonate (300 mg, 920.76 μmol) and trans-N,N-dimethylcyclohexyl-1,2-diamine (70 mg, 492.12 μmol) were added. The reaction mixture was stirred at 110° C. for 12 hours. After the reaction was completed, water (20 ml) and aqueous ammonia (3 ml) were added to the mixture. The mixture was extracted with ethyl acetate (20 mL) for 3 times. The combined organic phase was washed with saturated brine (20 mL) and then dried over anhydrous sodium sulfate, filtered and concentrated to give a crude product. The crude product was separated by thin layer chromatography (petroleum ether:ethyl acetate=1:1) to give the target compound 40-2. MS m/z: 564.1 [M+H]$^+$.

To a solution of 40-2 (100 mg, 177.17 μmol) in dichloromethane (5 ml), trimethyltin hydroxide (100 mg, 553.03 μmol) was added. The reaction mixture was stirred at 70° C. for 2 hours. After the reaction was completed, water (20 ml) was added. The mixture was extracted with dichloromethane (20 mL) for 3 times. The combined organic phase was washed with saturated brine (20 mL) and then dried over anhydrous sodium sulfate, filtered and concentrated to give a crude product. The crude product was separated by preparative chromatography to give the target compound 40. $^1$H NMR (400 MHz, METHANOL-d$_4$) δ=9.12 (br s, 1H), 8.54 (br d, J=5.3 Hz, 1H), 7.64-7.38 (m, 4H), 6.73 (br s, 1H), 6.52 (br d, J=7.0 Hz, 1H), 6.12 (br d, J=7.5 Hz, 1H), 4.83-4.79 (m, 2H), 3.00 (br s, 2H), 2.75 (br s, 2H), 2.30 (br s, 1H), 1.17 (br s, 4H). MS m/z: 550.0 [M+H]$^+$.

Example 41: Compound 41

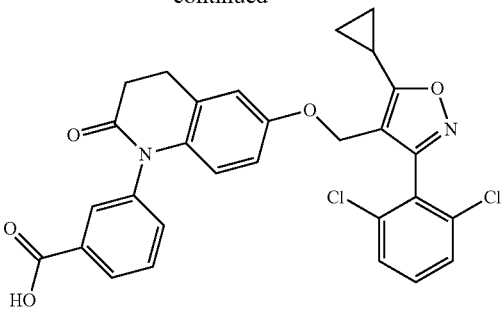

41

Synthetic Route:

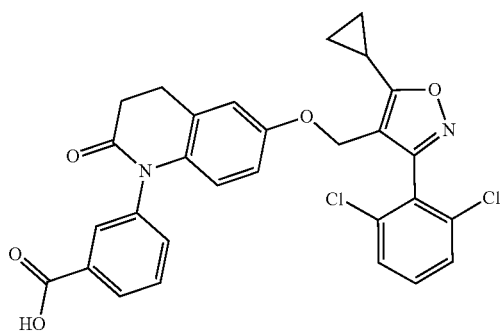 [SMILES: O=C(O)c1cccc(N2C(=O)CCc3cc(OCc4c(-c5c(Cl)cccc5Cl)noc4C4CC4)ccc32)c1]

31-2

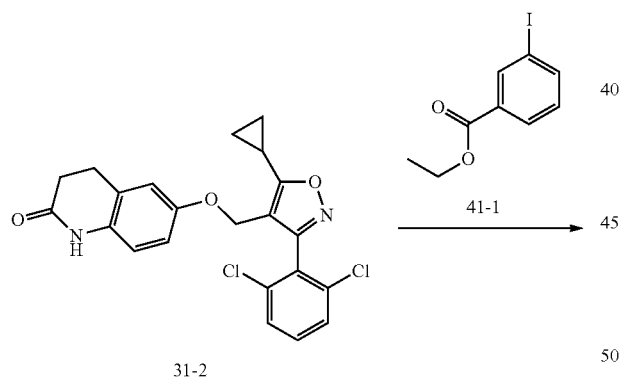

41-2

To a solution of 31-2 (200 mg, 465.88 μmol) and 41-1 (190 mg, 688.23 μmol) in toluene (5 mL), cuprous iodide (90 mg, 472.56 μmol), cesium carbonate (300 mg, 920.76 μmol) and trans-N,N-dimethylcyclohexyl-1,2-diamine (70 mg, 492.12 μmol) were added. The reaction mixture was stirred at 110° C. for 12 hours. After the reaction was completed, water (10 ml) and aqueous ammonia (3 ml) were added to the mixture. The mixture was extracted with ethyl acetate (20 mL) for 3 times. The combined organic phase was washed with saturated brine (30 mL) and then dried over anhydrous sodium sulfate, filtered and concentrated to give a crude product. The crude product was separated by thin layer chromatography (petroleum ether:ethyl acetate=2:1) to give the target compound 41-2. MS m/z: 577.1 [M+H]$^+$.

To a solution of 41-2 (200 mg, 346.35 mmol) in tetrahydrofuran (5 ml) and water (5 ml), lithium hydroxide monohydrate (145 mg, 3.46 mmol) was added. The reaction mixture was stirred at 20° C. for 12 hours. After the reaction was completed, water (10 ml) was added to the mixture, which was then adjusted with 1 M of hydrochloric acid to pH=6, and extracted with ethyl acetate (20 ml) for 3 times. The combined organic phase was washed with saturated brine (20 mL), dried over anhydrous sodium sulfate, filtered and concentrated to obtain a crude product. The crude product was separated by preparative chromatography to give the target compound 41. $^1$H NMR (400 MHz, METHANOL-d$_4$) δ=8.08 (br d, J=7.0 Hz, 1H), 7.84 (br s, 1H), 7.69-7.55 (m, 1H), 7.46 (br d, J=11.0 Hz, 4H), 6.70 (br s, 1H), 6.48 (br d, J=8.0 Hz, 1H), 6.13 (br d, J=8.5 Hz, 1H), 4.83-4.80 (m, 2H), 2.99 (br s, 2H), 2.74 (br s, 2H), 2.29 (br s, 1H), 1.17 (br d, J=6.0 Hz, 4H). MS m/z: 549.0 [M+H]$^+$.

Example 42: Compound 42

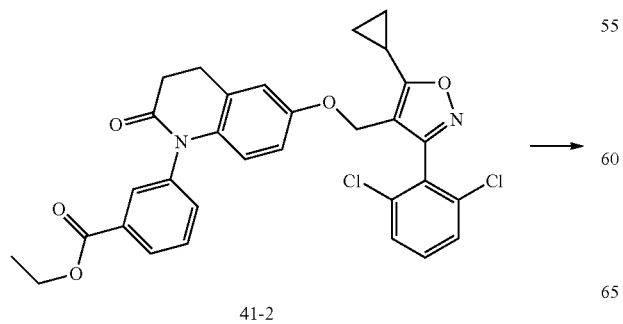

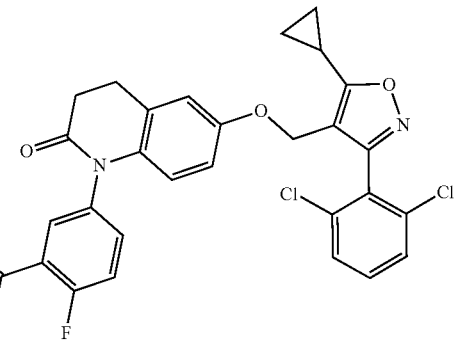

141

Synthetic Route:

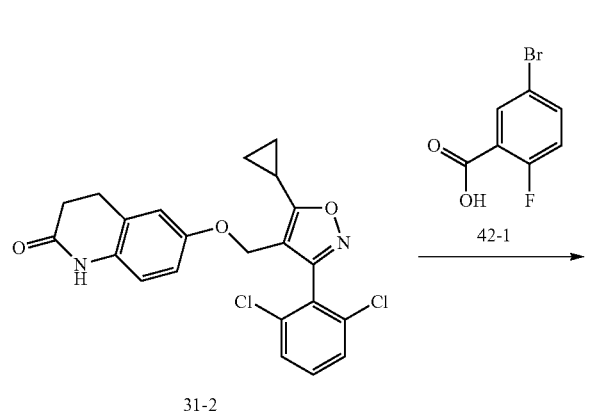

142

Example 43: Compound 43

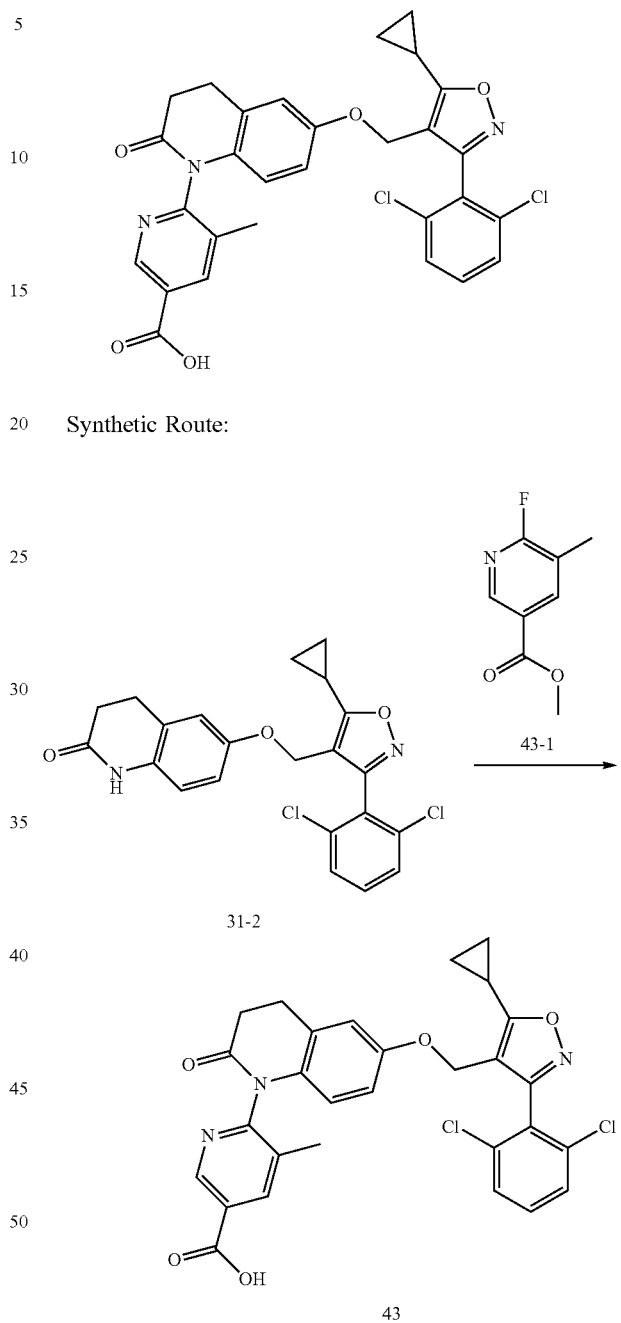

To a solution of 31-2 (200 mg, 465.88 µmol) and 42-1 (155 mg, 707.74 µmol) in toluene (5 mL), cuprous iodide (90 mg, 472.56 µmol), cesium carbonate (300 mg, 920.75 µmol) and trans-N,N-dimethylcyclohexyl-1,2-diamine (70 mg, 492.12 µmol) were added. The reaction mixture was stirred at 110° C. for 12 hours. After the reaction was completed, water (20 ml) and aqueous ammonia (3 ml) were added to the mixture. The mixture was extracted with ethyl acetate (30 mL) for 3 times. The combined organic phase was washed with saturated brine (20 mL) and then dried over anhydrous sodium sulfate, filtered and concentrated to give a crude product. The crude product was separated by preparative chromatography to give the target compound 42. $^1$H NMR (400 MHz, METHANOL-$d_4$) δ=7.76 (br s, 1H), 7.54-7.41 (m, 4H), 7.40-7.30 (m, 1H), 6.70 (br s, 1H), 6.50 (br d, J=8.0 Hz, 1H), 6.17 (br d, J=8.5 Hz, 1H), 4.84-4.83 (m, 2H), 2.98 (br s, 2H), 2.75 (br d, J=6.5 Hz, 2H), 2.30 (br s, 1H), 1.17 (br s, 4H). MS m/z: 567.0 [M+H]$^+$ To a solution of 31-2 (200 mg, 465.88 µmol) and 43-1 (120 mg, 709.42 µmol) in N,N-dimethylformamide (5 ml), cesium carbonate (455 mg, 1.40 mmol) was added. The reaction mixture was stirred at 110° C. for 12 hours. After the reaction was completed, the mixture was added with water (20 ml), adjusted with 1 M of hydrochloric acid to pH=6, and extracted with ethyl acetate (30 ml) for 3 times. The combined organic phase was washed with saturated brine (20 mL), dried over anhydrous sodium sulfate, filtered and concentrated to obtain a crude product. The crude product was separated by preparative chromatography to give the target compound 43. $^1$H NMR (400 MHz, METHA- NOL-d$_4$) δ=8.98 (s, 1H), 8.44 (s, 1H), 7.52-7.48 (m, 2H), 7.47-7.41 (m, 1H), 6.75 (d, J=2.0 Hz, 1H), 6.52 (dd, J=2.8, 8.8 Hz, 1H), 5.98 (d, J=8.5 Hz, 1H), 4.84-4.84 (m, 2H), 3.12-2.98 (m, 2H), 2.82-2.73 (m, 2H), 2.30 (td, J=6.8, 13.6 Hz, 1H), 2.18 (s, 3H), 1.22-1.14 (m, 4H). MS m/z: 564.0 [M+H]$^+$.

Example 44: Compound 44

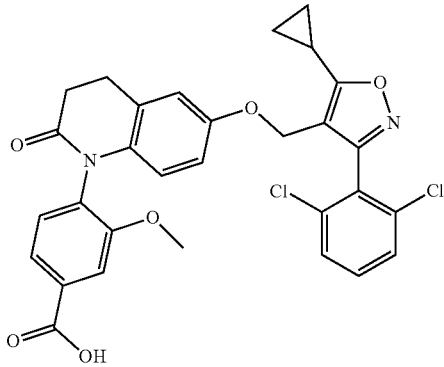 [SMILES: COc1cc(C(=O)O)ccc1N1C(=O)CCc2cc(OCc3c(-c4c(Cl)cccc4Cl)noc3C3CC3)ccc21]

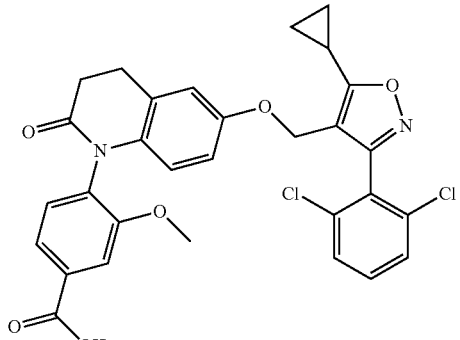

44

Synthetic Route:

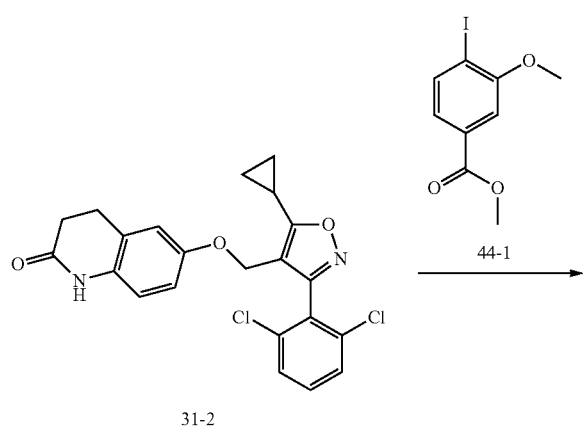

31-2

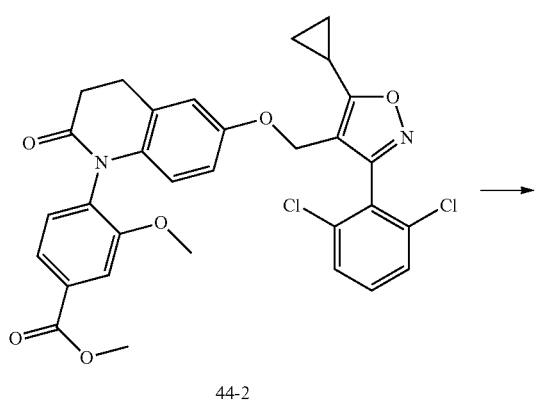

44-2

To a solution of 31-2 (200 mg, 465.88 μmol) and 44-1 (200 mg, 684.77 μmol) in toluene (5 mL), cuprous iodide (90 mg, 472.56 μmol), cesium carbonate (300 mg, 920.75 μmol) and trans-N,N-dimethylcyclohexyl-1,2-diamine (70 mg, 492.12 μmol) were added. The reaction mixture was stirred at 110° C. for 12 hours. After the reaction was completed, water (20 ml) was added to the mixture. The mixture was extracted with ethyl acetate (30 mL) for 3 times. The combined organic phase was washed with saturated brine (30 mL) and then dried over anhydrous sodium sulfate, filtered and concentrated to give a crude product. The crude product was separated by thin layer chromatography (petroleum ether:ethyl acetate=1:1) to give the target compound 44-2. MS m/z: 593.0 [M+H].

To a solution of 44-2 (40 mg, 67.40 μmol) in tetrahydrofuran (2 ml), methanol (2 ml) and water (5 ml), lithium hydroxide monohydrate (30 mg, 714.91 μmol) was added. The reaction mixture was stirred at 25° C. for 12 hours. After the reaction was completed, water (20 ml) was added to the mixture, which was then adjusted with 1 M of hydrochloric acid to pH=6, and extracted with ethyl acetate (30 ml) for 3 times. The combined organic phase was washed with saturated brine (20 mL), dried over anhydrous sodium sulfate, filtered and concentrated to obtain a crude product. The crude product was separated by preparative chromatography to give the target compound 44. $^1$H NMR (400 MHz, METHANOL-d$_4$) δ=7.84-7.69 (m, 2H), 7.53-7.38 (m, 3H), 7.22 (br d, J=7.5 Hz, 1H), 6.68 (br s, 1H), 6.47 (br d, J=8.5 Hz, 1H), 6.11 (d, J=8.5 Hz, 1H), 4.83 (br s, 2H), 3.78 (s, 3H), 3.04-2.92 (m, 2H), 2.78-2.65 (m, 2H), 2.35-2.22 (m, 1H), 1.17 (br d, J=6.5 Hz, 4H). MS m/z: 579.2 [M+H]$^+$.

Example 45: Compound 45

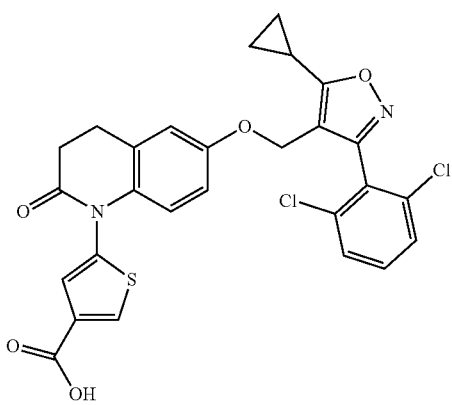 [SMILES: O=C(O)c1csc(N2C(=O)CCc3cc(OCc4c(-c5c(Cl)cccc5Cl)noc4C4CC4)ccc32)c1]

Synthetic Route:

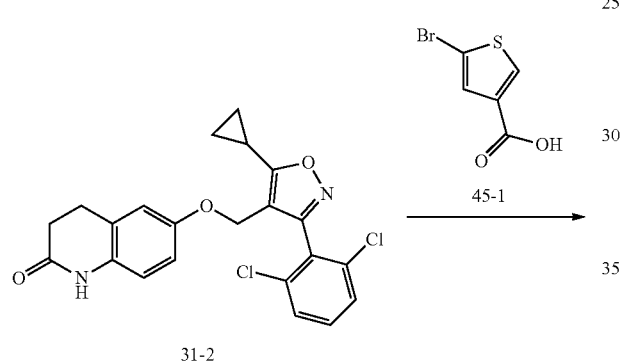

31-2 (200 mg, 0.46 mmol) and 45-1 (115 mg, 0.55 mmol) were dissolved in toluene (5 ml), and cuprous iodide (90 mg, 0.47 mmol), trans-N N-dimethylcyclohexyl-1,2-diamine (67 mg, 0.47 mmol) and cesium carbonate (450 mg, 1.38 mmol) were added. The reaction mixture was stirred at 110° C. for 14 hours under nitrogen atmosphere. The system was adjusted with 1 molar hydrochloric acid to pH=3. The system was extracted with ethyl acetate (30 mL×2). The organic phase was washed with saturated brine (50 mL×1). The organic phase was dried over anhydrous sodium sulfate, filtered and concentrated. The crude product was separated by preparative thin layer chromatography (petroleum ether: ethyl acetate=1:1) and high performance liquid chromatography (formic acid) to give the target compound 45. $^1$H NMR (400 MHz, METHANOL-$d_4$) δ=8.21 (s, 1H), 7.55-7.39 (m, 3H), 7.29 (br s, 1H), 6.69 (d, J=2.5 Hz, 1H), 6.63-6.46 (m, 2H), 4.91-4.89 (s, 2H), 3.02-2.92 (m, 2H), 2.79-2.73 (m, 2H), 2.31 (quin, J=6.8 Hz, 1H), 1.20-1.13 (m, 4H)

Example 46: Compound 46

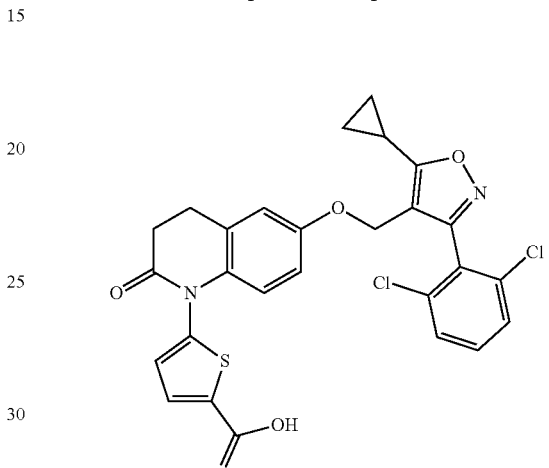

Synthetic Route:

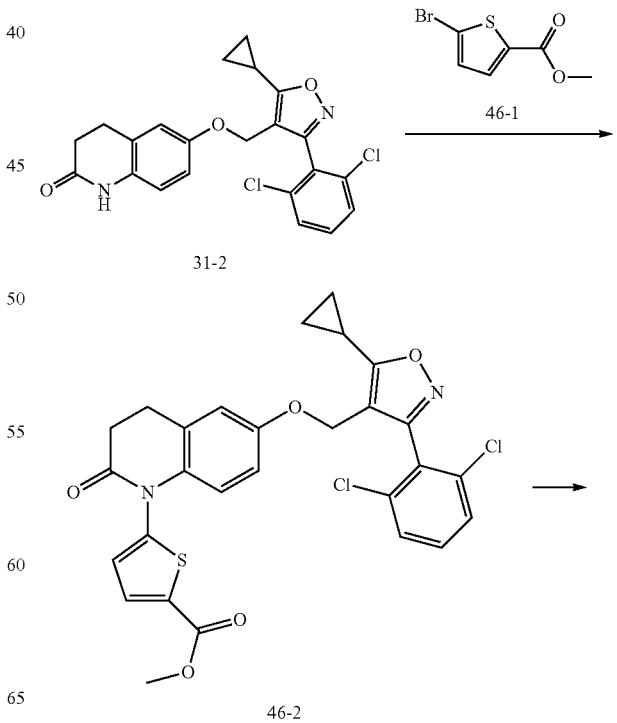

147
-continued

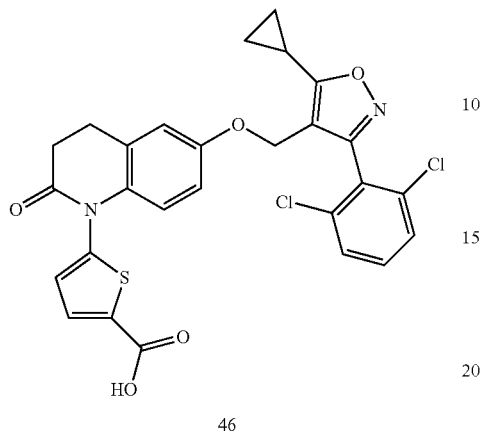

46

148
Example 47: Compound 47

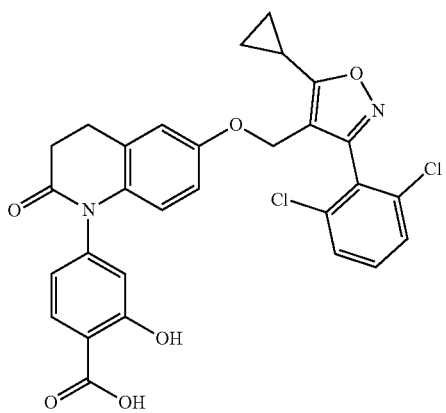 [SMILES: O=C(O)c1ccc(N2C(=O)CCc3cc(OCc4c(-c5c(Cl)cccc5Cl)noc4C4CC4)ccc32)cc1O]

Synthetic Route:

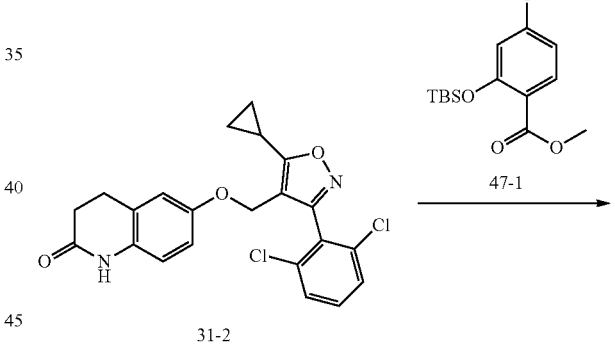

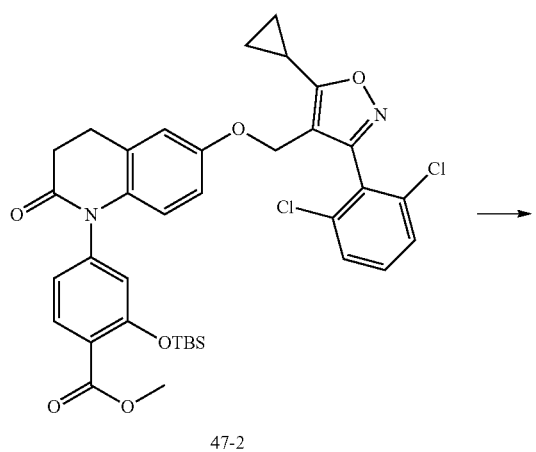

31-2 (200 mg, 0.46 mmol) and 46-1 (123 mg, 0.55 mmol) were dissolved in toluene (5 mL), and cuprous iodide (90 mg, 0.47 mmol), (1S, 2S))-(+)-1,2-cyclohexanediamine (56 mg, 0.49 mmol) and cesium carbonate (152 mg, 0.46 mmol) were added. The reaction mixture was stirred at 100° C. for 16 hours under a nitrogen atmosphere. Water (50 ml) and a 25% aqueous ammonia solution (1 mL) were added to the reaction mixture. The system was extracted with ethyl acetate (50 mL×2). The organic phase was washed with saturated brine (50 mL×1). The organic phase was dried over anhydrous sodium sulfate, filtered and concentrated. The crude product was separated by preparative thin layer chromatography (petroleum ether:ethyl acetate=3:2) to give the target compound 46-2.

To a solution of 46-2 (80 mg, 0.14 mmol) in tetrahydrofurane (0.28 mL), aqueous solution of sodium hydroxide (1 mol/L, 0.28 mL) was added. The reaction mixture was stirred at 25° C. for 3 hours. The system was adjusted with 1 mol of hydrochloric acid to pH=3. The system was extracted with ethyl acetate (30 mL×2). The organic phase was washed with saturated brine (50 mL×1). The organic phase was dried over anhydrous sodium sulfate, filtered and concentrated. The crude product was separated by preparative thin layer chromatography (petroleum ether:ethyl acetate=1:1) and separated by high performance liquid chromatography (formic acid) to give the title compound 46. $^1$H NMR (400 MHz, METHANOL-$d_4$) δ=7.72 (d, J=4.0 Hz, 1H), 7.54-7.39 (m, 3H), 6.97 (d, J=4.0 Hz, 1H), 6.70 (d, J=2.0 Hz, 1H), 6.62-6.52 (m, 2H), 4.93-4.89 (m, 2H), 3.00-2.92 (m, 2H), 2.79-2.70 (m, 2H), 2.31 (quin, J=6.7 Hz, 1H), 1.19 (d, J=7.0 Hz, 4H).

-continued

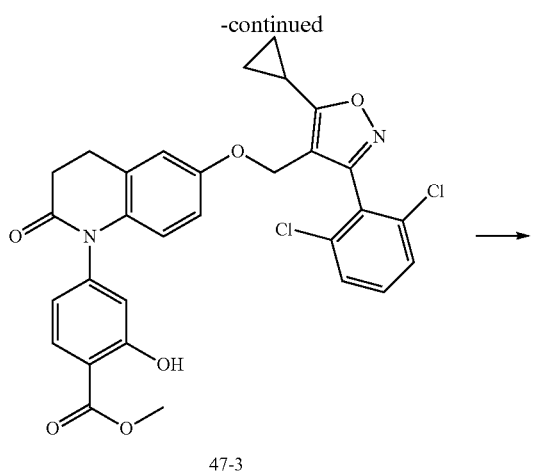

47-3

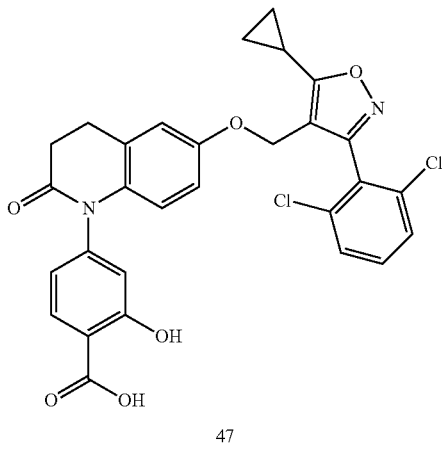

47

31-2 (200 mg, 0.46 mmol) and 47-1 (270 mg, 0.69 mmol) were dissolved in toluene (5 mL), and cuprous iodide (90 mg, 0.46 mmol), (1S, 2S))-(+)-1,2-cyclohexanediamine (56 mg, 0.49 mmol) and cesium carbonate (303 mg, 0.93 mmol) were added. The reaction mixture was stirred at 110° C. for 2.5 hours under a nitrogen atmosphere. Water (50 ml) and a 25% aqueous ammonia solution (0.5 mL) were added to the reaction mixture. The system was extracted with ethyl acetate (50 mL×2). The organic phase was washed with saturated brine (50 mL×1). The organic phase was dried over anhydrous sodium sulfate, filtered and concentrated. The crude product was separated by preparative thin layer chromatography (petroleum ether:ethyl acetate=3:2) to give the target compound 47-2. $^1$H NMR (400 MHz, CHLOROFORM-d) δ 7.86 (d, J=8.5 Hz, 1H), 7.42-7.38 (m, 2H), 7.36-7.29 (m, 1H), 6.83 (dd, J=2.0, 8.5 Hz, 1H), 6.76 (d, J=2.0 Hz, 1H), 6.65 (d, J=3.0 Hz, 1H), 6.49 (dd, J=2.8, 8.8 Hz, 1H), 6.26 (d, J=9.0 Hz, 1H), 4.77 (s, 2H), 3.89 (s, 3H), 3.03-2.88 (m, 2H), 2.83-2.71 (m, 2H), 2.23-2.11 (m, 1H), 1.32-1.28 (m, 2H), 1.18-1.10 (m, 2H), 1.00 (s, 9H), 0.21-0.19 (m, 6H).

To a solution of 47-2 (152 mg, 0.22 mmol) in tetrahydrofurane (5 mL), a solution of tetrabutylammonium fluoride in tetrahydrofuran (1 mol/L, 0.45 mL) was added. The reaction mixture was stirred at 25° C. for 15 min. Water (50 ml) was added to the mixture. The system was extracted with ethyl acetate (30 mL×2). The organic phase was washed with saturated brine (50 mL). The organic phase was dried over anhydrous sodium sulfate, filtered and concentrated to give the target compound 47-3.

47-3 (121 mg, 0.21 mmol) was dissolved in tetrahydrofuran (2 ml), methanol (2 ml) and water (2 ml), and lithium hydroxide monohydrate (88 mg, 2.1 mmol) was added. The reaction mixture was stirred at 25° C. for 2 hours. Water (10 ml) was added to the reaction mixture, which was then adjusted with 1 mole of diluted hydrochloric acid to pH=2, and then extracted with ethyl acetate (30 ml×2). The combined organic phase was washed with saturated brine (50 mL), dried over anhydrous sodium sulfate, filtered and concentrated. The crude product was separated by high performance liquid chromatography (formic acid) to give the target compound 47. $^1$H NMR (400 MHz, CHLOROFORM-d) δ=11.05 (s, 1H), 7.81 (br d, J=8.5 Hz, 1H), 7.44-7.29 (m, 3H), 6.85 (s, 1H), 6.77-6.63 (m, 2H), 6.51 (br d, J=9.0 Hz, 1H), 6.32 (d, J=8.5 Hz, 1H), 4.77 (s, 2H), 3.00 (br t, J=7.0 Hz, 2H), 2.87-2.79 (m, 2H), 2.15 (br s, 1H), 1.29 (br s, 2H), 1.14 (br d, J=8.0 Hz, 2H).

Biological Activity Test

FXR Biochemical Experiment

Experiment Objectives:

To test the effect of the compound on the activation of the FXR binding reaction by a Homogenous Proximity Luminescent Amplified Assay (alphascreen).

Experimental Materials:

1. Protein: glutathione-S-transferase-labeled FXR human protein (Invitrogen)
2. Coactivator: biotin-labeled steroid receptor coactivator (Anaspec)
3. Detection reagent: Homogenous Proximity Luminescent Amplified Assay (alphascreen) detection kit (PerkinElmer)

Experimental Method:

1. Dilution of compounds: The test compound was prepared as a 40 μM DMSO solution, which was then diluted 3-fold to 10 concentration points. The reference compound was prepared as a 400 μM DMSO solution, and then was 1.5-fold diluted to 10 concentration points. The diluted DMSO solution was added to the micro-wells of a 384-well plate at a volume of 150 nl per well.
2. Glutathione-S-transferase-labeled FXR human protein and biotin-labeled steroid receptor coactivator were prepared to a mixed solution at a concentration of 0.4 nM and 30 nM, respectively. The mixed solution was added to the micro-wells of the 384-well plate at a volume of 15 μL per well, and incubated for 1 hour at room temperature.
3. The receptor pellet mixture in the Homogenous Proximity Luminescent Amplified Assay (alphascreen) assay kit was 125-fold diluted and added to the micro-wells of a 384-well plate at a volume of 7.5 μL per well. The experiment process was protected from light. It was incubated for 1 hour at room temperature.
4. The receptor pellet mixture in the Homogenous Proximity Luminescent Amplified Assay (alphascreen) assay kit was 125-fold diluted and added to the micro-wells of a 384-well plate at a volume of 7.5 μL per well. The experiment process was protected from light. It was incubated for 1 hour at room temperature.
5. EC50 test: Envision was used to excite at 680 nm and the absorption signal at 520-620 nm was read.
6. Data analysis: Data analysis was conducted using Prism 5.0 to calculate the $EC_{50}$ value of the activation effect of the compound. Ratio of the highest signal value of the compound to the highest signal value of the reference compound was determined to give the activation efficacy percent of the compound (Efficacy).

Table 1 Test results of the biochemical experiment

TABLE 1

| Tested samples | FXR enzyme activity | |
|---|---|---|
| Title compounds | EC$_{50}$ (μM) | Efficacy |
| Chenodeoxycholic acid | 16.21 | 100% |
| Compound 1 | 0.2 | 156% |
| Compound 2 | 0.29 | 155% |
| Compound 3 | 0.18 | 165% |
| Compound 4 | 0.20 | 256% |
| Compound 5 | 0.15 | 242% |
| Compound 6 | 0.1 | 169% |
| Compound 7 | 0.24 | 144% |
| Compound 8 | 0.82 | 35% |
| Compound 9 | 1.56 | 229% |
| Compound 10 | 1.03 | 312% |
| Compound 11 | 0.58 | 82% |
| Compound 12 | 1.76 | 33% |
| Compound 13 | 0.09 | 163% |
| Compound 14 | 0.20 | 136% |
| Compound 15 | 0.23 | 152% |
| Compound 16 | 3.39 | 151% |
| Compound 17 | 1.88 | 169% |
| Compound 18 | 0.66 | 142% |
| Compound 19 | 2.56 | 95% |
| Compound 20 | 0.83 | 169% |
| Compound 21 | 0.95 | 96% |
| Compound 22 | 0.66 | 200% |
| Compound 23 | 0.31 | 120% |
| Compound 24 | 0.61 | 124% |
| Compound 25 | 0.41 | 130% |
| Compound 26 | 6.43 | 21% |
| Compound 27 | 0.41 | 218% |
| Compound 28 | 0.65 | 186% |
| Compound 29 | 0.56 | 211% |
| Compound 30 | 1.53 | 228% |
| Compound 31 | 0.043 | 115% |
| Compound 32 | 0.041 | 117% |
| Compound 33 | 0.143 | 127% |
| Compound 34 | 0.127 | 140% |
| Compound 35 | 0.009 | 161% |
| Compound 36 | 0.069 | 135% |
| Compound 37 | 0.013 | 118% |
| Compound 38 | 0.14 | 118% |
| Compound 39 | 0.035 | 140% |
| Compound 40 | 0.058 | 117% |
| Compound 41 | 0.444 | 95% |
| Compound 42 | 0.189 | 137% |
| Compound 43 | 0.02 | 153% |
| Compound 44 | 0.058 | 117% |
| Compound 45 | 0.108 | 117% |
| Compound 46 | 0.083 | 126% |
| Compound 47 | 0.02 | 153% |

* The reference compound of activation efficacy percent (Efficacy) in Examples 31-47 is obeticholic acid, and the reference compound of activation efficacy percent (Efficacy) in Examples 1-30 is chenodeoxycholic acid.

As can be seen from Table 1, the agonistic effect of the compounds in the present disclosure on the FXR receptor was remarkable.

In Vivo Efficacy Test:

In this test, NASH model was established on mice by two procedures of high-fat diet feeding and CCl$_4$ induction to test the effects of compounds on treating NASH. Briefly, the modeling process includes feeding C57/BL6 mice with high-fat diet to induce obesity in mice and produce non-alcoholic fatty liver disease; selecting 40 obese mice with a body weight >35 g when >80% of mice reached 35 g or more, continuously feeding with high-fat diet while intraperitoneal injection of CCl$_4$ twice a week for four weeks; as for 10 normal animals in the same batch, feeding intraperitoneally with olive oil as a healthy control. The day when CCl$_4$ feeding was started was set to the 0$^{th}$ day, and the time when CCl$_4$ feeding was started was set to 0$^{th}$ hour. On the day when CCl$_4$ feeding was started, the intragastric administration was started, 5 mL/kg once a day for 4 weeks, namely 28 days. Test doses of the compound were 15 mg/kg, 30 mg/kg, 60 mg/kg, respectively; healthy control and vehicle control were given vehicle 1% hydroxypropyl methylcellulose (HPMC). During the whole experiment period, the animals were weighed and their health was monitored every day. If there are special circumstances, the relevant project leader should be notified in time and the corresponding records should be made. On the 28$^{th}$ day, after all the animals were weighed, they were euthanized after narcotizing and blood collecting, and the liver was taken. After the blood sample was processed into serum, ALT/AST/TG/TC were tested; for parts of the liver samples, liver TG and TC and the relative expression of collagen-1 alpha gene were tested, and for the other part, liver samples was taken for pathological analysis.

Experimental results: The compounds of the present disclosure have significant in vivo pharmacodynamics activities.

What is claimed is:

1. A compound of formula (I), an optical isomer thereof or a pharmaceutically acceptable salt thereof,

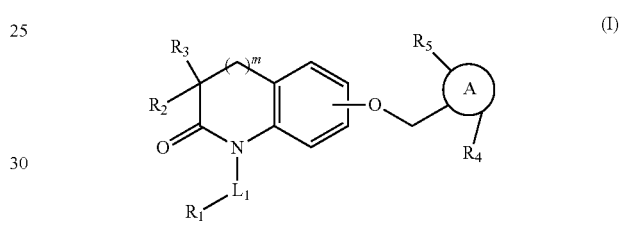

(I)

wherein, m is 1;

L$_1$ is selected from a single bond, —CH$_2$—,

R$_1$ is pyridyl which is optionally substituted with 1, 2 or 3 R;

R$_2$ is selected from H, or selected from C$_{1-3}$ alkyl which is optionally substituted with 1, 2 or 3 R;

R$_3$ is selected from H, or selected from C$_{1-3}$ alkyl which is optionally substituted with 1, 2 or 3 R;

R$_4$ is selected from H, halogen, OH, NH$_2$, or selected from the following groups which are optionally substituted with 1, 2 or 3 R: C$_{1-6}$ alkyl, or phenyl;

R$_5$ is selected from H, or selected from the following groups which are optionally substituted with 1, 2 or 3 R: C$_{1-6}$ alkyl or C$_{3-6}$ cycloalkyl;

ring A is isoxazolyl;

R is each independently selected from F, Cl, Br, I, OH, NH$_2$, CN, COOH or CONH$_2$, or selected from the following groups which are optionally substituted with 1, 2 or 3 R': C$_{1-6}$ alkyl or C$_{1-6}$ heteroalkyl;

R' is each independently selected from halogen, CN, OH, NH$_2$, COOH, NH(Me), N(CH$_3$)$_2$ or CF$_3$;

the "hetero" in the C$_{1-6}$ heteroalkyl refers to a hetero atom or a hetero atomic group selected from —NH—, —O—, —S—, —N—, —C(=O)NH—, —C(=O)O— or —C(=O)—;

in any of the above situations, the number of the hetero atom or hetero atomic group is respectively independently selected from 1, 2 or 3.

2. The compound, optical isomer thereof or pharmaceutically acceptable salt thereof according to claim 1, which is selected from:

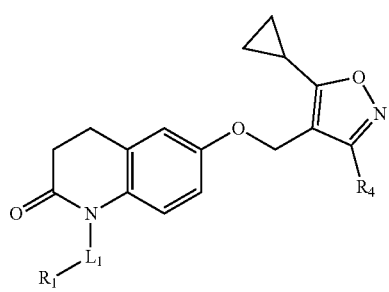

(III)

wherein, $L_1$ is selected from a single bond, —$CH_2$—,

$R_1$ is pyridyl which is optionally substituted with 1, 2 or 3 R;

$R_4$ is selected from H, halogen, OH, $NH_2$, or selected from the following groups which are optionally substituted with 1, 2 or 3 R: $C_{1-6}$ alkyl, or phenyl;

R is each independently selected from F, Cl, Br, I, OH, $NH_2$, CN, COOH or $CONH_2$, or selected from the following groups which are optionally substituted with 1, 2 or 3 R': $C_{1-6}$ alkyl or $C_{1-6}$ heteroalkyl;

R' is each independently selected from halogen, CN, OH, $NH_2$, COOH, NH(Me), $N(CH_3)_2$ or $CF_3$;

the "hetero" in the $C_{1-6}$ heteroalkyl refers to a hetero atom or a hetero atomic group selected from —NH—, —O—, —S—, —N—, —C(=O)NH—, —C(=O)O— or —C(=O)—;

in any of the above situations, the number of the hetero atoms or hetero atomic groups is respectively independently selected from 1, 2 or 3.

3. The compound, optical isomer thereof or pharmaceutically acceptable salt thereof according to claim 1, wherein R is selected from F, Cl, Br, I, OH, $NH_2$, CN, COOH, $CONH_2$, or selected from the following groups which are optionally substituted with 1, 2 or 3 R': $C_{1-3}$ alkyl, $C_{1-3}$ alkoxy or —C(=O)O—$C_{1-3}$ alkyl; or wherein R is selected from F, Cl, Br, I, CN, OH, $NH_2$, COOH, $CONH_2$, Me, Et, $CF_3$,

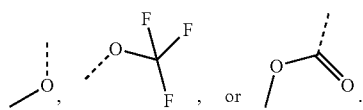

4. The compound, optical isomer thereof or pharmaceutically acceptable salt thereof according to claim 1, wherein $R_1$ is selected from the following groups which are optionally substituted with 1, 2 or 3 R:

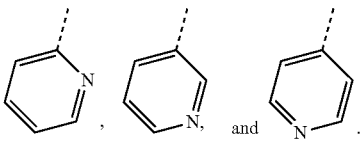

5. The compound, optical isomer thereof or pharmaceutically acceptable salt thereof according to claim 1, wherein $R_2$ is selected from Me or Et.

6. The compound, optical isomer thereof or pharmaceutically acceptable salt thereof according to claim 1, wherein $R_3$ is selected from Me or Et.

7. The compound, optical isomer thereof or pharmaceutically acceptable salt thereof according to claim 1, wherein $R_4$ is selected from H, F, Cl, Br, I, OH, or $NH_2$, or selected from the following groups which are optionally substituted with 1, 2 or 3 R: $C_{1-3}$ alkyl, and phenyl.

8. The compound, optical isomer thereof or pharmaceutically acceptable salt thereof according to claim 1, wherein $R_5$ is H, or selected from the following groups which are optionally substituted with 1, 2 or 3 R: Me or

9. The compound, optical isomer thereof or pharmaceutically acceptable salt thereof according to claim 7, wherein the structure unit

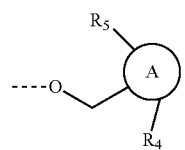

is selected from

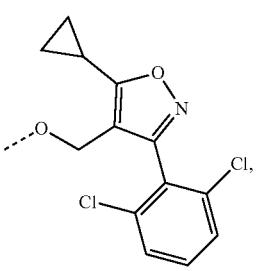

-continued
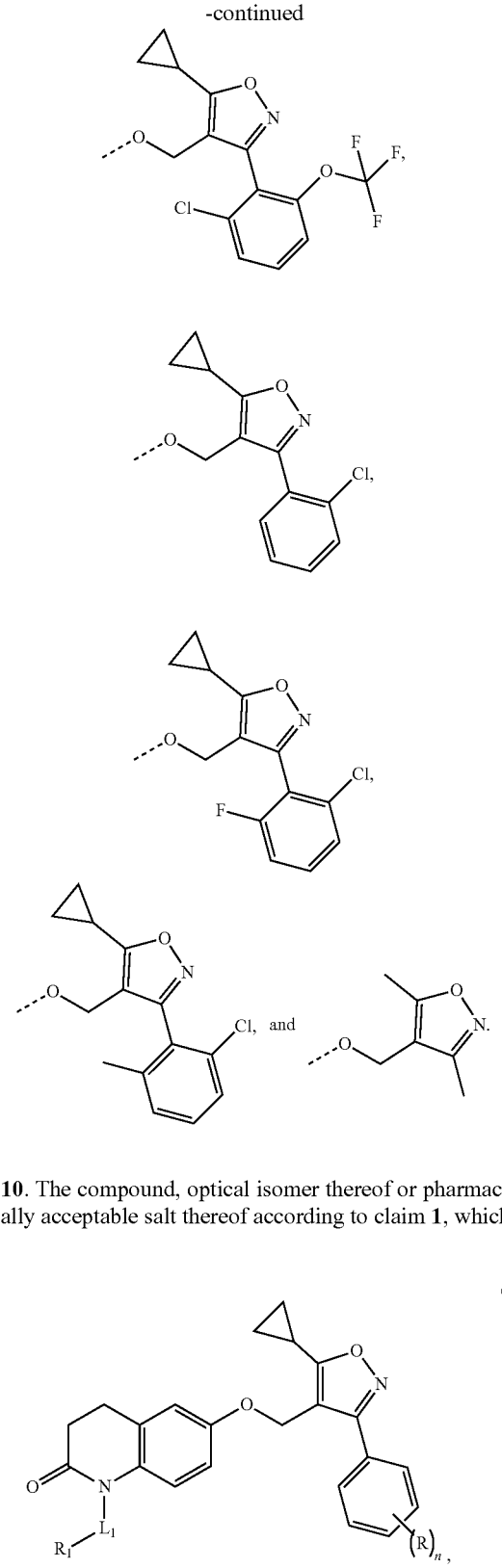
10. The compound, optical isomer thereof or pharmaceutically acceptable salt thereof according to claim 1, which is
(I-4)
wherein,
n is selected from 0, 1 or 2;
R, L₁, and R₁ are as defined in claim 1.
11. The compound, optical isomer thereof or pharmaceutically acceptable salt thereof according to claim 1, which is selected from
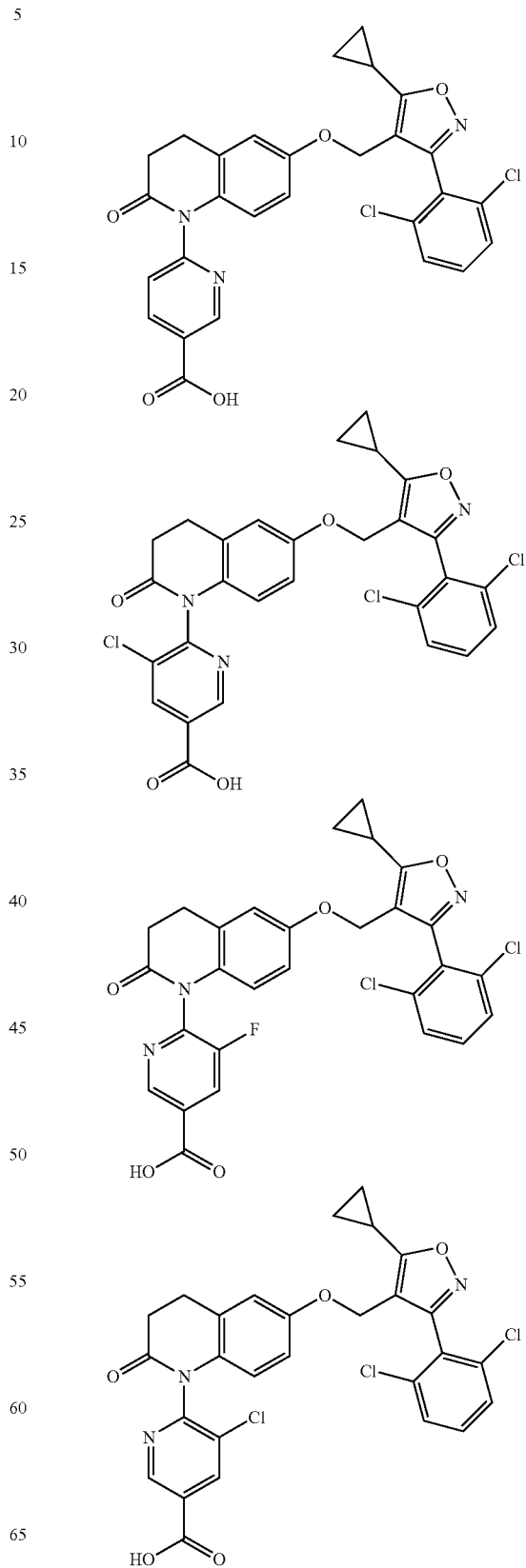

157

-continued

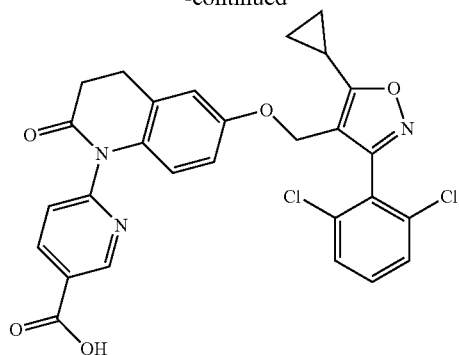

12. The compound, optical isomer thereof or pharmaceutically acceptable salt thereof according to claim 4, wherein $R_1$ is selected from the group consisting of

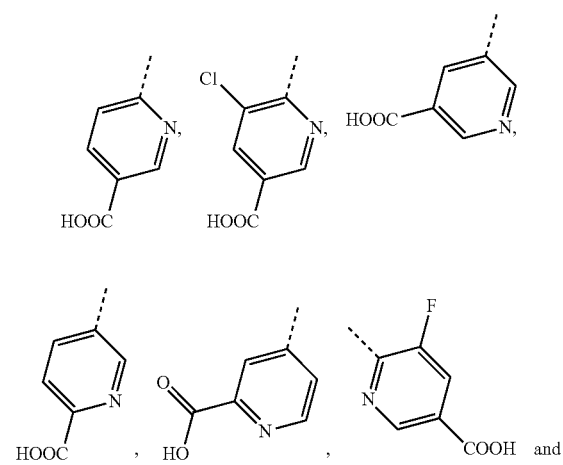

158

-continued

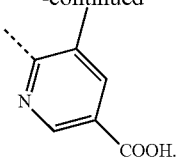

13. The compound, optical isomer thereof or pharmaceutically acceptable salt thereof according to claim 7, wherein $R_4$ is selected from H, F, Cl, Br, I, OH, or $NH_2$, or selected from the following groups which are optionally substituted with 1, 2 or 3 R: Me and

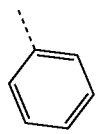

14. The compound, optical isomer thereof or pharmaceutically acceptable salt thereof according to claim 7, wherein $R_4$ is selected from H, Cl, Me,

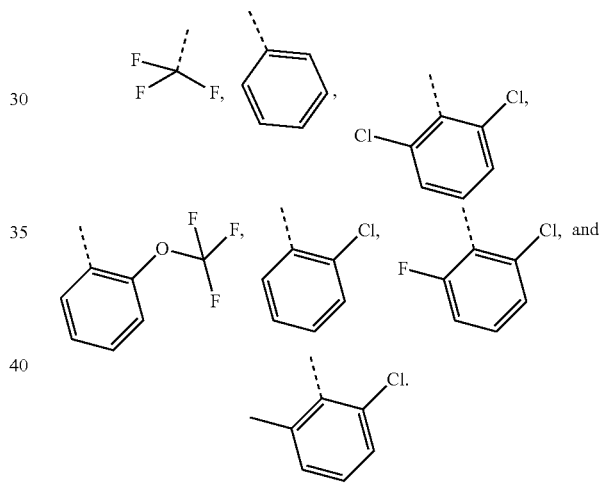

15. The compound, optical isomer thereof or pharmaceutically acceptable salt thereof according to claim 8, wherein $R_5$ is selected from H, Me and

* * * * *